US012527874B2

(12) United States Patent
Mejia Oneto et al.

(10) Patent No.: US 12,527,874 B2

(45) Date of Patent: Jan. 20, 2026

(54) BIOORTHOGONAL COMPOSITIONS

(71) Applicant: TAMBO, INC., San Francisco, CA (US)

(72) Inventors: Jose Mejia Oneto, San Francisco, CA (US); Robert Galemmo, Jr., Hong Kong (CN)

(73) Assignee: Tambo, Inc., San Francisco, CA (US)

( * ) Notice: Subject to any disclaimer, the term of this patent is extended or adjusted under 35 U.S.C. 154(b) by 0 days.

(21) Appl. No.: 17/554,792

(22) Filed: Dec. 17, 2021

(65) Prior Publication Data

US 2022/0105191 A1 Apr. 7, 2022

Related U.S. Application Data

(63) Continuation of application No. 17/032,966, filed on Sep. 25, 2020, now abandoned, which is a continuation of application No. 15/759,056, filed as application No. PCT/US2016/051394 on Sep. 12, 2016, now Pat. No. 10,828,373.

(60) Provisional application No. 62/381,442, filed on Aug. 30, 2016, provisional application No. 62/357,647, filed on Jul. 1, 2016, provisional application No. 62/344,341, filed on Jun. 1, 2016, provisional application No. 62/327,924, filed on Apr. 26, 2016, provisional application No. 62/387,480, filed on Dec. 24, 2015, provisional application No. 62/242,896, filed on Oct. 16, 2015, provisional application No. 62/216,858, filed on Sep. 10, 2015.

(51) Int. Cl.

| | |
|---|---|
| ***A61K 47/61*** | (2017.01) |
| ***A61K 9/00*** | (2006.01) |
| ***A61K 31/337*** | (2006.01) |
| ***A61K 31/35*** | (2006.01) |
| ***A61K 31/453*** | (2006.01) |
| ***A61K 38/08*** | (2019.01) |
| ***A61K 47/18*** | (2017.01) |
| ***A61K 47/54*** | (2017.01) |
| ***A61K 47/69*** | (2017.01) |
| ***A61K 49/00*** | (2006.01) |
| ***A61K 51/04*** | (2006.01) |
| ***A61K 51/12*** | (2006.01) |
| ***A61P 35/00*** | (2006.01) |
| ***C08B 37/00*** | (2006.01) |

(52) U.S. Cl.

CPC .............. *A61K 47/61* (2017.08); *A61K 47/18* (2013.01); *A61K 47/555* (2017.08); *A61K 47/6903* (2017.08); *A61K 47/6939* (2017.08); *A61K 49/0032* (2013.01); *A61K 49/0054* (2013.01); *A61K 49/0073* (2013.01); *A61K 51/0495* (2013.01); *A61K 51/1213* (2013.01); *A61K 51/1244* (2013.01); *A61P 35/00* (2018.01); *C08B 37/0084* (2013.01); *A61K 9/0019* (2013.01); *A61K 9/0024* (2013.01); *A61K 31/337* (2013.01); *A61K 31/35* (2013.01); *A61K 31/453* (2013.01); *A61K 38/08* (2013.01); *A61K 2300/00* (2013.01)

(58) Field of Classification Search

CPC ...... A61K 47/61; A61K 47/18; A61K 47/555; A61K 47/6903; A61K 47/6939; A61K 49/0032; A61K 49/0054; A61K 49/0073; A61K 51/0495; A61K 51/1213; A61K 51/1244; A61K 9/0019; A61K 9/0024; A61K 31/337; A61K 31/35; A61K 31/453; A61K 38/08; A61K 2300/00; A61K 45/00; A61K 47/542; A61K 47/543; A61K 47/545; A61P 35/00; C08B 37/0084; C07H 19/09; C07H 15/252; C07D 239/553; C07D 305/14; C07D 475/08; C07D 519/00; C07J 5/0076; C07J 41/0005

See application file for complete search history.

(56) References Cited

U.S. PATENT DOCUMENTS

| | | | |
|---|---|---|---|
| 5,770,229 | A | 6/1998 | Tanihara et al. |
| 8,552,183 | B2 | 10/2013 | Wiessler et al. |
| 9,421,274 | B2 | 8/2016 | Robillard et al. |
| 9,427,482 | B2 | 8/2016 | Rossin et al. |
| 9,463,256 | B2 | 10/2016 | Lub et al. |
| 10,130,711 | B2 | 11/2018 | Mejia Oneto et al. |
| 10,130,723 | B2 | 11/2018 | Mejia Oneto et al. |
| 10,342,882 | B2 | 7/2019 | Mejia Oneto et al. |
| 10,806,807 | B2 | 10/2020 | Mejia Oneto et al. |
| 10,828,373 | B2 | 11/2020 | Mejia Oneto et al. |

(Continued)

FOREIGN PATENT DOCUMENTS

| | | |
|---|---|---|
| EP | 1867638 A1 | 12/2007 |
| EP | 2716662 A1 | 4/2014 |

(Continued)

OTHER PUBLICATIONS

Al-Dubai et al., "Biocompatible medical implant materials with binding sites for a biodegradable drug-delivery system," Nanotechnology, Science and AQQlications, vol. 2011, No. 4, pp. 87-94 (2011).

(Continued)

*Primary Examiner* — Joseph K Mckane
*Assistant Examiner* — Meghan C Heasley
(74) *Attorney, Agent, or Firm* — Michael Best & Friedrich LLP

(57) ABSTRACT

The present disclosure provides bioorthogonal compositions for delivering agents in a subject. The disclosure also provides methods of producing the compositions, as well as methods of using the same.

7 Claims, 54 Drawing Sheets

(56) References Cited

U.S. PATENT DOCUMENTS

| | | | |
|---|---|---|---|
| 11,253,600 | B2 | 2/2022 | Mejia Oneto et al. |
| 2005/0014197 | A1 | 1/2005 | Agnew et al. |
| 2006/0153893 | A1 | 7/2006 | Matsuno et al. |
| 2009/0023916 | A1 | 1/2009 | Fox et al. |
| 2009/0304587 | A1 | 12/2009 | Rubinstein et al. |
| 2010/0016545 | A1 | 1/2010 | Wiessler et al. |
| 2010/0028435 | A1 | 2/2010 | Gavard Molliard |
| 2011/0223257 | A1 | 9/2011 | Zhao et al. |
| 2011/0268654 | A1 | 11/2011 | Hilderbrand et al. |
| 2012/0034161 | A1 | 2/2012 | Robillard et al. |
| 2012/0076727 | A1 | 3/2012 | McBride et al. |
| 2013/0281644 | A1 | 10/2013 | Kiessling et al. |
| 2013/0302246 | A1 | 11/2013 | Hilderbrand et al. |
| 2014/0093450 | A1 | 4/2014 | Robillard et al. |
| 2014/0199331 | A1 | 7/2014 | Robillard et al. |
| 2014/0303123 | A1 | 10/2014 | Baker, Jr. et al. |
| 2015/0037359 | A1 | 2/2015 | Schellenberger et al. |
| 2016/0114046 | A1 | 4/2016 | Brudno et al. |
| 2016/0120987 | A1 | 5/2016 | Mejia Oneto et al. |
| 2017/0087258 | A1 | 3/2017 | Oneto et al. |
| 2017/0095580 | A1 | 4/2017 | Mejia Oneto et al. |
| 2017/0189581 | A1* | 7/2017 | Desai ...................... A61L 27/54 |
| 2019/0111163 | A1 | 4/2019 | Mejia Oneto et al. |
| 2021/0128733 | A1 | 5/2021 | Mejia Oneto et al. |
| 2022/0168426 | A1* | 6/2022 | Mejia Oneto ...... A61K 49/0043 |

FOREIGN PATENT DOCUMENTS

| | | | |
|---|---|---|---|
| EP | 2719400 | A2 | 4/2014 |
| JP | 2009-513696 | A | 4/2009 |
| JP | 2010-036032 | A | 2/2010 |
| WO | WO2003/000708 | A1 | 1/2003 |
| WO | WO2003/084571 | A1 | 10/2003 |
| WO | 2009064738 | A2 | 5/2009 |
| WO | WO 2010/051530 | A2 | 5/2010 |
| WO | WO 2011/127149 | A1 | 10/2011 |
| WO | WO 2012/012612 | A2 | 1/2012 |
| WO | WO 2012/049624 | A1 | 4/2012 |
| WO | WO 2012/074840 | A2 | 6/2012 |
| WO | WO 2012/085789 | A1 | 6/2012 |
| WO | WO 2012/153254 | A1 | 11/2012 |
| WO | WO 2012/156918 | A1 | 11/2012 |
| WO | WO 2012/156919 | A1 | 11/2012 |
| WO | WO 2012/156920 | A1 | 11/2012 |
| WO | WO 2012/165462 | A1 | 12/2012 |
| WO | WO 2012/168512 | A2 | 12/2012 |
| WO | WO 2013/187954 | A1 | 12/2013 |
| WO | WO 2014/065860 | A1 | 5/2014 |
| WO | WO 2014/081299 | A1 | 5/2014 |
| WO | WO 2014/081300 | A1 | 5/2014 |
| WO | WO 2014/081301 | A1 | 5/2014 |
| WO | WO 2014/081303 | A1 | 5/2014 |
| WO | WO 2014/117001 | A1 | 7/2014 |
| WO | WO 2014/138186 | A1 | 9/2014 |
| WO | WO 2014/200767 | A1 | 12/2014 |
| WO | WO 2014/205126 | A1 | 12/2014 |
| WO | WO 2014/134689 | A1 | 8/2015 |
| WO | WO 2015/117235 | A1 | 8/2015 |
| WO | WO 2015/139025 | A1 | 9/2015 |
| WO | WO 2015/154082 | A1 | 10/2015 |
| WO | 2016014799 | A1 | 1/2016 |
| WO | 2017004192 | A1 | 6/2016 |

OTHER PUBLICATIONS

Alge et al., "Synthetically tractable click hydrogels for three-dimensional cell culture formed using tetrazine-norbornene chemistry," Biomacromolecules, 2013, 14(4):949-953.

Altin et al., "Fabrication of "Clickable" Hydrogels via Dendron-Polymer Conjugates," Macromolecules, 2010, vol. 43, No. 8, pp. 3801-3808.

Antoci et al., "The inhibition of *Staphylococcus* epidermidis biofilm formation by vancomycin-modified titanium alloy and implications for the treatment of periprosthetic infection," Biomaterials, vol. 29, pp. 4684-4690 (2008).

Berge et al., "Pharmaceutical Salts," J. Pharm. Sci., 1977, vol. 66, pp. 1-19.

Blackman et al., "Tetrazine Ligation: Fast Bioconjugation Based on Inverse-Electron-Demand Diels-Alder Reactivity," J. Am. Chem. Soc., 2008, vol. 130, pp. 13518-13519.

Brudno et al., "In Vivo Targeting through Click Chemistry," Chem. Med. Chem., 2015, vol. 10, pp. 617-620.

Brudno et al., "On-demand drug delivery from local depots," J. Control. Release, 2015, http://dx.doi.org/10.1016/j.jconrel.2015.09.011, 10 pages.

Brudno et al., "Refilling drug delivery depots through the blood," PNAS, 2014, 111(35):12722-12727.

Brudno et al., "Replenishable drug depot to combat post-resection cancer recurrence," Biomaterials, 2018, 178:373-382.

Burdick et al., "Acellular Biomaterials: An Evolving Alternative to Cell-Based Therapies," Science Translation Medicine, Mar. 13, 2013, vol. 5, Issue 176, 4 pages.

Carlson et al., "Unraveling Tetrazine-Triggered Bioorthogonal Elimination Enables Chemical Tools for Ultrafast Release and Universal Cleavage," J. Am. Chem. Soc., 2018, 140(10):3603-3612.

Chung et al., "Ubiquitous Detection of Gram-Positive Bacteria with Bioorthogonal Magnetofluorescent Nanoparticles," ACS NANO, 2011, vol. 5, No. 11, pp. 8834-8841, Supporting Documentation Included.

Cok et al., "Synthesis of Model Network Hydrogels via Tetrazine-Olefin Inverse Electron Demand Diels-Alder Cycloaddition," Macromol Symp, 2013, 329:108-112.

Coviello et al., "Polysaccharide hydrogels for modified release formulations," Journal of Controlled Release, 2007, vol. 119, pp. 5-24.

Deforest et al., "Sequential click reactions for synthesizing and patterning three-dimensional cell microenvironments," Nature materials: Letters, 2009, vol. 8, pp. 659-664.

Desai et al., "Versatile click alginate hydrogels crosslinked via tetrazine-norbornene chemistry," Biomaterials, 2015, vol. 50, pp. 30-37.

Devaraj et al., "Fast and Sensitive Pretargeted Labeling of Cancer Cells through a Tetrazine/trans-Cyclooctene Cycloaddition," Angew. Chem. Int. Ed., 2009, vol. 48, pp. 7013-7016.

Devaraj et al., "Reactive polymer enables efficient in vivo bioorthogonal chemistry," PNAS, 2012, vol. 109, No. 13, pp. 4762-4767.

Eckhouse et al., "Local Hydrogel Release of Recombinant TIMP-3 Attenuates Adverse Left Ventricular Remodeling After Experimental Myocardial Infarction," Science Translation Medicine, 2014, vol. 6, Issue 223, 10 pages.

Eschenhagen et al., "Physiological aspects of cardiac tissue engineering," Am. J. Physiol. Heart Circ. Physiol., vol. 30, 2012, pp. H133-H143.

European Application No. 14813532.0, Extended European Search Report mailed Dec. 2, 2016, 9 pages.

Extended European Search Report from the European Patent Office for Application No. 16845300.9 dated Apr. 17, 2019 (13 pages).

Extended European Search Report mailed on Aug. 10, 2017, for EP Application No. 15761367.0, filed Aug. 10, 2017, 12 pages.

Godoy et al., "Enhanced activity of an immobilized lipase promoted by site-directed chemical modification with polymers," Process Biochemistry, 2010, 45(4):534-541.

Guo Hua et al: "Functional alginate nanoparticles for efficient intracellular release of doxorubicin and hepatoma carcinoma cell targeting therapy", International Journal of Pharmaceutics, Els ev i er, N L, vol. 451, No. 1, Apr. 22, 2013 (Apr. 22, 2013), pp. 1-11.

Hashida et al., "Timed-Release of Mitomycin C from Its Agarose Bead Conjugate," Chem Pharm Bull, 1977, 25:2456-2458.

Hofmann et al., "Targeted delivery of vancomycin to *Staphylococcus* epidermidis biofilms using a fibrinogen-derived peptide," J Biomed Mater Res A, 2012, 100(9):2517-2525.

Hu et al., "Mitochondria-Targeted Cancer Therapy Using a Light-Up Probe with Aggregation-Induced-Emission Characteristics," Angew. Chem. Int. Ed., 2014, 53:14225-14229.

International Application No. PCT/US2015/020718 , "International Search Report and Written Opinion", mailed Jun. 10, 2015, 8 pages.

(56) References Cited

OTHER PUBLICATIONS

International Search Report and Written Opinion for Application No. PCT/US2016/051394 dated Feb. 16, 2017 (21 pages).
International Search Report and Written Opinion for International Application No. PCT/US2014/043020 dated Oct. 6, 2014 (9 pages).
IUPAC 1974 Recommendations for Section E, Fundamental Stereochemistry, in Pure Appl. Chem., 1976, 45: 13-30.
Jose M. Mejia Oneto et al: In Vivo Bioorthogonal Chemistry Enables Local Hydrogel and Systemic Pro-Drug To Treat Soft Tissue Sarcoma11 , ACS Central Science, vol. 2, No. 7, Jul. 13, 2016 (Jul. 13, 2016), pp. 476-482.
Kharkar et al., "Designing degradable hydrogels for orthogonal control of cell microenvironments," Chem. Soc. Rev., vol. 42, No. 17, pp. 7335-7372 (2013).
Kojima et al., "Antitumor activity of timed-release derivative of mitomycin C, agarose bead conjugate," Chem Pharm Bull, 1978, 26(6): 1818-1824.
Koo et al., "Bioorthogonal Copper-Free Click Chemistry In Vivo for Tumor-Targeted Delivery of Nanoparticles," Angew. Chem. Int. Ed., 2012, vol. 51, pp. 11836-11840.
Korpela et al., "A simple method to introduce aldehydic function to agarose," Anal Biochem, 1976, 71 (1):322-323.
Koshy et al., "Click-Crosslinked Injectable Gelatin Hydrogels," Advanced Healthcare Materials, 2016, DOI: 10.1002/adhm.201500757, 7 pages.
Landa et al., "Effect of Injectable Alginate Implant on Cardiac Remodeling and Function After Recent and Old Infarcts in Rat," Circulation, 2008, vol. 117, pp. 1388-1396.
Li et al., "Designing hydrogels for controlled drug delivery," Nature Reviews Materials, 2016, 1(12): 38 pages.
Li et al., "Diels-Alder reaction-triggered bioorthogonal protein decaging in living cells," Natural Chemical Biology, Advanced Online Publication, 2014, vol. 10, 5 pages.
Li et al., "Monodispersed PEG-DOTA Conjugated Anti-Tag-72 Diabody Has Low Kidney Uptake and High Tumor to Blood Ratios Resulting in Inproved $^{64}$Cu PET Imaging," J. Nucl. Med., 2010, vol. 51, No. 7, pp. 1139-1146.
Lueckgen et al., "Hydrolytically-degradable click-crosslinked alginate hydrogels," Biomaterials, 2018, 181: 189-198.
Matikonda et al., "Bioorthogonal prodrug activation driven by a strain-promoted 1,3-dipolar cycloaddition," Chem. Sci., 2015, vol. 6, pp. 1212-1218.
Mejia Oneto et al., "Implantable biomaterial based on click chemistry for targeting small molecules," Acta Biomaterialia, 2014, vol. 10, pp. 5099-5105.
Neves et al., "Imaging Cell Surface Glycosylation in Vivo Using "Double Click" Chemistry," Bioconjugate Chem., May 5, 2013, vol. 24, pp. 934-941.
Niska et al., "Vancomycin-rifampin combination therapy has enhanced efficacy against an experimental *Staphylococcus aureus* prosthetic joint infection," Antimicrob Agents Chemother, 2013, 57(10):5080-5086.
Patterson et al., "Finding the Right (Bioorthogonal) Chemistry," ACS Chem. Biol., 2014, vol. 9, pp. 592-605.
Pretze et al., "Recent Trends in Bioorthogonal Click-Radiolabeling Reactions Using Fluorine-18," Molecules, vol. 18, 2013, pp. 8618-8665; doi:I0.3390/molecules18078618.
Reiner et al., "The inverse electron demand Diels-Alder click reaction in radiochemistry," J. Labelled Comp. Radiopharm., 2014, vol. 57, No. 4, pp. 285-290.
Rohatagi et al., "Pharmacokinetic and Pharmacodynamic Evaluation of Triamcinolone Acetonide After Intravenous, Oral, and Inhaled Administration," J. Clin. Pharmacol., 1995, 35:1187-1193.
Rossin et al., "Chemically triggered drug release from an antibody-drug conjugate leads to potent antitumour activity in mice," Nat Commun, 2018, 9:1484, Supplementary Information Included, 120 pages.
Rossin et al., "In Vivo Chemistry for Pretargeted Tumor Imagining in Live Mice," Angew. Chem. Int. Ed., vol. 49, pp. 3375-3378 (2010) Supporting Information Sections S1-S6, pp. S2-S21.
Rossin et al., "Triggered Drug Release from an Antibody-Drug Conjugate Using Fast "Click- to-Release" Chemistry in Mice," Bioconjugate Chemistry, 2016, 27:1697-1706.
Royzen et al., "A Photochemical Synthesis of Functionalized trans-Cyclooctenes Driven by Metal Complexation," J. Am. Chem. Soc., vol. 130, pp. 3760-3761 (2008).
Seif-Naraghi et al., "Safety and Efficacy of an Injectable Extracellular Matrix Hydrogel for Treating Myocardial Infarction," Science Translation Medicine, 2013, vol. 5, Issue 173, 10 pages.
Selvaraj et al., "Tetrazine-tans-cyclooctene ligation for the rapid construction of integrin $\alpha_v\beta_3$ targeted PET tracer based on a cyclic RGD peptide," Bioorg. Med. Chem. Lett., 2011; 21 (17), pp. 5011-5014; doi:10.1016/j.bmcl.2011.04.116.
Selvaraj et al., "trans-Cyclooctene—a stable, voracious dienophile for bioorthogonal labeling", Current Opinion in Chemical Biology, vol. 17, Issue 5, 2013, pp. 753-760; doi: 10.1016/j.cbpa.2013.07.031.
Shelke et al., "Polysaccharide biomaterials for drug delivery and regenerative engineering," Polym. Adv. Technol., 2014, vol. 25, pp. 448-460; DOI: 10.1002/pat.3266.
Sluyterman et al., "Chromatofocusing: a preparative protein separation method," TIBS, 1982, pp. 168-170.
Thalhammer et al., "Reaktivitat Einfacher Offenkettiger und Cyclischer Dienophile Bei Diels-Alder-Reaktionen Mit Inversem Elektronenbedarf," Tetrahedron Letters, 1990, vol. 31, No. 47, pp. 6851-6854.
Thomas et al., "Polyvalent Dendrimer-Methotrexate as a Folate Receptor-Targeted Cancer Therapeutic" Molecular Pharmaceutics, 2012, vol. 9 pp. 2669-2676.
Tjwa, "Budesonide inhaled via Turbuhaler: a more effective treatment for asthma than beclomethasone dipropionate via Rotahaler," Ann. Allergy Asthma Immunol., 1995, 75(2): 107-111.
Triton et al., "The anticancer agent adriamycin can be actively cytotoxic without entering cells," Science, 1982, 217(4556):248-250.
Verbeke et al., "Multicomponent Injectable Hydrogels for Antigen-Specific Tolerogenic Immune Modulation," Adv Healthc Mater, 2017, 6 (6), 34 pages.
Versteegen et al., "Click to Release: Instantaneous Doxorubicin Elimination upon Tetrazine Ligation," Angew. Chem. Int. Ed., 2013, vol. 52, pp. 14112-14116.
Versteegen et al., "Click-to-Release from trans-Cyclooctenes: Mechanistic Insights and Expansion of Scope from Established Carbamate to Remarkable Ether Cleavage," Angew. Chem. Int. Ed., 2018, 57:10494-10499.
Zeglis et al., "A Pretargeted PET Imaging Strategy Based on Bioorthogonal Diels-Alder Click Chemistry," J. Nucl. Med., 2013, vol. 54, No. 8, pp. 1389-1396.
Zeglis et al., "Building Blocks for the Construction of Bioorthogonally Reactive Peptides via Solid-Phase Peptide Synthesis," Chemistry Open Communications, 2014, vol. 3, pp. 48-53, DOI: 10.1002/open.201402000.
Zeglis et al., "Modular Strategy for the Construction of Radiometalated Antibodies for Positron Emission Tomography Based on Inverse Electron Demand Diels-Alder Click Chemistry," Bioconjugate Chemistry, 2011, vol. 22, pp. 2048-2059.
Zhang et al., "An ionically crosslinked hydrogel containing vancomycin coating on a porous scaffold for drug delivery and cell culture," International Journal of Pharmaceutics, 2008, vol. 353, pp. 74-87.
Japanese Patent Office Action for Application No. 2018-532532 dated Aug. 26, 2020 (14 pages, English translation and pending claims included).
Chinese Patent Office Action for Application No. 201680056941.4 dated Jul. 24, 2020 (15 pages, brief English translation and pending claims included).
Australian Patent Office Examination Report for Application No. 2016321431 dated May 12, 2021 (4 pages).
Chinese Patent Office Action for Application No. 201680056941.4 dated Mar. 2, 2021 (X pages, brief English translation and pending claims included).
Japanese Patent Office Notification of Reasons for Rejection for Application No. 2021-000729 dated Jan. 27, 2022 (9 pages including English translation).

(56) References Cited

OTHER PUBLICATIONS

Australian Patent Office Action for application No. 2021282425, dated Feb. 17, 2023 (5 pages).
Australian Patent Office Action for application No. 2021282425, dated Oct. 16, 2023 (7 pages).
Japanese Patent Office Decision of Rejection for application No. 2021-000729, dated Oct. 21, 2022 (5 pages with translation).
Zhang, H., et al. "Interfacial bioorthogonal cross-linking." ACS macro letters 3.8 (2014): 727-731.

* cited by examiner

Alginate hydrogel modified with tetrazines (HMT, 1)

Doxorubicin (doxo, 2)

*trans*-cyclooctene modified doxorubicin (pro-drug, 3)

TCO-Non-Releasable-Fluorescein
TCO-NR-Fl

TCO-Releasable-Rhodamine
TCO-R-Rh

TCO-Gemcitabine

TCO-Taxane

TCO-Methotrexate-A

TCO-Methotrexate-B

Adipic acid dihydrazide (Commercially available) | TCO-Adipic acid hydrazide | TCO-Adipic-Dexamethasone A = O, S, SR, $SR_3$
B = C, $CR_2$
D = O, S, nothing
E = $(CR_2)_{0-30}$, O, SR, $SR_3$, $NR_2$,
R = H, alkyl, aryl, O, $NR_2$ pH & carbamate Releasable
TCO-Adipic-Doxorubicin only pH dependent
TCO-Adipic-Doxorubicin 5 6 7 3a

Synthetic route to an analog of 4

5 6 7 4a

BIOORTHOGONAL COMPOSITIONS

CROSS REFERENCE TO RELATED APPLICATION

This application is a continuation of U.S. patent application Ser. No. 17/032,966, filed Sep. 25, 2020, which is a continuation of U.S. patent application Ser. No. 15/759,056, filed on Mar. 9, 2018, which is a U.S. national stage entry of International Patent Application No. PCT/US2016/051394, filed on Sep. 12, 2016, which claims priority to U.S. Provisional Application No. 62/216,858, filed Sep. 10, 2015; U.S. Provisional Application No. 62/242,896, filed Oct. 16, 2015; U.S. Provisional Application No. 62/387,480, filed Dec. 24, 2015; U.S. Provisional Application No. 62/327,924, filed Apr. 26, 2016; U.S. Provisional Application No. 62/344,341, filed Jun. 1, 2016; U.S. Provisional Application No. 62/357,647, filed Jul. 1, 2016; and U.S. Provisional Application No. 62/381,442, filed Aug. 30, 2016; each of which is herein incorporated by reference in its entirety.

STATEMENT OF GOVERNMENT INTEREST

This invention was made with government support under Contract No. 1549133, awarded by the National Science Foundation. The government has certain rights in the invention.

TECHNICAL FIELD

The present disclosure provides bioorthogonal compositions and methods of using the bioorthogonal compositions for delivering agents in a subject. Aspects of the bioorthgonal compositions as well as methods of producing the bioorthogonal compositions are also described herein.

BACKGROUND

Typically, physicians rely on systemic medications for the treatment of various medical conditions. The use of physical drug delivery systems may assist the physician in optimizing the delivery of therapeutic agents to specific sites of the body, as well as facilitating the delivery of therapeutic agents at desired times or intervals. However, after the initial intervention, physicians still rely on systemic medications that need frequent dosing and may have noxious side effects. Existing biomaterials can serve as depots for therapeutic agents, which can be released to the body through diffusion or degradation. However, most biomaterials cannot be modulated or modified after implantation, and usually exhibit an initial burst of activity shortly after implantation. These issues may limit the application of biomaterials for medical conditions that require a particular dosing regimen, such as doses that are to be administered at different time points, or for medical conditions where the most effective therapeutic agent is identified hours or days after implantation of the biomaterial, e.g., after culture or pathology results are obtained.

Bioorthogonal conjugation or click reactions are selective and orthogonal (non-interacting with) functionalities found in biological systems, and have found use in various applications in the fields of chemistry, chemical biology, molecular diagnostics, and medicine, where they can be used to facilitate the selective manipulation of molecules, cells, particles and surfaces, and the tagging and tracking of biomolecules in vitro and in vivo. These reactions include the Staudinger ligation, the azide-cyclooctyne cycloaddition, and the inverse-electron-demand Diels-Alder reaction.

SUMMARY

The present disclosure provides bioorthogonal compositions for delivering agents in a subject. The disclosure also provides methods of producing the compositions, as well as methods of using the same.

Aspects of the present disclosure include a support composition that includes a support, where the support is a hydrogel support or a support particle. The support composition also includes a first binding agent attached to the support and comprising a first bioorthogonal functional group that is a member of a first complementary binding pair; a second binding agent attached to the support and comprising a second bioorthogonal functional group that is a member of a second complementary binding pair different from the first complementary binding pair. In addition, if the support comprises the support particle, then the support composition can comprise a targeting agent attached to the support particle.

In some embodiments, the support is a hydrogel support. In some embodiments, the support is a support particle and the support composition includes the targeting agent attached to the support particle. In some embodiments, the support composition includes a first linker covalently linking the first binding agent to the support. In some embodiments, the support composition includes a second linker covalently linking the second binding agent to the support. In some embodiments, the first bioorthogonal functional group and the second bioorthogonal functional group are a trans-cyclooctene and an azide. In some embodiments, the first bioorthogonal functional group and the second bioorthogonal functional group are a trans-cyclooctene and an alkyne. In some embodiments, the first bioorthogonal functional group and the second bioorthogonal functional group are a tetrazine and an azide. In some embodiments, the first bioorthogonal functional group and the second bioorthogonal functional group are a tetrazine and an alkyne. In some embodiments, the first binding agent is covalently bound to a first functionalized payload. In some embodiments, the first functionalized payload comprises a first complementary binding agent that selectively binds to the first binding agent, a first payload, and'a linker covalently linking the first complementary binding agent to the first payload. In some embodiments, the first payload includes a therapeutic agent, a diagnostic agent or a targeting agent. In some embodiments, the linker comprises a releasable linker. In some embodiments, the second binding agent is covalently bound to a second functionalized payload. In some embodiments, the second functionalized payload comprises a second complementary binding agent that selectively binds to the second binding agent, a second payload, and a linker covalently linking the second complementary binding agent to the second payload. In some embodiments, the second payload comprises a therapeutic agent, a diagnostic agent or a targeting agent. In some embodiments, the linker comprises a releasable linker. In some embodiments, the support particle is a nanoparticle or a microparticle.

Aspects of the present disclosure include a method for delivering an effective amount of a payload to a target location in a subject, where the method includes administering to the subject a support composition. The support composition includes a support, where the support is a hydrogel support or a support particle. The support composition also includes a first binding agent attached to the support and comprising a first bioorthogonal functional group that is a member of a first complementary binding pair; a second binding agent attached to the support and comprising a second bioorthogonal functional group that is a member of a second complementary binding pair different from the first complementary binding pair. In addition, if the support comprises the support particle, then the support composition further can comprise a targeting agent attached to the support particle. The method also includes administering to the subject a first functionalized payload comprising a first complementary binding agent that selectively binds to the first binding agent, a first payload, and a linker covalently linking the first complementary binding agent to the first payload, such that the first functionalized payload binds to the support composition.

In some embodiments, the linker includes a releasable linker, and the method also includes releasing the first payload, thereby delivering the first payload to the target location in the subject. In some embodiments, the method includes administering to the subject a second functionalized payload comprising a second complementary binding agent that selectively binds to the second binding agent, a second payload, and a linker covalently linking the second complementary binding agent to the second payload, such that the second functionalized payload binds to the support composition. In some embodiments, the linker includes a releasable linker, and the method also includes releasing the second payload, thereby delivering the second payload to the target location in the subject. In some embodiments, the method includes administering to the subject a second support composition, where the second support composition includes a second support, a second complementary binding agent attached to the second support that selectively binds to the second binding agent, and a third binding agent attached to the second support and comprising a third bioorthogonal functional group, such that the second support composition binds to the support composition. In some embodiments, the first binding agent has a shorter in vivo half life than the second binding agent. In some embodiments, the first binding agent has a longer in vivo half life than the second binding agent.

Aspects of the present disclosure also include a kit. The kit includes a support composition that includes a support, where the support is a hydrogel support or a support particle. The support composition also includes a first binding agent attached to the support and comprising a first bioorthogonal functional group that is a member of a first complementary binding pair; a second binding agent attached to the support and comprising a second bioorthogonal functional group that is a member of a second complementary binding pair different from the first complementary binding pair. In addition, if the support comprises the support particle, then the support composition further comprises a targeting agent attached to the support particle. The kit also includes a packaging containing the support composition.

In some embodiments, the kit includes a first functionalized payload. In some embodiments, the first functionalized payload comprises a first complementary binding agent that selectively binds to the first binding agent, a first payload, and a linker covalently linking the first complementary binding agent to the first payload. In some embodiments, the kit includes a second functionalized payload. In some embodiments, the second functionalized payload comprises a second complementary binding agent that selectively binds to the second binding agent, a second payload, and a linker covalently linking the second complementary binding agent to the second payload.

BRIEF DESCRIPTION OF THE DRAWINGS

FIG. 17A, FIG. 17 B, and FIG. 17C show in vitro activation of doxorubicin pro-drug when mixed with HMT. FIG. 17A shows chemical structures of an alginate monosaccharide modified with tetrazine, doxorubicin, and doxorubicin pro-drug.

FIG. 18A shows NCR/nu:nu mice were injected with human HT-1080 fibrosarcoma cells at day 0. Tumors were then injected with HMT and started on intravenous doses of either doxorubicin pro-drug or a maximum tolerable dose of doxorubicin. Tumor sizes were monitored for more than 16 weeks (n=5-10). FIG. 18B shows the tumor size of the members of each cohort at relevant time points in a logarithmic scale illustrate the differences between standard chemotherapy treatment and the material pro-drug approach. P values were determined by unpaired t test. Solid bars represent the mean for each cohort (n=5-10). FIG. 18C shows the evaluation of reticulocyte counts as a surrogate for bone marrow suppression in a xenograft model of soft tissue sarcoma. Mice were given vehicle, doxorubicin, or doxorubicin pro-drug after injection of HMT. Samples were collected 3 days after the last treatment. Data are means±SD (n=2). FIG. 18D shows the body weight changes in response to therapy. Data are mean body weight changes as a percentage of initial weight±SD (n=5-10). P values were determined by unpaired t test.

FIG. 22 shows the chemical reaction and protocol. FIG. 23 shows a comparison of reacted TCO—NR—F in alginate control vs HMT at different time points. HMT and unmodified alginate 2% (w/w) gels were challenged with non releasable fluorescently labeled TCO to determine the functional amount of tetrazines that remain active after incubation in PBS at 37° C. for different time periods (0, 2, 3, 14 days). In short, the hydrogels were prepared as outlined above for in-vitro analysis. Disks of hydrogel (50 mg) were placed in well plates with 1 mL of PBS. Then the plates were maintained at a 37° C. incubator until the period was over. Then, the hydrogels were challenged with 50 nmoles of a solution of TCO—NR—F for 90 min in a shaker. The resulting supernatant (approximately 1 mL) was transferred to another well plate leaving the hydrogel behind. The radiance of the supernatant in each well plate was measured via an IVIS Spectrum. The data are average±SEM, n=3. P values were determined by unpaired t-test. These data suggests that more than 70% of the tetrazine moieties remain stable and reactive after 14 days.

DETAILED DESCRIPTION

Figure 1:
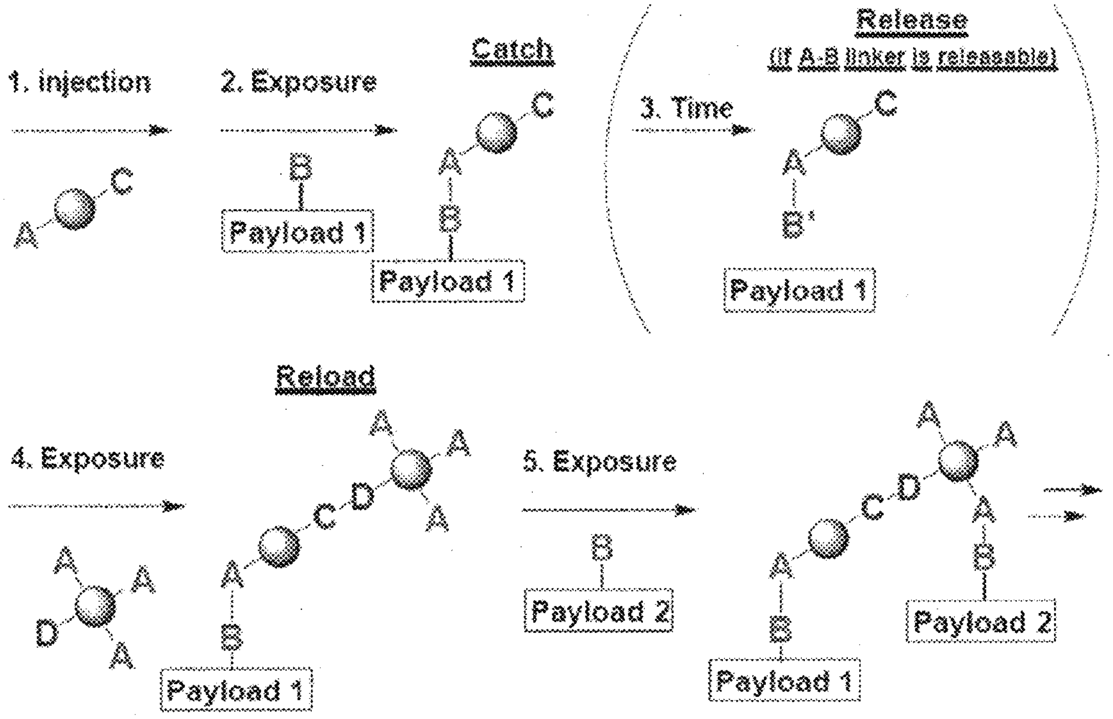
FIG. 1 shows a schematic of an administration protocol using support compositions and functionalized payloads, according to embodiments of the present disclosure.

The present disclosure provides bioorthogonal compositions for delivering agents in a subject. The disclosure also provides methods of producing the compositions, as well as methods of using the same. Embodiments of each are described in more detail in the sections below.

The bioorthogonal compositions of the present disclosure may be used to deliver a payload to a target location in a subject, such as selectively delivering a payload to a specific target location in the subject. In certain embodiments, the bioorthogonal compositions include a support composition having different bioorthogonal functional groups, which may be administered to a subject (e.g., injected or implanted) at a desired target location in the subject, or may be administered systemically and targeted to a specific location or targeted to specific cells in the subject via a targeting agent.

The present disclosure also provides functionalized payload compositions that include a payload linked to a bioorthogonal functional group, which is complementary to one of the bioorthogonal functional groups of the support composition. Upon administration of the functionalized payload to the subject (e.g., systemic administration), selective binding between complementary bioorthogonal binding partners (e.g., between a bioorthogonal functional group of the support composition and its complementary bioorthogonal functional group of a functionalized payload) may occur, thus localizing the payload to the desired target location or cells in the subject.

In certain embodiments, the support composition includes two different bioorthogonal functional groups, and as such a second functionalized payload may be administered to the subject and similarly localized to the desired target location or cells in the subject through selective binding between complementary bioorthogonal binding partners.

In certain embodiments, a second support composition may be administered to the subject, where, similar to the first support composition, the second support composition also includes two different bioorthogonal functional groups. One of the bioorthogonal functional groups of the second support composition may be complementary to a bioorthogonal functional group on the first support composition, such that selective binds occurs between the first and second support compositions, thus reloading the first support composition. For example, the second support composition can include additional different bioorthogonal functional groups that may selectively bind to additional functionalized payloads or additional support compositions.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrases "at least one of A, B, . . . and N" or "at least one of A, B, . . . N, or combinations thereof" are defined in the broadest sense to mean one or more elements selected from the group comprising A, B, . . . and N, that is to say, any combination of one or more of the elements A, B, . . . or N including any one element alone or in combination with one or more of the other elements which may also include, in combination, additional elements not listed.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, $5^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, $3^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 30 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a hydrocarbon chain containing from 2 to 30 carbon atoms with at least one carbon-carbon double bond. The alkenyl group may be substituted or unsubstituted. For example, the alkenyl group may be substituted with an aryl group, such as a phenyl.

The term "alkynyl," as used herein, refers to straight or branched monovalent hydrocarbyl groups having from 2 to 30 carbon atoms, such as 2 to 20, or 2 to 10 carbon atoms and having at least 1 site of triple bond unsaturation. The term "alkyne" also includes non-aromatic cycloalkyl groups of from 5 to 20 carbon atoms, such as from 5 to 10 carbon atoms, having single or multiple rings and having at least one triple bond. Examples of such alkynyl groups include, but are not limited to acetylenyl ($-C \equiv CH$), and propargyl ($-CH_2C \equiv CH$), and cycloalkynyl moieties, such as, but not limited to, substituted or unsubstituted cyclooctyne moieties.

The term "alkoxyalkyl" as used herein, refers to an alkoxy group, as defined herein, appended to the parent molecular moiety through an alkyl group, as defined herein.

The term "alkylene", as used herein, refers to a divalent group derived from a straight or branched chain hydrocarbon of 1 to 30 carbon atoms, for example, of 2 to 10 carbon atoms. Representative examples of alkylene include, but are not limited to, $-CH_2CH_2-$, $-CH_2CH_2CH_2-$, $-CH_2CH_2CH_2CH_2-$, and $-CH_2CH_2CH_2CH_2CH_2-$.

The term "amino acid" refers to both natural and unnatural amino acids. It also includes protected natural and unnatural amino acids.

The term "aryl" as used herein, refers to a phenyl group, or bicyclic aryl or tricyclic aryl fused ring systems. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl. The monocyclic, bicyclic, and tricyclic aryls are connected to the parent molecular moiety through any carbon atom contained within the rings, and can be unsubstituted or substituted.

The term "azide" as used herein, refers to the functional group $-N_3$.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl. "Cycloalkyl" also includes carbocyclic ring systems in which a cycloalkyl group is appended to the parent molecular moiety and is fused to an aryl group as defined herein, a heteroaryl group as defined herein, or a heterocycle as defined herein.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "cyclooctene" as used herein, refers to a substituted or unsubstituted non-aromatic cyclic alkyl group of 8 carbon atoms, having a single ring with a double bond. Examples of such cyclooctene groups include, but are not limited to, substituted or unsubstituted trans-cyclooctene (TCO).

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "alkoxyfluoroalkyl" as used herein, refers to an alkoxy group, as defined herein, appended to the parent molecular moiety through a fluoroalkyl group, as defined herein.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" or "halo" as used herein, means Cl, Br, I, or F.

The term "haloalkyl" as used herein, means an alkyl group, as defined herein, in which one, two, three, four, five, six, seven or eight hydrogen atoms are replaced by a halogen.

The term "haloalkoxy" as used herein, means at least one haloalkyl group, as defined herein, is appended to the parent molecular moiety through an oxygen atom.

The term "heteroalkyl" as used herein, means an alkyl group, as defined herein, in which one or more of the carbon atoms has been replaced by a heteroatom selected from S, Si, O, P and N. The heteroatom may be oxidized. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a monocyclic heteroaryl ring appended to the parent molecular moiety and fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings, and can be unsubstituted or substituted.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4 (1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[$3.3.1.1^{3,7}$]decane), and oxa-adamantane (2-oxatricyclo[$3.3.1.1^{3,7}$]decane). The monocyclic, bicyclic, and tricyclic heterocycles are connected to the parent molecular moiety through any carbon atom or any nitrogen atom contained within the rings, and can be unsubstituted or substituted.

The term "hydroxyl" as used herein, means an —OH group.

The term "hydroxyalkyl" as used herein, means an alkyl group, as defined herein, in which one, two, three, four, five, six, seven or eight hydrogen atoms are replaced by a hydroxyl group.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

The term "tetrazine" refers to a substituted or unsubstituted aromatic cyclic group of 2 carbon atoms and 4 nitrogen atoms, having a single ring with three double bonds. Examples of tetrazine groups include 1,2,3,4-tetrazine and 1,2,4,5-tetrazine. As used herein, 1,2,4,5-tetrazine is referred to as a "Tz" group.

The term "selectively delivering" refers to delivering an agent (e.g., a payload) to an organ or tissue (or portion thereof) in need of treatment or diagnosis, without significant binding to other non-target organs or tissues (or portions thereof).

The term "payload" refers to an agent for delivery to a target site in a subject. Payloads include therapeutic agents, diagnostic agents, targeting agents, and the like.

The term "therapeutic agent" refers to an agent capable of treating and/or ameliorating a condition or disease, or one or more symptoms thereof, in a subject. Therapeutic agents of the present disclosure also include prodrug forms of therapeutic agents.

The term "diagnostic agent" refers to agents that assist in diagnosing conditions or diseases. Representative diagnostic agents include imaging agents such as paramagnetic agents, optical probes, radionuclides, and the like. Paramagnetic agents are imaging agents that are magnetic under an externally applied field. Examples of paramagnetic agents include, but are not limited to, iron particles including iron nanoparticles and iron microparticles. Optical probes are fluorescent compounds that can be detected by excitation at one wavelength of radiation and detection at a second, different, wavelength of radiation. Optical probes of the present disclosure include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo detectable radioactive decay. Radionuclides useful in embodiments of the present disclosure include, but are not limited to, $^{3}H$, $^{11}C$, $^{13}N$, $^{18}F$, $^{19}F$, $^{60}Co$, $^{64}Cu$, $^{67}Cu$, $^{68}Ga$, $^{82}Rb$, $^{90}Sr$, $^{90}Y$, $^{99}Tc$, $^{99m}Tc$, $^{111}In$, $^{123}I$, $^{124}I$, $^{125}I$, $^{129}I$, $^{131}I$, $^{137}Cs$, $^{177}Lu$, $^{186}Re$, $^{188}Re$, $^{211}At$, Rn, Ra, Th, U, Pu and $^{241}Am$.

The term "targeting agent" refers to a chemical or biological agent that specifically binds to a target (e.g., a targeted organ or tissue), thereby forming a stable association between the targeting agent and the specific target. By "stably associated" or "stable association" is meant that a moiety is bound to or otherwise associated with another moiety or structure under standard physiological conditions. Bonds may include covalent bonds and non-covalent interactions, such as, but not limited to, ionic bonds, hydrophobic interactions, hydrogen bonds, van der Waals forces (e.g., London dispersion forces), dipole-dipole interactions, and the like. A targeting agent may be a member of a specific binding pair, such as, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like.

The term "targeted organ or tissue" refers to an organ or tissue that is being targeted for delivery of the payload. Representative organs and tissues for targeting include those that can be targeted by chemical or biological targeting agents, as well as those organs and tissues that cannot be targeted by chemical or biological targeting agents.

The term "implanting" refers to surgical implantation into a subject's body.

The term "biocompatible support" refers a support material capable of implantation into a subject's body and supporting binding agents, as well as payloads after the binding agents conjugate. The support is compatible with the subject's body. Representative biocompatible supports include, but are not limited to, hydrogels such as polysaccharide hydrogels, alginate, cellulose, chitosan, hyaluronic acid, chondroitin sulfate, heparin, and the like. Biocompatible supports also include particles, such as nanoparticles, microparticles, and the like.

The term "contacting" or "contact" refers to the process of bringing into contact at least two distinct species such that they can interact with each other, such as in a non-covalent or covalent binding interaction or binding reaction. It should be appreciated, however, the resulting complex or reaction product can be produced directly from an interaction or a reaction between the added reagents or from an intermediate from one or more of the added reagents or moieties, which can be produced in the contacting mixture.

The term "linker", "linked" or "linking" refers to a chemical moiety that attaches two moieties together, such as a compound of the present disclosure to a biological material that targets a specific type of cell, such as a cancer cell, other type of diseased cell, or a normal cell type. The linking can be via covalent bonds, ionic bonds, hydrophobic interactions, hydrogen bonds, van der Waals forces (e.g., London dispersion forces), dipole-dipole interactions, and the like. The linking can be direct linkage between to the two moieties being linked, or indirectly, such as via a linker. Linkers useful in embodiments of the present disclosure include linkers having 30 carbon atoms or less in length. In some embodiments, the linkers are 1-15 carbon atoms in length, such as 1-12 carbon atoms, or 1-10 carbon atoms, or 5-10 carbon atoms in length. The types of bonds used to link the linker to the compound and biological molecule of the present disclosure include, but are not limited to, amides, amines, esters, carbamates, ureas, thioethers, thiocarbamates, thiocarbonate and thioureas. Other types of bonds may also be used in embodiments of the present disclosure.

The term "binding agent" refers to an agent having a functional group capable of forming a covalent bond to a complementary functional group of another binding agent in a biological environment. Binding between binding agents in a biological environment may also be referred to as bioconjugation. Representative binding agents include, but are not limited to, an amine and an activated ester, an amine and an isocyanate, an amine and an isothiocyanate, thiols for formation of disulfides, an aldehyde and amine for enamine formation, an azide for formation of an amide via a Staudinger ligation. Binding agents also include bioorthogonal binding agents, which are binding agents having bioorthogonal functional groups. Bioorthogonal functional groups of bioorthogonal binding agents selectively react with a complementary bioorthogonal functional group of another bioorthogonal binding partner. Selective reaction between bioorthogonal binding partners can minimize side reactions with other binding agents, biological compounds, or other non-complementary bioorthogonal binding agents or non-complementary bioorthogonal functional groups.

Bioorthogonal functional groups of bioorthogonal binding agents include, but are not limited to, an azide and alkyne for formation of a triazole via Click-chemistry reactions, trans-cyclooctene (TCO) and tetrazine (Tz) (e.g., 1,2,4,5-tetrazine), and others. The binding agents useful in the present disclosure may have a high reactivity with the corresponding binding agent so that the reaction is rapid.

The term "functionalized" refers to a moiety having a functional group attached to the moiety, such as for example a moiety having a binding agent functional group (e.g., a bioorthogonal functional group) attached thereto.

The term "administering" refers to any suitable route of administration to a subject, such as, but not limited to, oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

The term "leaving group" refers to an atom (or a group of atoms) with electron withdrawing ability that can be displaced as a stable species, taking with it the bonding electrons. Examples of suitable leaving groups include halides (e.g., Br, Cl, I), sulfonate esters (e.g., triflate, mesylate, tosylate, and brosylate), and nitrophenols.

The term "pharmaceutically effective amount" and "therapeutically effective amount" refer to an amount of a compound sufficient to treat a specified disorder or disease or one or more of its symptoms and/or to prevent or reduce the risk of the occurrence or reoccurrence of the disease or disorder or symptom(s) thereof. In reference to tumorigenic proliferative disorders, a pharmaceutically or therapeutically effective amount comprises an amount sufficient to, among other things, cause the tumor to shrink or decrease the growth rate of the tumor.

The term "patient" as used herein refers to human and non-human subjects, especially mammalian subjects.

The term "treating" or "treatment" as used herein means the treating or treatment of a disease or medical condition or symptom(s) thereof in a patient, such as a mammal (particularly a human) that includes: (a) preventing or reducing the risk of the occurrence or reoccurrence of the disease or medical condition or symptom(s) thereof from occurring, such as, prophylactic treatment of a subject; (b) ameliorating the disease or medical condition or symptom(s) thereof, such as, eliminating or causing regression of the disease or medical condition or symptom(s) thereof in a patient; (c) suppressing the disease or medical condition or symptom(s) thereof, for example by, slowing or arresting the development of the disease or medical condition or symptom(s) thereof in a patient; or (d) alleviating a symptom of the disease or medical condition or symptom(s) thereof in a patient.

The term "physiological conditions" is meant to encompass those conditions compatible with living cells, e.g., predominantly aqueous conditions of a temperature, pH, salinity, etc. that are compatible with living cells.

The term "particle" as used herein is used in its broadest sense and it may take the form of any fabricated material, a polymer, a protein, a synthetic hydrogel, a biological hydrogel, an organogel, a ceramic, a composite, a metal, a wood, or a glass material, a molecule, cryptophan, a virus, a phage, etc. Further, a particle may be of any shape, for example, spheres, rods, non-symmetrical shapes, etc. In some examples, the particles may be magnetic and can be formed from a paramagnetic, super-paramagnetic or ferromagnetic material or any other material that responds to a magnetic field. The particles, or a group of several particles in a complex, may be functionalized with a receptor that has a specific affinity to bind to or interact with a clinically relevant substrate. The receptor may be inherent to the particle itself. For example, the particle itself may be a virus or a phage with an inherent affinity for certain substrates. Additionally or alternatively, the particles can be functionalized by covalently or otherwise attaching or associating a receptor that specifically binds or otherwise recognizes a particular clinically relevant substrate. The functionalized receptor can be an antibody, peptide, nucleic acid, phage, bacteria, virus, or any other molecule with a defined affinity for a target substrate. Examples of material that may be used for the "particles" and/or "carrier" include polylactic acid, polyglycolic acid, PLGA polymers, alginates and alginate derivatives, gelatin, collagen, fibrin, hyaluronic acid, laminin rich gels, agarose, natural and synthetic polysaccharides, polyamino acids, polypeptides, polyesters, poly anhydrides, polyphosphazines, poly(vinyl alcohols), poly(alkylene oxides), poly(allylamines) (PAM), poly(acrylates), modified styrene polymers, pluronic polyols, polyoxamers, poly (uronic acids), poly(vinylpyrrolidone) and copolymers or graft copolymers of any of the above. These examples do not limit their concentration, their cross-linking with different agents, their method of administration, their tailored degradation profiles and other characteristics known to those skilled in the art.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

2. Compositions

The present disclosure provides compositions for delivering agents in a subject. The compositions can include a functionalized payload composition and a support composition. In certain embodiments, the composition is used to selectively deliver one or more agents to a specific location in a subject, for example a targeted organ or tissue (or portion thereof) in a subject. The targeted delivery of the agent may be such that an effective amount of the agent is delivered to the targeted organ or tissue to produce a desired effect on the targeted organ or tissue (or targeted portion thereof). As such, compositions of the present disclosure facilitate selective targeting and treatment of a targeted organ or tissue (or portion thereof) in a subject.

The support compositions can include one or more different binding agents (e.g., a. first binding agent and a second binding agent). In certain embodiments, the support compositions include two or more different binding agents (e.g., a first binding agent and a second binding agent). In certain embodiments, the support composition is attached to a functionalized payload composition. For example, the first binding agent of the support composition may be bound (e.g., covalently bound) to a functionalized payload (e.g., a first functionalized payload). In some instances, the functionalized payload includes a complementary binding agent that selectively binds to one of the binding agents present on the support composition. For example, the functionalized payload may include a first complementary binding agent that selectively binds to the first binding agent of the support composition. As described above, a binding reaction may occur between a binding agent and its complementary binding agent to form a covalent bond between the binding agent and its complementary binding agent. As such, when the support composition and the functionalized payload each include a member of a complementary binding pair (e.g., complementary bioorthogonal functional groups), a binding reaction may occur between the binding agent on the support composition and the complementary binding agent on the functionalized payload to form a covalent bond between the binding agent on the support composition and the complementary binding agent on the functionalized payload, thus binding the functionalized payload to the support composition.

In certain embodiments, the functionalized payload includes a payload. The payload may be attached to the complementary binding agent. For instance, the payload may be linked to the complementary binding agent through a linker that covalently attaches the complementary binding agent to the payload.

Accordingly, as described above, in certain embodiments, the first binding agent of the support composition may be covalently bound to a first functionalized payload (e.g., through a bioorthogonal binding interaction between the first binding agent and the first complementary binding agent as described herein). In these embodiments, the payload is indirectly attached to the support through the bioorthogonal binding interaction between the first binding agent of the support composition and the first complementary binding agent of the first functionalized payload.

Similarly, in certain embodiments, the second binding agent of the support composition may be covalently bound to a second functionalized payload (e.g., through a bioorthogonal binding interaction between the second binding agent and the second complementary binding agent as described herein). In these embodiments, the payload is indirectly attached to the support through the bioorthogonal binding interaction between the second binding agent of the support composition and the second complementary binding agent of the second functionalized payload.

If present, additional binding agents attached to the support composition may be covalently bound to additional functionalized payloads through different bioorthogonal binding interactions as described herein, thus indirectly attaching additional payloads to the support composition.

As described above, the payload may be attached to the complementary binding agent through a linker. Any suitable linker can be used to link the payload to the complementary binding agent. Representative linkers can have 1 to 100 linking atoms, and can include ethylene-oxy groups, amines, esters, amides, carbamates, carbonates, and ketone functional groups. For example, linkers may have from 1 to 50 linking atoms, or from 5 to 50 linking atoms, or from 10 to 50 linking atoms.

In certain embodiments, the linker between the payload and the complementary binding agent is a non-releasable linker. A non-releasable linker is a linker that forms an attachment between at least two moieties, where the attachment is not significantly disrupted under the conditions that compositions using the non-releasable linker are used (e.g., covalent bonds in the linker remain intact and are not cleaved). For instance, a non-releasable linker may include one or more covalent bonds between at least two moieties, such that the moieties are; covalently bound to each other and remain covalently bound to each other under the conditions that compositions are used. For example, in certain embodiments, a non-releasable linker may be used with a payload, such as a payload having a prodrug form of a therapeutic agent, where release of the therapeutic agent from the prodrug provides for delivery of the therapeutic agent to the target site in the subject.

In certain embodiments, the linker between the payload and the complementary binding agent is a releasable linker. A releasable linker is a linker that forms an attachment between at least two moieties, where the attachment may be disrupted under releasing conditions such that the moieties are no longer attached to each other (e.g., one or more covalent bonds in the linker may be cleaved). Releasable linkers may have the attachment between the moieties. disrupted by exposure of the releasable linker to releasing conditions, such as, but not limited to, light, heat, sound, a releasing agent (e.g., chemical releasing agent (e.g., an acid, a base, an oxidizing agent, a reducing agent), a solvent, an enzyme, etc.), combinations thereof, and the like. In some embodiments, the releasable linker may not require the application of an external stimulus or contact with releasing conditions to disrupt the attachment between the moieties. For example, a releasable linker may include one or more unstable bonds or functional groups in the linker that can be cleaved spontaneously without contact with an external stimulus or releasing conditions, thereby releasing the payload from the support composition. Examples of bonds or functional groups that can be spontaneously cleaved as described above include, but are not limited to, carbamates and carbonates, which release carbon dioxide upon spontaneous cleavage. Functionalized payloads of the present disclosure that include a releasable linker may facilitate delivery of a payload to a target location in a subject.

In some cases, the payload may be released as described above by contacting the releasable linker to releasing conditions. The releasing conditions can be target specific, such as releasing conditions that are directly applied to a desired target location in a subject (e.g., a target location where the support composition is present). In some embodiments, the releasing conditions may be non-specific, such as by exposure of the releasable linker to an extracellular mechanism (e.g., low pH in tumor tissue, hypoxia, enzymes, and the like). In other instances, release of the payload can be achieved through intracellular, such as lysosomal, release mechanisms (e.g., glutathione, proteases (e.g., cathepsin), catabolismand the like). In these cases, the support composition may be internalized within a cell and subsequently exposed to releasing conditions present within the cell. Intracellular releasing conditions (e.g., glutathione, cathepsin, and the like) may result in release of the payload from the support composition such that the payload can be dispersed from the cell and provide a therapeutic effect on neighboring cells. Examples of these types of releasable linkers include, but are not limited to, hydrazones (acid labile), peptide linkers (cathepsin B cleavable), disulfide moieties (thiol cleavable), and the like. This type of release mechanism of action may facilitate providing treatment to diseases or conditions, such as tumors (e.g., tumors with heterogeneous receptor expression, or with poor mAb penetration).

A. Functionalized Payloads

As described above, functionalized payloads of the present disclosure may include a payload, a complementary binding agent, and optionally a linker attaching the payload to the complementary binding agent. A payload is an agent capable of producing a desired effect in a subject. For example, payloads of the present disclosure include therapeutic agents, diagnostic agents, targeting agents, and the like.

A therapeutic agent is an agent capable of treating and/or ameliorating a condition or disease in a subject. The therapeutic agent included of the present disclosure may be any desired therapeutic agent. Selection of a therapeutic agent may depend on various factors, for example, the disease or condition to be treated in the subject, functional groups on the therapeutic agent that may be used to attach a linker or binding agent, compatibility with other components of the compositions (e.g., low cross-reactivity with binding agents or complementary binding agents), and the like.

Representative therapeutic agents include, but are not limited to, therapeutic agents for treating cancer (e.g., paclitaxel, doxorubicin, daunorubicin, etoposide, irinotecan, SN-38, docetaxel, paclitaxel, gemcitabine, podophyllotoxin, Carmustine, Ixabepilone, Patupilone (epothelone class), platinum drugs, and the like), immunosuppressants (e.g., cyclosporin A, rapamycin, and the like), anti-fungal agents (e.g., Amphotericin, and the like), antibiotics (e.g., vancomycin, daptomycin, doxycycline, ceftriaxone, trimethoprim, sulfamethoxazole, acyclovir, nystatin, amphotericin B, flucytosine, emtricitabine, gentamicin, colistin, and the like), etc.. Still other therapeutic agents include, but are not limited to, matrix metalloproteinase (MMP) inhibitors, L-dopa, oseltamivir, cefalexin, 5-aminolevulinic acid, cysteine, celecoxib, nimodipine, among others. In some embodiments, the therapeutic agent is vancomycin. In some embodiments, the therapeutic agent is daptomycin. In some embodiments, the therapeutic agent is doxorubicin. In some embodiments, the therapeutic agent is gemcitabine. In some embodiments, the therapeutic agent is docetaxel. In some embodiments, the therapeutic agent is cyclic-adenosine monophosphatidyl (c-AMP).

Therapeutic agents of the present disclosure also include pro drug forms of the therapeutic agent. In some cases, the therapeutic agent may include a functional group for attachment of the therapeutic agent to a linker or binding agent. For example, the therapeutic agent may be attached to the linker or the binding agent through a covalent bond, such as an amide, amine, ester, carbonate, carbamate, urea, thioether, thiocarbamate, thiocarbonate, thiourea, etc. In some instances, the therapeutic agent is covalently attached to the linker or binding agent through an amide bond; e.g., the therapeutic agent may be an amine-containing therapeutic agent for attachment of the therapeutic agent to a carboxyl group of the linker or binding agent, or, in other cases, the therapeutic agent may be a carboxyl-containing therapeutic agent for attachment of the therapeutic agent to an amine group of the linker or binding agent. In some instances, the therapeutic agent is covalently attached to the linker or binding agent through a carbamate group; e.g., the therapeutic agent may be an amine-containing therapeutic agent for attachment of the therapeutic agent to an acyloxy group of the linker or binding agent.

Diagnostic agents suitable for embodiments of the present disclosure are agents that facilitate diagnosing conditions or diseases in a subject. Representative diagnostic agents include imaging agents such as paramagnetic agents, optical probes, radionuclides, and the like. Paramagnetic agents are imaging agents that are magnetic under an externally applied field. For example, paramagnetic agents may produce a detectable magnetic field under an externally applied magnetic field. Examples of paramagnetic agents include, but are not limited to, iron particles including iron nanoparticles and iron microparticles. Optical probes are fluorescent compounds that can be detected by excitation at one wavelength of radiation and detection at a second, different, wavelength of radiation. Optical probes of the present disclosure include, but are not limited to, fluorescein, rhodamine, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo detectable radioactive decay. Radionuclides useful in embodiments of the present disclosure include, but are not limited to, $^{3}H$, $^{11}C$, $^{13}N$, $^{18}F$, $^{19}F$, $^{60}Co$, $^{64}Cu$, $^{67}Cu$, $^{68}Ga$, $^{82}Rb$, $^{90}Sr$, $^{90}Y$, $^{99}Tc$, $^{99m}Tc$, $^{111}In$, $^{123}I$, $^{124}I$, $^{125}I$, $^{129}I$, $^{131}I$, $^{137}Cs$, $^{177}Lu$, $^{186}Re$, $^{188}Re$, $^{211}At$, Rn, Ra, Th, U, Pu and $^{241}Am$. Other radionucleotide agents that may be used include, for example, DOTA (1,4,7,10-tetraazacyclododecane-1,4,7,10-tetraacetic acid) and TETA (1,4,8,11-tetraazacyclotetradecane-1,4,8,11-tetraacetic acid); e.g., DOTA-$^{64}Cu$, TETA-$^{64}Cu$, DOTA-$^{111}In$, and the like. Diagnostic agents also include detectable labels, which may themselves be detectable or may elicit accumulation of detectable compounds at a target site. For instance, detectable labels include fluorophores or autofluorescent or luminescent markers. An example of a detectable label that elicits accumulation of detectable compounds at a target site is 5-aminolevulinic acid, which elicits accumulation of fluorescent porphyrins (e.g., protoporphyrin IX) in neoplastic tissues.

A targeting agent is a chemical or biological targeting agent that specifically binds to a target (e.g., a targeted organ or tissue), thereby forming a stable association between the targeting agent and the specific target. Stable associations between a targeting agent and its target may include covalent bonds and non-covalent interactions, such as, but not limited to, ionic bonds, hydrophobic interactions, hydrogen bonds, van der Waals forces (e.g., London dispersion forces), dipole-dipole interactions, and the like. Targeting agents may include members of specific binding pairs, such as, but not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin;

digoxin/antidigoxin; a member of a DNA or RNA aptamer binding pair; a member of a peptide aptamer binding pair; and the like.

Targeting agents include ligands that specifically bind (or substantially specifically bind) a particular clinically-relevant target receptor or cell surface target. The ligand can be an antibody, peptide, nucleic acid, phage, bacteria, virus, or other molecule with a specific affinity for a target receptor or cell surface target. Examples of receptors and cell surface targets include, but are not limited to, PD-1, CTLA-4, HER2/neu, HER1/EGFR, VEGFR, BCR-ABL, SRC, JAK2, MAP2K, EML4-ALK, BRAF V600E, 4-1BB, GITR, GSK3beta, or other cellular receptors or cell surface targets.

As described above, the payload may be attached to the complementary binding agent through a linker. Any suitable linker can be used to link the payload to the complementary binding agent. Representative linkers can have 1 to 100 linking atoms, and can include ethylene-oxy groups, amines, esters, amides, carbamates, carbonates, and ketone functional groups. For example, linkers may have from 1 to 50 linking atoms, or from 5 to 50 linking atoms, or from 10 to 50 linking atoms.

In certain embodiments, the linker between the payload and the complementary binding agent is a non-releasable linker. A non-releasable linker is a linker that forms an attachment between at least two moieties, where the attachment is not significantly disrupted under the conditions that compositions using the non-releasable linker are used (e.g., covalent bonds in the linker remain intact and are not cleaved). For instance, a non-releasable linker may include one or more covalent bonds between at least two moieties, such that the moieties are covalently bound to each other and remain covalently bound to each other under the conditions that compositions are used. For example, in certain embodiments, a non-releasable linker may be used with a payload, such as a payload having a prodrug form of a therapeutic agent, where release of the therapeutic agent from the prodrug provides for delivery of the therapeutic agent to the target site in the subject.

In certain embodiments, the linker between the payload and the complementary binding agent is a releasable linker. A releasable linker is a linker that forms an attachment between at least two moieties, where the attachment may be disrupted under releasing conditions such that the moieties are no longer attached to each other (e.g., one or more covalent bonds in the linker may be cleaved). Releasable linkers may have the attachment between the moieties disrupted by exposure of the releasable linker to releasing conditions, such as, but not limited to, light, heat, sound, a releasing agent (e.g., chemical releasing agent (e.g., an acid, a base, an oxidizing agent, a reducing agent), a solvent, an enzyme, etc.), combinations thereof, and the like. In some embodiments, the releasable linker may not require the application of an external stimulus or contact with releasing conditions to disrupt the attachment between the moieties. For example, a releasable linker may include one or more unstable bonds or functional groups in the linker that can be cleaved spontaneously without contact with an external stimulus or releasing conditions, thereby releasing the payload from the support composition. Examples of bonds or functional groups that can be spontaneously cleaved as described above include, but are not limited to, carbamates, which release carbon dioxide upon spontaneous cleavage. Functionalized payloads of the present disclosure that include a releasable linker may facilitate delivery of a payload to a target location in a subject.

In some cases, the payload may be released as described above by contacting the releasable linker to releasing conditions. The releasing conditions can be target specific, such as releasing conditions that are directly applied to a desired target location in a subject (e.g., a target location where the support composition is present). In some embodiments, the releasing conditions may be non-specific, such as by exposure of the releasable linker to an extracellular mechanism (e.g., low pH in tumor tissue, hypoxia, enzymes, and the like). In other instances, release of the payload can be achieved through intracellular, such as lysosomal, release mechanisms (e.g., glutathione, proteases (e.g., cathepsin), catabolismand the like). In these cases, the support composition may be internalized within a cell and subsequently exposed to releasing conditions present within the cell. Intracellular releasing conditions (e.g., glutathione, cathepsin, and the like) may result in release of the payload from the support composition such that the payload can be dispersed from the cell and provide a therapeutic effect on neighboring cells. Examples of these types of releasable linkers include, but are not limited to, hydrazones (acid labile), peptide linkers (cathepsin B cleavable), disulfide moieties (thiol cleavable), and the like. This type of release mechanism of action may facilitate providing treatment to diseases or conditions, such as tumors (e.g., tumors with heterogeneous receptor expression, or with poor mAb penetration).

In certain embodiments, the linker between the payload and the complementary binding agent is an immolative linker.

In certain embodiments, the linker between the payload and the complementary binding agent is a pH tunable linker.

In certain embodiments, the functionalized payload compositions have formula:

(I)

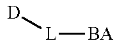

wherein

D is a payload as defined herein;

L is a linker as defined herein; and

BA is a complementary binding agent as defined herein.

In certain embodiments, the functionalized payload compositions comprise a trans-cyclooctene (TCO) as the complementary binding agent. The compounds can include one or more therapeutic agents. The compounds can include one or more cell permeation agents. The compounds can include one or more diagnostic agents. The compounds can optionally include a linker group (e.g., a self-immolative linker) attaching the one or more agents to the trans-cyclooctene.

In certain embodiments, the functionalized payload compositions have formula (I), (I)

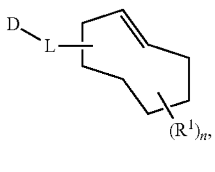

wherein

D is a payload as defined herein;

L is a linker as defined herein;

$R^1$, at each occurrence, is independently selected from the group consisting of halogen, cyano, nitro, alkyl, alkenyl, alkynyl, heteroalkyl, aryl, heteroaryl, heterocycle, cycloalkyl, cycloalkenyl, —$OR^{1a}$, —$NR^{1b}R^{1c}$, —$SR^{1d}$, —$SO_2R^{1e}$, —$S(O)R^{1f}$, and —$P(O)OR^{1g}R^{1h}$;

$R^{1a}$, $R^{1b}$, $R^{1c}$, $R^{1d}$, $R^{1e}$, $R^{1f}$, $R^{1g}$, and $R^{1h}$, are each independently selected from the group consisting of hydrogen, alkyl, alkenyl, alkynyl, heteroalkyl, aryl, heteroaryl, heterocycle, cycloalkyl, and cycloalkenyl; and n is 0, 1, 2, 3, 4, 5, 6, 7, 8, 9, 10, 11, 12, or 13;

wherein said alkyl, alkenyl, alkynyl, heteroalkyl, aryl, heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In certain embodiments, the functionalized payload compositions have formula:

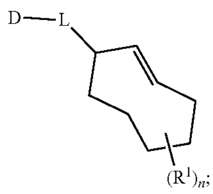

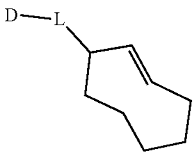

;

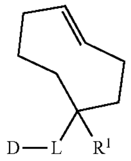

;

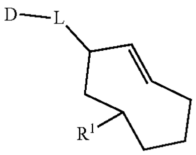

;

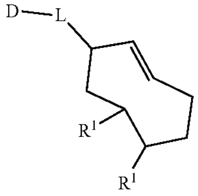

;

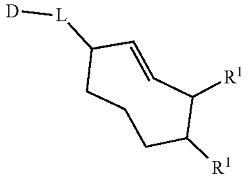

;

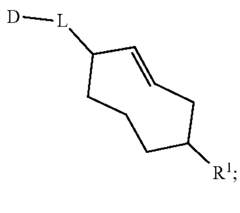

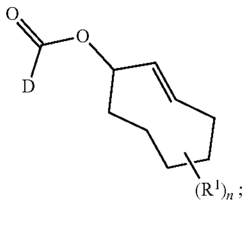

-continued

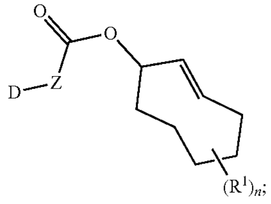

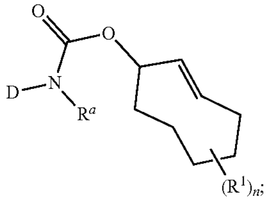

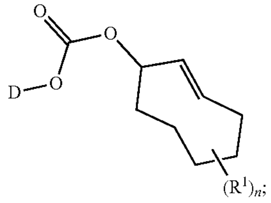

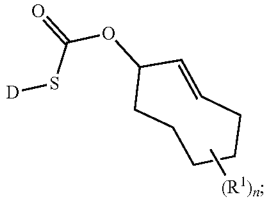

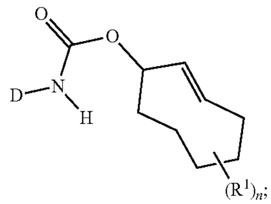

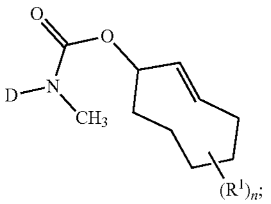

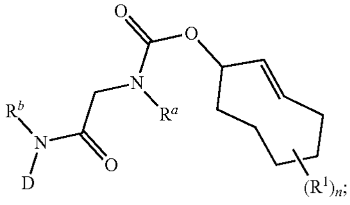

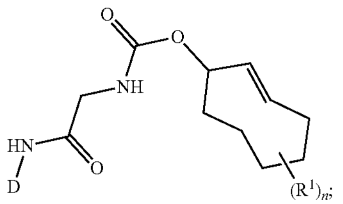

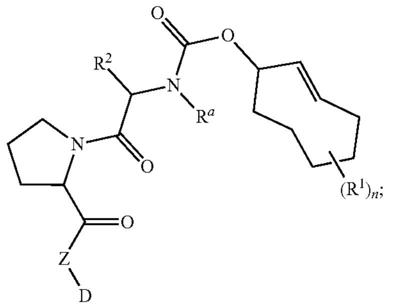

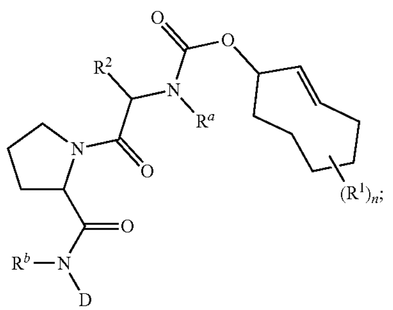

-continued
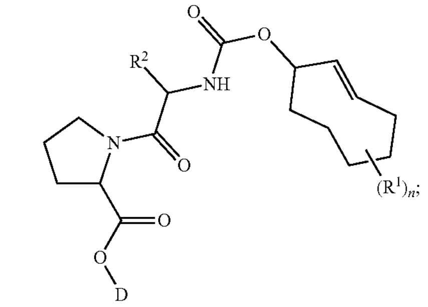
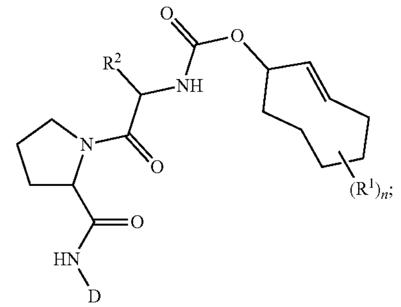
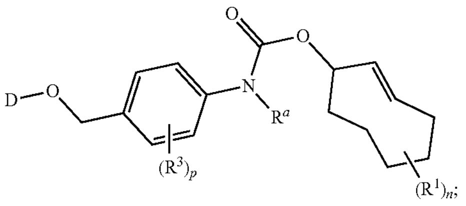
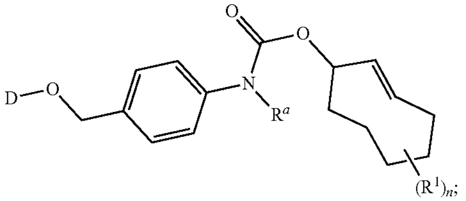
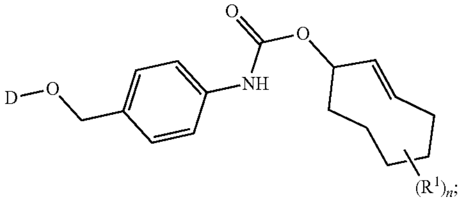
-continued
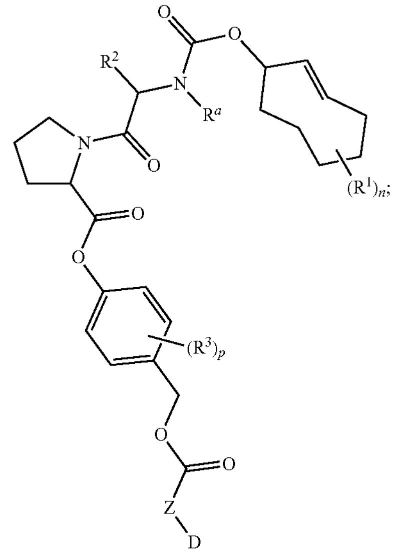
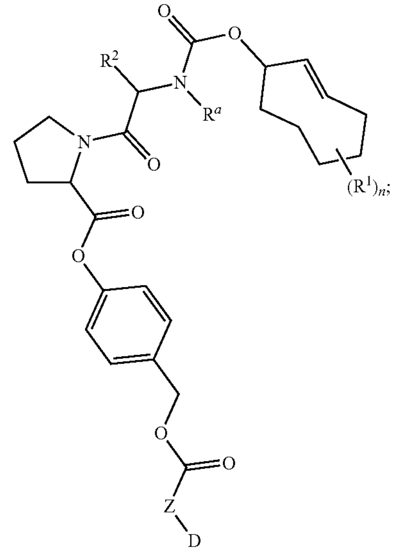
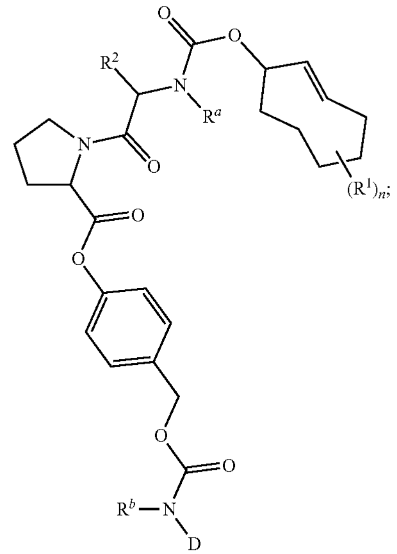

-continued
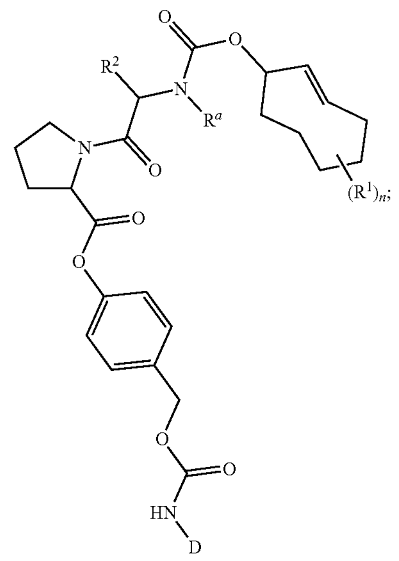
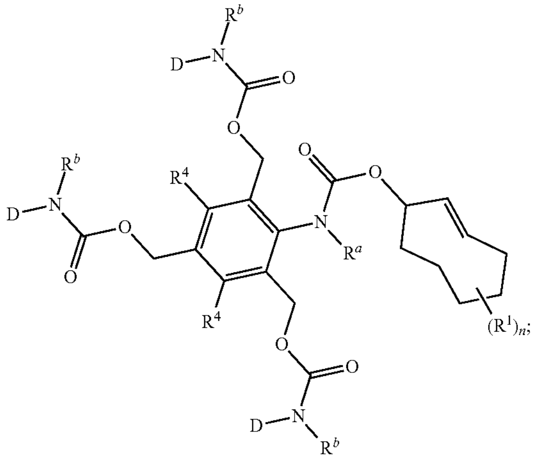
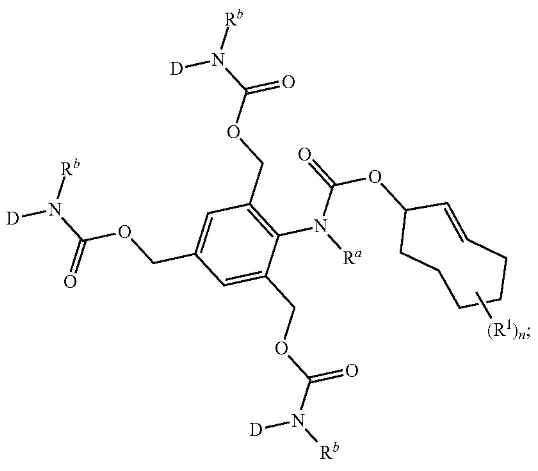
-continued
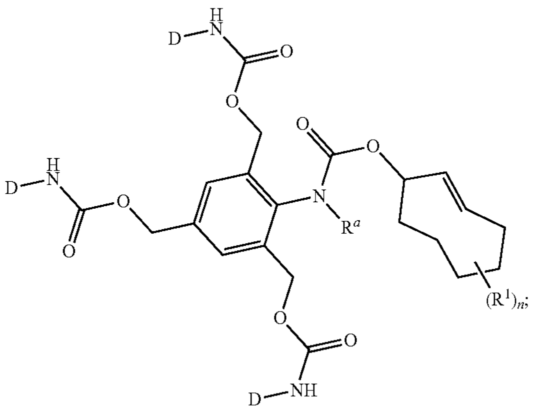
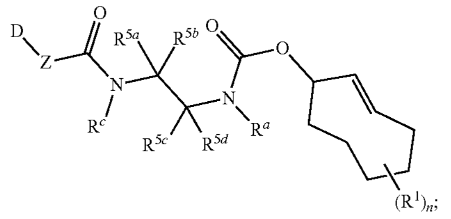
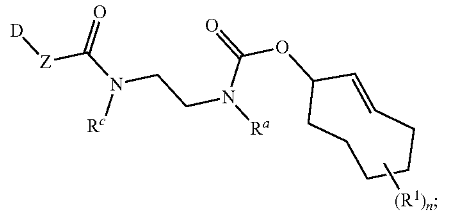
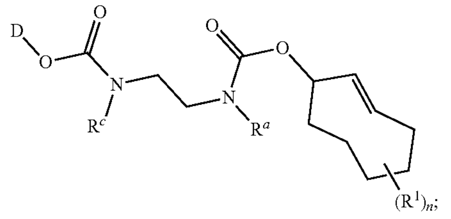
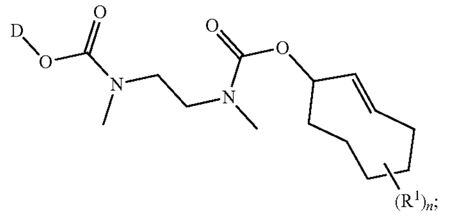
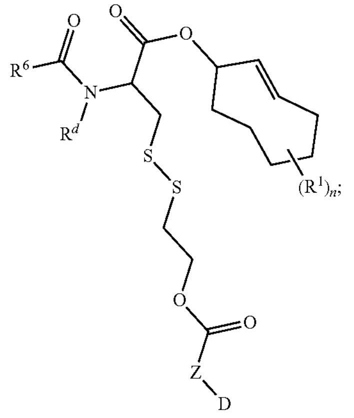

-continued
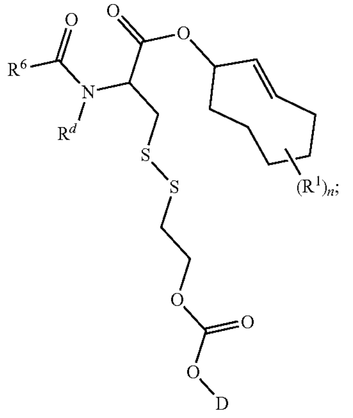
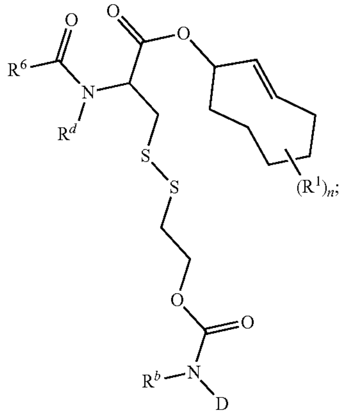
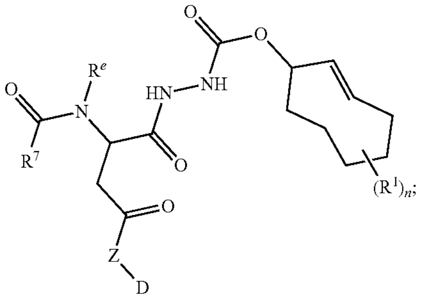
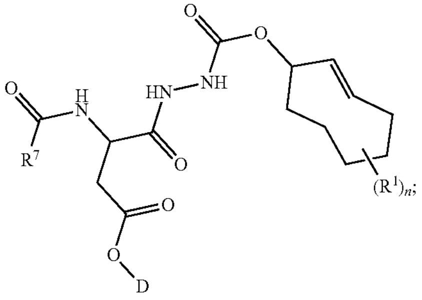
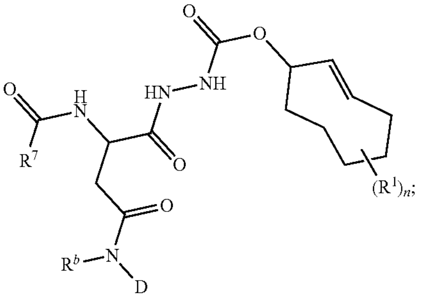
-continued
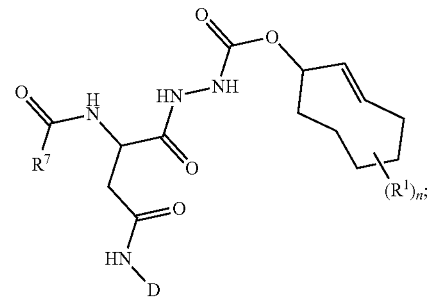
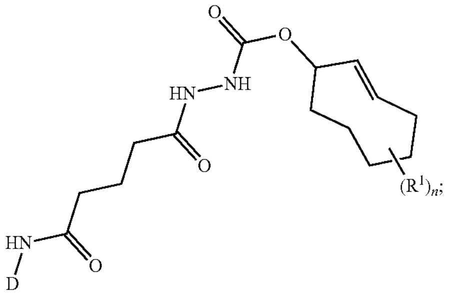
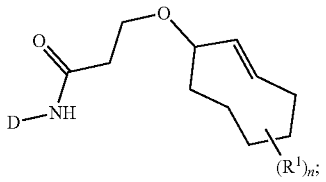
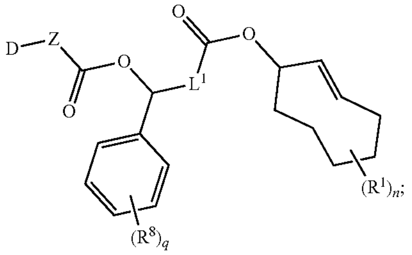
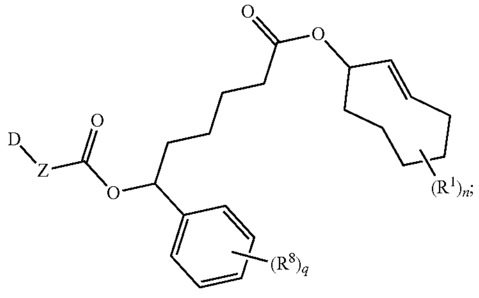
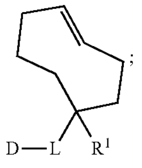

-continued

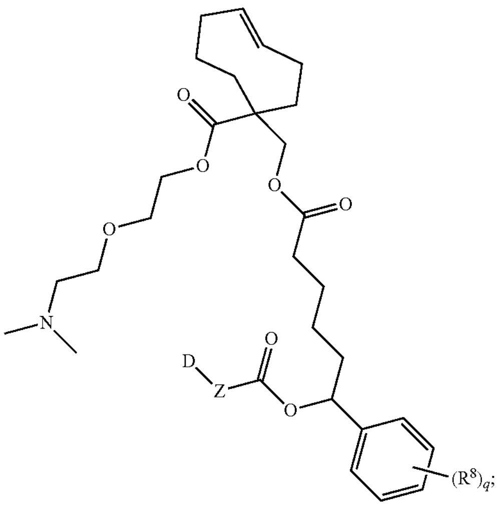

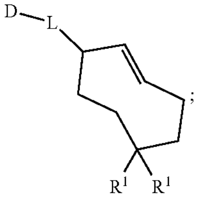

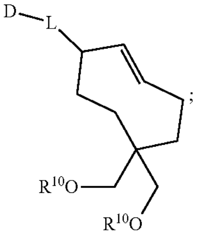

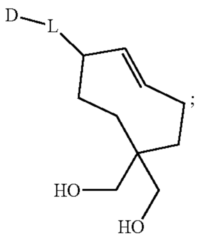

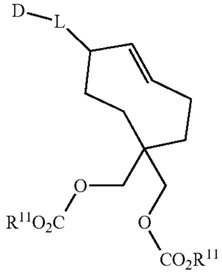

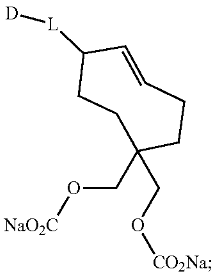

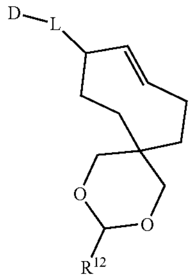

; or

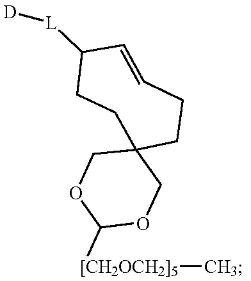

-continued

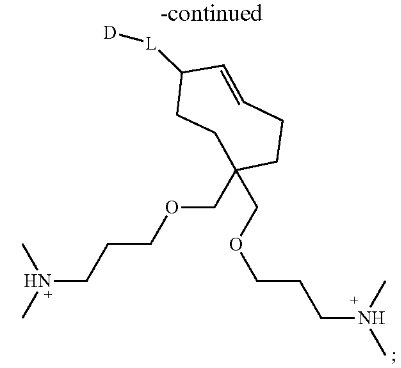

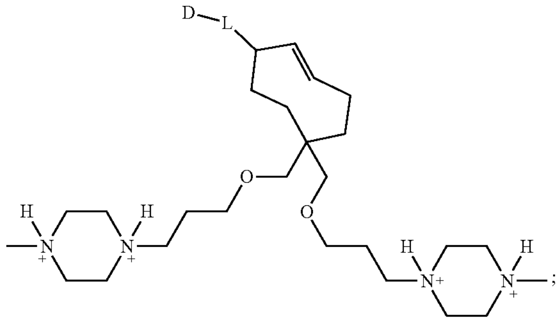

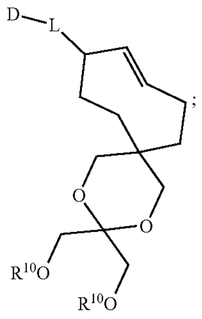

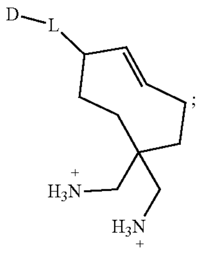

or

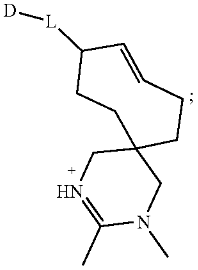

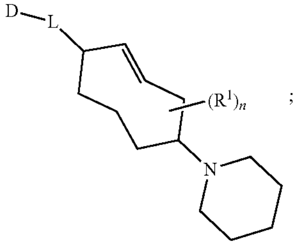

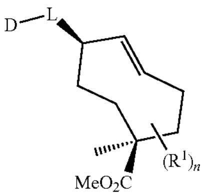

wherein $R^1$, at each occurrence, is independently selected from the group consisting of halogen, cyano, nitro, alkyl, alkenyl, alkynyl, heteroalkyl, aryl, heteroaryl, heterocycle, cycloalkyl, cycloalkenyl, —$OR^{1a}$, —$NR^{1b}R^{1c}$, —$SR^{1b}$, —$SO_2R^{1e}$, —$S(O)R^{1f}$, and —$P(O)OR^{1g}R^{1h}$;

$R^2$, at each occurrence, is independently selected from the group consisting of hydrogen, halogen, cyano, nitro, alkyl, alkenyl, alkynyl, heteroalkyl, aryl, heteroaryl, heterocycle, cycloalkyl, cycloalkenyl, —$OR^{2a}$, —$NR^{2b}R^{1c}$, —$SR^{2d}$, —$SO_2R^{2e}$, —$S(O)R^{2f}$, and —$P(O)OR^{2g}R^{2h}$;

$R^3$, at each occurrence, is independently selected from the group consisting of halogen, cyano, nitro, alkyl, alkenyl, alkynyl, heteroalkyl, aryl, heteroaryl, heterocycle, cycloalkyl, cycloalkenyl, —$OR^{3a}$, —$NR^{3b}R^{3c}$, —$SR^{3d}$, —$SO_2R^{3e}$, —$S(O)R^{3f}$, and —$P(O)OR^{3g}R^{3h}$, $R^4$, at each occurrence, is independently selected from the group consisting of hydrogen, halogen, cyano, nitro, alkyl, alkenyl, alkynyl, heteroalkyl, aryl, heteroaryl, heterocycle, cycloalkyl, cycloalkenyl, —$OR^{4a}$, —$NR^{4b}R^{4c}$, —$SR^{4d}$, —$SO_2R^{4c}$, —$S(O)R^{4f}$, and —$P(O)OR^4BR^{4h}$, $R^5$, at each occurrence, is independently selected from the group consisting of hydrogen, halogen, cyano, nitro, alkyl, alkenyl, alkynyl, heteroalkyl, aryl, heteroaryl, heterocycle, cycloalkyl, cycloalkenyl, —$OR^{5a}$, —$NR^{5b}R^{5c}$, —$SR^{5d}$, —$SO_2R^{5e}$, —$S(O)R^{5f}$, and —$P(O)OR^{5g}R^{5h}$, $R^6$, at each occurrence, is independently selected from the group consisting of hydrogen, halogen, cyano, nitro, alkyl, alkenyl, alkynyl, heteroalkyl, aryl, heteroaryl, heterocycle, cycloalkyl, cycloalkenyl, —$OR^{6a}$, —$NR^{6b}R^{6c}$, —$SR^{6d}$, —$SO_2R^{6e}$, —$S(O)R^{6f}$, and —$P(O)OR^{6g}R^{6h}$;

$R^7$, at each occurrence, is independently selected from the group consisting of hydrogen, halogen, cyano, nitro, alkyl, alkenyl, alkynyl, heteroalkyl, aryl, heteroaryl, heterocycle, cycloalkyl, cycloalkenyl, —$OR^{7a}$, —$NR^{7b}R^{7c}$, —$SR^{7d}$, —$SO_2R^{7e}$, —$S(O)R^{7f}$, and —$P(O)OR^{7g}R^{7h}$;

$R^8$, at each occurrence, is independently selected from the group consisting of hydrogen, halogen, cyano, nitro, alkyl, alkenyl, alkynyl, heteroalkyl, aryl, heteroaryl, heterocycle, cycloalkyl, cycloalkenyl, —$OR^{8a}$, —$NR^{8b}R^{8c}$, —$SR^{8d}$, —$SO_2R^{8e}$, —$S(O)R^{8f}$, and —$P(O)OR^{8g}R^{8h}$;

$R^{10}$, at each occurrence, is independently selected from the group consisting of hydrogen, alkyl, alkenyl, alkynyl, heteroalkyl, aryl, heteroaryl, heterocycle, cycloalkyl, and cycloalkenyl;

$R^{11}$, at each occurrence, is independently selected from the group consisting of hydrogen, alkyl, alkenyl, alkynyl, heteroalkyl, aryl, heteroaryl, heterocycle, cycloalkyl, and cycloalkenyl;

$R^{12}$, at each occurrence, is independently selected from the group consisting of hydrogen, halogen, cyano, nitro, alkyl, alkenyl, alkynyl, heteroalkyl, aryl, heteroaryl, heterocycle, cycloalkyl, cycloalkenyl, —$OR^{12a}$, —$NR^{12b}R^{12c}$, —$SR^{12d}$, —$SO_2R^{12e}$, —$S(O)R^{12f}$, and —$P(O)OR\ ^{12g}R^{12h}$, $R^{1a}$, $R^{1b}$, $R^{1c}$, $R^{1d}$, $R^{1e}$, $R^{1f}$, $R^{1g}$, $R^{1h}$, $R^{2a}$, $R^{2b}$, $R^{2c}$, $R^{2d}$, $R^{2e}$, $R^{2f}$, $R^{2g}$, $R^{2h}$, $R^{3a}$, $R^{3b}$, $R^{3c}$, $R^{3d}$, $R^{3e}$, $R^{3f}$, $R^{3g}$, $R^{3h}$, $R^{4a}$, $R^{4b}$, $R^{4c}$, $R^{4d}$, $R^{4e}$, $R^{4f}$, $R^{4g}$, $R^{4h}$, $R^{5a}$, $R^{5b}$, $R^{5c}$, $R^{5d}$, $R^{5e}$, $R^{5f}$, $R^{5g}$, $R^{5h}$, $R^{6a}$, $R^{6b}$, $R^{6c}$, $R^{6d}$, $R^{6e}$, $R^{6f}$, $R^{6g}$, $R^{6h}$, $R^{7a}$, $R^{7b}$, $R^{7c}$, $R^{7d}$, $R^{7e}$, $R^{7f}$, $R^{7g}$, $R^{7h}$, $R^{8a}$, $R^{8b}$, $R^{8c}$, $R^{8d}$, $R^{8e}$, $R^{8f}$, $R^{8g}$, $R^{8h}$, $R^{12a}$, $R^{12b}$, $R^{12c}$, $R^{12d}$, $R^{12e}$, $R^{12f}$, $R^{12g}$, $R^{12h}$, are each independently selected from the group consisting of hydrogen, alkyl, alkenyl, alkynyl, heteroalkyl, aryl, heteroaryl, heterocycle, cycloalkyl, and cycloalkenyl Z is selected from the group consisting of O, $N(R^a)$, $N(R^b)$, or S;

$R^a$, $R^b$, $R^c$, $R^d$, and $R^e$ are each independently selected from the group consisting of hydrogen, $C_1$-$C_6$-alkyl, and $C_1$-$C_6$-haloalkyl;

$L^1$ is alkylene;

n is 0, 1, 2, 3, 4, 5, 6, 7, 8, 9, 10, 11, 12, or 13;

p is 0, 1, 2, 3, or 4;

q is 0, 1, 2, 3, 4, or 5;

wherein said alkyl, alkylene, alkenyl, alkynyl, heteroalkyl, aryl, heteroaryl, heterocycle, cycloalkyl, and cycloalkenyl, at each occurrence, are independently substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, and acyl.

In certain embodiments, n is 0. In certain embodiments, n is 1. In certain embodiments, n is 2.

In certain embodiments, D is an antibiotic agent, antifungal agent, antiviral agent, anticancer agent, cardiovascular agent, CNS agent, anti-inflammatory/anti-arthritic agent, anti-TB/anti-leprosy agent, anti-histaminic/respiratory disorder agent, a corticosteroid agent, immunosuppressant agent, or anti-ulcer agent.

In certain embodiments, D is an antibiotic. Suitable antibiotics include, but are not limited to β-lactams, including penicillins and cephalosporins, such as thienamycins, monobactams, β-lactamade inhibitors and methoxypeniciuins; aminoglycosides, including streptomycin, gentamicin, kanamycin, tobramycin, amikacin, neomycin, ribostamycin, micronomicin and astromicin; tetracyclines, including tetracycline, oxytetracycline, chlortetracycline and doxycycline; chloramphenicols, including chloramphenicol and thiamphenicol; macrolides, including erythromycin, albomycin, erythromycin estolate, erythromycin ethylsuccinate, azithromycin, acetylspiramycin, midecamycin and josamycin; other antibiotics acting on Gram-positive bacteria, such as lincomycin, clindamycin, vancomycin and bacitracin; other antibiotics acting on Gram bacteria, such as polymyxin, fosfomycin, ciramycin, cycloserine and rifampicin; antifungal antibiotics, such as griseofulvin; anticancer antibiotics, such as mitomycin, actinomycin D, bleomycin and Adriamycin; and immunosuppressive antibiotics, such as cyclosporine.

In certain embodiments, D is an anticancer drug, an anticoagulant, a microbial immunosuppressive drug, or an anti-restenosis drug. The anticancer drug may be one or more selected from methotrexate, purines, pyrimidines, plant alkaloids, epothilones, triptolide compounds, antibiotics (notably actinomycin D), hormones and antibodies. From among the plant alkaloids, mention may notably be made of paclitaxel, doxorubicin, maytansin, auristatin, calicheamycin, duocarmycin, tubulysin and camptothecin. The anticoagulant may be one or more selected from heparin, aspirin, hirudin, colchicine and platelet GPIIb/IIIa receptor antagonists. The platelet GPIIb/IIIa receptor antagonists may be one or more selected from tirofiban, abciximab and eptifibatide. The microbial immunosuppressive drug may be one or more selected from cyclosporin A, tacrolimus and its analogues, despergualin, mycophenolate esters, rapamycin and its derivatives, FR-900520 substance from *Streptomyces* strains, FR-900523 substance from *Streptomyces* strains, daclizumab, pentanamide, kanglemycin C, spergualin, prodigiosin-25C, tranilast, myriocin, cyclosporin C, bredinin, mycophenolic acid, brefeldin A and ketosteroids. The anti-restenosis drug may be one or more selected from batimastat, metalloproteinase inhibitors, 17ß-estradiol, NO donors, 2-chlorodeoxyadeno sine, 2-deoxycoformycin, fingolimod, mycophenolate sodium, $ISA_{TX}$247 (a cyclosporin A derivative), elsibucol, daclizumab, basiliximab, anti-thymocyte globulin, everolimus, methotrexate, neoral, cyclophosphamide, brequinar sodium, leflunomide and mizoribine.

In certain embodiments, D is an anticancer drug. Exemplary anti-cancer drugs include, but are not limited to, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Bendamustine Hydrochloride, BEP, Bevacizumab, Bexarotene, Bexxar (Tositumomab and I 131 Iodine Tositumomab), Bicalutamide, Bleomycin, Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPOX, Carboplatin, Carboplatin-Taxol, Carfilzomib, Casodex (Bicalutamide), CeeNU (Lomustine), Cerubidine (Daunorubicin Hydrochloride), Cervarix (Recombinant HPV Bivalent Vaccine), Cetuximab, Chlorambucil, Chlorambucil-Prednisone, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), Folfiri, Folfiri-Bevacizumab, Folfiri-Cetuximab, Folfirinox, Folfox (Leucovorin, Fluorouracil, Oxaliplatin), Folotyn (Pralatrexate), FU-LV, Fulvestrant, Gardasil (Recombinant HPV Quadrivalent Vaccine), Gazyva (Obinutuzumab), Gefitinib, Gemcitabine Hydrochloride, Gemcitabine-Cisplatin, Gemcitabine-Oxaliplatin, Gemtuzumab Ozogamicin, Gemzar (Gemcitabine Hydrochloride), Gilotrif (Afatinib Dimaleate), Gleevec (Imatinib Mesylate), Glucarpidase, Goserelin Acetate, Halaven (Eribulin Mesylate), Herceptin (Trastuzumab), HPV Bivalent Vaccine, Recombinant, HPV Quadrivalent Vaccine, Recombinant, Hycamtin (Topotecan Hydrochloride), Hyper-CVAD, Ibritumomab Tiuxetan, Ibrutinib, ICE, Iclusig (Ponatinib Hydrochloride), Ifex (Ifosfamide), Ifosf amide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Kyprolis (Carfilzomib), Lapatinib Ditosylate, Lenalidomide, Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nolvadex (Tamoxifen Citrate), Nplate (Romiplostim), Obinutuzumab, Ofatumumab, Omacetaxine Mepesuccinate, Oncaspar (Pegaspargase), Ontak (Denileukin Diftitox), OEPA, OPPA, Oxaliplatin, Paclitaxel, Paclitaxel Albumin-stabilized Nanoparticle Formulation, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Radium 223 Dichloride, Raloxifene Hydrochloride, Rasburicase, R—CHOP, R—CVP, Recombinant HPV Bivalent Vaccine, Recombinant HPV Quadrivalent Vaccine, Recombinant Interferon Alfa-2b, Regorafenib, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Sipuleucel-T, Sorafenib Tosylate, Sprycel (Dasatinib), Stanford V, Sterile Talc Powder (Talc), Steritalc (Talc), Stivarga (Regorafenib), Sunitinib Malate, Sutent (Sunitinib Malate), Sylatron (Peginterferon Alfa-2b), Synovir (Thalidomide), Synribo (Omacetaxine Mepesuccinate), Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Toposar (Etoposide), Topotecan Hydrochloride, Toremifene, Torisel (Temsirolimus), Tositumomab and 1 131 Iodine Tositumomab, Totect (Dexrazoxane Hydrochloride), Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VelP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), Xelox, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), and Zytiga (Abiraterone Acetate).

In certain embodiments, D is a PBD dimer, calicheamicin, speromycin, tubulysin B, 1 rhizoxin, dolastatin, didemnin B, camptothecin, CBI, temsirolimus, actinomycin D, epothilone B, taxol, cryptophycin, SN38, velcade, bruceantin, DAVLBH, DM1, Phyllanthoside, Alimta, T2 Toxin, MMC, vantalanib, vinorelbine, brefeldin, sunitinib, daunomycin, semaxanib, tarceva, iressa, irinotecan, LY-541503, geldanomycin, gemcitabine, methotrexate, gleevec, topotecan, bleomycin, doxorubicin, cisplatin, N-mustards, etoposide, or 5-FU.

In certain embodiments, D is an anthracycline. In certain embodiments, D is a taxane. In certain embodiments, D is gemcitabine. In certain embodiments, D is doxorubicin. In certain embodiments, D is docetaxel. In certain embodiments, D is SN38. In certain embodiments, D is monomethyl auristatin E. In certain embodiments, D is dexamethasone. In certain embodiments, D is celecoxib. In certain embodiments, D is gentamicin.

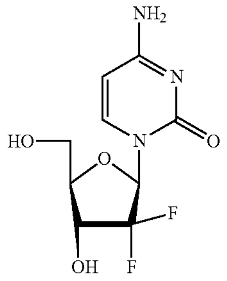

Gemcitabine
Nucleoside analog

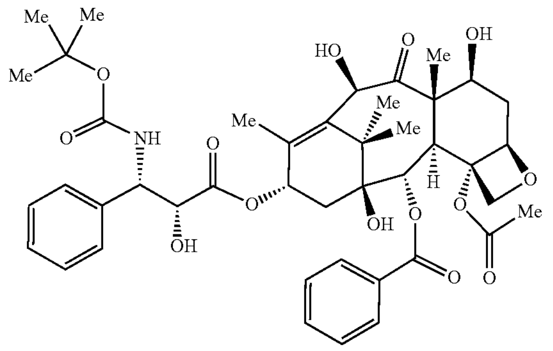

Docetaxel
Microtubule inhibitor

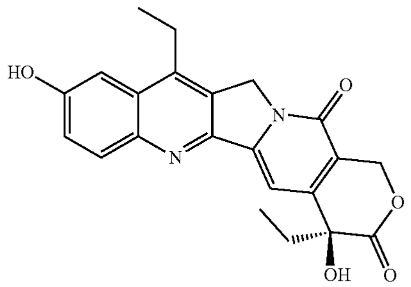

SN38
Topoisomerase 1 inhibitor

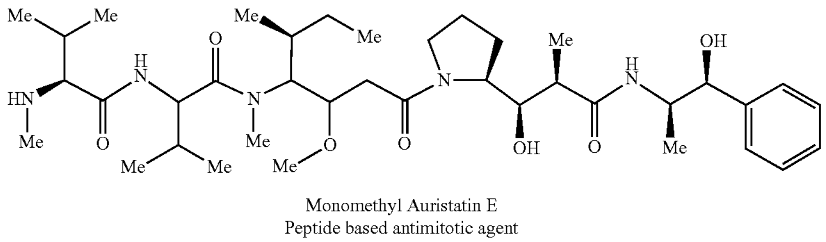

Monomethyl Auristatin E
Peptide based antimitotic agent

-continued

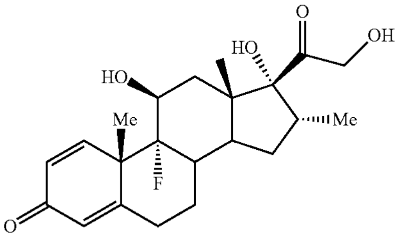

Dexamethasone
Corticosteroid

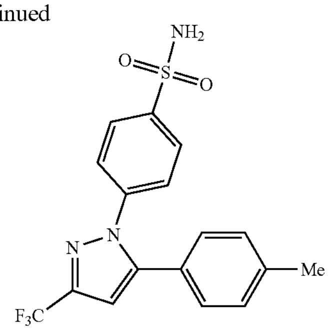

Celecoxib
COX-2 Inhibitor

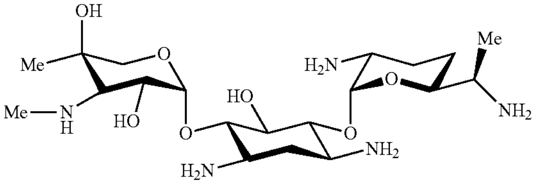

Gentamicin
Antibiotic against Gram (-) Bacteria

In certain embodiments, D is an intracellular permeation enhancing agent. For example, D may be a functionalized ketoacid, 6-Oxo-6-phenylhexanoic acid, 8-Oxo-8-phenyloctanoic acid, 8-(2,5-Dichlorophenyl)-8-oxooctanoic acid, a functionalized ketoester or aldehyde, a modified amino acid, modified amino acids, N-[8-(2-hydroxybenzoyl)aminooctanoic acid, N-[8-(2-hydroxybenzoyl)aminodecanoic acid, N-(5-chlorosalicyloyl)-8-minocaprylic acid, N-[4-(4-chloro-2hydroxybenzoyl)amino1 butanoic acid, 2-ethylhexyl 2-hydroxybenzoate, 5-Cyclohexyl-5-oxovaleric acid, 6-Cyclohexyl-6-oxohexanoic acid, 7-Cyclohexyl-7-oxoheptanoic acid, 8-Cyclohexyl-8-oxooctanoic acid, 4-Cyclopentyl-4-oxobutyric acid, 5-Cyclopentyl-5-oxovaleric acid, 6-Cyclopentyl-6-oxohexanoic acid, 7-Cyclopentyl-7-oxoheptanoic acid, 8-Cyclopentyl-8-oxooctanoic acid, 4-Cyclobutyl-4-oxobutyric acid, 5-Cyclobutyl-5-oxovaleric acid, 6-Cyclobutyl-6-oxohexanoic acid, 7-Cyclobutyl-7-oxoheptanoic acid, 8-Cyclobutyl-8-oxooctanoic acid, 4-Cyclopropyl-4-oxobutyric acid, 5-Cyclopropyl-5-oxovaleric acid, 6-Cyclopropyl-6-oxohexanoic acid, 7-Cyclopropyl-7-oxoheptanoic acid, 8-Cyclopropyl-8-oxooctanoic acid, 8-[(3-methylcyclohexyl)oxy]octanoic acid, 7-[(3-methylcyclohexyl)oxy]heptanoic acid, 6-[(3-methylcyclohexyl)oxy] hexanoic acid, 5-[(3-methylcyclohexyl)oxy]pentanoic acid, 4-[(3-methylcyclohexyl)oxy]butanoic acid, 3-[(3-methylcyclohexyl)oxy]propanoic acid, octisalate, a diketopiperazines, saponin, an acylcarnitine, an alkanoylcholine, a taurodihydrofusidate, a sulphoxide, an oxazolidinone, a pyrrolidone, an alcohol or alkanol, a benzoic acid, a glycol, a surfactant, a terpene, a functionally effective salt of any of the foregoing, a derivative of any of the foregoing, or combinations thereof.

In certain embodiments, the functionalized payload composition is one or more of:

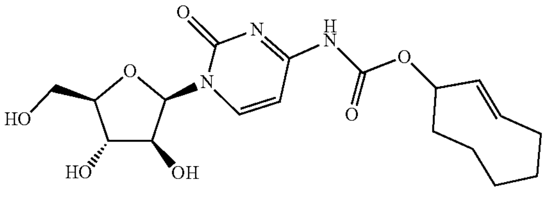

;

(payload = cytarabine)

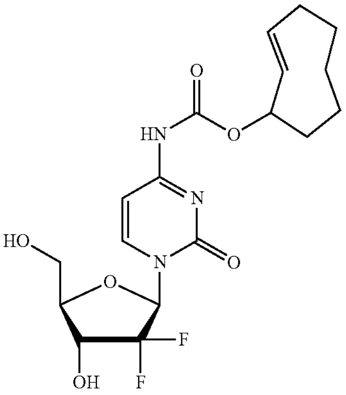

;

(payload = gemcitabine)

-continued
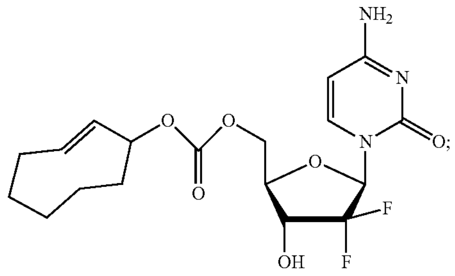
(payload = gemcitabine)
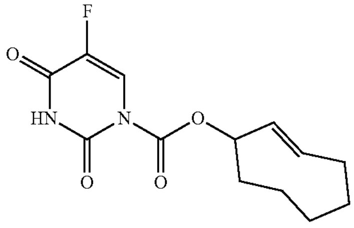
;
(payload = 5-fluorouracil)
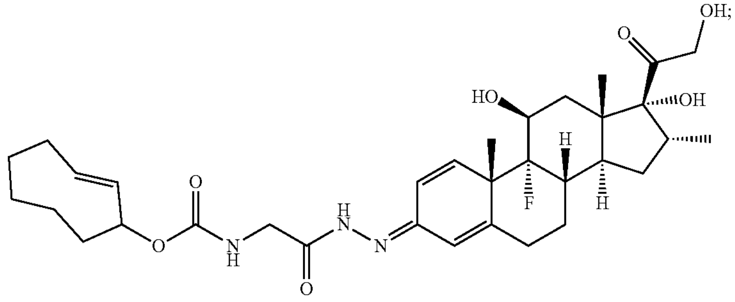
(payload = dexamethasone)
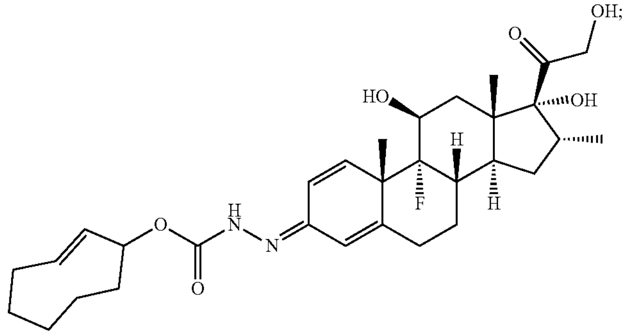
(payload = dexamethasone)
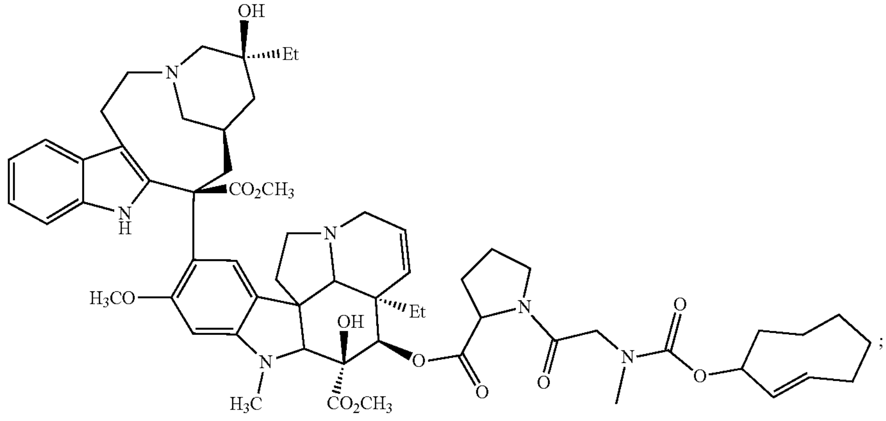
;
(payload = des-acteyl-vinblastine)

-continued
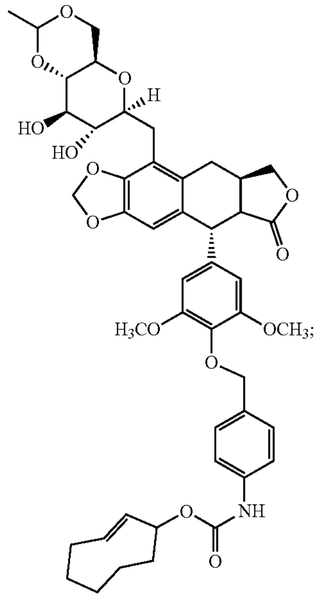
(payload = etoposide)
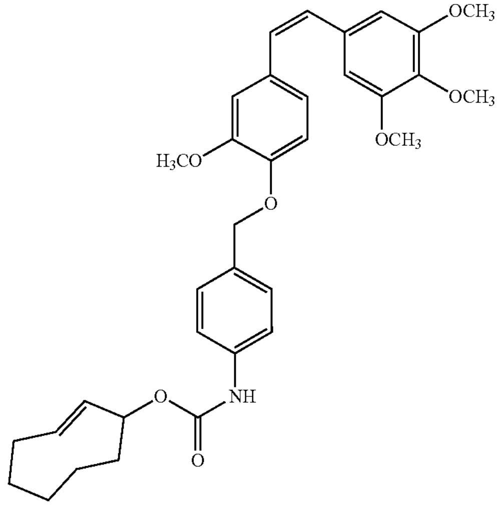
(payload = combrestatin-A4)
;
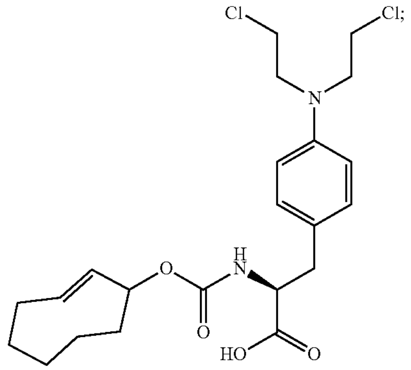
(payload = melphalan)
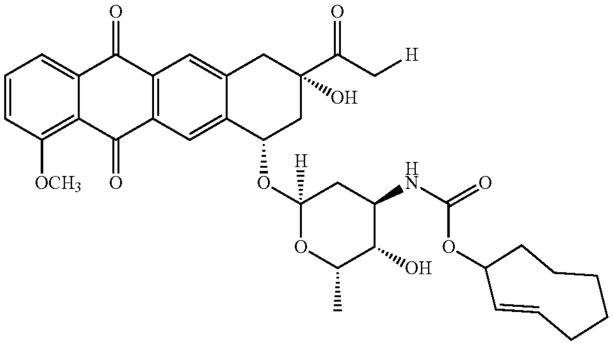
(payload = daunorubicin)
;
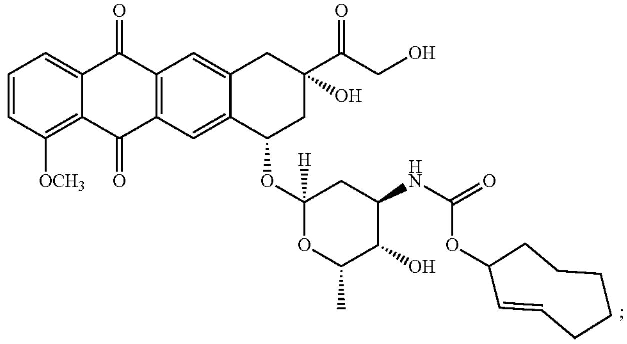
;
(payload = doxorubicin)

-continued
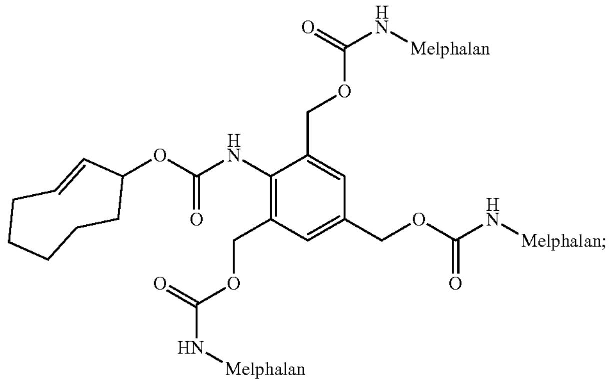
(payload = melphalan)
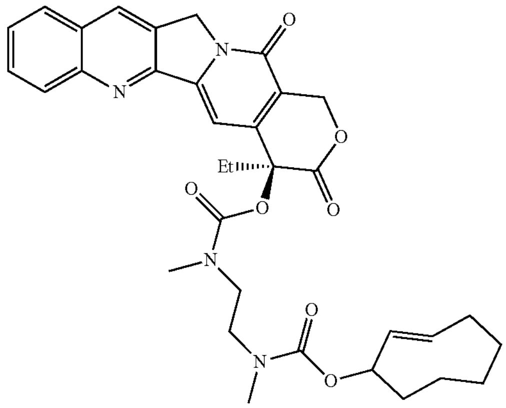
;
(payload = camptothecin)
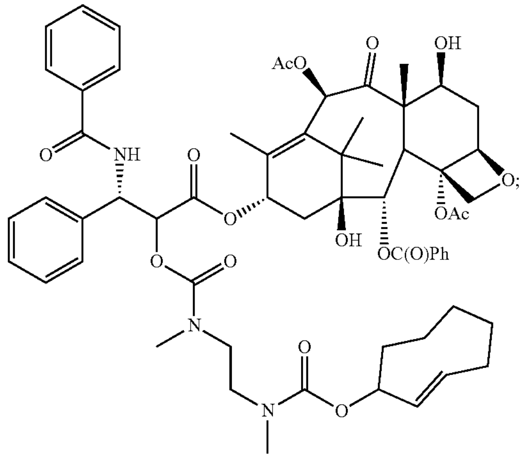
(payload = paclitaxel)
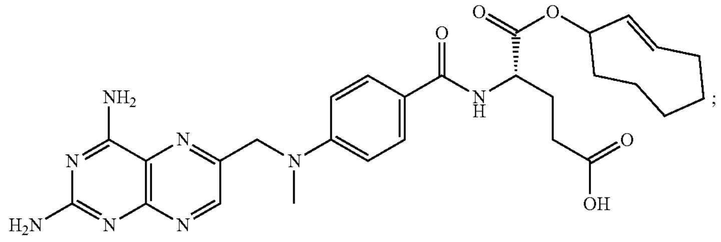
(payload = methotrexate)
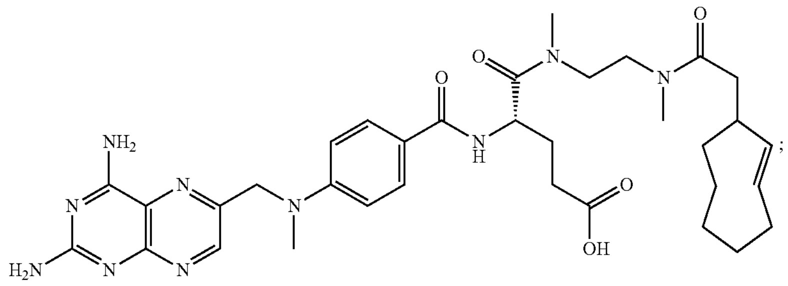
(payload = methotrexate)

-continued
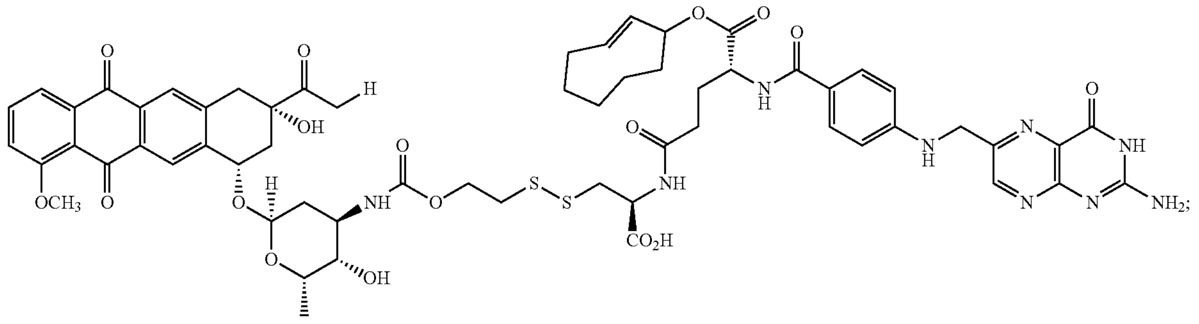
(payload = daunorubicin-folic acid)
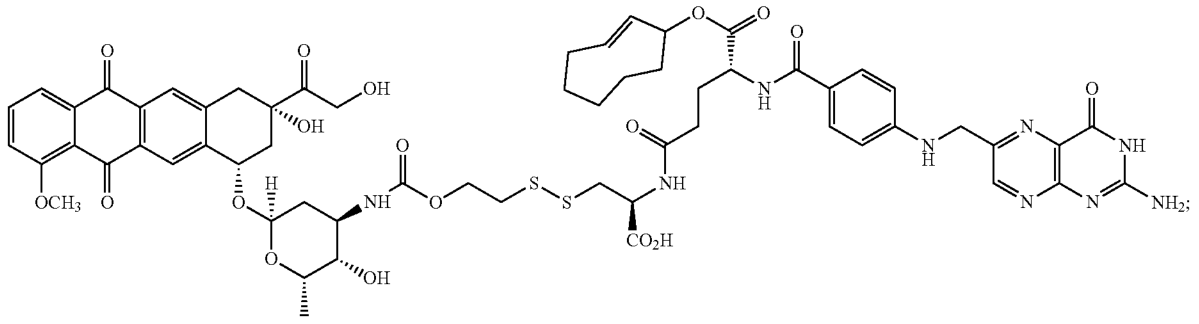
(payload = doxorubicin-folic acid)
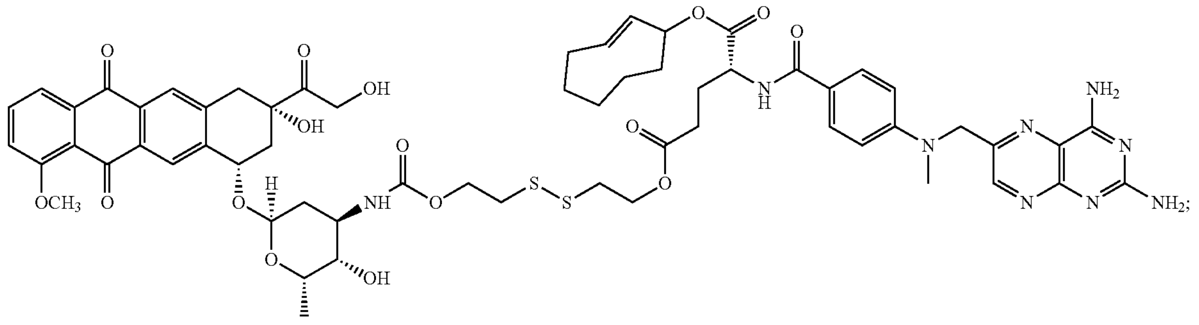
(payload = DOX-MTX)
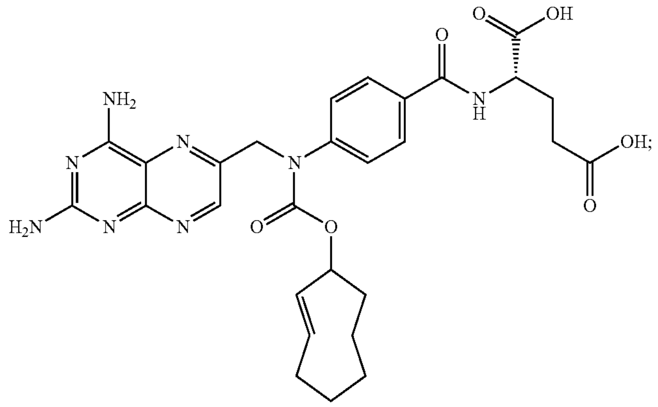
(payload = aminopterin)

-continued
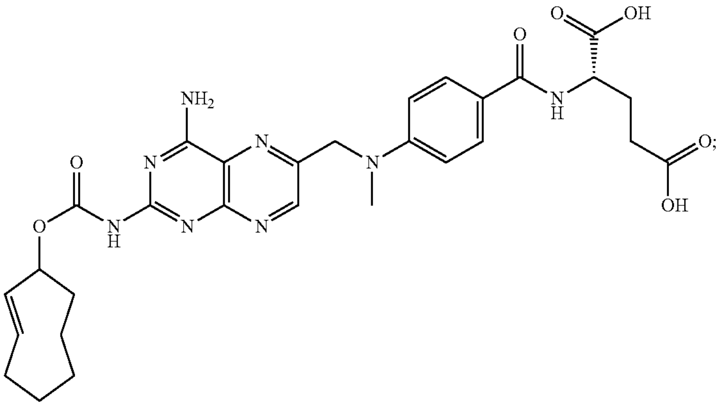
(payload = methotrexate)
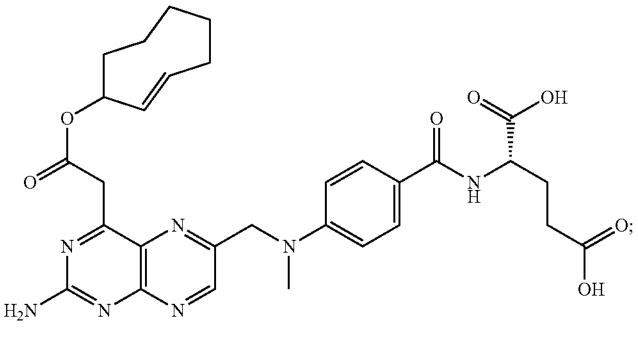
(payload = methotrexate)
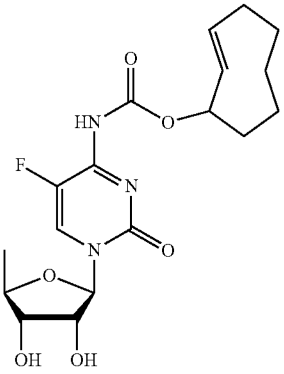
(payload = 5′-deoxy-5-fluorocytidine)
;
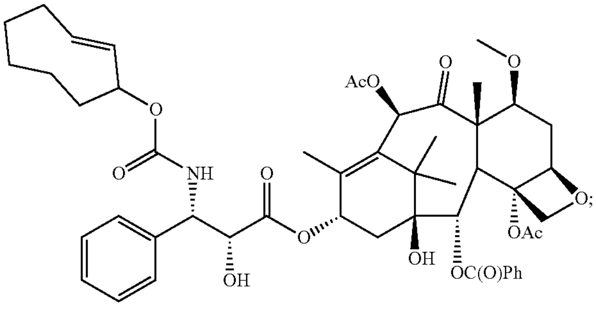
(payload = taxane)

-continued
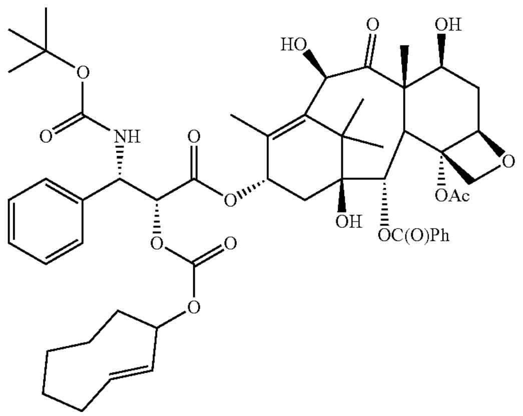
;
(payload = docetaxel)
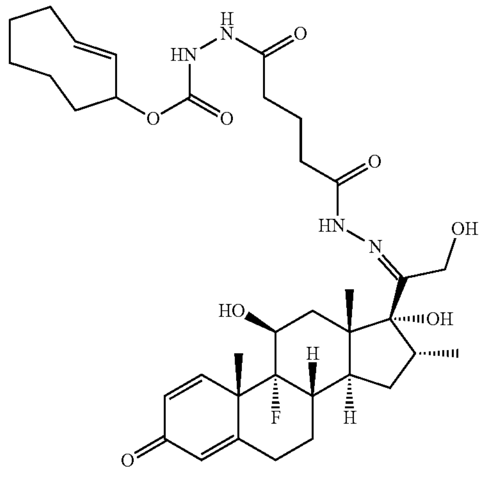
;
(payload = dexamethasone)
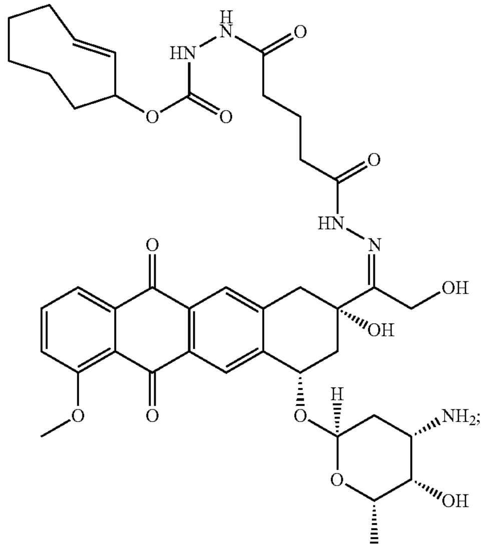
(payload = doxorubicin)
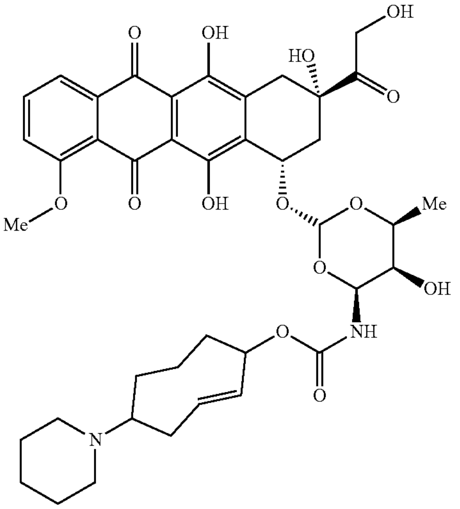
;
(payload = doxorubicin)
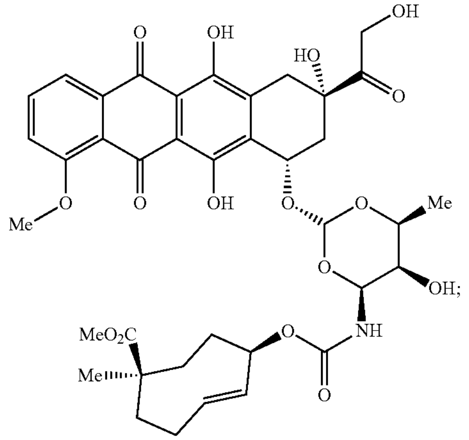
(payload = doxorubicin)
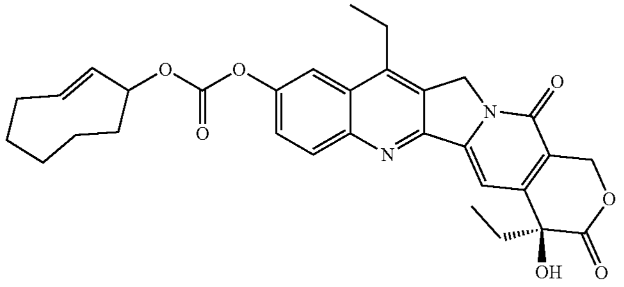
;
(payload = SN-38)

-continued
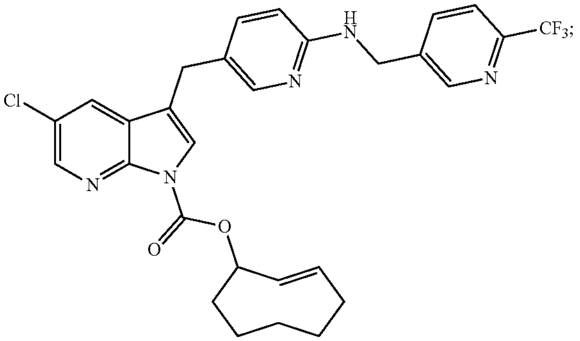
(payload = CFS-1R inhibitor)
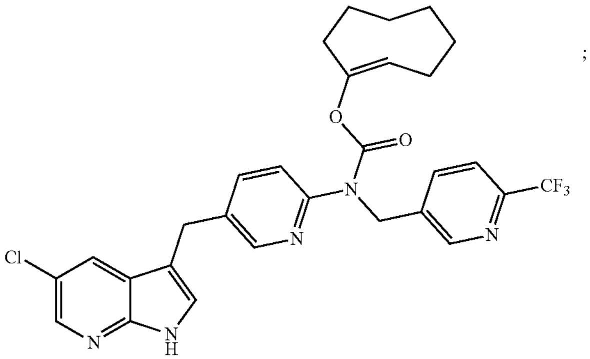
(payload = CFS-1R inhibitor)
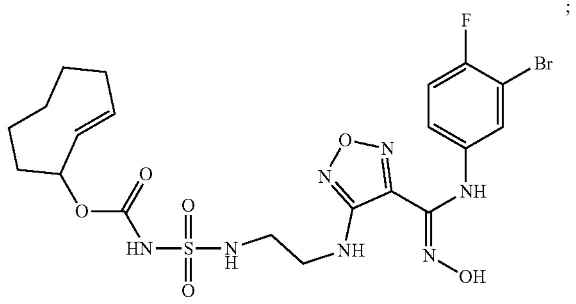
(payload = IDO inhibitor)
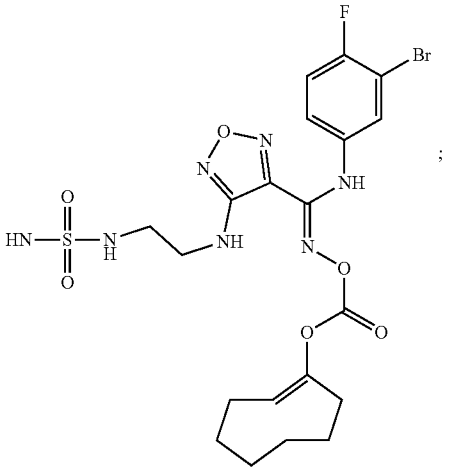
(payload = IDO inhibitor)
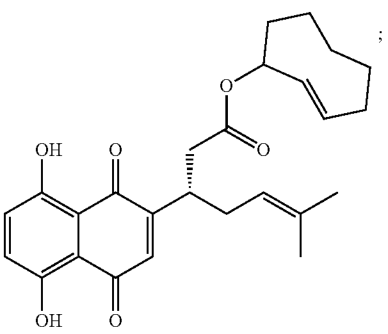
(payload = Shikonin PMK inhibitor)
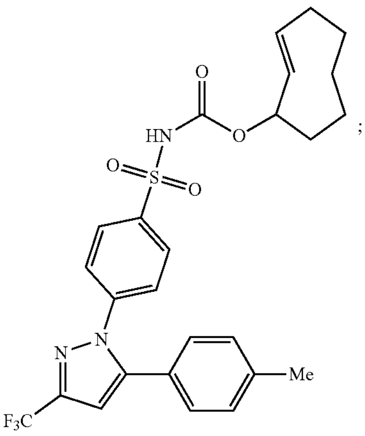
(payload = Cox-2 inhibitor)

-continued

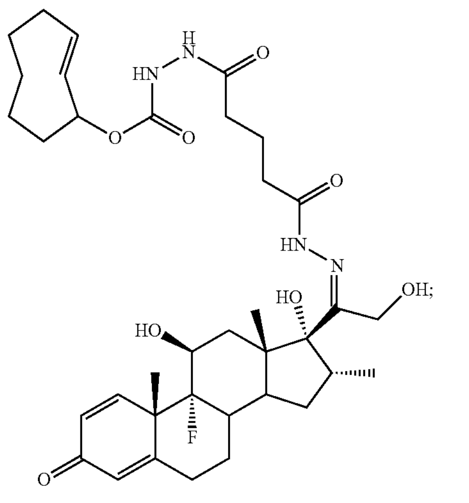

(double pH & carbamate releasable, payload = dexamethasone)

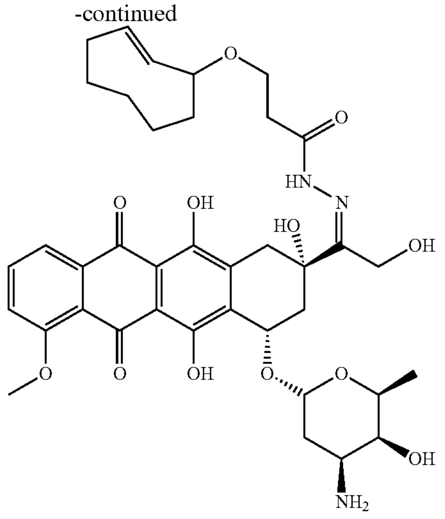

; or (pH & carbamate releasable TCO-Adipic-Doxorubicin)

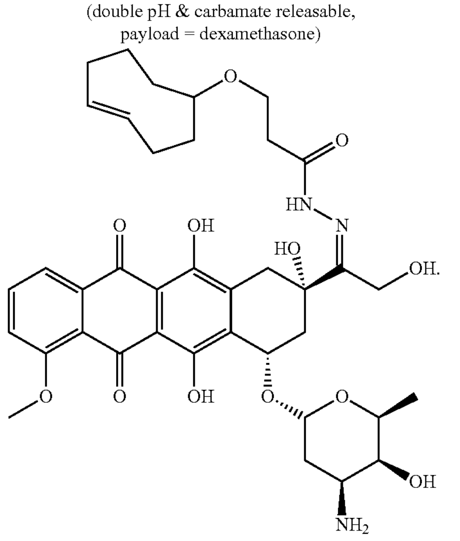

(pH dependent TCO-Adipic-Doxorubicin)

The compounds may exist as stereoisomers wherein asymmetric or chiral centers are present. The stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45:13-30. The disclosure contemplates various stereoisomers and mixtures thereof, and these are specifically included within the scope of this invention. Stereoisomers include enantiomers and diastereomers and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography, and optional liberation of the optically pure product from the auxiliary as described in Furniss, Hannaford, Smith, and Tatchell, "Vogel's Textbook of Practical Organic Chemistry", 5$^{th}$ edition (1989), Longman Scientific & Technical, Essex CM20 2JE, England, or (2) direct separation of the mixture of optical enantiomers on chiral chromatographic columns, or (3) fractional recrystallization methods.

It should be understood that the compounds may possess tautomeric forms as well as geometric isomers, and that these also constitute an aspect of the invention.

The present disclosure also includes isotopically-labeled compounds, which are identical to those recited herein, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$, and 36Cl, respectively. Substitution with heavier isotopes such as deuterium, i.e., 2H, can afford certain therapeutic advantages resulting from greater metabolic stability, for example increased in vivo half-life or reduced dosage requirements, and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds disclosed herein can generally be prepared by conventional techniques known to those skilled in the art or by processes analogous to those described in the accompanying Examples using appropriate isotopically-labeled reagent in place of non-isotopically-labeled reagent.

B. Support Compositions

In certain embodiments, the composition is a support composition. The support composition may be a biocompatible support composition. Biocompatible support compositions are compatible with the subject's body. In some instances, a biocompatible support composition is non-toxic to the subject and does not substantially react with tissue or biological compounds in the subject. Any suitable biocompatible support can be used. For example, the biocompatible support can be a hydrogel, a cross-linked polymer matrix, a metal, a ceramic, a plastic, a bone graft material, among others.

Hydrogels include, but are not limited to, polysaccharide hydrogels, alginate, cellulose, hyaluronic acid, chitosan, chitosin, chitin, hyaluronic acid, chondroitin sulfate, heparin, and the like. Other suitable sugar-based biomaterials include those described in Polymer *Advanced Technology,* 2014, 25, 448-460. Polymers that may be used as the biocompatible support can include, but are not limited to, polyphosphazenes, polyanhydrides, polyacetals, poly(ortho esters), polyphosphoesters, polycaprolactones, polyurethanes, polylactides, polycarbonates, polyamides, and polyethers, and blends/composites/co-polymers thereof. Representative polyethers include, but are not limited to, poly(ethylene glycol) (PEG), polypropylene glycol) (PPG), triblock Pluronic ($[PEG]_n$-$[PPG]_m$-$[PEG]_n$), PEG diacrylate (PEGDA), and PEG dimethacrylate (PEGDMA). The biocompatible support can also include proteins and other poly(amino acids), such as collagen, gelatin, elastin and elastin-like polypeptides, albumin, fibrin, poly(gamma-glutamic acid), poly(L-lysine), poly(L-glutamic acid), poly (aspartic acid), and the like.

In some embodiments, the support is a hydrogel. In some embodiments, the support is alginate. In some embodiments, the support is chitin. In some embodiments, the support is hyaluronic acid. In some embodiments, the support is chitosin.

In certain embodiments, the support is a particle. Particles of the present disclosure can have a diameter that is 2 cm or less, such as 1.5 cm or less, or 1 cm or less, or 0.5 cm or less. For example, the particles can be nanoparticles or microparticles. Nanoparticles include particles having average dimensions in the nanometer scale (e.g., 1000 nm or less). Microparticles are particles having average dimensions in the micrometer scale (e.g., 1000 μm or less). By "average" is meant the arithmetic mean. In some embodiments, the nanoparticles have a diameter ranging from 1 nm to 1 μm, such as from 10 nm to 1 μm, or 25 nm to 1 μm, or 50 nm to 1 μm, or 75 nm to 1 μm, or 100 nm to 1 μm, or 150 nm to 1 μm, or 200 nm to 1 μm, or 250 nm to 1 μm, or 300 nm to 1 μm, or 350 nm to 1 μm, or 400 nm to 1 μm, or 450 nm to 1 μm, or 500 nm to 1 μm. In other embodiments, the microparticles have a diameter ranging from 1 μm to 1 mm, such as from 10 μm to 1 mm, or 25 μm to 1 mm, or 50 μm to 1 mm, or 75 μm to 1 mm, or 100 μm to 1 mm, or 150 μm to 1 mm, or 200 μm to 1 mm, or 250 μm to 1 mm, or 300 μm to 1 mm, or 350 μm to 1 mm, or 400 μm to 1 mm, or 450 μm to 1 mm, or 500 μm to 1 mm. In further embodiments, small particles on the order of 10-100 nm in diameter may be assembled to form larger complexes, such as clusters or assemblies on the order of 1-10 μm. Particles of the present disclosure may be substantially spherical, such that the particles have a substantially circular cross-section. Other particle shapes may also be used, such as, but not limited to, ellipsoid, cubic, cylindrical, conical, needle, or other irregular shapes.

A "particle" may take the form of any fabricated material, a molecule, cryptophan, a virus, a phage, etc. The particle may be composed of a material, such as, but not limited to, a metal, a ceramic, a plastic, a polymer, a hydrogel, and the like. For example, the particles may be made of an inert material, such as alginate or iron oxide. In some examples, the particles may be magnetic and can be formed from a paramagnetic, super-paramagnetic or ferromagnetic material, or other material that responds to a magnetic field.

The particles, or a group of several particles in a complex, may be functionalized with a targeting agent (e.g., a ligand or antibody) that specifically binds (or substantially specifically binds) to a target (e.g., a target receptor or a cell surface target, such as a clinically relevant receptor or cell surface target (e.g., antigen)). The targeting agent may be attached directly to the particle itself. The targeting agent can be an antibody, peptide, nucleic acid, phage, bacteria, virus, or any other molecule with a specific affinity for a target receptor or cell surface target. In some instances, the receptor or cell surface target is PD-1, CTLA-4, HER2/neu, HER1/EGFR, VEGFR, BCR-ABL, SRC, JAK2, MAP2K, EML4-ALK, BRAF V600E, 4-1BB, GITR, GSK3beta, or other cellular receptors or cell surface targets. Other compounds or molecules, such as fluorophores or autofluorescent or luminescent markers, which may assist in detecting the particles (e.g., in vivo detection), may also be attached to the particles. The ligands and/or detectable labels may be attached directly to the particle or attached to the particle through bioorthogonal functional groups as described herein.

In certain embodiments, the support is a bone graft material, such as a bone graft substitute material. A bone graft substitute material is a biocompatible material structurally similar to bone. In some instances, a bone graft substitute material is bioresorbable such that the bone graft substitute material can dissolve or be absorbed in the body over time. A bone graft substitute material can be osteoconductive, such that it facilitates blood vessel and new bone formation into the bone graft substitute material. In some instances, the bone graft substitute material is osteoinductive, such that facilitates the formation of new bone through active recruitment of mesenchymal stem cells from the surrounding tissue. For example, growth factors, such as bone morphogenetic proteins, may be included in the bone graft substitute material. Bone graft substitute materials include, but are not limited to, hydroxyapatite, tricalcium phosphate, demineralized bone matrix, bovine collagen, calcium sulfate, calcium phosphate, cancellous bone chips, and the like, and combinations thereof.

In certain embodiments, the support composition is a bioorthogonal composition. A bioorthogonal composition includes compositions having a bioorthogonal binding agent. In some embodiments, the support composition includes one or more binding agents (e.g., bioorthogonal binding agents). In certain cases, the support composition includes 2 or more binding agents (e.g., 2 or more different binding agents), such as 3 or more binding agents (e.g., 3 or more different binding agents), or 4 or more binding agents (e.g., 4 or more different binding agents), or 5 or more binding agents (e.g., 5 or more different binding agents), or 6 or more binding agents (e.g., 6 or more different binding agents), or 7 or more binding agents (e.g., 7 or more different binding agents), or 8 or more binding agents (e.g., 8 or more different binding agents), or 9 or more binding agents (e.g., 9 or more different binding agents), or 10 or more binding agents (e.g., 10 or more different binding agents). In certain embodiments, the support composition includes two binding agents (e.g., two different binding agents). For example, the composition may include a support as described herein, a first binding agent attached (e.g., covalently linked) to the support, and a second binding agent different from the first binding agent attached (e.g., covalently linked) to the support.

Any suitable binding agent can be used. Representative binding agents are described, for example, in "Bioconjugate Techniques", Greg T. Hermanson, 1996 and *ACS Chemical Biology,* 2014, 9, 592-605. For example, binding agents include, but are not limited to, binding agents having bioorthogonal functional groups, such as cyclooctene, tetrazine, azide, alkyne, amine, activated ester, isocyanate, isothiocyanate, thiol, aldehyde, amide, and the like. In some instances, the binding agent includes a cyclooctene bioorthogonal functional group. In some instances, the binding agent includes a tetrazine bioorthogonal functional group. In some instances, the binding agent includes an azide bioorthogonal functional group. In some instances, the binding agent includes an alkyne bioorthogonal functional group.

In some embodiments, the first binding agent and the second binding agent have different bioorthogonal functional groups. For example, the first binding agent may have a first bioorthogonal functional group, and the second binding agent may have a second bioorthogonal functional group different from the first bioorthogonal functional group. A "different" bioorthogonal functional group refers to a bioorthogonal functional group that is a member of a different bioorthogonal binding pair. For example, a cyclooctene or a tetrazine bioorthogonal functional group is a different bioorthogonal functional group than an azide or an alkyne bioorthogonal functional group. A "different" bioorthogonal functional group does not refer to the complementary bioorthogonal functional group of a bioorthogonal functional group. For instance, a cyclooctene bioorthogonal functional group is not a "different" bioorthogonal functional group from a tetrazine bioorthogonal functional group; a cyclooctene and a tetrazine are referred to herein as "complementary" bioorthogonal functional groups. Similarly, an azide bioorthogonal functional group is not a "different" bioorthogonal functional group from an alkyne bioorthogonal functional group; an azide and an alkyne are referred to herein as "complementary" bioorthogonal functional groups.

Bioorthogonal functional groups may selectively react with their respective complementary binding partners. A binding reaction may occur between the binding agent and its complementary binding agent (e.g., between the complementary bioorthogonal functional groups) to form a covalent bond between the binding agent and its complementary binding agent. For example, a cyclooctene (e.g., trans-cyclooctene; TCO) may selectively react with its complementary binding partner, a tetrazine (e.g., 1,2,4,5-tetrazine; Tz), to form a covalent bond between the binding partners, or an alkyne may selectively react with its complementary binding partner, an azide, to form a covalent bond between the binding partners. In embodiments where the first binding agent and the second binding agent have different bioorthogonal functional groups, the first binding agent selectively reacts with its complementary binding partner (e.g., a first complementary binding agent), and the second binding agent selectively reacts with its complementary binding partner (e.g., a second complementary binding agent). In these embodiments, there is substantially no cross-reactivity between different binding agents; e.g., the first binding agent may not significantly react with the second binding agent or the second complementary binding agent, the first complementary binding agent may not significantly react with the second binding agent or the second complementary binding agent, the second binding agent may not significantly react with the first binding agent or the first complementary binding agent, and the second complementary binding agent may not significantly react with the first binding agent or the first complementary binding agent.

For instance, in some embodiments, the first binding agent may be a cyclooctene (e.g., trans-cyclooctene) and the second binding agent may be an azide. As such, in these embodiments, the first complementary binding agent may be a tetrazine (e.g., 1,2,4,5-tetrazine) and the second complementary binding agent may be an alkyne.

In some embodiments, the first binding agent may be a cyclooctene (e.g., trans-cyclooctene) and the second binding agent may be an alkyne. As such, in these embodiments, the first complementary binding agent may be a tetrazine (e.g., 1,2,4,5-tetrazine) and the second complementary binding agent may be an azide.

In some embodiments, the first binding agent may be a tetrazine (e.g., 1,2,4,5-tetrazine) and the second binding agent may be an azide. As such, in these embodiments, the first complementary binding agent may be a cyclooctene (e.g., trans-cyclooctene) and the second complementary binding agent may be an alkyne.

In some embodiments, the first binding agent may be a tetrazine (e.g., 1,2,4,5-tetrazine) and the second binding agent may be an alkyne. As such, in these embodiments, the first complementary binding agent may be a cyclooctene (e.g., trans-cyclooctene) and the second complementary binding agent may be an azide.

In certain embodiments, the first binding agent and the second binding agent are present on the support composition in a ratio of the first binding agent to the second binding agent of 1:100, or 1:75, or 1:50, or 1:25, or 1:10, or 1:5, or 1:4, or 1:3, or 1:2, or 1:1, or 2:1, or 3:1, or 4:1, or 5:1, or 10:1, or 25:1, or 50:1, or 75:1, or 100:1.

As described above, support compositions of the present disclosure include a support and two or more different binding agents attached (e.g., covalently linked) to the support (e.g., a first binding agent covalently linked to the support, and a second binding agent covalently linked to the support). The binding agents may be attached to the support on a surface of the support, such as a solvent-accessible surface of the support (e.g., a surface of the support that is in contact with the surrounding solvent). In some cases, the binding agent is attached directly to the support. For example, the binding agent may be covalently attached to the surface of the support, e.g., through a covalent bond, such as an amide, amine, ester, carbamate, urea, thioether, thiocarbamate, thiocarbonate, thiourea, etc. In some instances, the binding agent is covalently attached to the support through an amide bond. In other instances, the binding agent may be linked to the support via a linker. Any suitable linker can be used to link the binding agent to the support. Representative linkers can have from 1 to 100 linking atoms, and can include ethylene-oxy groups, amines, esters, amides, carbamates, carbonates, and ketone functional groups. For example, linkers may have from 1 to 50 linking atoms, or from 5 to 50 linking atoms, or from 10 to 50 linking atoms. Representative linkers include, but are not limited to, those shown below:

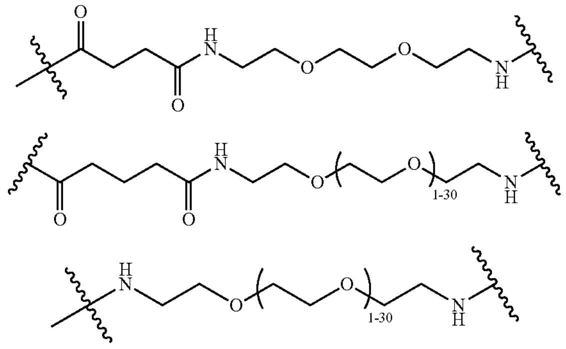

In certain embodiments, the support compositions comprise a tetrazine-containing group of formula:

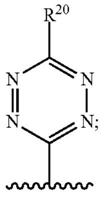

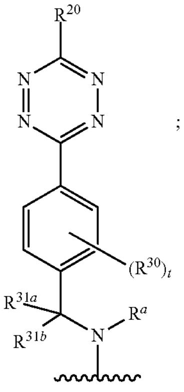

; or

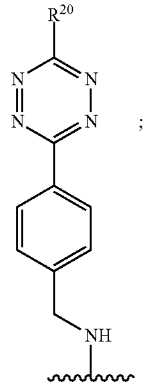

;

wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(=O)R', C(=S)R', OC(=O)R''', SC(=O)R''', OC(=S)R''', SC(=S)R''', S(=O)R', $S(=O)_2R'''$, $S(=O)_2NR'R''$, C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O) SR'', NR'C(=S)SR'', OC(=O)NR'R'', SC(=O)NR'R'', OC(=S)R'R''', SC(=S)R'R'', NR'C(=O)NR''R'', and NR'C(=S)NR''R''; R' and R'' at each occurrence are independently selected from hydrogen, aryl and alkyl; and R''' at each occurrence is independently selected from aryl and alkyl; $R^{30}$ is halogen, cyano, nitro, hydroxy, alkyl, haloalkyl; alkenyl, alkynyl, alkoxy; halalkoxy; heteroalkyl, aryl, heteroaryl, heterocycle, cycloalkyl, or cycloalkenyl; $R^a$, $R^{31a}$ and $R^{31b}$ are each independently hydrogen, $C_1$-$C_6$-alkyl, or $C_1$-$C_6$-haloalkyl; and t is 0, 1, 2, 3, or 4.

In certain embodiments, the support compositions have formula:

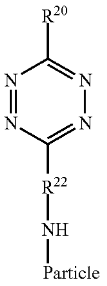

wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(=O)R', C(=S)R', OC(=O)R''', SC(=O)R''', OC(=S)R''', SC(=S)R''', S(=O)R', $S(=O)_2R'''$, $S(=O)_2NR'R''$, C(=O)O—R', C(=O)S—R', C(=S)O—R', C(=S)S—R', C(=O)NR'R'', C(=S)NR' R'', NR'R'', NR'C(=O)R'', NR'C(=S)R'', NR'C(=O)OR'', NR'C(=S)OR'', NR'C(=O) SR'', NR'C(=S)SR'', OC(=O)NR'R'', SC(=O)NR'R'', OC(=S)R'R'', SC(=S)R'R'', NR'C(=O)NR''R'', and NR'C(=S)NR''R''; R' and R'' at each occurrence are independently selected from hydrogen, aryl and alkyl; R''' at each occurrence is independently selected from aryl and alkyl; and $R^{22}$ is a linker of 1 to 100 linking atoms, and can include ethylene-oxy groups, amines, esters, amides, carbamates, carbonates, and ketone functional groups. For example, linkers may have from 1 to 50 linking atoms, or from 5 to 50 linking atoms, or from 10 to 50 linking atoms.

In certain embodiments, the support compositions have formula:

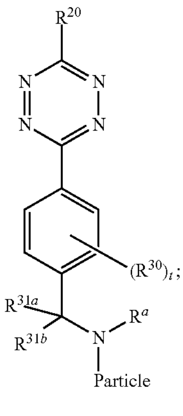

or

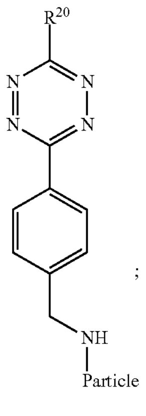

;

wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(=O)R', C(=S)R', OC(=O)R''', SC(=O)R''', OC(=S)R''', SC(=S)R''', S(=O)R', $S(=O)_2R''$, $S(=O)_2NR'$ R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O) SR'', NR'C(=S)SR'', OC(=O)NR'R'', SC(=O)NR'R'', OC(=S)R'R'', SC(=S)R'R'', NR'C(=O)NR''R'', and NR'C(=S)NR''R''; R' and R'' at each occurrence are independently selected from hydrogen, aryl and alkyl; R''' at each occurrence is independently selected from aryl and alkyl; $R^{30}$ is halogen, cyano, nitro, hydroxy, alkyl, haloalkyl; alkenyl, alkynyl, alkoxy; halalkoxy; heteroalkyl, aryl, heteroaryl, heterocycle, cycloalkyl, or cycloalkenyl; $R^a$, $R^{31a}$ and $R^{31b}$ are each independently hydrogen, $C_1$-$C_6$-alkyl, or $C_1$-$C_6$-haloalkyl; and t is 0, 1, 2, 3, or 4.

In certain embodiments, the support compositions comprise units of formula:

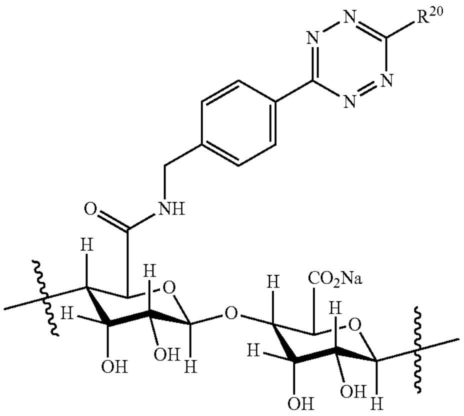

wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(═O)R', C(═S)R', OC(═O)R''', SC(═O)R''', OC(═S)R''', SC(═S)R''', S(═O)R', $S(═O)_2R'''$, $S(═O)_2NR'R''$, C(═O)O—R', C(═O)S—R', C(═S)O—R', C(═S)S—R', C(═O)NR'R'', C(═S)NR'R'', NR'R'', NR'C(═O)R'', NR'C(═S)R'', NR'C(═O)OR'', NR'C(═S)OR'', NR'C(═O) SR'', NR'C(═S)SR'', OC(═O)NR'R'', SC(═O)NR'R'', OC(═S)R'R'', SC(═S)R'R'', NR'C(═O)NR''R'', and NR'C(═S)NR''R''; R' and R'' at each occurrence are independently selected from hydrogen, aryl and alkyl; and R''' at each occurrence is independently selected from aryl and alkyl.

In certain embodiments, the support compositions comprise units of formula:

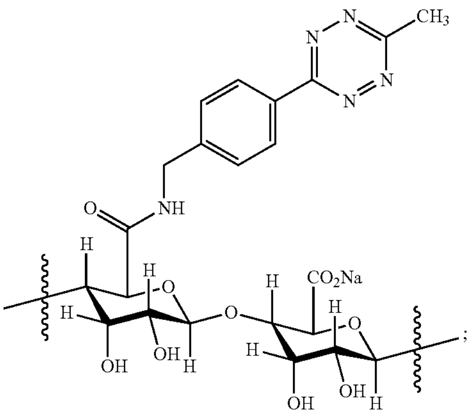
;
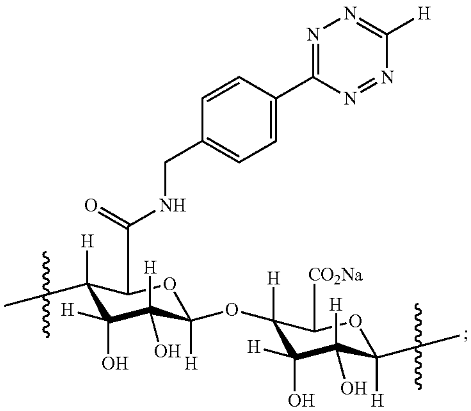
;
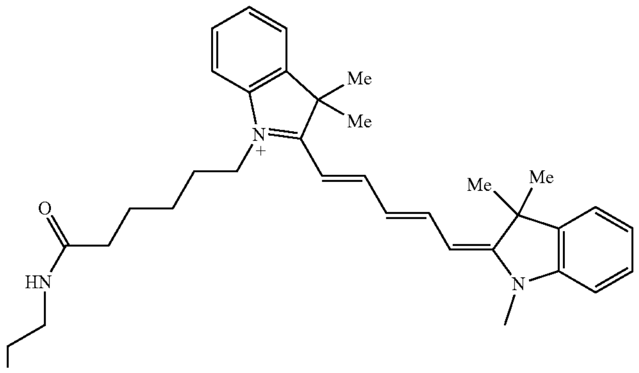

-continued

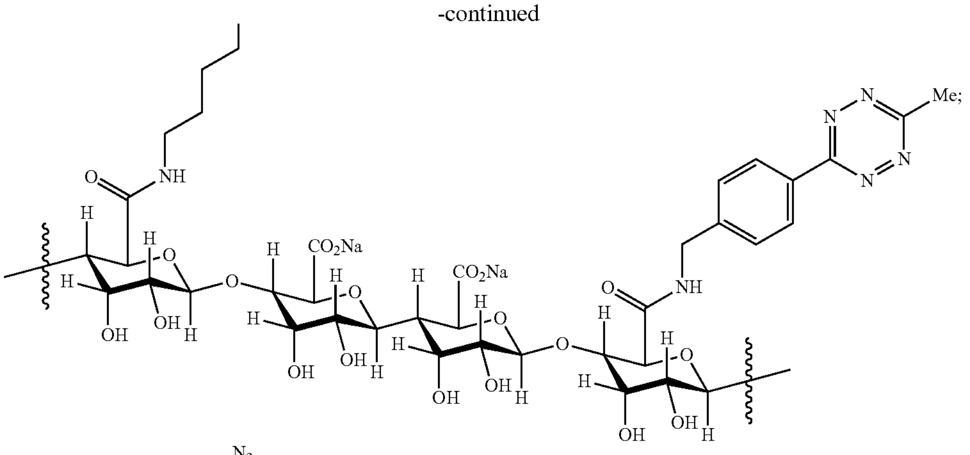

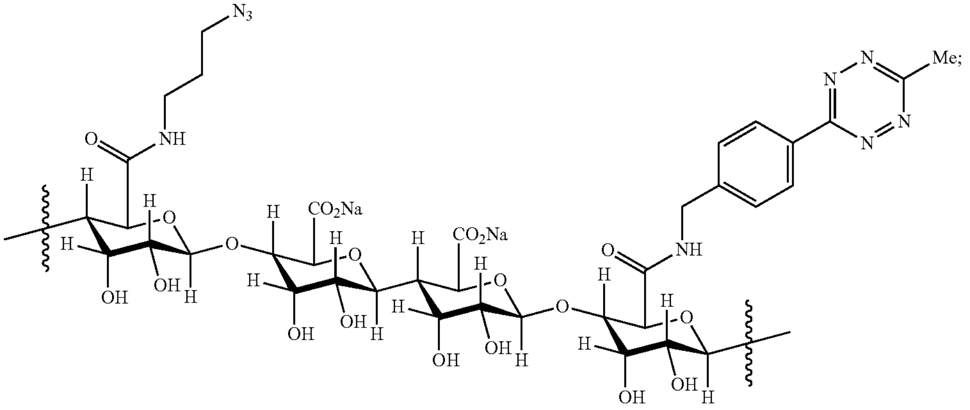

Additional support compositions are exemplified in WP/2015/139025A1 and WO/2014/205126A1, the entire contents of each of which is incorporated herein by reference in their entirety.

3. Synthetic Methods

The compounds of the present disclosure can be better understood in connection with the following synthetic schemes and methods which illustrate a means by which the compounds can be prepared.

In another aspect, disclosed are methods of preparing the disclosed compositions.

In general, compounds of formula (I) can be prepared by reacting a payload having a primary amine, secondary amine, or a hydroxyl group with an activated complementary binding agent (e.g., an activated trans-cyclooctene). It is to be understood that the reactive group of the active complementary binding agent (e.g., ester, carbonate, acyl chloride, carboxylic acid) can be located on any selected position of the complementary binding agent or the linker group.

In certain embodiments, as shown below, a trans-cyclooctene activated for nucleophilic addition can be reacted with a suitable payload (D) in the presence of a base to provide a functionalized payload. The payload can include a primary amine, secondary amine, or hydroxyl group that reacts with the activated TCO, wherein $R^a$: is hydrogen, $C_1$-$C_6$-alkyl, or $C_1$-$C_6$-haloalkyl. In certain embodiments, the leaving group (LG) is a chloro leaving group or a p-nitrophenol leaving group. Exemplary bases for use in the reaction include organic and inorganic bases, such as for example, triethylamine, pyridine, sodium hydroxide, and sodium bicarbonate.

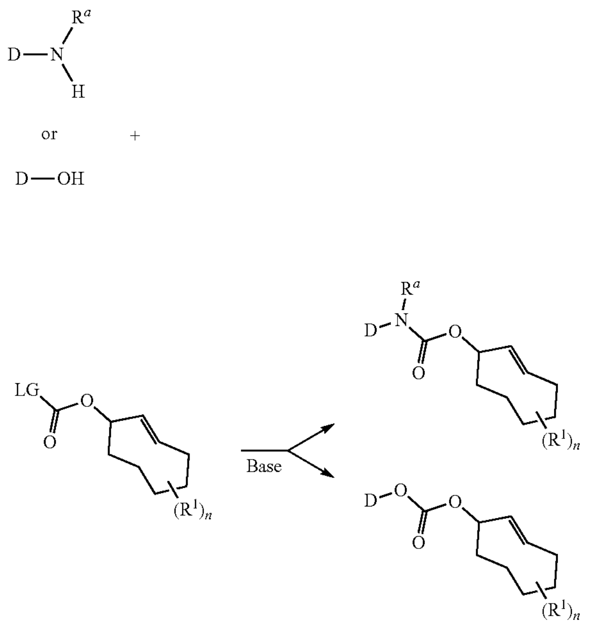

In certain embodiments, as shown below, a trans-cyclooctene including a carboxylic acid substituted linker can be coupled with a payload having an amine through use of (2-(1H-benzotriazol-1-yl)-1,1,3,3-tetramethyluronium hexafluorophosphate) ("HBTU"). Alternatively, coupling with a hydroxyl-containing payload can be affected with the use of N,N'-Dicyclohexylcarbodiimide ("DCC").

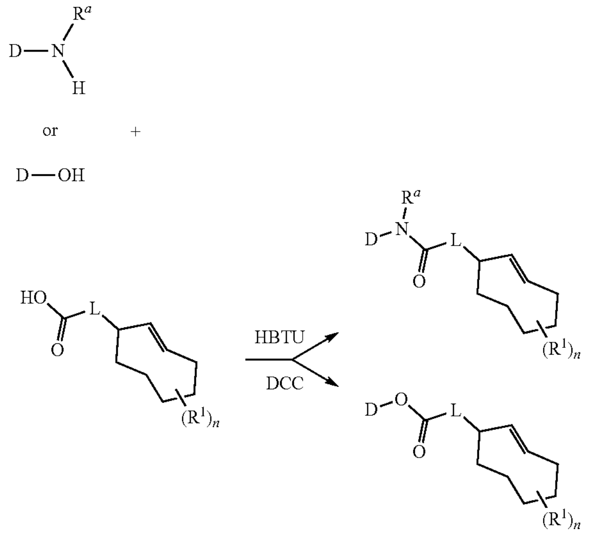

In certain embodiments, compounds of formula (I) incorporating cytarabine can be prepared as shown below.

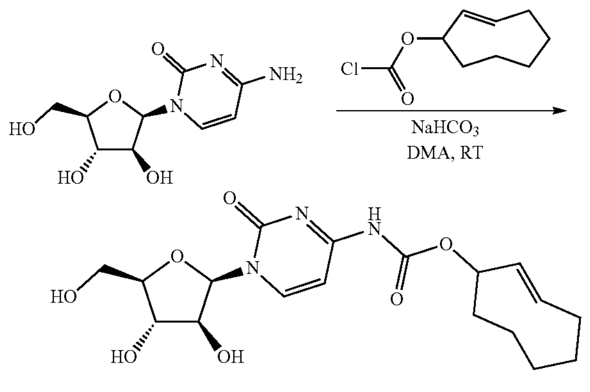

In certain embodiments, compounds of formula (I) incorporating 5-fluorouracil can be prepared as shown below.

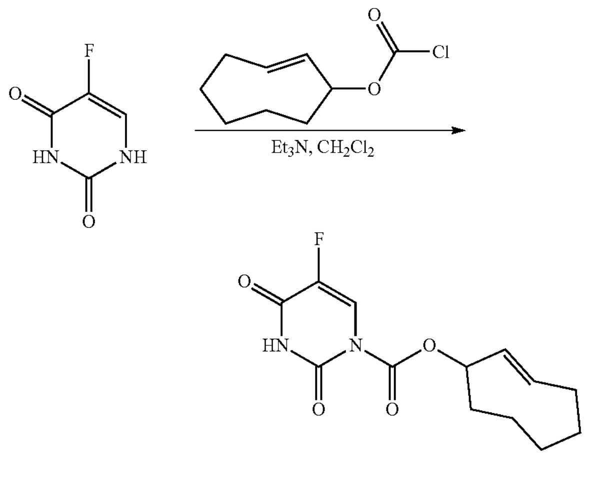

In certain embodiments, compounds of formula (I) incorporating dexamethasone can be prepared as shown below.

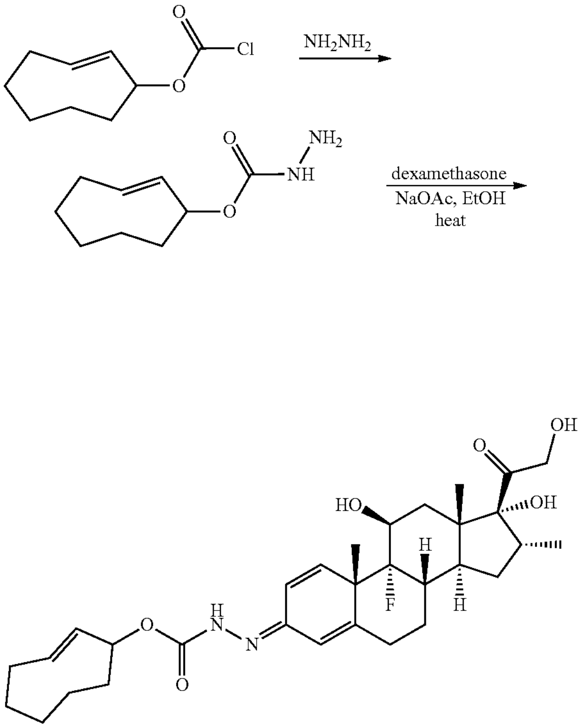

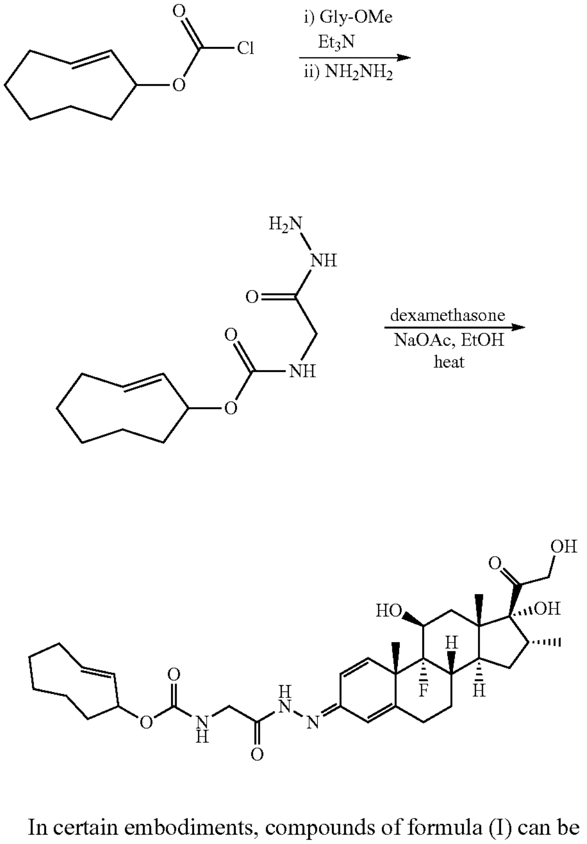

In certain embodiments, compounds of formula (I) can be prepared as shown below. Such compounds may include immolative linkers.

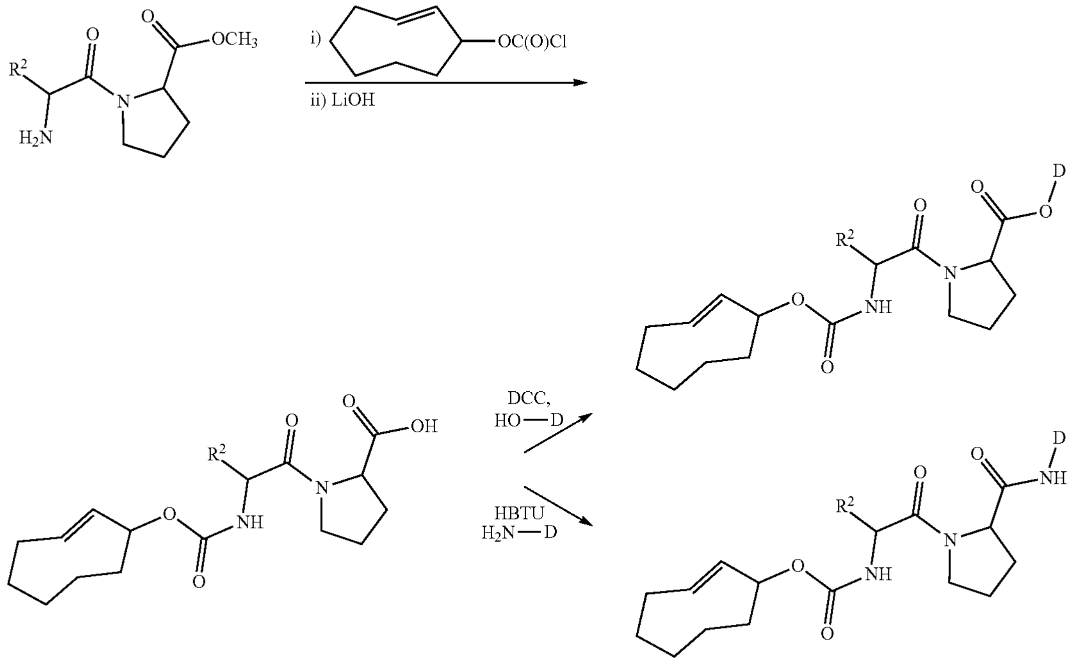
wherein D (i.e., the payload) and $R^2$ are as defined above.
In certain embodiments, compounds of formula (I) incorporating vinblastine can be prepared as shown below.
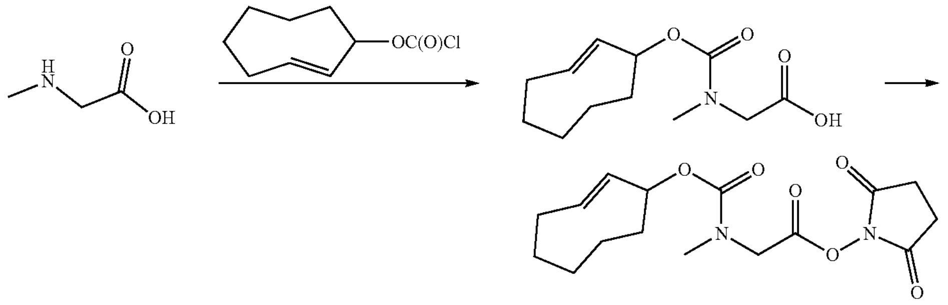
A
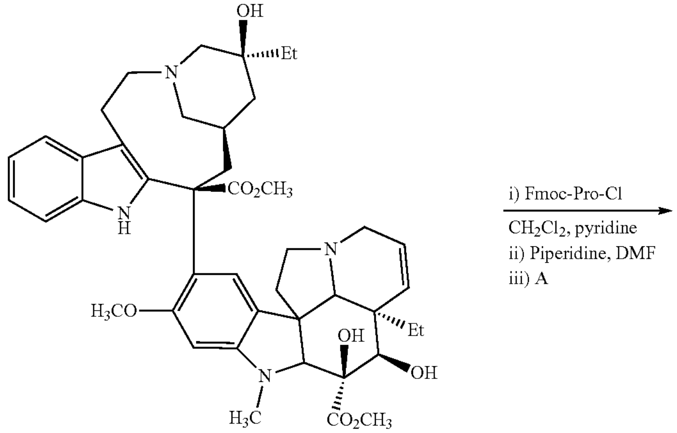

-continued
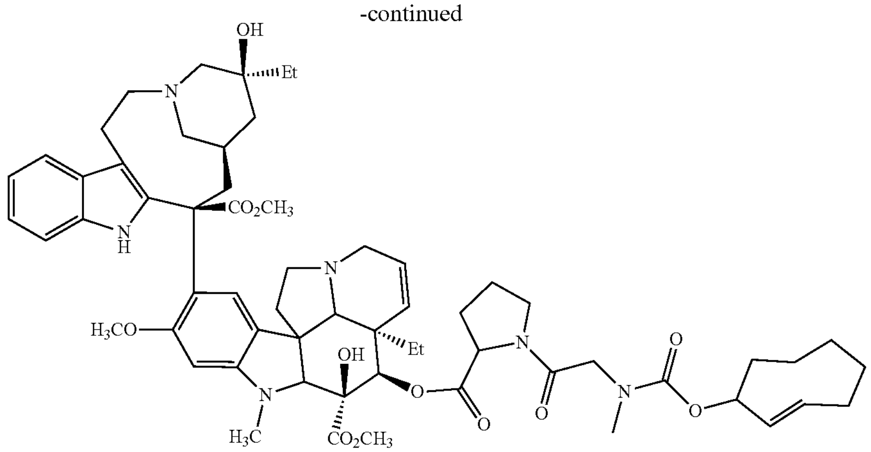
In certain embodiments, compounds of formula (I) incorporating etoposide can be prepared as shown below.
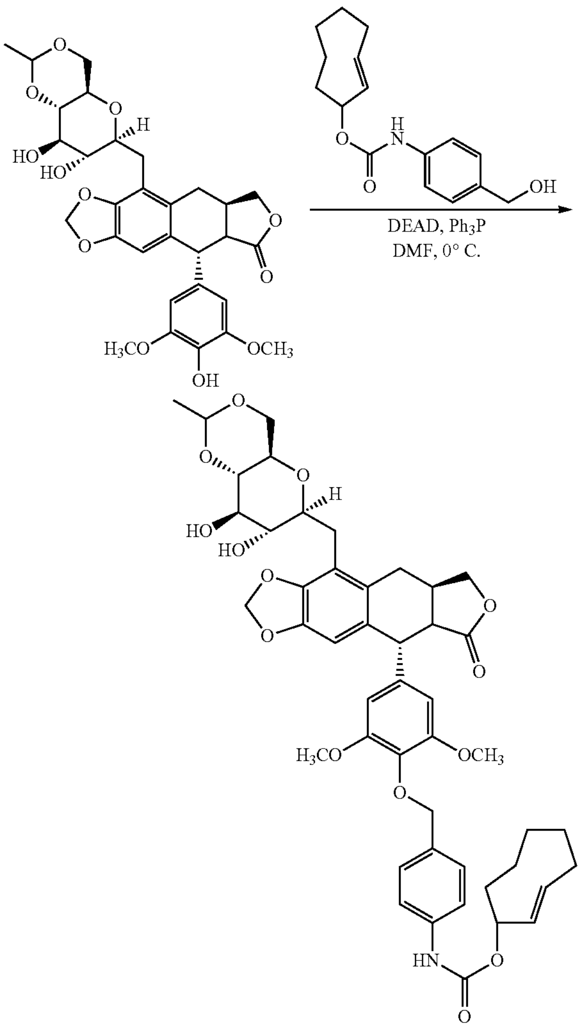
In certain embodiments, compounds of formula (I) incorporating combretastatin-A4 can be prepared as shown below.
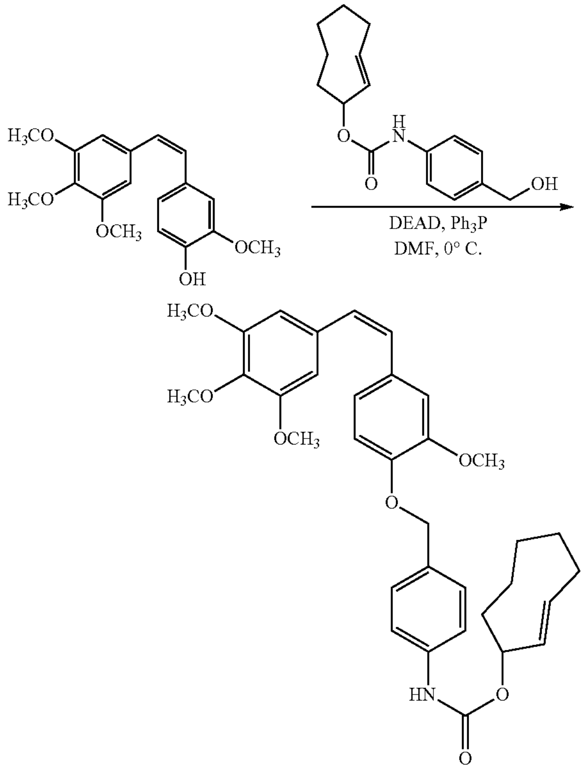
In certain embodiments, compounds of formula (I) incorporating melphalin can be prepared as shown below.
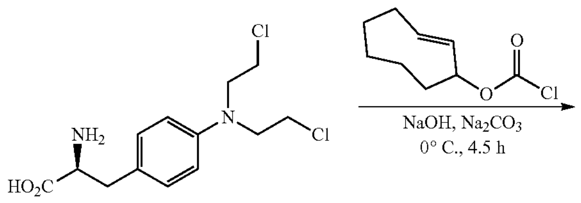

-continued
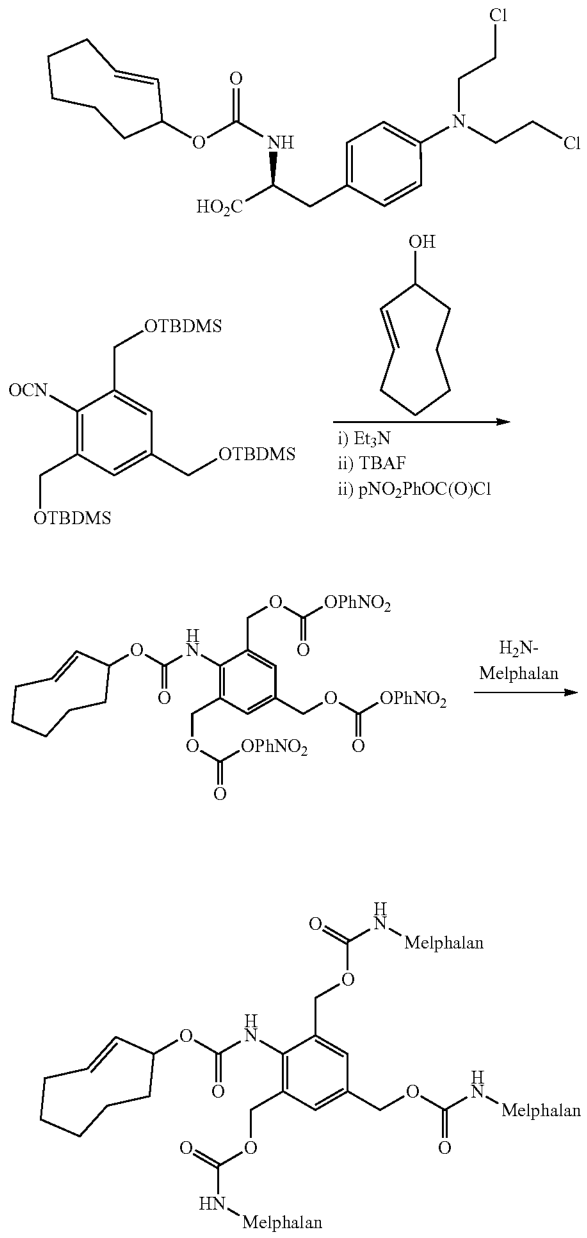
In certain embodiments, compounds of formula (I) incorporating camptothecin can be prepared as shown below.
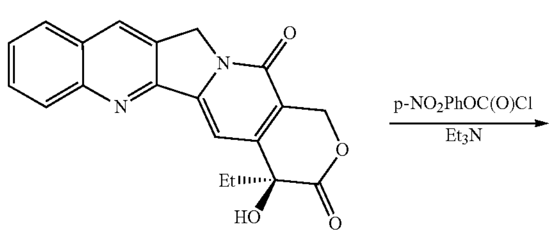
-continued
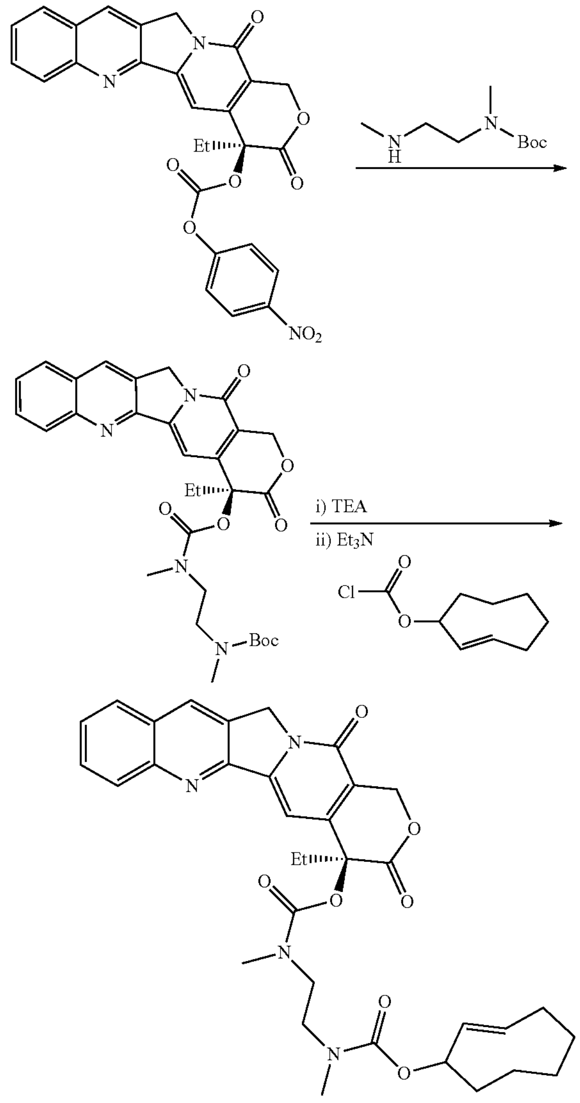
In certain embodiments, compounds of formula (I) incorporating paclitaxel can be prepared as shown below.
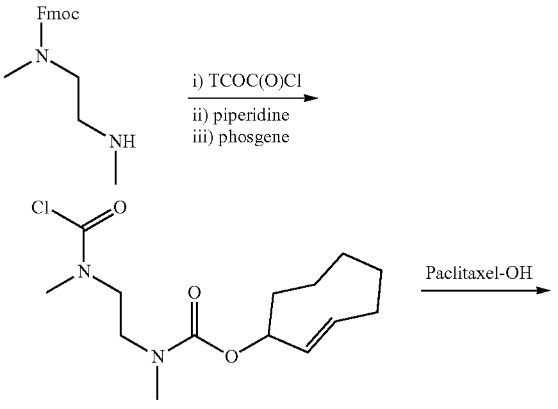

-continued
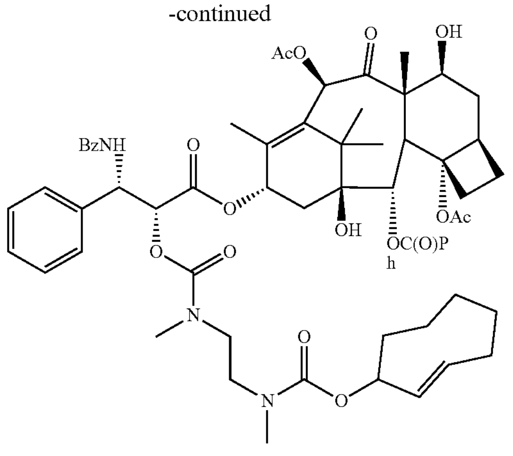
In certain embodiments, compounds of formula (I) incorporating methotrexate can be prepared as shown below.
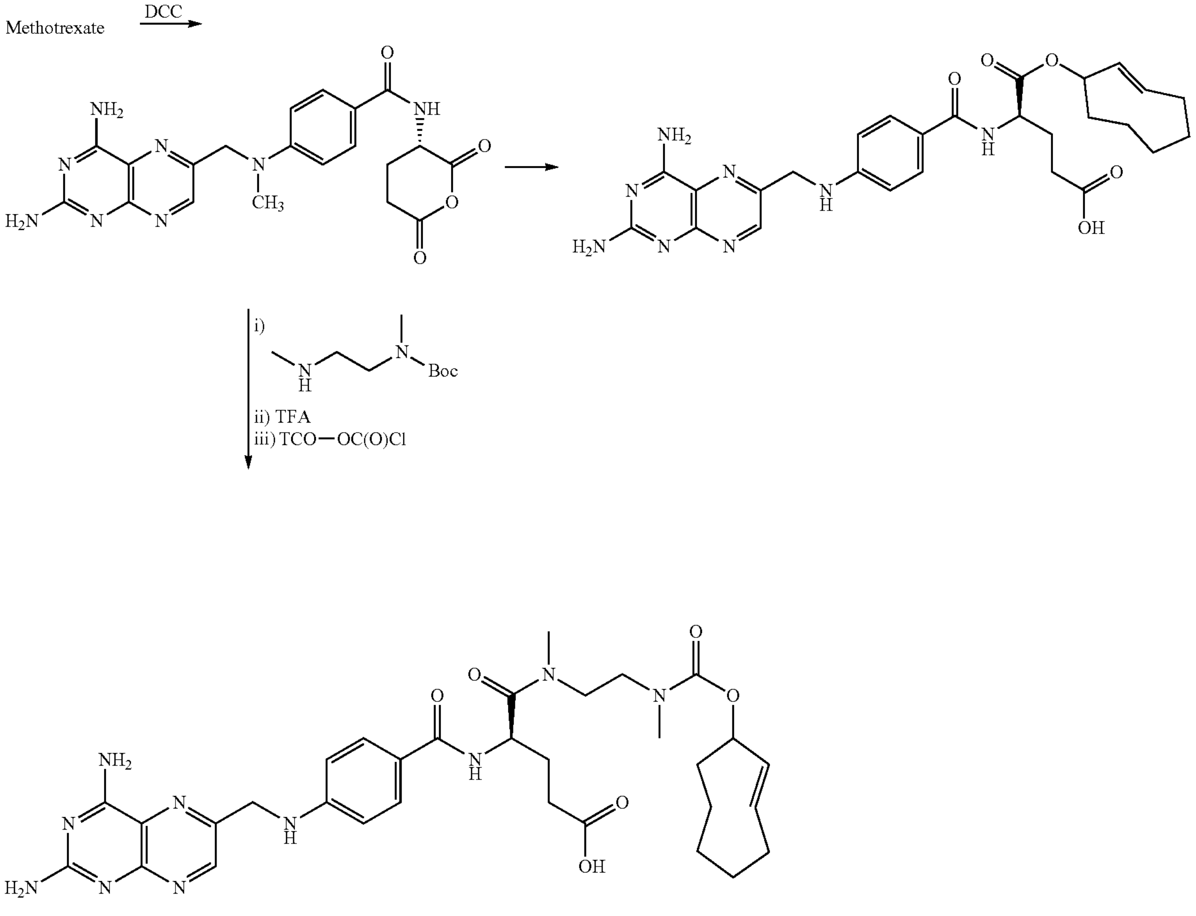
In certain embodiments, compounds of formula (I) incorporating doxorubicin can be prepared as shown below.

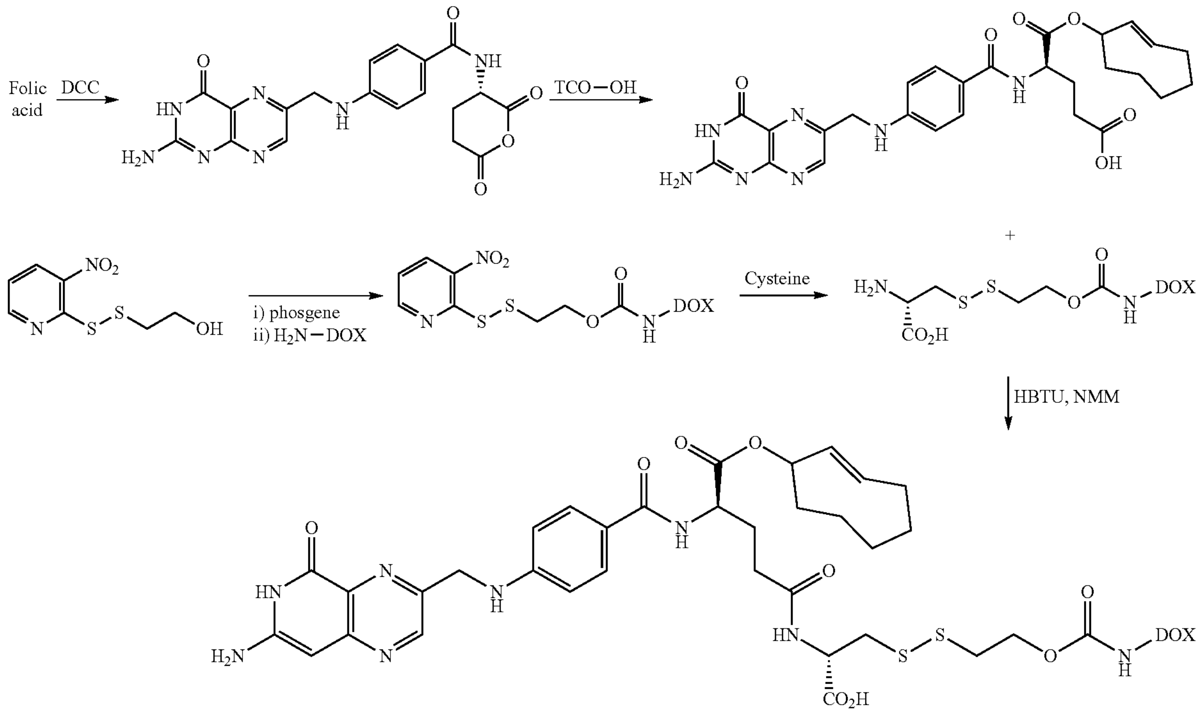
In certain embodiments, compounds of formula (I) incorporating doxorubicin and methotrexate can be prepared as shown below.
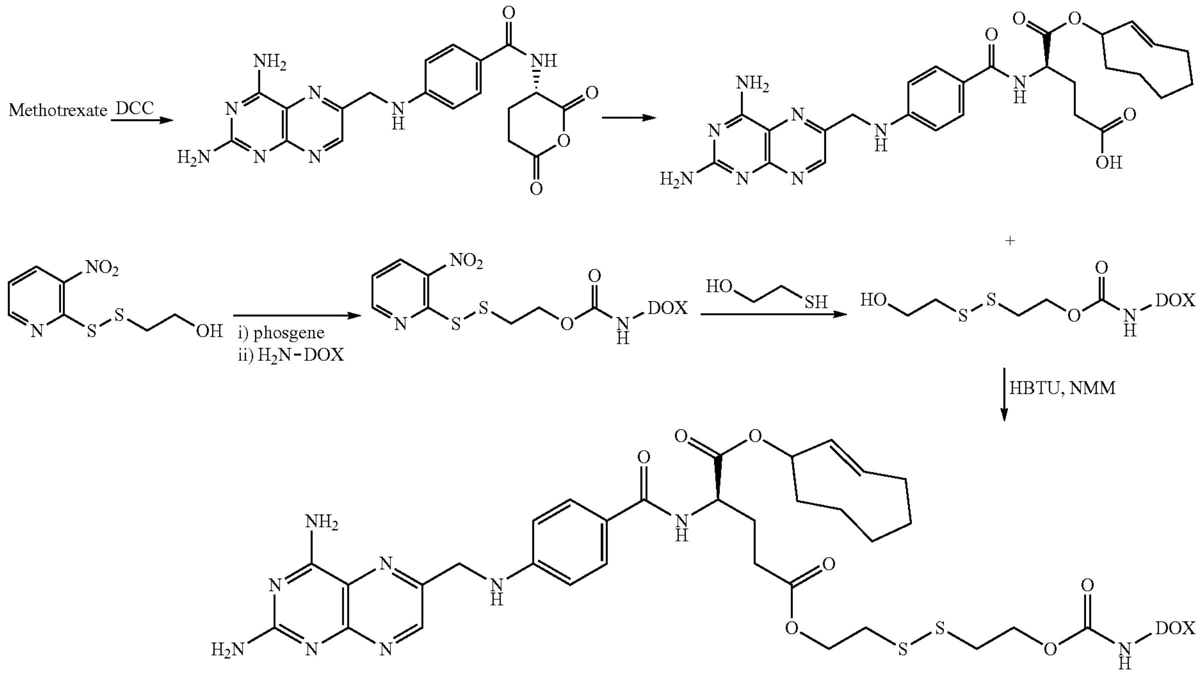
In certain embodiments, compounds of formula (I) incorporating gemcitabine can be prepared as shown below.

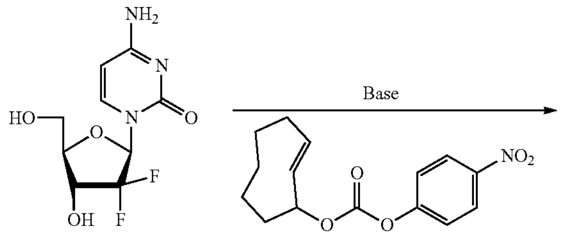
Gemcitabine
-continued
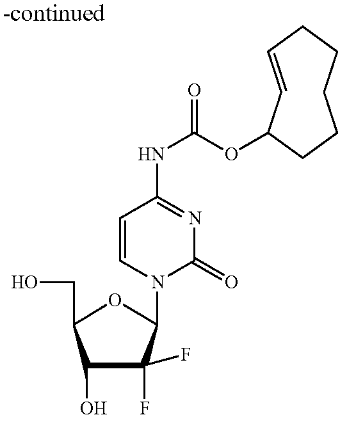
In certain embodiments, compounds of formula (I) incorporating SN38 can be prepared as shown below.
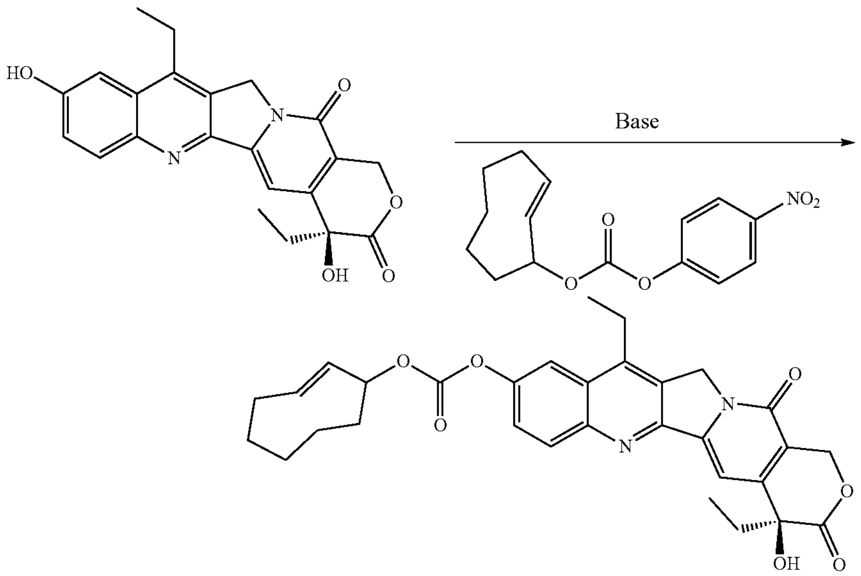
In certain embodiments, compounds formula (I) incorporating taxane can be prepared as shown below.
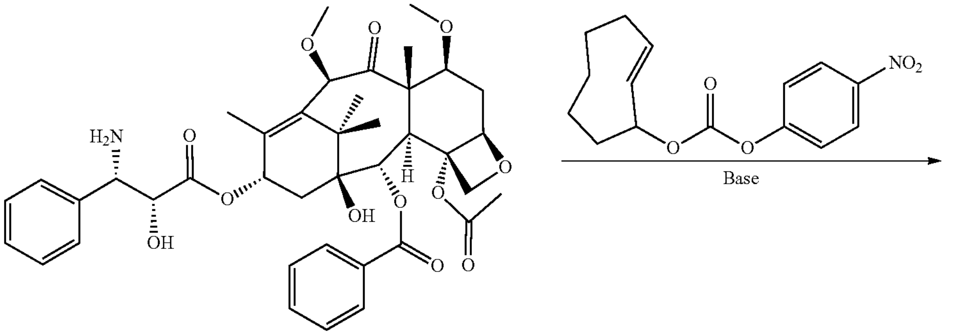

-continued

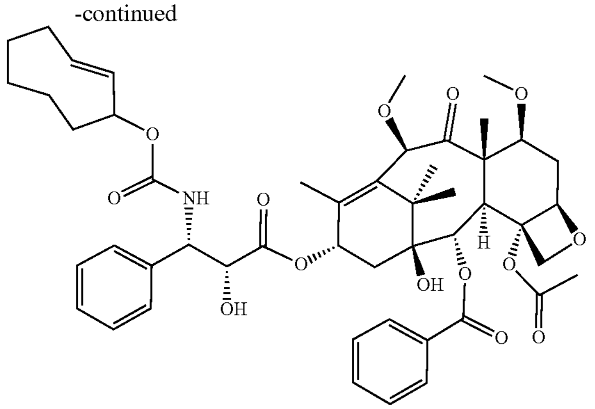

Additional functionalized payloads may be prepared by complementary methods, for example, as shown in FIGS. 33-48.

The disclosed compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

A compound described herein can be in the form of a salt, e.g., a pharmaceutically acceptable salt. The term “pharmaceutically acceptable salt” includes salts of the active compounds that are prepared with relatively nontoxic acids or bases, depending on the particular substituents found on the compounds described herein. Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure. Examples of pharmaceutically acceptable salts are discussed in Berge et al, 1977, “Pharmaceutically Acceptable Salts.” J. Pharm. Sci. Vol. 66, pp. 1-19.

For example, if the compound is anionic, or has a functional group which may be anionic (e.g., —COOH may be —$COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations. Examples of suitable organic cations include, but are not limited to, ammonium ion (i.e., $NH^{4+}$) and substituted ammonium ions (e.g., $NH^3R_1^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine.

If the compound is cationic, or has a functional group that may be cationic (e.g., —$NH^2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, gluchep tonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

It may be convenient or desirable to prepare, purify, and/or handle an active compound in a chemically protected form. The term “chemically protected form” is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999). Unless otherwise specified, a reference to a particular compound also includes chemically protected forms thereof.

A wide variety of such “protecting,” “blocking,” or “masking” methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxy group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—$OC(O)CH_3$, —OAc).

An aldehyde or ketone group may be protected as an acetal ($RCH(OR)_2$) or ketal ($R_2C(OR)_2$), respectively, in which the carbonyl group ($R_2C{=}O$) is converted to a diether ($R_2C(OR)_2$), by reaction with, for example, a primary alcohol. The aldehyde or ketone group is readily regenerated by hydrolysis using a large excess of water in the presence of acid.

An amine group may be protected, for example, as an amide (—NRC(O)R) or a urethane (—NRC(O)OR), for example, as: a methyl amide (—$NHC(O)CH_3$); a benzyloxy amide (—$NHC(O)OCH_2C_6H_5$, —NH-Cbz); as a t-butoxy amide (—$NHC(O)OC(CH_3)_3$, —NH-Boc); a 2-biphenyl-2-propoxy amide (—$NHCO(O)C(CH_3)_2C_6H_4C_6H_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2 (-phenylsulphonyl)ethyloxy amide (—NH—Psec); or, in suitable cases (e.g., cyclic amines), as a nitroxide radical (>N–0«).

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; an acetamidomethyl ether (—S—$CH_2NHC(O)CH_3$)

A compound described herein can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

In certain embodiments, the products may be further modified, for example, by manipulation of substituents. These manipulations may include, but are not limited to, reduction, oxidation, organometallic cross-coupling, alkylation, acylation, and hydrolysis reactions which are commonly known to those skilled in the art. In some cases, the order of carrying out the foregoing reaction schemes may be varied to facilitate the reaction or to avoid unwanted reaction products.

4. Methods

Aspects of the present disclosure include methods for delivering a payload to a target location in a subject. In certain embodiments, the method includes selectively delivering a payload to the target location in a subject. Selective delivery of the payload includes delivering the payload to the target location (e.g., an organ or tissue, or portion thereof), without targeting other locations in the subject (e.g., other organs or tissues, or portions thereof) that do not need administration of the payload. Selective delivery of the payload may be achieved through use of the support compositions and the functionalized payloads described herein.

In some instances, a support composition of the present disclosure may be localized to a desired target location in a subject. For example, methods of the present disclosure may include administering to a subject a support composition as described herein. The support composition may be administered to the subject at a desired target location in the subject. In some instances, the support composition may be implanted into the subject at the desired target location in the subject. In some embodiments, the support composition may be attached to a targeting agent as described herein, and the method may include administering the support composition to the subject (e.g., administered systemically). In these embodiments, the support composition that is attached to a targeting agent may localize at a desired target location in the subject through specific binding of the targeting agent to its target (e.g., antibody-antigen interaction, and the like), or may localize on the surface of a desired target (e.g., a cell surface) through specific binding of the targeting agent to its target (e.g., antibody-antigen interaction, and the like).

As described herein, selective binding between bioorthogonal binding partners (e.g., between a binding agent of the support composition and its complementary binding agent of a functionalized payload) may occur. Due to the localized administration of the support composition to a desired location in the subject as described above, the selective binding between the binding agent of the support composition and its complementary binding agent of the functionalized payload will localize the payload to the desired target location. Accordingly, in certain embodiments, the method includes administering to the subject a functionalized payload such that the functionalized payload binds to the support composition to form a support complex. For example, the functionalized payload may be administered systemically to the subject. Upon administration of the functionalized payload to the subject, contact between the binding agent of the support composition and the complementary binding agent of the functionalized payload may occur, such that the binding agent and its complementary binding agent bind to one another to form a support complex, thereby selectively delivering the payload to the target location in the subject. In some embodiments, selective delivery of the functionalized payload results in a concentration of the payload at the target location that is greater than the concentration of the payload elsewhere in the subject (e.g., at non-targeted areas in the subject).

For example, as described above, the support composition may include a first binding agent and a second binding agent different from the first binding agent. In these embodiments, the method may include administering a first functionalized payload to a subject, where the first functionalized payload includes a first complementary binding agent covalently linked to a first payload. After administration of the first functionalized payload to the subject, contact may occur between the first binding agent of the support composition and the first complementary binding agent of the first functionalized payload, such that the first binding agent and the first complementary binding agent selectively bind to one another upon contact to form a support complex, thus indirectly linking the first payload to the support composition and selectively delivering the first payload to the desired target location in the subject.

Similarly, the method may include administering a second functionalized payload to a subject, where the second functionalized payload includes a second complementary binding agent covalently linked to a second payload. After administration of the second functionalized payload to the subject, contact may occur between the second binding agent of the support composition and the second complementary binding agent of the second functionalized payload, such that the second binding agent and the second complementary binding agent selectively bind to one another upon contact to form a support complex, thus indirectly linking the second payload to the support composition and selectively delivering the second payload to the desired target location in the subject.

As described herein, the first binding agent and the second binding agent may be different bioorthogonal binding agents. As such, the method may include selectively delivering payloads to the desired target location in the subject. For example, the first payload may be different from the second payload. The first and second payloads may be selectively delivered to the target location at the same time or at different times.

In other embodiments, the payloads may be the same. In these embodiments, the method may include selectively delivering the payload to the desired target location in the subject at different times. For instance, the payload may be selectively delivered to the desired target location at an initial time point, and then additional payload may be selectively delivered to the desired target location at a subsequent time point. Combinations of the above selective delivery protocols are also possible.

In certain embodiments, different bioorthogonal binding agents used in the methods of the present disclosure have different in vivo half lives in the subject. For example, a binding agent (and its complementary binding agent) may have a relatively short in vivo half life in a subject, such as a half-life of 10 days or less, or 9 days or less, or 8 days or less, or 7 days or less, or 6 days or less, or 5 days or less, or 4 days or less, or 3 days or less, or 2 days or less, or 1 day or less, or 20 hours or less, or 16 hours or less, or 12 hours or less, or 8 hours or less, or 4 hours or less. In some instances, a binding agent having a shorter half life as described above includes binding agents such as a cyclooctene (e.g., trans-cyclooctene) or a tetrazine (e.g., 1,2,4,5-tetrazine). In other instances, a binding agent (and its complementary binding agent) may have a relatively long in vivo half life in a subject, such as a half-life of 7 days or more, such as 10 days or more, or 12 days or more, or 14 days or more, or 16 days or more, or 18 days or more, or 20 days or more, or 22 days or more, or 24 days or more, or 26 days or more, or 28 days or more, or 30 days or more, or even longer, such as 2 months or more, or 3 months or more, or 4 months or more, or 5 months or more, or 6 months or more. In some instances, a binding agent having a longer half life as described above includes binding agents such as an azide or an alkyne.

As described above, embodiments of the method include administering a first functionalized payload to a subject, such that the first functionalized payload binds to the support composition. In addition, in some embodiments, the method may include administering a second functionalized payload to a subject, such that the second functionalized payload binds to the support composition. In some cases, the first functionalized payload and the second functionalized payload may be administered to the subject at different times. For example, the first functionalized payload may be administered at a first time point, and the second functionalized payload may be administered at a later point in time, such as minutes, days or even weeks later. In some instances, the timing of the initial administration of the first payload and later administration of the second payload may depend on the particular dosing regimen desired for treatment or diagnosis of the disease or condition in the subject.

As described herein, a functionalized payload may include a complementary binding agent linked to a payload, where the linker is a releasable linker. As such, additional aspects of the methods of the present disclosure include releasing the payload from the support composition, thereby delivering the payload to the target location in the subject. Releasing the payload may include exposing the functionalized payload (e.g., contacting the releasable linker) to conditions sufficient to cause the releasable linker to be disrupted and thereby release the payload from the support composition. Contacting the releasable linker to releasing conditions may include exposing the releasable linker to light, heat, sound, a releasing agent (e.g., chemical releasing agent, solvent, etc.), combinations thereof, and the like. In some embodiments, as described above, the releasable linker may not require the application of an external stimulus or contact with releasing conditions to disrupt the attachment between the moieties. For example, a releasable linker may include one or more unstable bonds or functional groups (e.g., carbamate) in the linker that can be cleaved spontaneously without contact with an external stimulus or releasing conditions, thereby releasing the payload from the support composition.

As described above, the method may include administering a support composition to a desired target location in a subject. In some embodiments, the method also includes administering a second support composition to the subject (e.g., to reload the first support composition with additional binding agents). The second support composition may include a complementary binding agent that selectively binds to one of the binding agents on the first support composition. As such, administration of the second support composition may produce binding of the second support composition to the first support composition through a selective binding interaction between a binding agent of the first support composition and a complementary binding agent of the second support composition (e.g., through a binding interaction between complementary bioorthogonal functional groups). In addition, the second support composition may include one or more additional binding agents as described herein. Accordingly, binding of the second support composition to the first support composition may provide additional binding agents at the target location in the subject. The binding agents on the second support composition may then be bound to additional complementary binding agents, for example complementary binding agents linked to payloads or other support compositions.

An example of an administration protocol according to embodiments of the present disclosure is shown in FIG. 1. As shown in FIG. 1, step 1, a first support composition is administered to a subject, for example by injection at a desired target location in the subject or by systemic administration. The first support composition includes a first binding agent, A, and a different second binding agent, C, each attached (e.g., covalently linked) to the support composition. In FIG. 1, step 2, a first functionalized payload is administered to the subject. The first functionalized payload includes a first payload (payload 1) covalently linked to a first complementary binding agent, B, which selectively binds to the first binding agent, A, on the first support composition. In some instances, as shown in FIG. 1, step 3, if the linker between the first complementary binding agent, B, and the first payload (payload 1) is a releasable linker, the first payload (payload 1) may be released and delivered to the target location by disrupting the releasable linker. As shown in FIG. 1, step 4, the first support composition may be reloaded with a second support composition carrying additional binding agents, A. In FIG. 1, step 4, the second support composition may be administered to the subject. The second support composition includes a second complementary binding agent, D, that selectively binds to the second binding agent, C, on the first support composition. As shown in FIG. 1, step 5, a second functionalized payload may be administered to the subject, where the second functionalized payload includes a second payload (payload 2) covalently linked to a first complementary binding agent, B, which selectively binds to the additional binding agents, A, on the second support composition, thus delivering the second payload (payload 2) to the target location in the subject.

Figure 2:
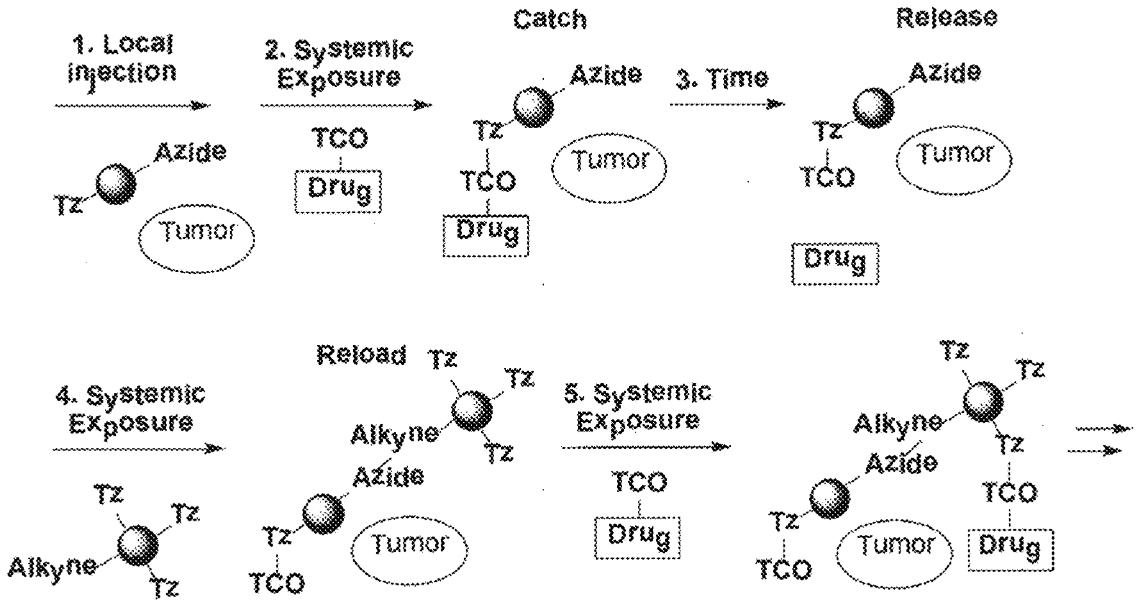
FIG. 2 shows a schematic of an administration protocol for targeted drug delivery to a local tumor site using support compositions and functionalized payloads, according to embodiments of the present disclosure.

Another example of an administration protocol according to embodiments of the present disclosure is shown in FIG. 2, which depicts an administration protocol for targeted drug delivery to a local tumor site. As shown in FIG. 2, step 1, a first support composition is administered to a subject, for example by local injection to the subject at the site of a tumor. The first support composition includes two different bioorthogonal binding agents, 1,2,4,5-tetrazine (Tz) and an azide, each attached (e.g., covalently bound) to the support composition. In FIG. 2, step 2, a first functionalized payload is administered to the subject, such as by systemic exposure. The first functionalized payload includes a first payload (drug) linked (e.g., covalently linked) to a first complementary binding agent, trans-cyclooctene (TCO), which selectively binds to the Tz bioorthogonal binding agent on the first support composition, thus localizing the first functionalized payload (including the first payload) at the site of the tumor in the subject. As shown in FIG. 2, step 3, the linker between the first complementary binding agent, TCO, and the first payload (drug) may be a releasable linker, and as such after a desired period of time the first payload (drug) may be released and delivered to the target location by disrupting the releasable linker. As shown in FIG. 2, step 4, a second support composition may be administered to the subject, such as by systemic exposure. The second support composition may include an alkyne bioorthogonal binding agent that selectively binds to the azide bioorthogonal binding agent of the first support composition, thus reloading the first support composition with a second support composition. The second support composition also includes additional tetrazine (Tz) bioorthogonal binding agents. As shown in FIG. 2, step 5, a second functionalized payload may be administered to the subject, where the second functionalized payload includes a second payload (drug) covalently linked to a trans-cyclooctene bioorthogonal binding agent, which selectively binds to the additional Tz binding agents on the second support composition, thus delivering the second payload (drug) to the site of the tumor in the subject. The first and second payloads may be the same drug or different drugs.

Figure 3:
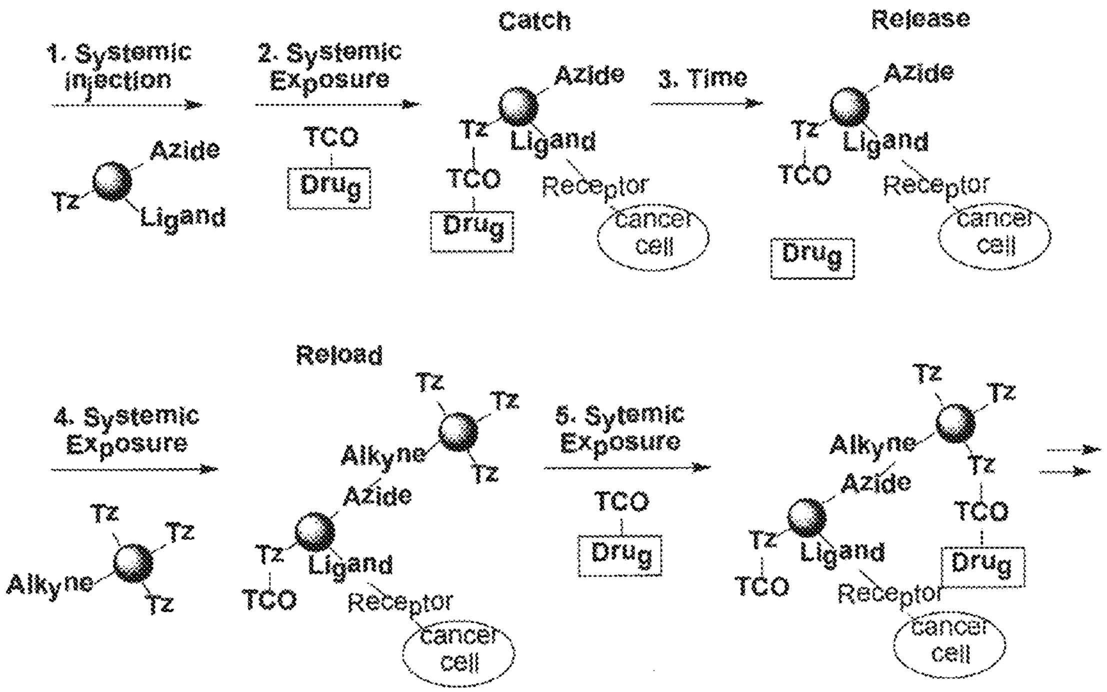
FIG. 3 shows a schematic of an administration protocol for targeted drug delivery to metastic cancer cells using support compositions and functionalized payloads, according to embodiments of the present disclosure.

Another example of an administration protocol according to embodiments of the present disclosure is shown in FIG. 3, which depicts an administration protocol for targeted drug delivery to metastic cancer cells. As shown in FIG. 3, step 1, a first support composition is administered to a subject, for example by systemic injection to the subject. The first support composition may be a particle, such as a nanoparticle or a microparticle, which optionally includes targeting agent (e.g., a ligand or antibody) attached (e.g., covalently bound) to the particle that specifically binds to a desired target receptor or cell surface target (e.g., antigen) on a target cell, such as a cancer cell, thus capturing the first support composition on a cell surface (e.g., cancer cell surface) in the subject.

The first support composition also includes two different bioorthogonal binding agents, 1,2,4,5-tetrazine (Tz) and an azide, each attached (e.g., covalently linked) to the support composition. In FIG. 3, step 2, a first functionalized payload may be administered to the subject, such as by systemic exposure. The first functionalized payload includes a first payload (drug) covalently linked to a first complementary binding agent, trans-cyclooctene (TCO), which selectively binds to the first binding agent, Tz, on the first support composition, thus indirectly attaching the first functionalized payload (including the first payload) to the cancer cells in the subject. As shown in FIG. 3, step 3, the linker between the first complementary binding agent, TCO, and the first payload (drug) may be a releasable linker, and as such after a desired amount of time, the first payload (drug) may be released and delivered to the target cells (e.g., target cancer cells) by disrupting the releasable linker. As shown in FIG. 3, step 4, a second support composition may be administered to the subject, such as by systemic exposure. The second support composition may include an alkyne bioorthogonal binding agent that selectively binds to the azide bioorthogonal binding agent of the first support composition, thus reloading the first support composition with a second support composition. The second support composition also includes additional tetrazine (Tz) bioorthogonal binding agents. As shown in FIG. 3, step 5, a second functionalized payload may be administered to the subject, where the second functionalized payload includes a second payload (drug) covalently linked to a trans-cyclooctene bioorthogonal binding agent, which selectively binds to the additional Tz binding agents on the second support composition, thus delivering the second payload (drug) to the target cells in the subject. The first and second payloads may be the same drug or different drugs.

Indications for this approach, include cancer, both hematological and solid cancers, infections, wound healing, revascularization, myocardial infarction, arrhythmias, vascular occlusion (thrombi, through anticoagulants), inflammation through anti-proliferative drugs, corticosteroids and derivatives, and/or NSAIDS, autoimmune disorders, transplants, macular degeneration, rheumatoid arthritis, osteoarthritis, peri-prosthetic infections, through coating of implants, paste, wax, polymethylmethacrylate (PMMA) constructs, and others. In certain embodiments, the approach can be used for the treatment and/or diagnosis of soft tissue sarcomas: rhabdomyosarcoma, fibrosarcoma, Ewing's sarcoma, and all the different subtypes of soft tissue sarcoma as well as osteosarcoma. The compositions can be for the treatment and/or diagnosis of pigmented vilonodular synovitis.

5. Formulations

The compositions of the present disclosure can be formulated in a variety of different ways. In general, compositions that include one or more binding agents or complementary binding agents are formulated in a manner compatible with the binding agents and complementary binding agents, the condition to be treated, and the route of administration to be used. In addition, where the composition includes a payload, the composition is formulated in a manner compatible with the payload, the condition to be treated, and the route of administration to be used.

The composition (e.g., support composition and/or functionalized payload) can be provided in any suitable form, e.g., in the form of a pharmaceutically acceptable formulation, and can be formulated for any suitable route of administration, e.g., oral, topical or parenteral administration. Where the composition is provided as a liquid injectable (such as in those embodiments where they are administered intravenously or directly into a tissue), the composition can be provided as a ready-to-use dosage form, or as a reconstitutable storage-stable powder or liquid that may include pharmaceutically acceptable carriers and excipients.

Methods for formulating compositions can be adapted from those readily available. For example, compositions can be provided in a pharmaceutical formulation that includes a therapeutically effective amount of a composition and a pharmaceutically acceptable carrier (e.g., saline). The pharmaceutical formulation may optionally include other additives (e.g., buffers, stabilizers, preservatives, and the like). In some embodiments, the formulations are suitable for administration to a mammal, such as those that are suitable for administration to a human.

The compositions of the present disclosure can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the subject. The compositions of the present disclosure can also be administered by injection, that is, intravenously, intramuscularly, intracutaneously, subcutaneously, intraduodenally, or intraperitoneally. In some instances, the compositions described herein can be administered by inhalation, for example, intranasally. In some instances, the compositions of the present disclosure can be administered transdermally. In some instances, the compositions can be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present disclosure also provides pharmaceutical formulations including a composition as described herein and a pharmaceutically acceptable carrier or excipient.

For preparing pharmaceutical formulations from the compositions of the present disclosure, pharmaceutically acceptable carriers can be solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are found, for example in Remington's Pharmaceutical Sciences, Maack Publishing Co, Easton PA ("Remington's").

6. Methods of Treatment

The compositions of the present disclosure find use in treatment and/or diagnosis of a condition or disease in a subject that is amenable to treatment or diagnosis by administration of the payload (e.g., the parent drug (i.e., the drug prior to conjugation to the composition)). By "treatment" is meant that at least an amelioration of the symptoms associated with the condition afflicting the subject is achieved, where amelioration is used in a broad sense to refer to at least a reduction in the magnitude of a parameter, e.g., symptom, associated with the condition being treated. As such, treatment also includes situations where the pathological condition, or at least symptoms associated therewith, are completely inhibited, e.g., prevented from happening, or stopped, e.g., terminated, such that the subject no longer suffers from the condition, or at least the symptoms that characterize the condition. Thus, treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms. For example, in the context of cancer, the term "treating" includes any or all of: reducing growth of a solid tumor, inhibiting replication of cancer cells, reducing overall tumor burden, prolonged survival and ameliorating one or more symptoms associated with a cancer.

The subject to be treated can be one that is in need of therapy, where the subject to be treated is one amenable to treatment using the parent drug. Accordingly, a variety of subjects may be amenable to treatment using the compositions disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of composition administered to a subject can be initially determined based on guidance of a dose and/or dosage regimen of the parent drug. In general, the compositions can provide for targeted delivery and/or enhanced serum half-life of the bound drug, thus providing for at least one of reduced dose or reduced administrations in a dosage regimen. Thus, the compositions can provide for reduced dose and/or reduced administration in a dosage regimen relative to the parent drug prior to being conjugated in a composition of the present disclosure.

The compositions of the present disclosure can be delivered by any suitable means, including oral, parenteral and topical methods. For example, transdermal administration methods, by a topical route, can be formulated as applicator sticks, solutions, suspensions, emulsions, gels, creams, ointments, pastes, jellies, paints, powders, and aerosols.

The pharmaceutical formulation may be provided in unit dosage form. In such form the pharmaceutical formulation may be subdivided into unit doses containing appropriate quantities of the compositions of the present disclosure. The unit dosage form can be a packaged preparation, the package containing discrete quantities of the preparation, such as packeted tablets, capsules, and powders in pouches, vials or ampoules. Also, the unit dosage form can be a capsule, tablet, dragee, cachet, or lozenge, or it can be the appropriate number of any of these in packaged form.

Compositions of the present disclosure can be present in any suitable amount, and can depend on various factors including, but not limited to, weight and age of the subject, state of the disease, etc. Suitable dosage ranges for the composition of the present disclosure include from 0.1 mg to 10,000 mg, or 1 mg to 1000 mg, or 10 mg to 750 mg, or 25 mg to 500 mg, or 50 mg to 250 mg. For instance, suitable dosages for the composition of the present disclosure include 1 mg, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg or 1000 mg.

In some embodiments, multiple doses of a composition are administered. The frequency of administration of a composition can vary depending on any of a variety of factors, e.g., severity of the symptoms, condition of the subject, etc. For example, in some embodiments, a composition is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The compositions of the present disclosure can be administered at any suitable frequency, interval and duration. For example, the composition of the present disclosure can be administered once an hour, or two, three or more times an hour, once a day, or two, three, or more times per day, or once every 2 days, 3 days, 4 days, 5 days, 6 days, or 7 days, so as to provide the desired dosage level to the subject. When the composition of the present disclosure is administered more than once a day, representative intervals include 5 min, 10 min, 15 min, 20 min, 30 min, 45 min and 60 minutes, as well as 1 hr, 2 hr, 4 hr, 6 hr, 8 hr, 10 hr, 12 hr, 16 hr, 20 hr, and 24 hours. The composition of the present disclosure can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The compositions of the present disclosure can be co-administered with another active agent. Co-administration includes administering the composition of the present disclosure and active agent within 0.5 hr, 1 hr, 2 hr, 4 hr, 6 hr, 8 hr, 10 hr, 12 hr, 16 hr, 20 hr, or 24 hours of each other. Co-administration also includes administering the composition of the present disclosure and active agent simultaneously or approximately simultaneously (e.g., within about 1 min, 5 min, 10 min, 15 min, 20 min, or 30 minutes of each other), or sequentially in any order. In addition, the composition of the present disclosure and the active agent can each be administered once a day, or two, three, or more times per day so as to provide the desired dosage level per day.

In some embodiments, co-administration can be accomplished by co-formulation, e.g., preparing a single pharmaceutical formulation including both the composition of the present disclosure and the active agent. In other embodiments, the composition of the present disclosure and the active agent can be formulated separately and co-administered to the subject.

The composition of the present disclosure and the active agent can be present in a formulation in any suitable weight ratio, such as from 1:100 to 100:1 (w/w), or 1:50 to 50:1, or 1:25 to 25:1, or 1:10 to 10:1, or 1:5 to 5:1 (w/w). The composition of the present disclosure and the other active agent can be present in any suitable weight ratio, such as 1:100 (w/w), 1:75, 1:50, 1:25, 1:10, 1:5, 1:4, 1:3, 1:2, 1:1, 2:1, 3:1, 4:1, 5:1, 10:1, 25:1, 50:1, 75:1, or 100:1 (w/w). Other dosages and dosage ratios of the composition of the present disclosure and the active agent are suitable in the formulations and methods described herein.

The functionalized payloads, therapeutics support compositions, and methods can be used for the treatment, prevention, and/or diagnosis of any targeted disease. Indications for this approach, include cancer, both hematological and solid cancers, infections, wound healing, re-vascularization, myocardial infarction, arrhythmias, vascular occlusion (thrombi, through anticoagulants), inflammation through anti-proliferative drugs, corticosteroids and derivatives, and/or NSAIDS, autoimmune disorders, transplants, macular degeneration, rheumatoid arthritis, osteoarthritis, peri-prosthetic infections, through coating of implants, paste, wax, polymethylmethacrylate (PMMA) constructs, and others. In certain embodiments, the functionalized payloads, therapeutics support compositions, and methods can be used for the treatment, prevention, and/or diagnosis of soft tissue sarcomas: rhabdomyosarcoma, fibrosarcoma, Ewing's sarcoma, and all the different subtypes of soft tissue sarcoma as well as osteosarcoma. The compositions can be for the treatment and/or diagnosis of pigmented vilonodular synovitis.

In certain embodiments, the functionalized payloads, therapeutics support compositions, and methods can be used for the treatment, prevention, and/or diagnosis of solid tumors, including but not limited to, melanoma (e.g., unresectable, metastatic melanoma), renal cancer (e.g., renal cell carcinoma), prostate cancer (e.g., metastatic castration resistant prostate cancer), ovarian cancer (e.g., epithelial ovarian cancer, such as metastatic epithelial ovarian cancer), breast cancer (e.g., triple negative breast cancer), glioblastoma, and lung cancer (e.g., non-small cell lung cancer), soft tissue sarcoma, fibrosarcoma, osteosarcoma, pancreatic cancer, among others. The disclosed approach lends itself well as an adjuvant/neoadjuvant system. For example, particles as disclosed herein could be placed during the biopsy, once the results from the study come back, the practitioner could deliver the appropriate cocktail to the desired site in the body. This would minimize the size of the tumor particularly in the context of a surgically resectable tumor. Then at the end of the surgery, the surgeon could place more particles around the surgical cavity and treat the patient with further doses of treatment (e.g. chemotherapy through the disclosed approach) to minimize the risk of any cancer cells that may have been missed in the surgical margins.

In certain embodiments, the disclosed methods provide the ability to place particles as disclosed herein at the time of the biopsy. When the results return, the practitioner can deliver through to the biopsy site chemokines (agents that attract cancerous cells and/or immune cells) and adjuvants to enhance the immune system with fewer side effects as well as the chemotherapeutics agents combined with immunotherapy agents. This combination approach would be beneficial to patients. The chemotherapy agent would treat the solid tumor or specific location, while the enhanced response of the immunotherapy would help with distant metastatic sites. For example, in certain embodiments, the disclosed compositions and methods could employ or be used with anthracyclines, taxanes, gemcitabine and other agents to enhance the efficacy of ipilimunab, nivolumab, pembrolizumab, avelumab (also known as MSB0010718C; Pfizer) and other checkpoint inhibitors.

7. Kits

Aspects of the present disclosure include kits that have a composition as described herein. For example, a kit may include a support composition as described herein. Embodiments of the kit may also include a functionalized payload as described herein. In certain embodiments, the kit may include a composition (e.g., support composition and/or functionalized payload) and a packaging configured to contain the composition (e.g., support composition and/or functionalized payload). The support composition and the functionalized payload may be in separate containers in the packaging. One or more support compositions may be provided in a kit. Similarly, one or more functionalized payloads may be provided in a kit. The packaging may be a sealed packaging, such as a sterile sealed packaging. By "sterile" is meant that there are substantially no microbes (such as fungi, bacteria, viruses, spore forms, etc.). In some instances, the packaging may be configured to be sealed, e.g., a water vapor-resistant packaging, optionally under an air-tight and/or vacuum seal.

In certain embodiments, the kit includes a reagent that may be used as the releasing agent for a releasable linker as described herein. The releasing reagent may be any one of the releasing agents described herein, such as, but not limited to, a chemical releasing agent (e.g., an acid, a base, an oxidizing agent, a reducing agent, etc.), a solvent, and the like. The releasing reagent in the kit may be provided in any convenient form, such as, but not limited to, a gas, a solution, a solid, granules, a powder, a suspension, and the like. The releasing reagent may be packaged in a separate container from the composition(s) in the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another form for the instructions would be a computer readable medium, e.g., CD, DVD, Blu-Ray, computer-readable memory (e.g., flash memory), etc., on which the information has been recorded or stored. Yet another form for the instructions that may be present is a website address which may be used via the Internet to access the information at a removed site. Any convenient means may be present in the kits.

8. Examples

The present disclosure has multiple aspects, illustrated by the following non-limiting examples. The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

Example 1

Efficacy in Athymic Mice Carrying MCF7 Subcutaneous Breast Cancer Xenografts

Animal Husbandry

Animals were housed in a temperature-controlled room with a 12-hour light/dark cycle, with ad libitum access to filtered water and irradiated food.

Study Design

MCF7 cells were grown in culture and implanted into the flank of approximately 20 female athymic NCR: nu/nu mice in an equal volume of matrigel. Once the tumors reached an average tumor volume of 100 $mm^3$+/−20 $mm^3$ by caliper measurement, 15 animals were selected and randomized into three groups of five animals each. Following randomization, animals were administered appropriate treatment regimen as per study design described in table below. Tumor growth was recorded two times per week and extended one to two weeks after dosing completion. Animals were humanely euthanized, blood and tumors harvested after completion of study (two weeks after dosing was complete).

TABLE

| Study design | | | | |
|---|---|---|---|---|
| Gp # | Cell line | # mice | Treatment & dose every 3 days × 3 (IV) | Tumor & body weight measurements |
| 1 | MCF7 | 5 | Vehicle | 2x/week |
| 2 | MCF7 | 5 | TCO-Doxorubicin | 2x/week |
| 3 | MCF7 | 5 | Doxorubicin | 2x/week |

Procedure

Female, athymic, NCR: nu/nu mice approximately 5-7 weeks of age were obtained and allowed to acclimatize to the animal facility for 3 to 5 days. Prior to the start of the study, the mice were ear tagged and the body weight of each mouse was recorded. Three days prior to MCF7 implantation, estradiol pellets were implanted on the shoulder area of each mouse. The MCF7 cell line was expanded in tissue culture media+10% FBS supplemented with Pen-Strep and incubated in a 37° C. incubator with 5% $CO_2$ using standard tissue culture techniques. On the day of injection, MCF7 cells were trypsinized, washed in HBSS+1% FBS, followed by 2 subsequent washes in HBSS without serum. The cells were counted and suspended HBSS. Approximately $5\times10^6$ MCF7 cells in 0.050 ml volume were mixed with an equivalent volume of Matrigel (BD Biosciences) and injected subcutaneously into flank region of each mouse. Following MCF7 cell implantation, tumor growth was monitored two times weekly once the tumors became palpable. Tumor growth was measured using a digital caliper and palpable tumor mass was calculated using the following formula:

$$\text{Palpable tumor mass}(mm^3)=d^2\times D/2$$

where d and D are the shortest and longest diameter in mm, respectively, of the tumor All animals were observed daily for general activity levels and clinical symptoms of morbidity and ambulatory discomfort. Body weights were measured and recorded two times per week (along with tumor measurement) throughout study duration. Once the tumors reach an average volume of 100 $mm^3$+/−20 $mm^3$, 15 animals were selected and distributed into three groups of five animals each, so that each group had a similar average tumor volume. Following randomization, animals were treated as per the following:

Group 1: Saline (Q3 day, 3 doses, intravenous route)

Group 2: TCO-doxorubicin (5 mg/kg×Q3 day×3 doses, intravenous route)

Group 3: doxorubicin (5 mg/kg×Q3 day×3 doses, intravenous route)

Note: hydrogel was inoculated at tumor site before starting systemic therapy

Hydrogel

The hydrogel was modified to include tetrazine bioorthogonal functional groups.

Hydrogel injection sets were stored at 4° C. without light. Prior to administration, tumor volume was measured.

An hour prior to either doxorubicin, or TCO-doxorubicin treatment; hydrogel was thoroughly mixed by following procedure.

1. Syringe filled with hydrogel was detached from the 3-way stopcock.
2. Hydrogel was pushed into the empty space of syringe edge to minimize air bubbles.
3. The syringe was reconnected back to the 3-way stopcock and the dial turned so that 2 syringes ports were open.
4. The hydrogel was forced back and forth through the 3-way stopcock to the other syringe for 30 times to mix the two materials.
5. The hydrogel was pushed into the syringe formerly containing the white aqueous material.
6. The syringe formally contained hydrogel was detached from the 3-way stopcock and all the material was aspirated into the other syringe.
7. The volume of hydrogel was filled into the 23-gage needle and recap.

The syringe with needle with a cap was weighed and tared. 100 μL of hydrogel was injected subcutaneously adjacent to the tumor. The needle was recapped and the syringe weighed after the injection to determine the weight of hydrogel injected. The remaining hydrogel was stored at 4° C. without light for a possible reapplication.

Doxorubicin and TCO-Doxorubicin

The TCO-Doxorubicin was doxorubicin modified with a trans-cyclooctene bioorthogonal functional group.

Doxorubicin and the TCO-Doxorubicin were stored at −80° C. On the day of use, the powder form of doxorubicin and TCO-Doxorubicin were reconstituted at a concentration of 2 mg/mL in sterile water. These solutions were further diluted with 0.9% saline solution according to the required dosage calculation. The doxorubicin and the test compound were administered at 5 mg/kg in 100 μL volume via tail vein.

Animals were observed for an additional one or two weeks after dosing and tumor measurements and body weights were recorded. On study termination, animals were euthanized humanely. Tumors were dissected, measured and weighed. Half of the tumor was frozen and stored at −80° C., the other half was fixed in 10% NBF.

Figure 4:
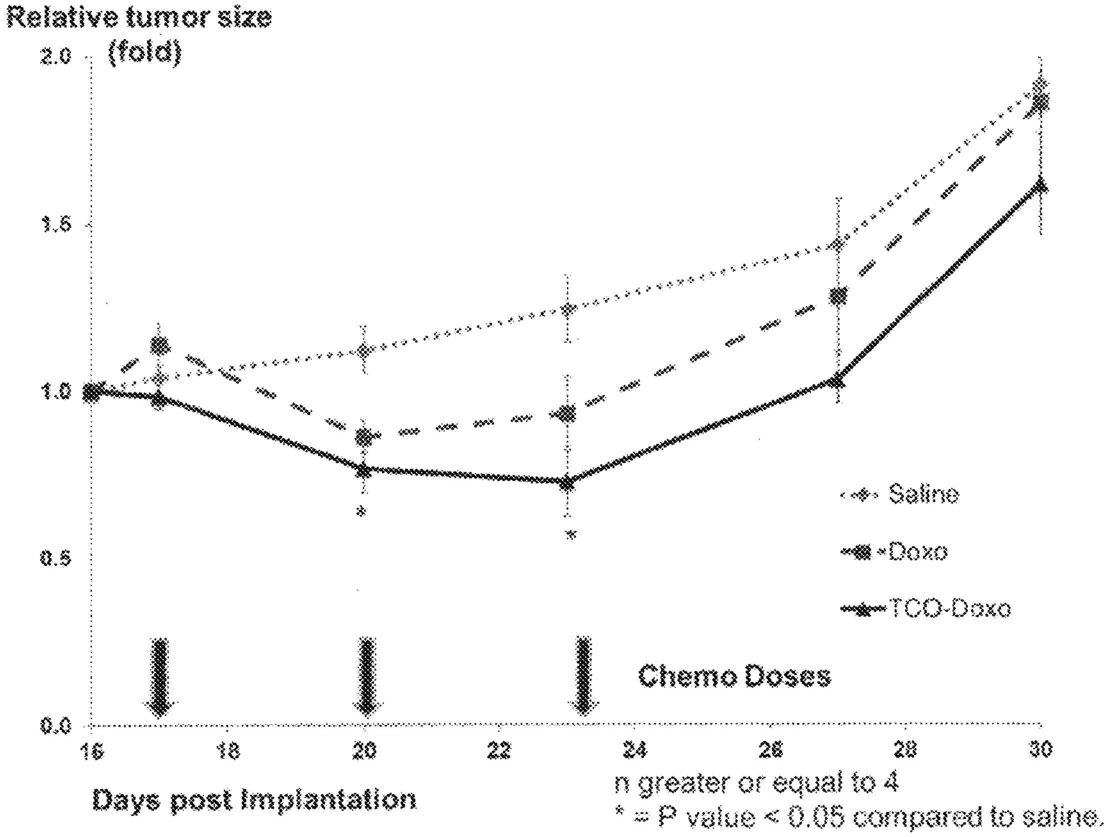
FIG. 4 shows a graph of the relative tumor size change (relative to day of randomization; day before first chemo treatment) for the experiments performed in Example 1, according to embodiments of the present disclosure.

A graph of the relative tumor size change (relative to day of randomization; day before first chemo treatment) is shown in FIG. 4.

Figure 5:
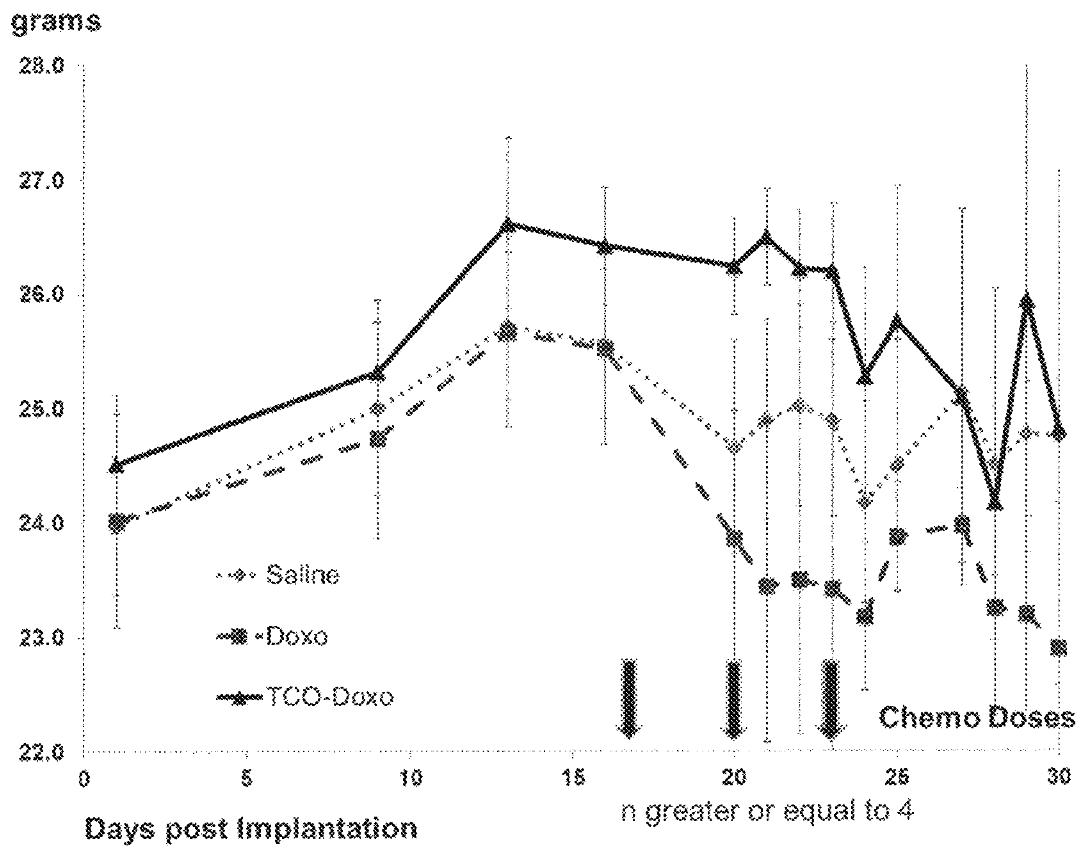
FIG. 5 shows a graph of a body weight analysis, where the average body weight per treatment group is plotted vs. days post-implantation.
Figure 6:
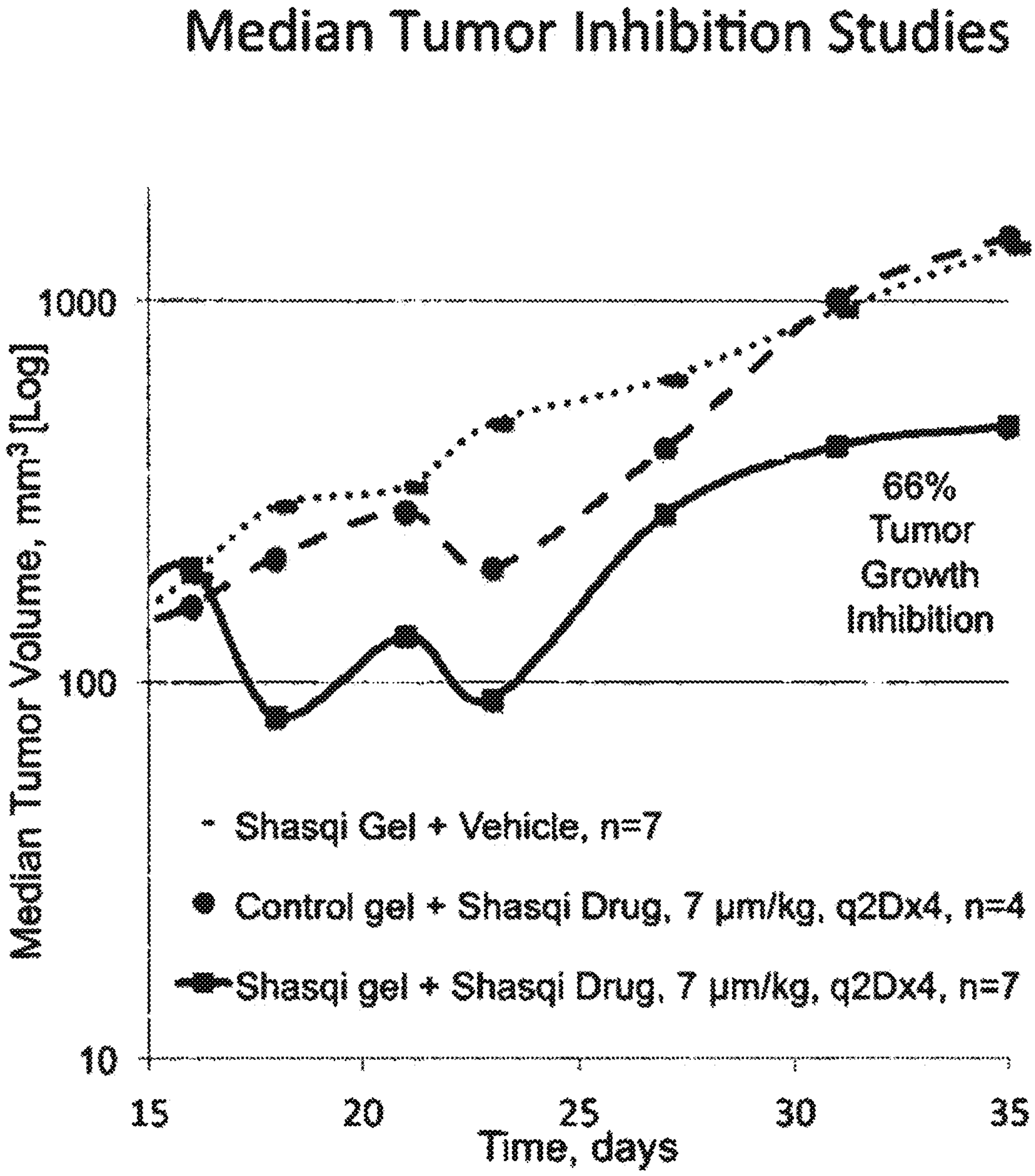
FIG. 6 and FIG. 7 show result from multiple studies with TCO-doxorubicin and a saracoma xenograft mouse model (HT1080). The figures demonstrate the the disclosed compositions and methods can shrink tumors. Dosing started at day 16 and stopped at day 22. Three groups of mice with a subcutaneous xenograft of HT1080 were treated as described herein and their median tumor volumes ($mm^3$) were measured over time. The disclosed support composition combined with a functionalized payload demonstrated a 66% inhibition of median tumor volume, demonstrating the efficacy of the disclosed systems.
Figure 7:
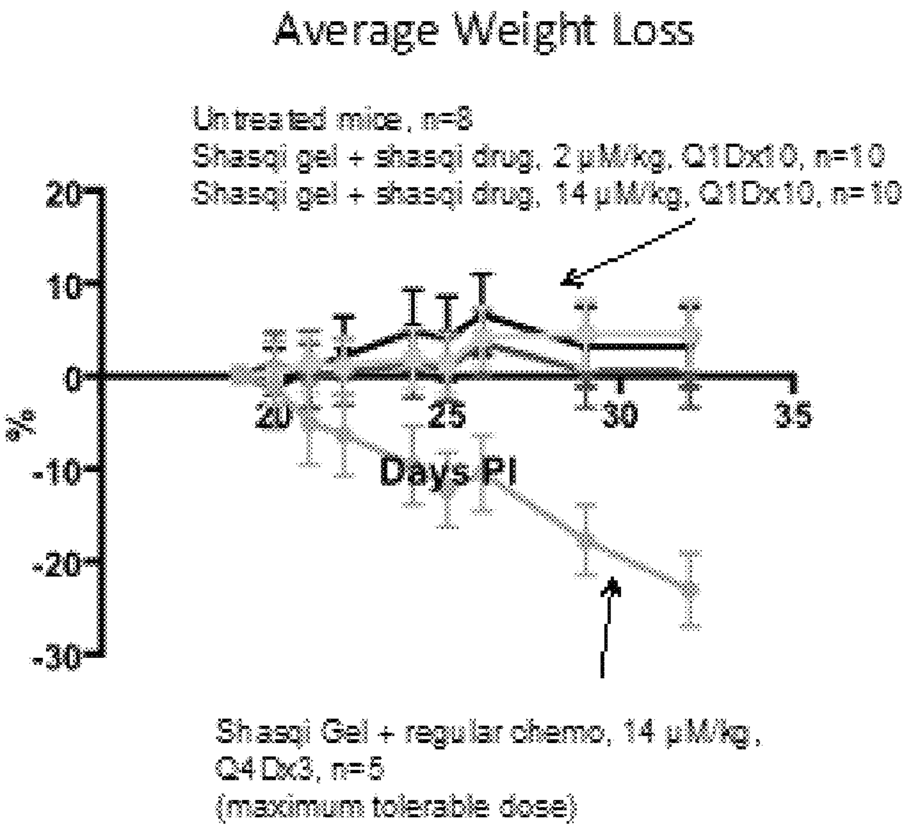
Figure 8:
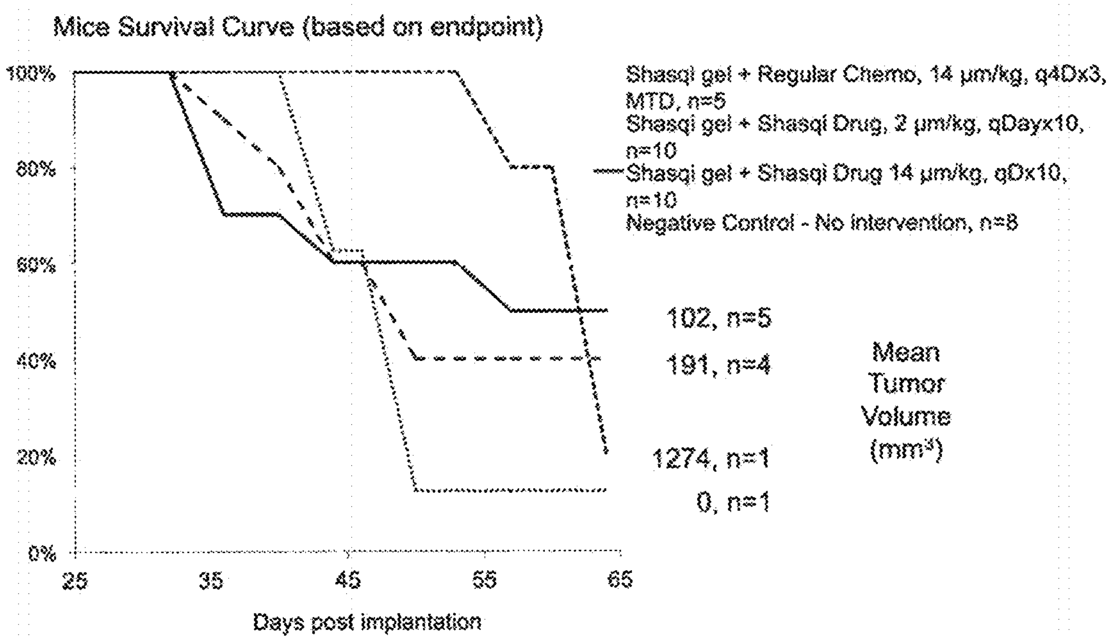
FIG. 8 shows a mice survival curve based on reaching endpoints for 3 different treatment groups using TCO-doxorubicin and Tz-gel.

FIG. 5 shows a graph of a body weight analysis, where the average body weight per treatment group is plotted vs. days post-implantation.

Example 2

Treatment of Soft Tissue Sarcomas (STS)

The efficacy of many cytotoxic agents for the treatment of soft tissue sarcoma (STS) is limited by their poor delivery and systemic side effects. Soft tissue sarcomas have remarkable heterogeneity, thus an approach focused on factors exogenous to the body or the tumor would be ideal for local control. A system was evaluated that combines the spatial control of a locally placed biomaterial with the flexibility of systemic pro-drugs. In-vivo chemistry was used to develop an injectable hydrogel (HMT) capable of concentrating and activating doxorubicin pro-drug doses. This approach was tested for the treatment of soft tissue sarcoma in a mouse xenograft model. After implanting the HTM near the tumor site, mice were treated for 10 days with daily doses of a doxorubicin pro-drug leading to significantly greater tumor growth inhibition without bone marrow suppression or cachexia in contrast to the standard of clinical care, maximum tolerable dose of doxorubicin. This strategy should be considered as a neoadjuvant approach to minimize the tumor burden before surgery and optimize clean surgical margins after resection. The low systemic toxicity observed also makes this approach appealing as an adjuvant therapy for frail patients who failed first line treatments, have unresectable tumors or palliative needs secondary to soft tissue sarcoma.

Materials and Methods

Chemical and Material Synthesis. See SI Materials and Methods for detailed protocols on chemical precursors and HMT synthesis.

Doxorubicin was purchased from LC Laboratories (Woburn, MA), cat. #D-4000. All other chemicals were purchased from Krackeler Scientific and used without further purification. Chromatographic purifications were conducted using SiliaSphere™ spherical silica gel 5 μm, 60 Å silica gel (Silicycle). Thin layer chromatography (TLC) was performed on SiliaPlate™ silica gel TLC plates (250 μm thickness) purchased from Silicycle. Preparative TLC was performed on SiliaPlate™ silica gel TLC plates (1000 μm thickness). Analytical HPLC was performed using Phenomenex Kinetex 2.6u XB-C18 100 A analytical column (50×2.1 mm). COSTAR® Spin-X spin columns (0.22 μm Cellulose Acetate), purchased from Fisher Scientific (cat #07-200-385), were used for kinetic experiment. 1H and 13C NMR spectroscopy was performed on a Bruker NMR at 400 ($^1$H), 100 ($^{13}$C) MHz. All 13C NMR spectra were proton decoupled. Fluorescence microscopy experiments were carried out using Zeiss LSM 710 Pascal laser confocal microscope (Carl Zeiss Microscopy, Thornwood, NY, USA). Image acquisition and analyses were performed using Zeiss ZEN 2012 Confocal Microscopy Software (Release 2.02). The MTT reagent was purchased from Sigma-Aldrich, cat. #M5655.

Cell culture. HT1080 cells were purchased from ATCC (cat. #CCL-121), and propagated in Dulbecco's modified Eagle's medium (DMEM; Meditech, Inc. Corning, Manassas, VA) containing 5% fetal bovine serum (FBS; HyClone, Logan Utah), supplemented with 100 U/ml penicillin, and 100 μg/ml streptomycin (Life Tech Corp., Grand Island, NY) at 37° C. in a 5% $CO_2$ incubator.

Synthesis of Alginate hydrogel modified with tetrazine. Each gram of UP MVG alginate was combined with 176 μmoles of (4-(6-Methyl-1,2,4,5-tetrazin-3-yl)phenyl) methanamine (Tz-Me-amine) under standard carbodiimide chemistry conditions as previously described in Royzen, M.; Mejia Oneto, J. M. PCT/US2015/020718, WO2015139025 A1, the contents of which is incorporated herein by reference in its entirety. The alginate product was purified by dialysis against deionized water containing decreasing salt concentrations for 4 days, frozen and lyophilized for 5-10 days until dry. A 2.5% alginate solution was obtained by adding dd$H_2O$. Covalent modification of alginate was confirmed through $^1$H-NMR and IR studies (see FIG. 25 and FIG. 26). The same protocol without the tetrazine addition was used for the construction of control alginate gels.

Figure 27:
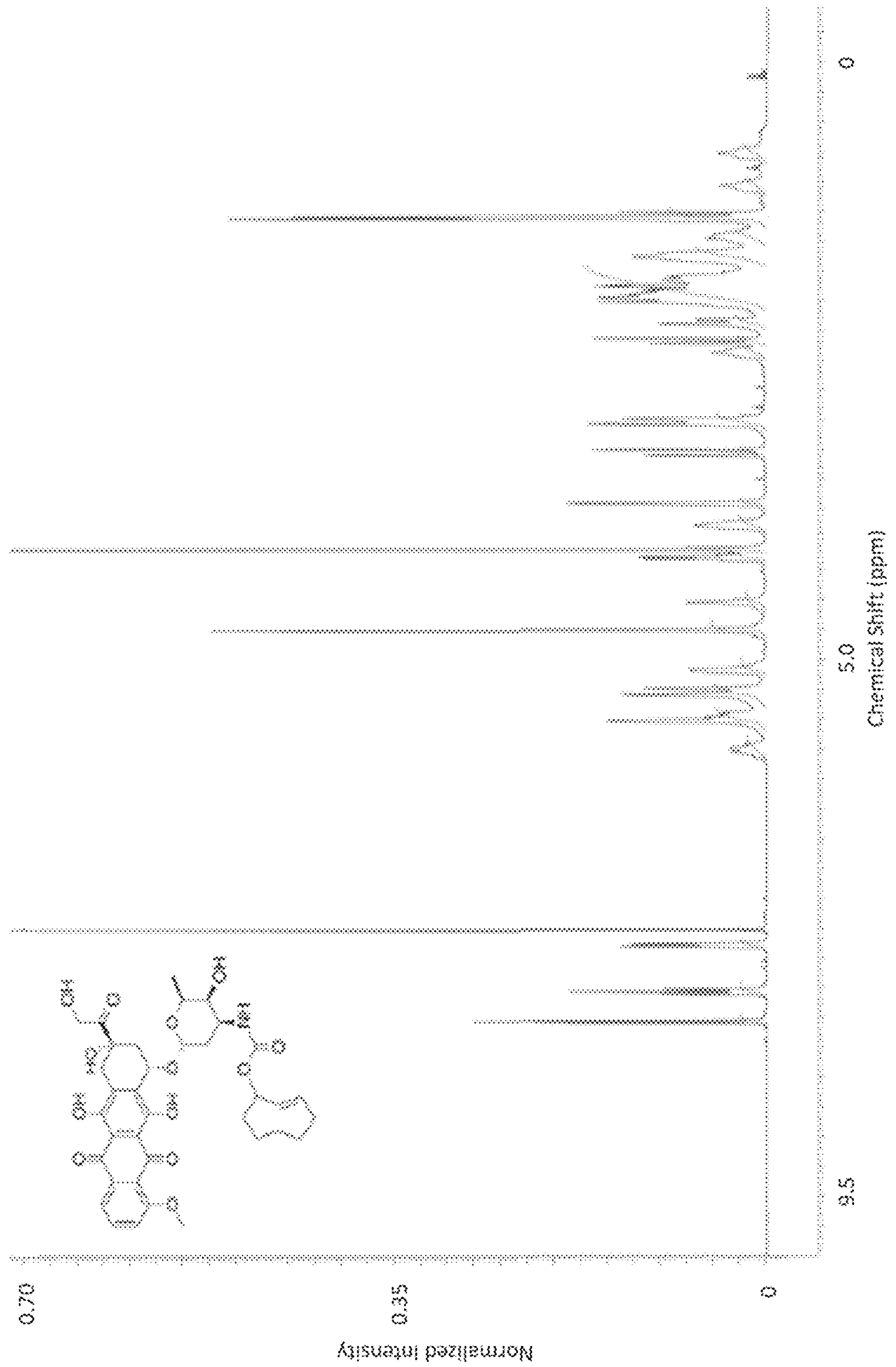
FIG. 27 shows a $^1$H NMR spectrum of the doxorubicin pro-drug.
Figure 28:
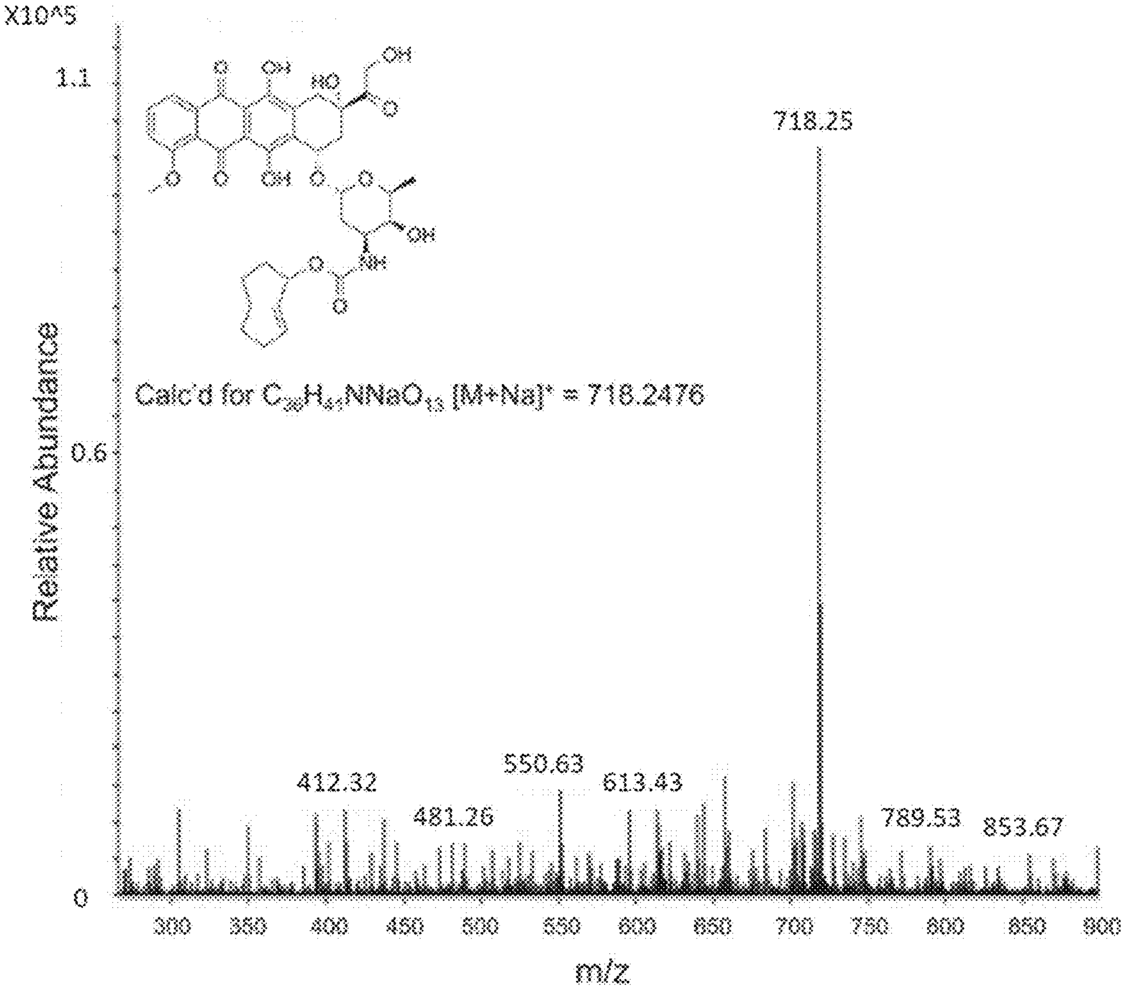
FIG. 28 shows high resolution ESI-MS spectrum of the doxorubicin pro-drug. The major observed peak corresponds to the expected value for the sodium adduct of the doxorubicin pro-drug.
Figure 29:
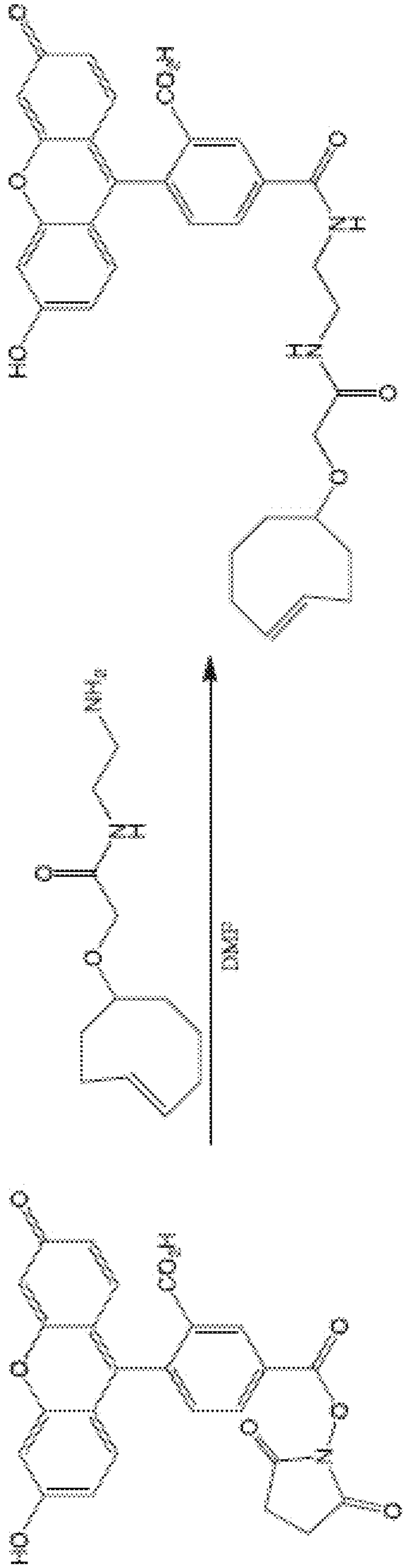
FIG. 29 shows the synthesis of TCO—NR—FI. Dissolved 2-((Z)-cyclooct-2-enyloxy)-N-(2-aminoethyl) acetamide (50.0 mg, 0.221 mmol) and fluorescein-NHS ester (105 mg, 0.221 mmol) in DMF (5 mL). Added triethylamine (60 μL, 0.442 mmol) and stirred at rt for 18 h. Evaporated the solvent under high vacuum and redissolved the reaction mixture in methanol. Purified by preparatory thin layer chromatography using 1:9 MeOH: CH2Cl2 mixture as mobile phase. Yield=51 mg (39.5%).
Figure 30:
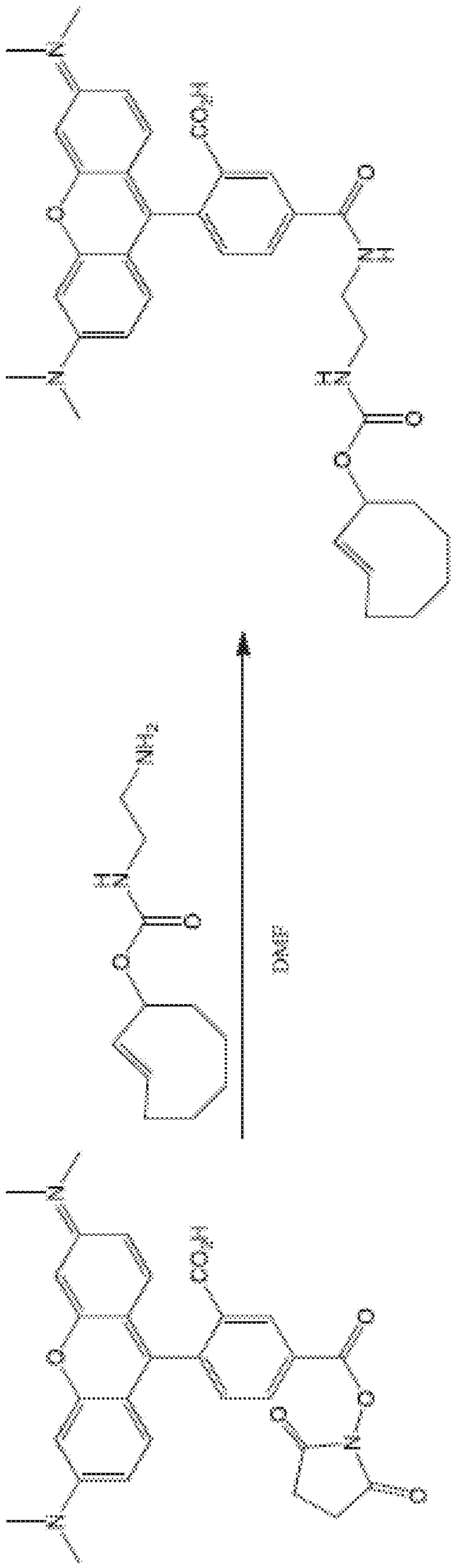
FIG. 30 shows the synthesis of TCO—R—Rh. Dissolved rhodamine-NHS ester (50 mg, 0.095 mmol) and (E)-cyclooct-2-enyl-2-aminoethylcarbamate (40.0 mg, 0.190 mmol) in CH2C12 (5 mL). Added triethylamine (129 μL, 0.95 mmol) and stirred at rt for 18 h. Evaporated the solvent under high vacuum and redissolved the reaction mixture in methanol. Purified by preparatory thin layer chromatography using 7.5:2.5:90 MeOH: Et3N: CH2C12 mixture as mobile phase. Yield=28 mg (47%).
Figure 31A:
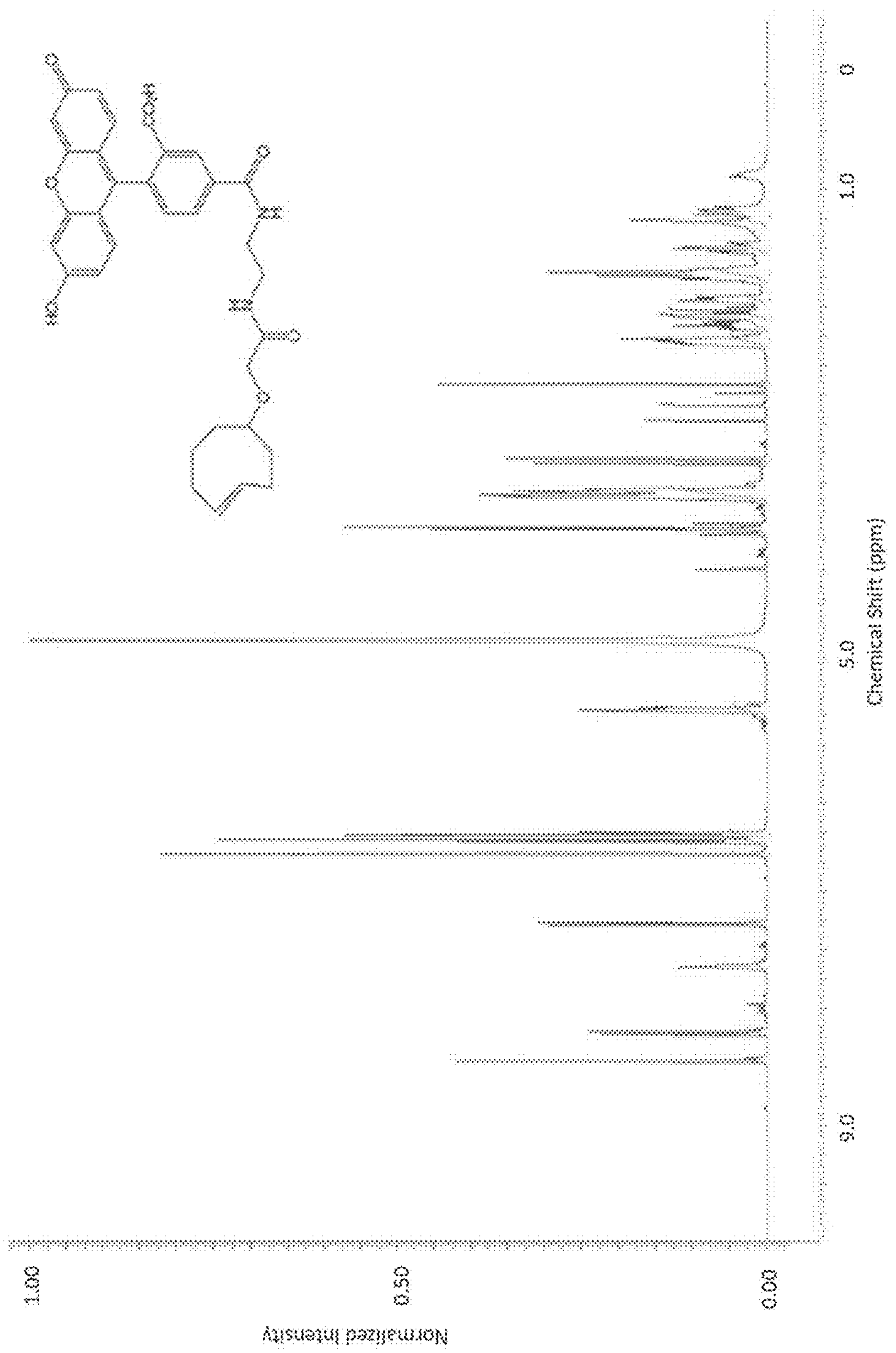
FIG. 31A and FIG. 31B show NMR spectra of TCO—NR-FI.
Figure 31B:
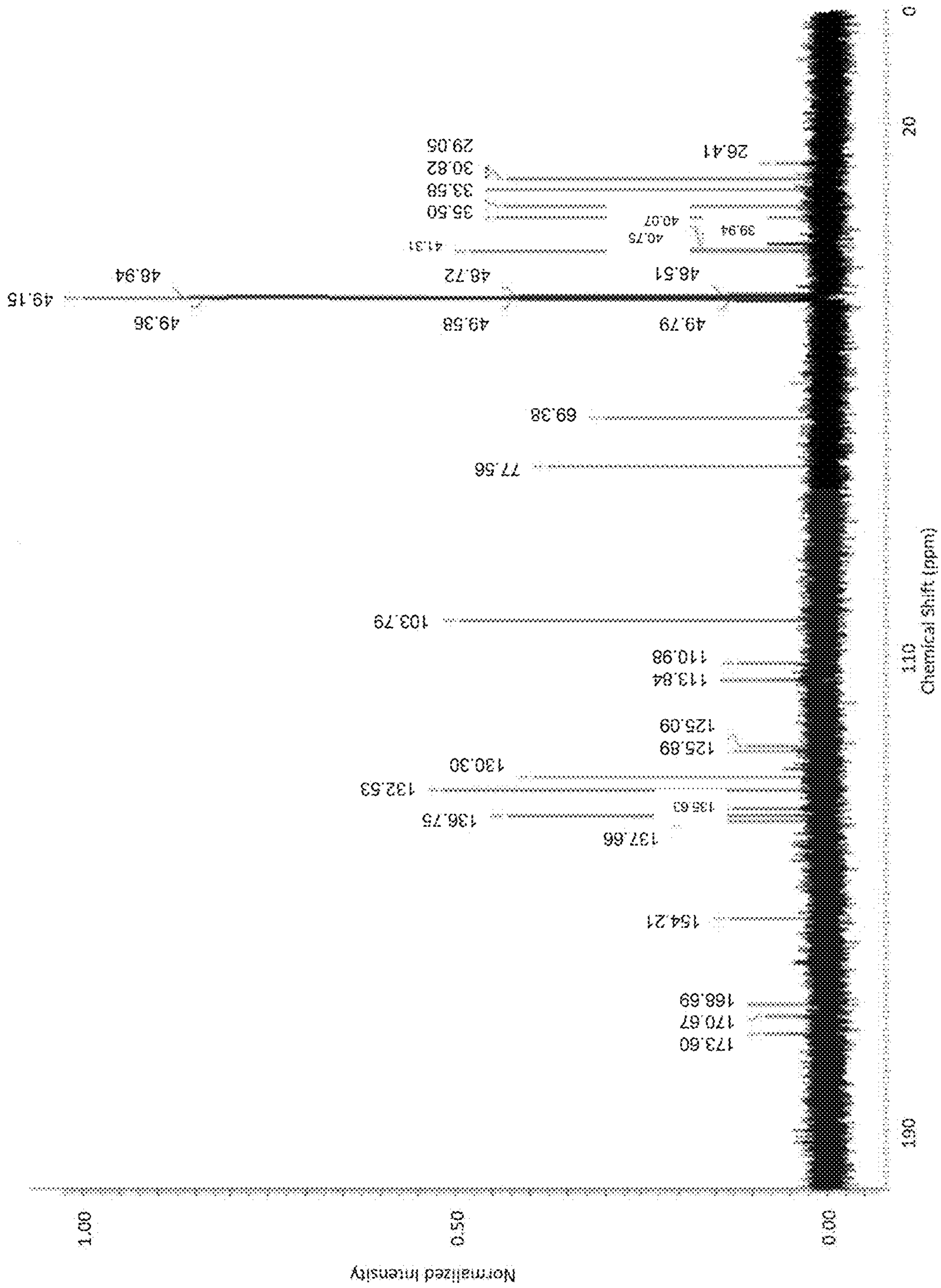
Figure 32A:
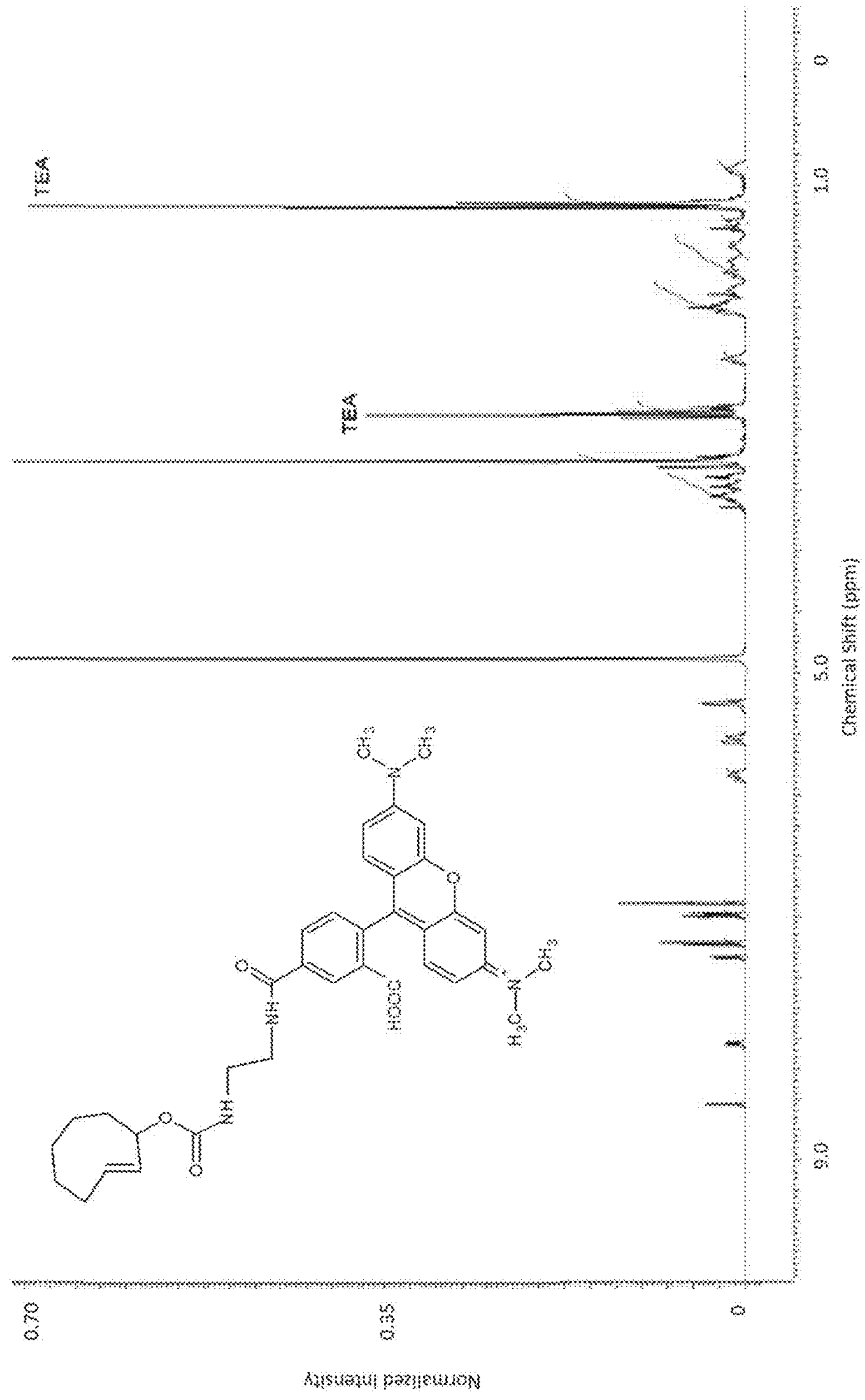
FIG. 32A and FIG. 32B show NMR spectra of TCO—R—Rh.
Figure 32B:
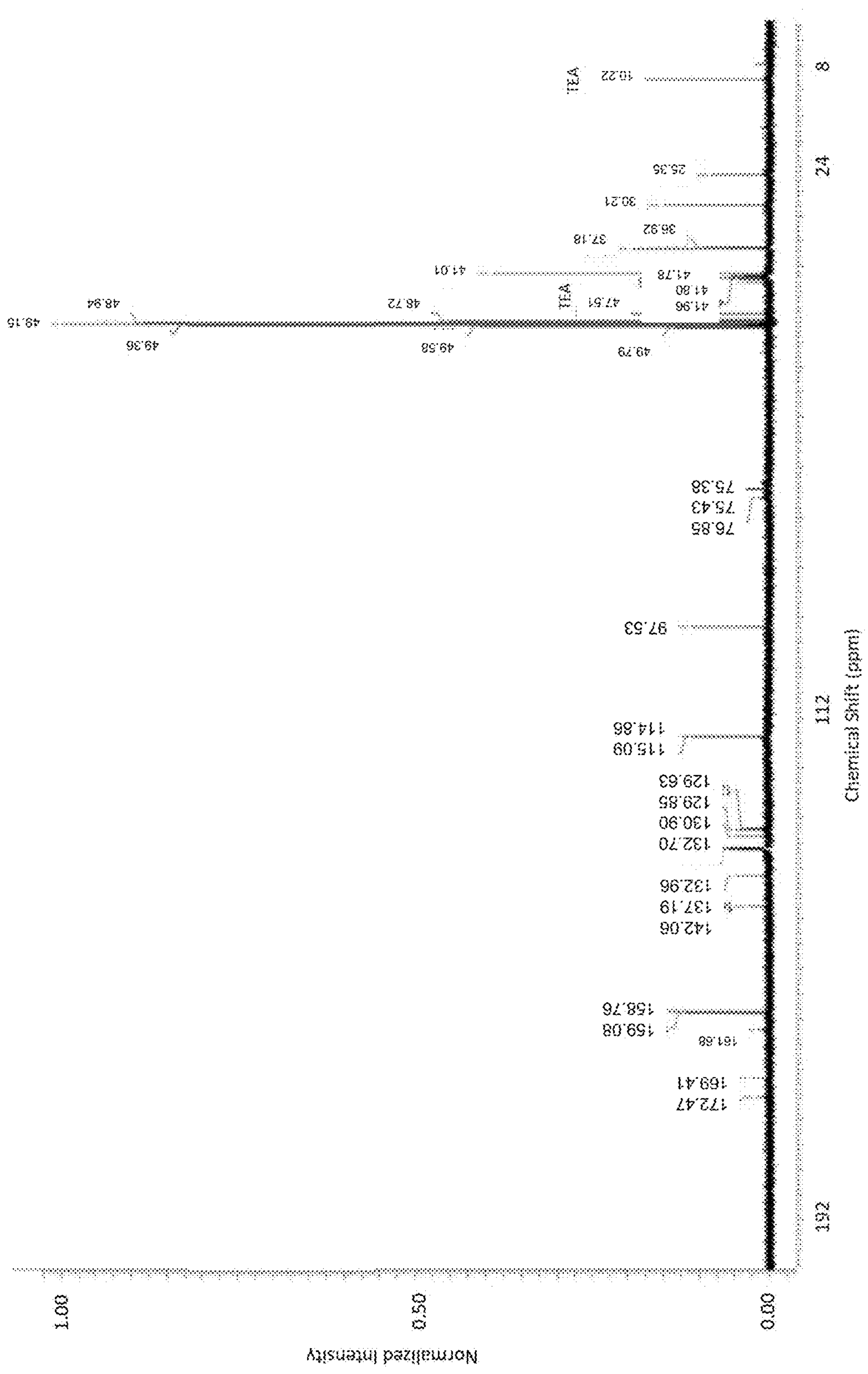
Figure 33:
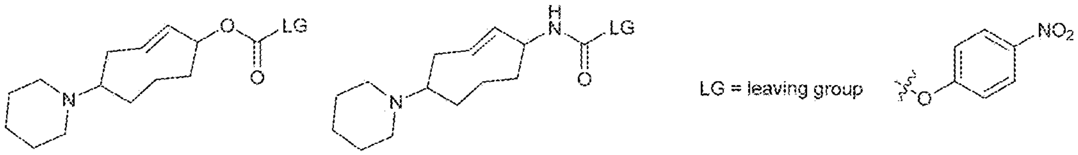
FIGS. 33-48 show exemplary synthetic methods for producing functionalized payloads with various linker types.
Figure 33:
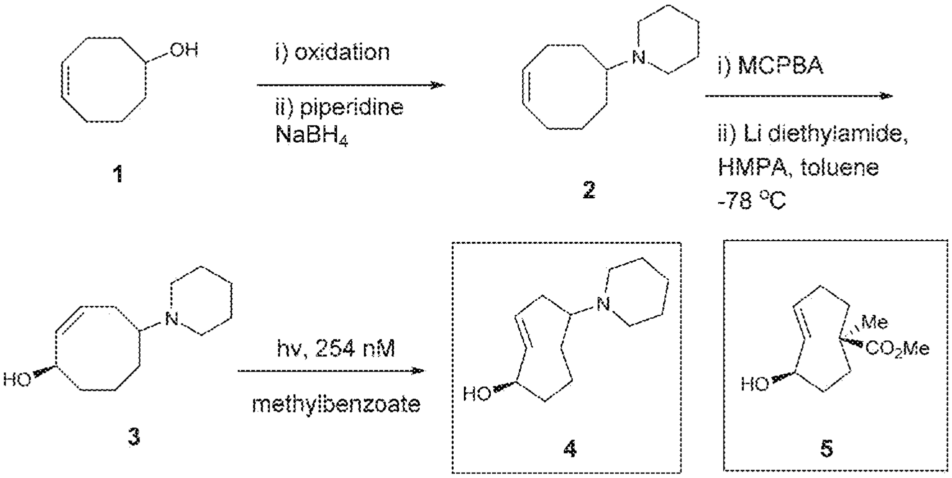
Figure 33:
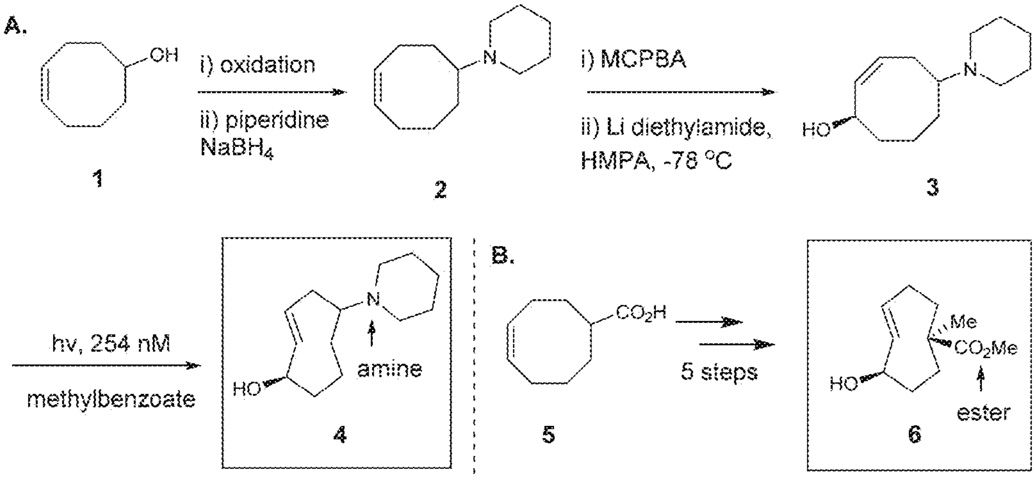
Figure 34:
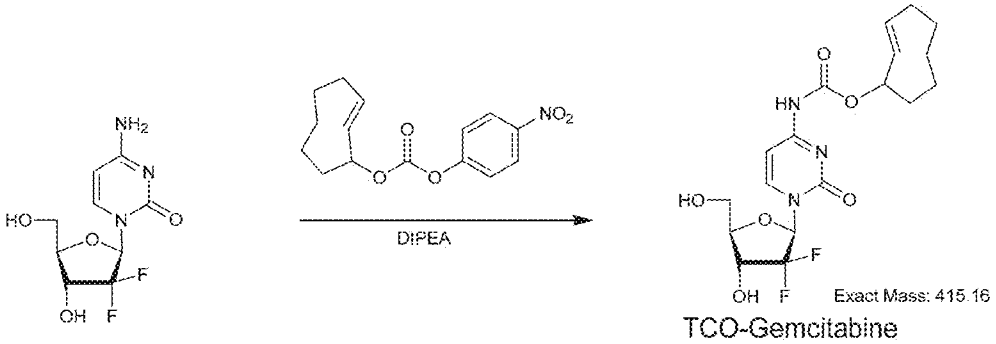
Figure 34:
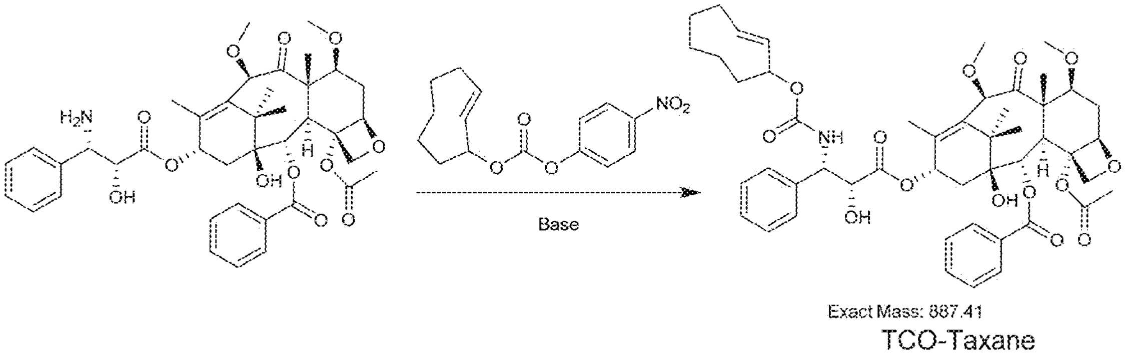
Figure 34:
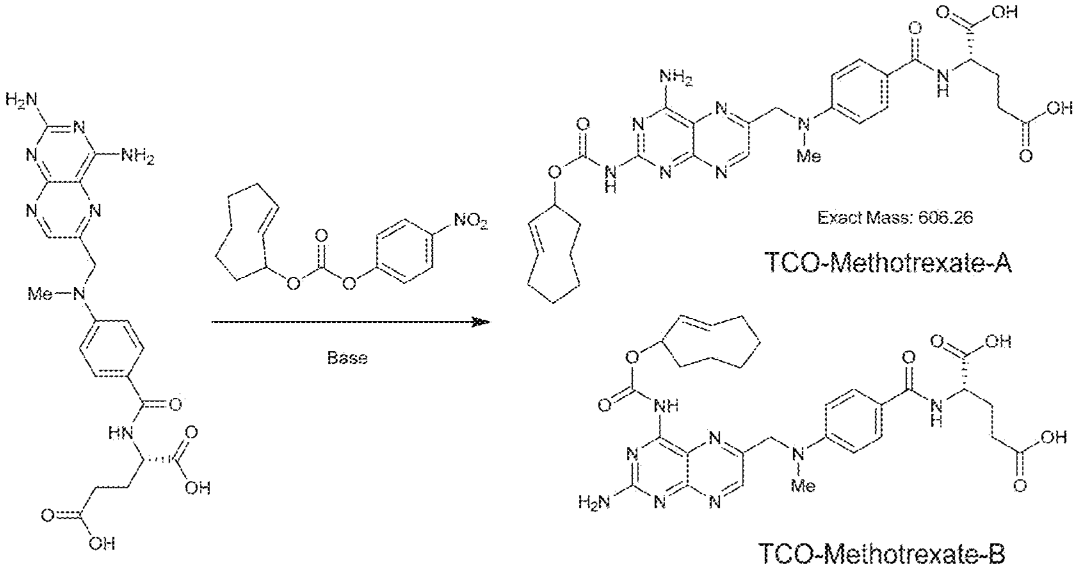
Figure 35:
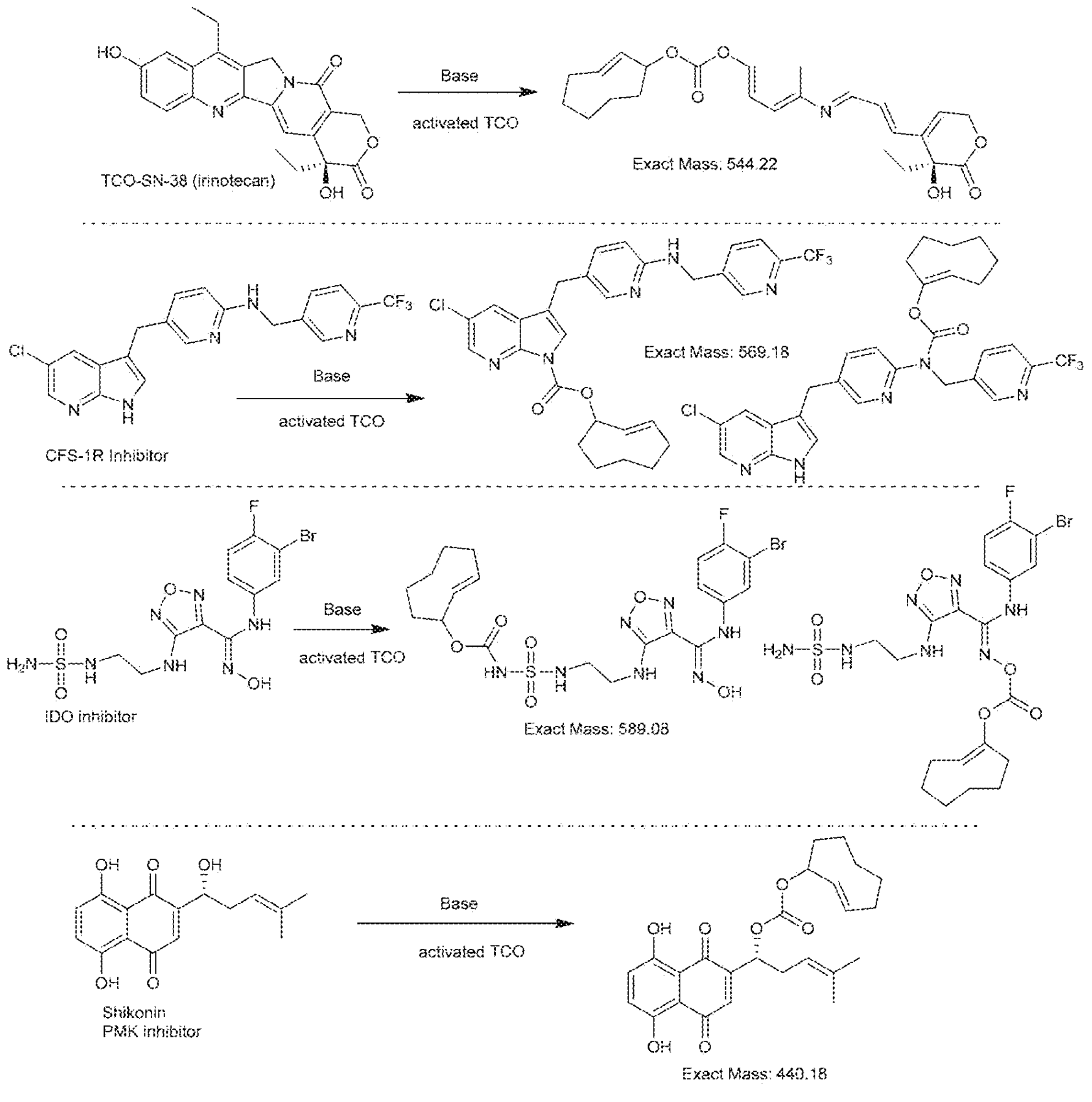
Figure 36:
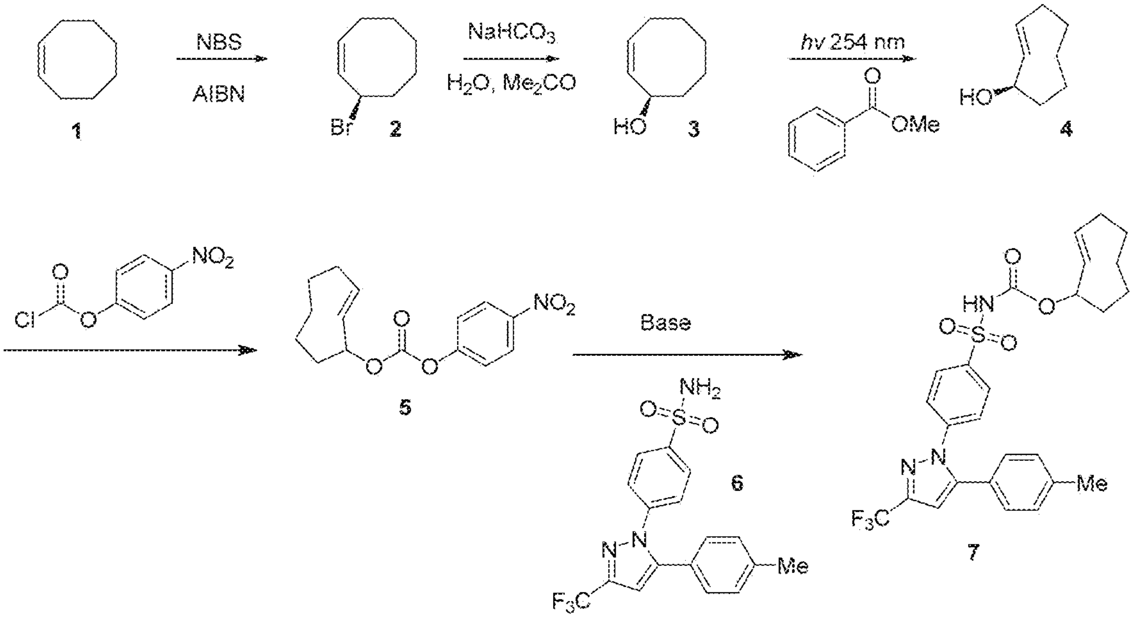
Figure 37:
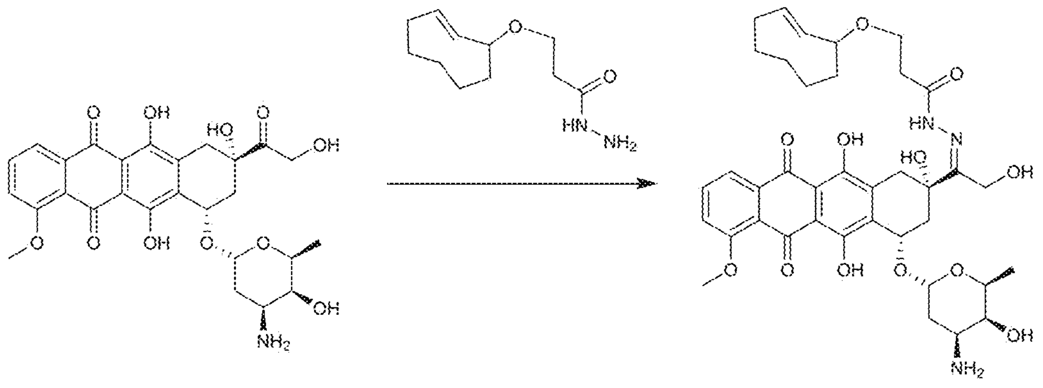
Figure 37:
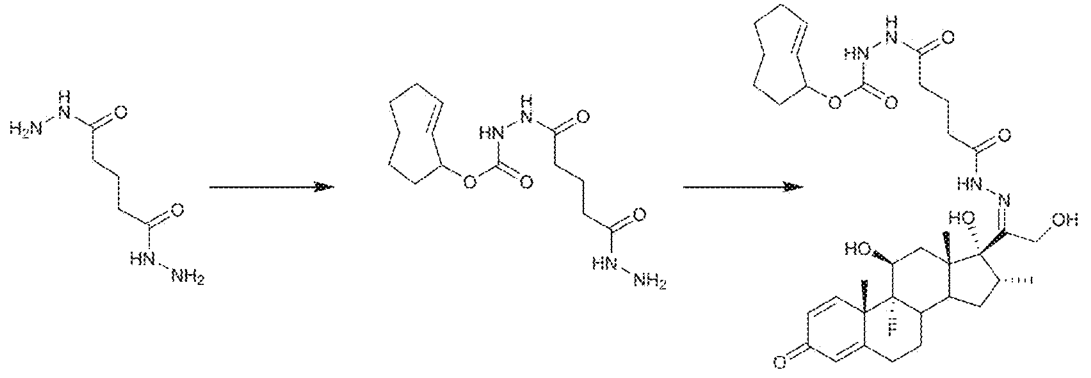
Figure 38:
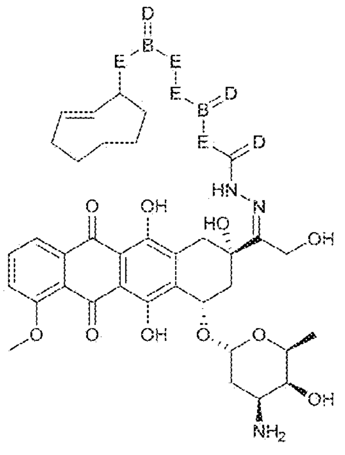
Figure 38:
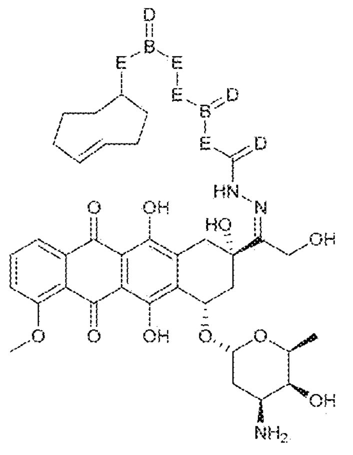
Figure 38:
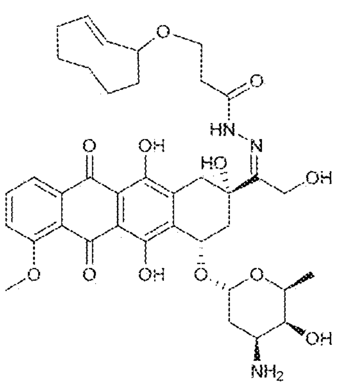
Figure 38:
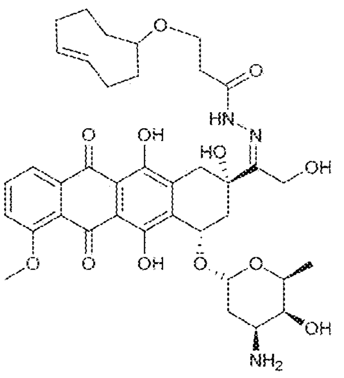
Figure 39:
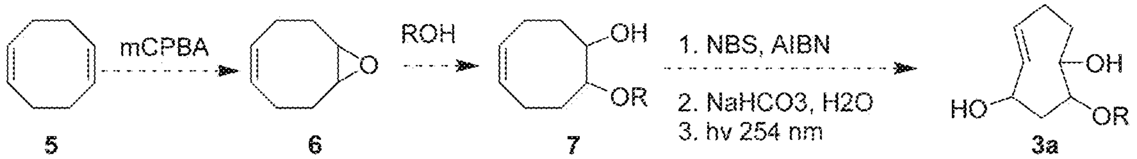
Figure 39:
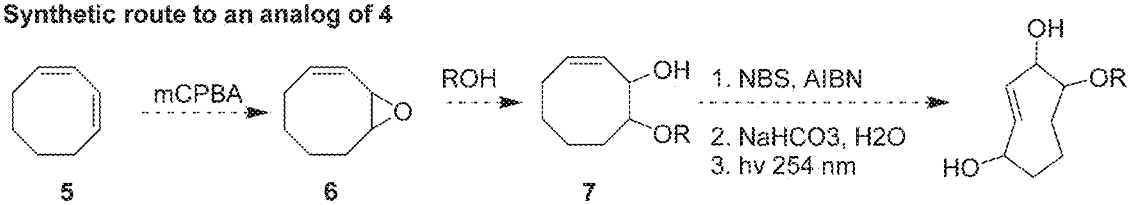
Figure 40:
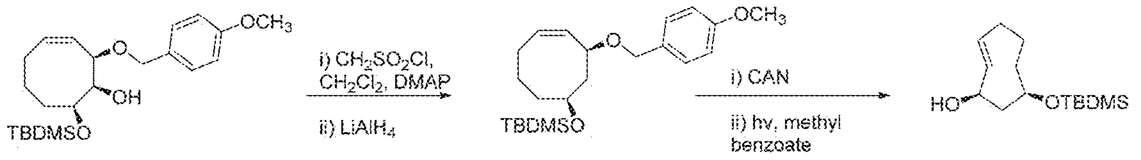
Figure 41:
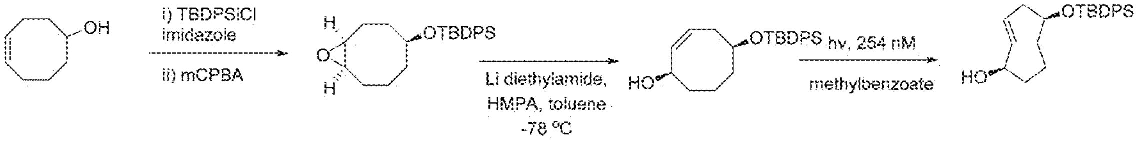
Figure 42:
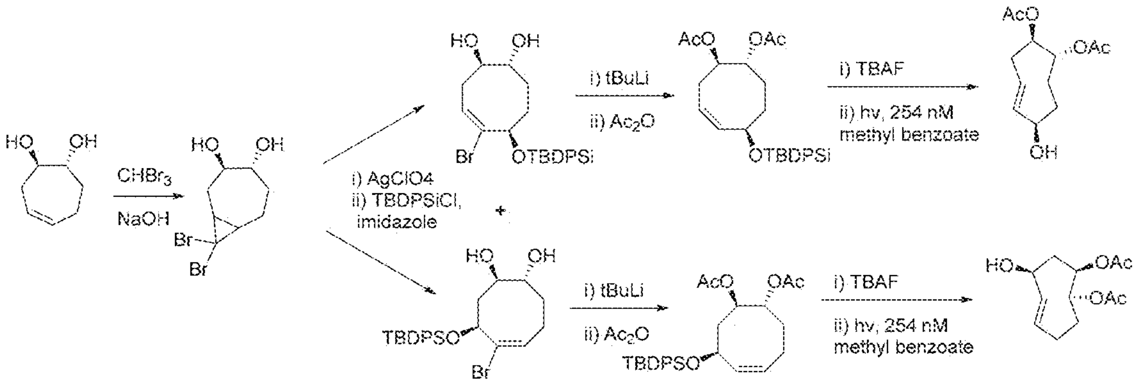
Figure 43:
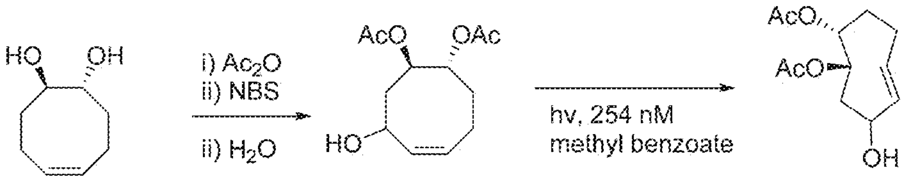
Figure 44:
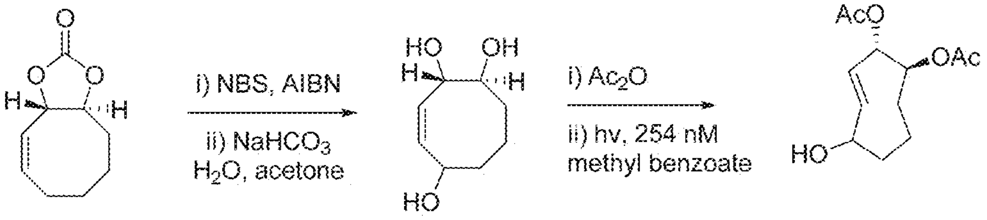
Figure 45:
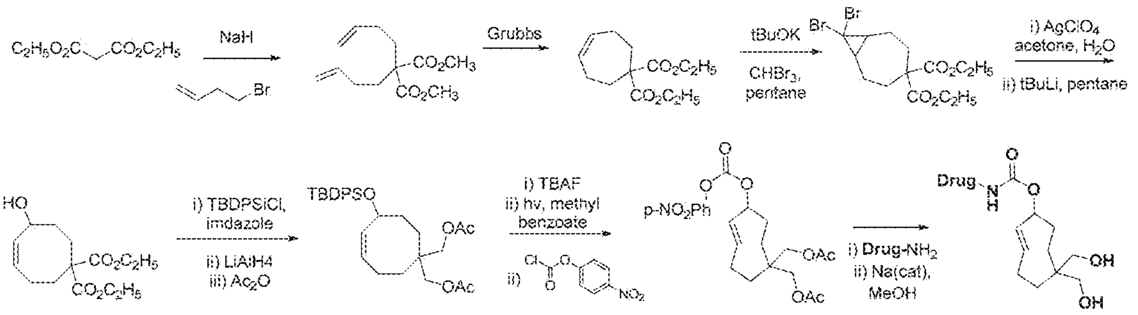
Figure 46:
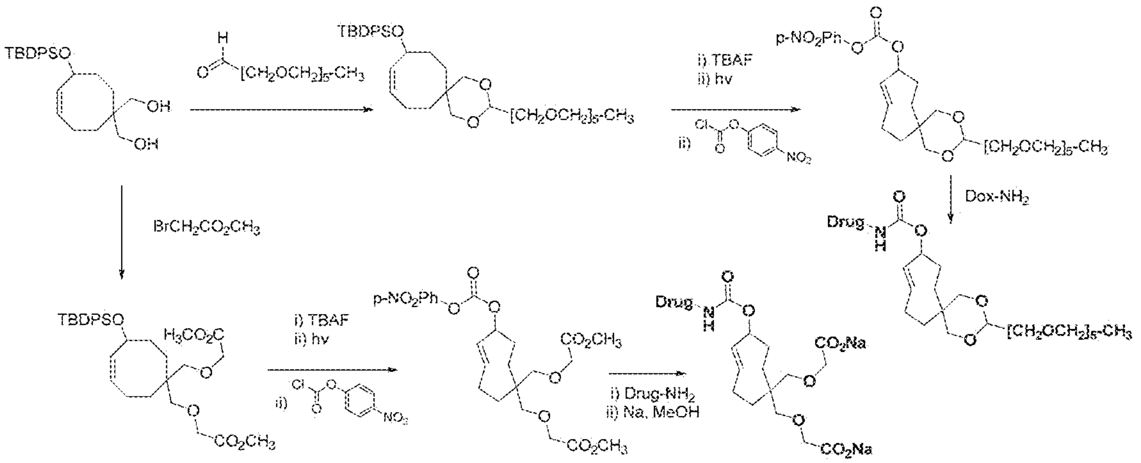
Figure 47:
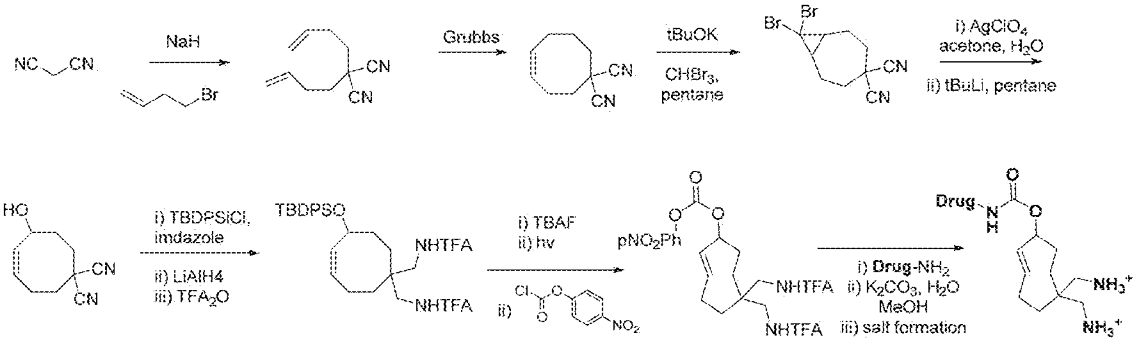
Figure 48:
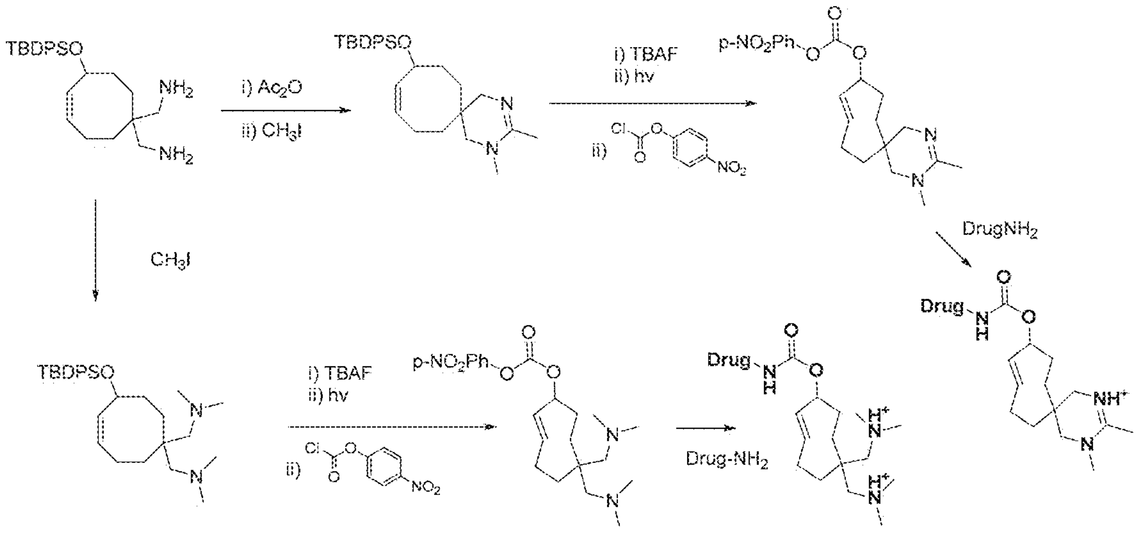
Figure 49:
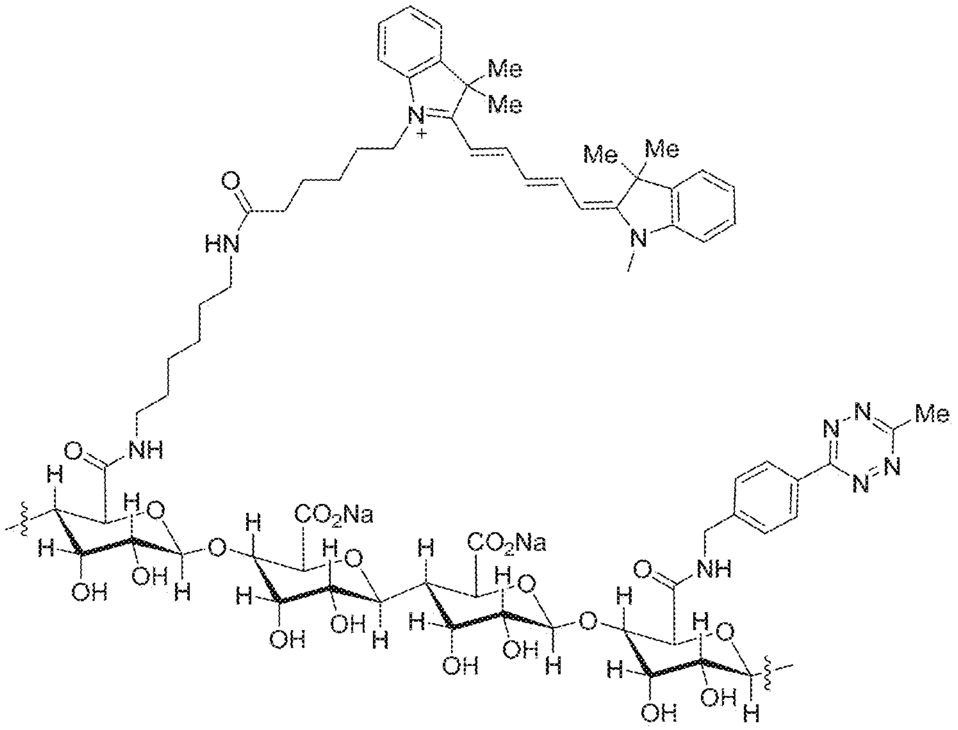
FIG. 49 shows an exemplary support composition prepared by a modified standard protocol to modify alginate polysaccharides with both tetrazines and a near infrared fluorophore (cyanine 5). At the amidation step both tetrazine amines and cyanine 5 amines were added in a ratio that maintained the reactivity of the gel, and added the property of being able be detected in-vitro and in-vivo (excitation and emission around 650 nm range).
Figure 50:
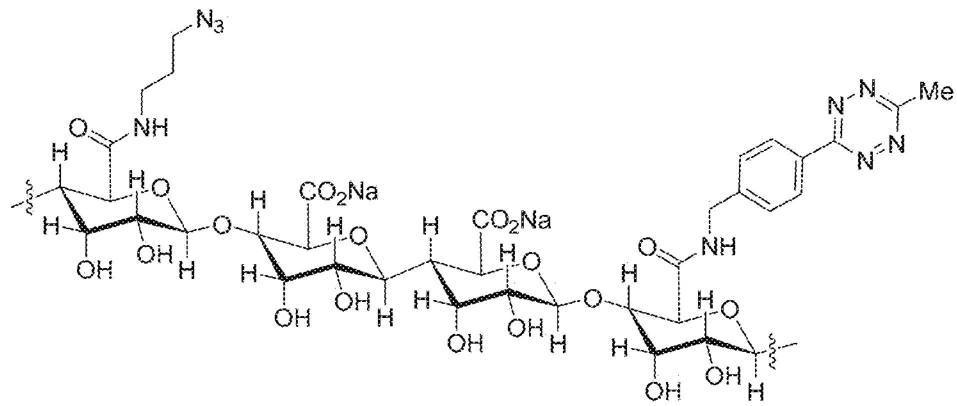
FIG. 50 shows an exemplary support composition prepared by a modified standard protocol to modify alginate polysaccharides with both tetrazines and azide propylamines. At the amidation step both tetrazine amines and azide propylamines were added in a ratio that maintained the reactivity of the gel, and added the property of being able be detected in-vitro and in-vivo (excitation and emission around 650 nm range).
Figure 51:
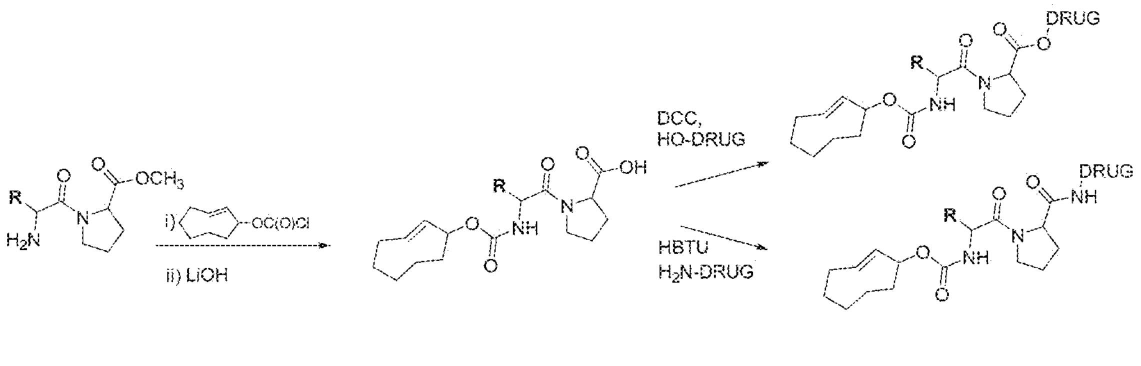
FIG. 51 shows a general synthetic strategy for an immolative linker.
Figure 52:
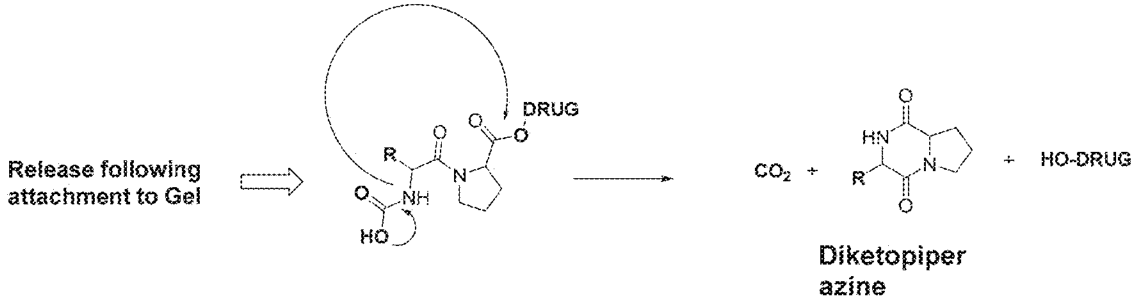
FIG. 52 shows an immolative linker system with a dipeptide release linker.
Figure 53:
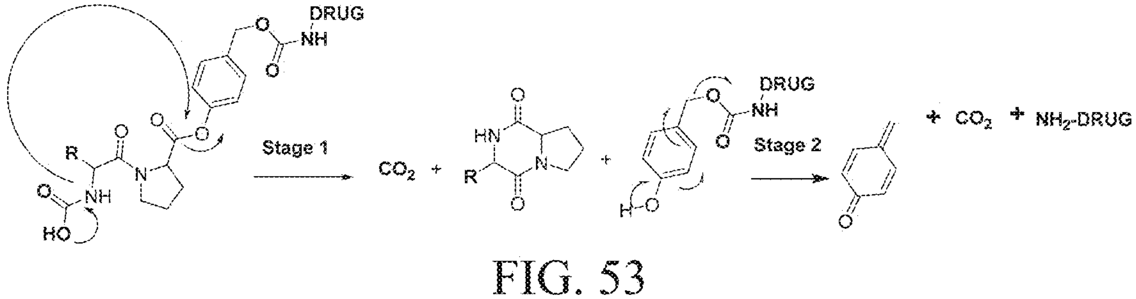
FIG. 53 shows an immolative linker system with a phenoxymethylene carbamate linker.
Figure 54:
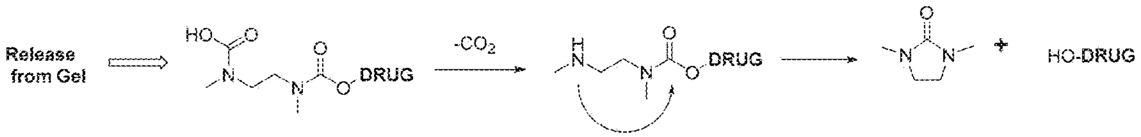
FIG. 54 shows an immolative linker system with an ethylene diamine linker.
Figure 55:
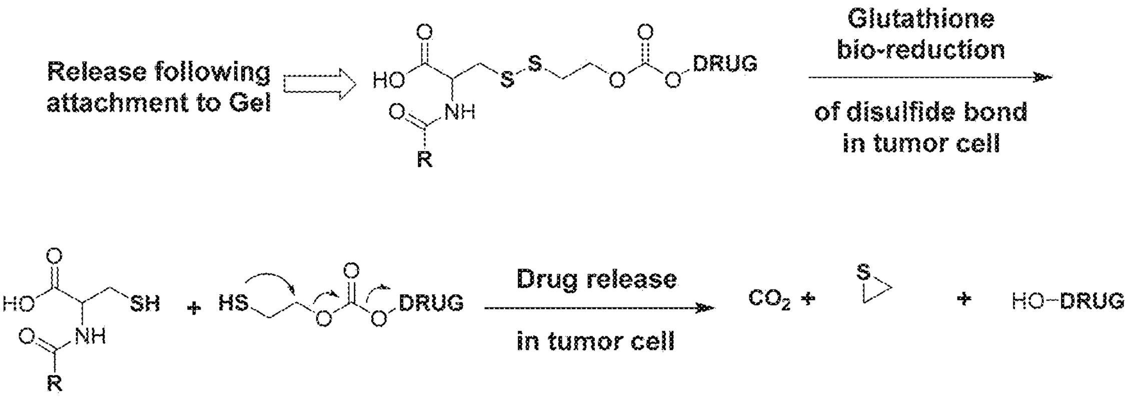
FIG. 55 shows an immolative linker system based on intracellular disulfide bond reduction.
Figure 56:
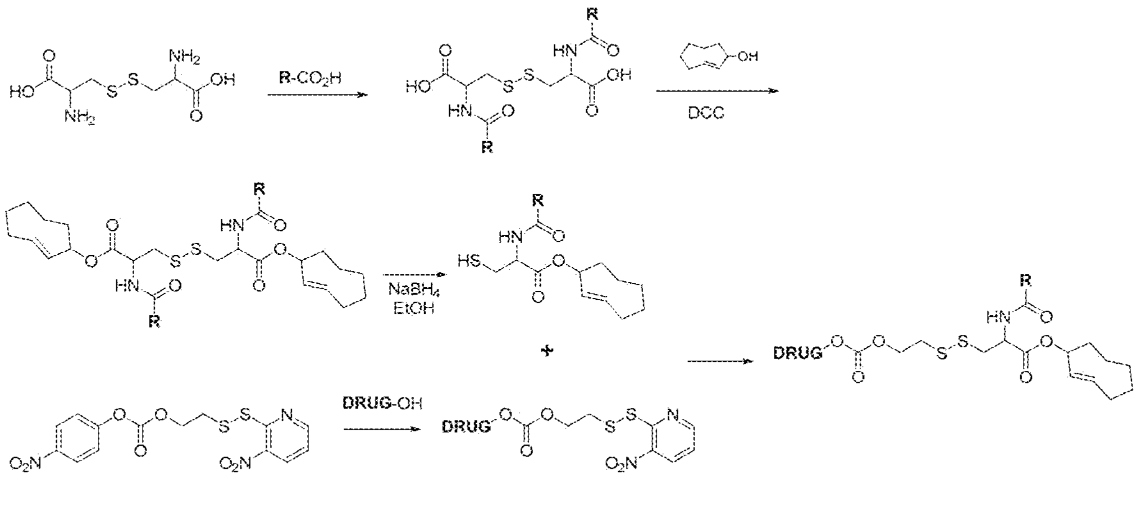
FIG. 56 shows a general synthesis of a TCO-modified cysteine linker.
Figure 57:
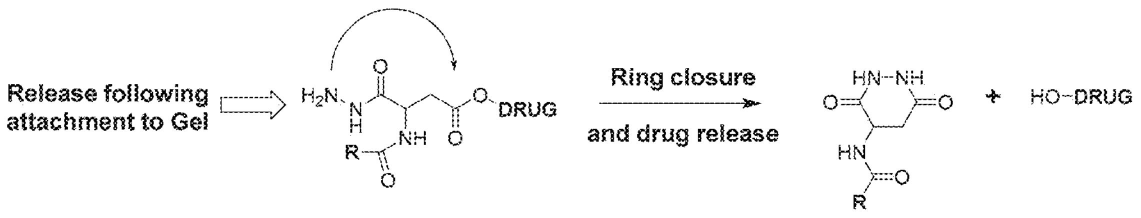
FIG. 57 shows an immolative linker system based on aspartyl hydrazide ring closure.
Figure 58:
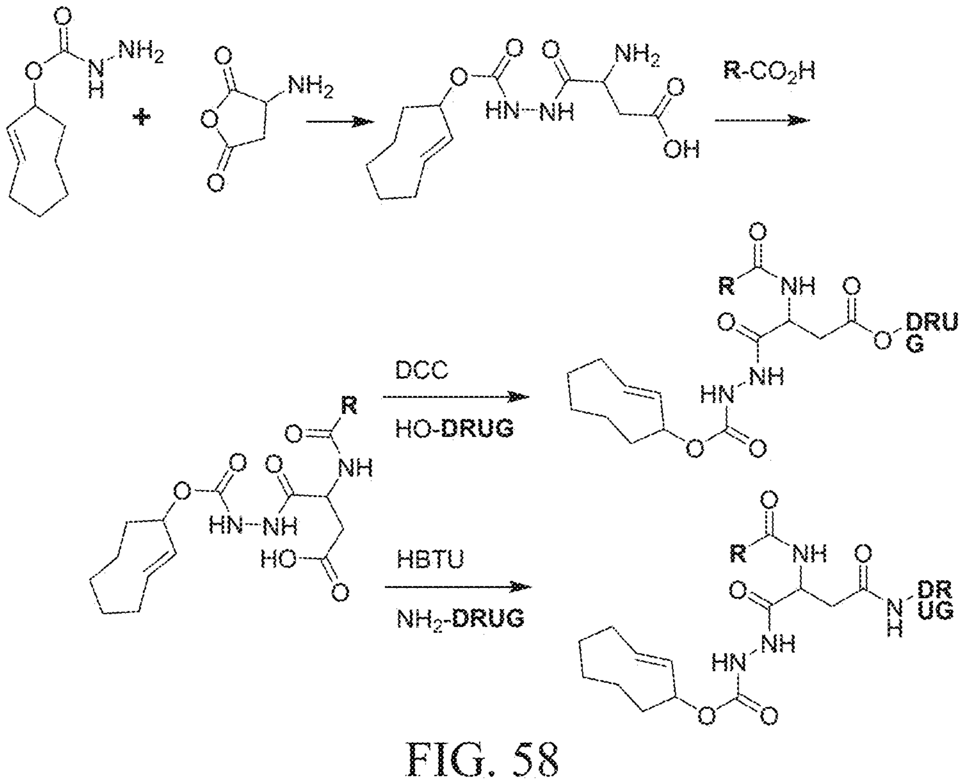
FIG. 58 shows a general synthesis of TCO-modified aspartyl hydrazide analogs.
Figure 59:
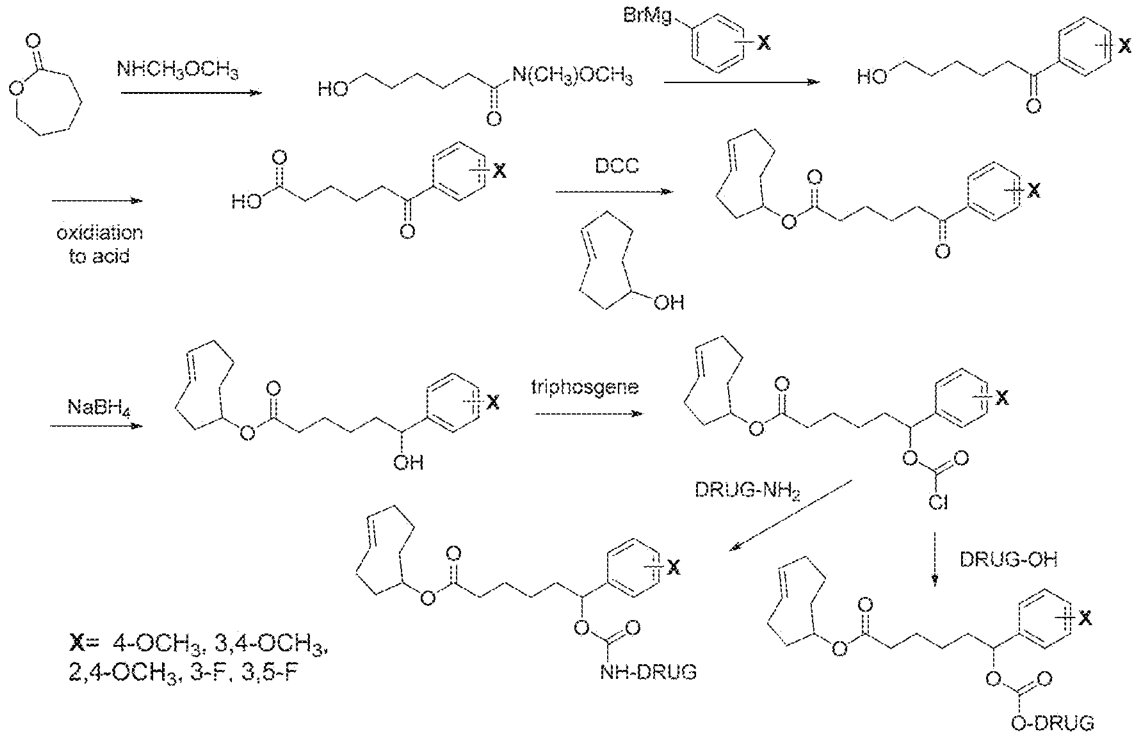
FIG. 59 shows a pH tunable linker synthesized from e-caprolactone.
Figure 60:
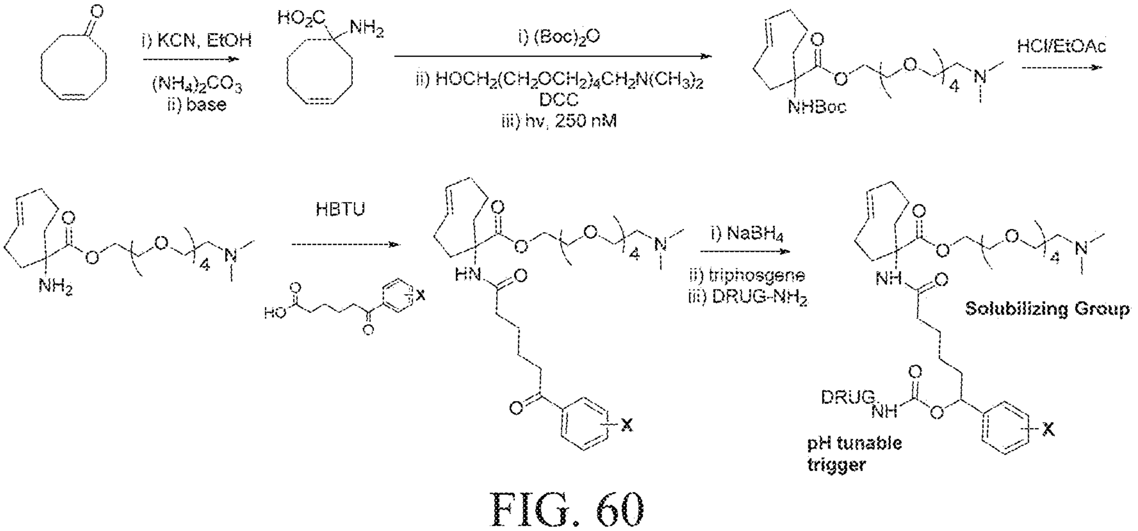
FIG. 60 shows a pH tunable linker incorporating a TCO amino acid. Bivalency of the amino acid allows for attachment of a trigger and a solubilizing group.
Figure 61:
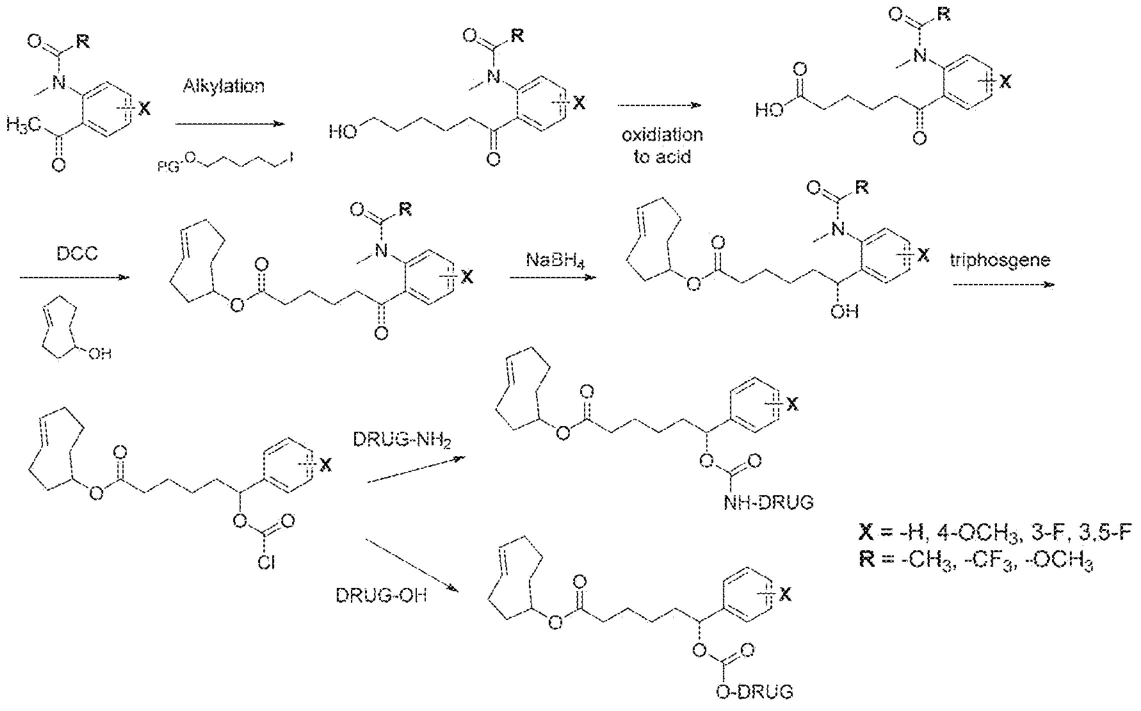
FIG. 61 shows a pH tunable linker with an NPG linker synthesis from acetophenones.
Figure 62:
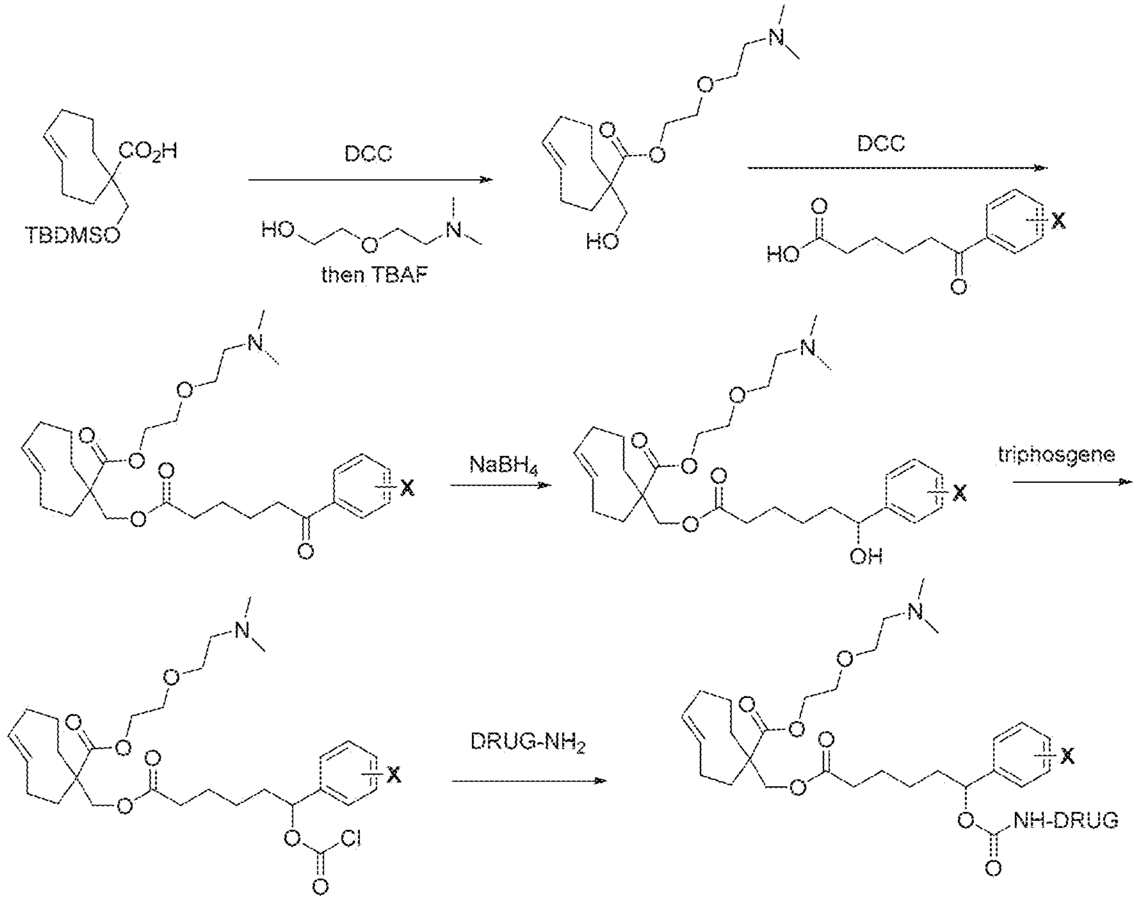
FIG. 62 shows a pH tunable linker with gem-disubstituted TCO linkers.
Figure 63:
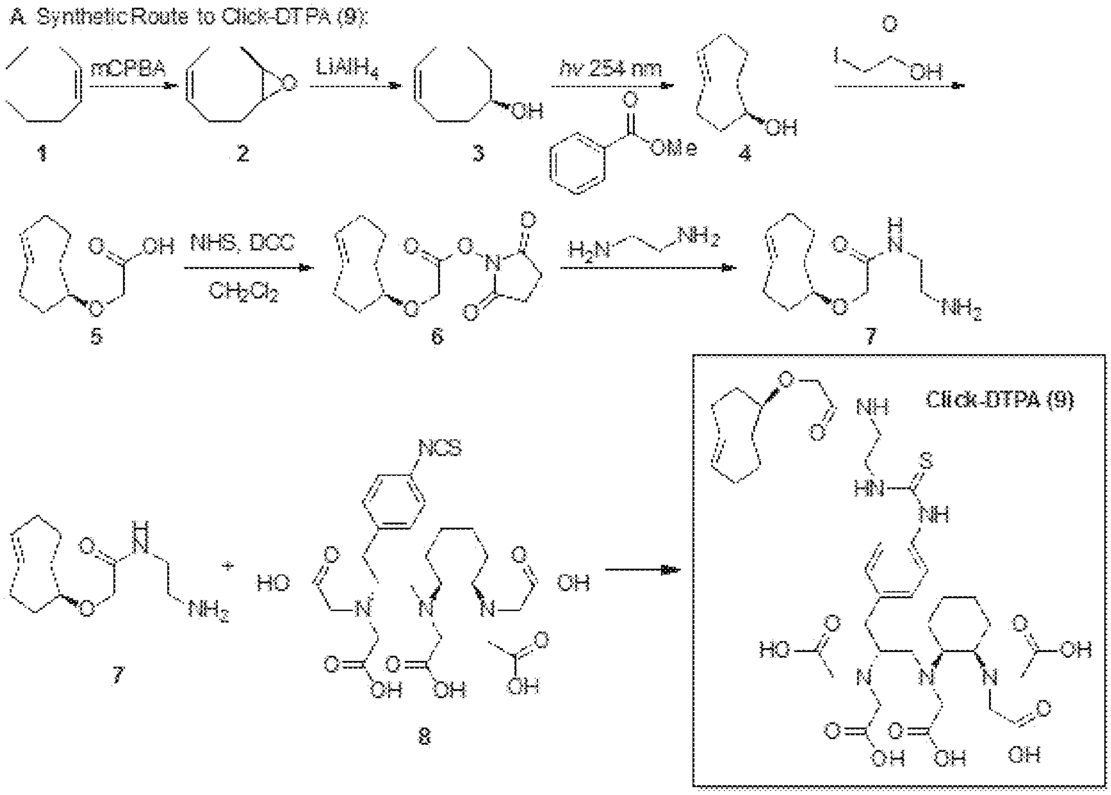
FIG. 63 shows an exemplary synthetic route to "click-DPTA".

Synthesis of Doxorubicin pro-drug. Doxorubicin was conjugated with trans-cyclooctene as described by: Versteegen, R. M. et. al., Angew. Chem. Int. Ed. 2013, 52, 14112-14116. The spectra from $^1$H NMR ($CDCl_3$) and high resolution mass spectrometry matched the published data (FIG. 27 and FIG. 28).

Cytotoxicity Assay. The colorimetric, 3-(4,5-dimethylthiazol-2-yl)-2,5-diphenyltetrazolium bromide (MTT), assay was used to evaluate the cytotoxicities of doxorubicin and doxorubicin pro-drug. Day one: using 96-well format, plated~100 cells/well in 100 μL DMEM and incubated for 24 h. Day two: DMEM was removed and the cells were treated with variable concentrations of doxorubicin and doxorubicin pro-drug in 100 μL DMEM for 48 h. Day four: the medium was replaced with 100 μL of fresh DMEM and the cells were incubated for 48 h. Day six: DMEM was removed and the cells were incubated with 100 μL of MTT solution (0.6 mg/mL in DMEM) per well for 4 h at 37° C. The MTT solution was then replaced with 100 μL of DMSO containing 4% aqueous ammonia per well to dissolve the purple formazan crystals. After 30 min, the absorbance of each well at 550 nm was recorded using BioTek Synergy HT multi detection microplate reader. Results were averaged from three independent arrays of triplicate experiments.

In vitro DOX release from alginate. A 2.5% w/w solution of alginate hydrogel (200 μL) was placed inside of a spin column and treated with 30 μL doxorubicin pro-drug (14 nmol). After 30 min, the supernatant was collected after a quick centrifugation at 6,000 RPM and the hydrogel was resuspended in PBS (30 μL). The supernatants were collected after 4 hours, 24 hours, and once daily for 7 more days, while the hydrogel was resuspended in fresh PBS (30 μL). The supernatant fractions were analyzed by HPLC.

Figure 20:
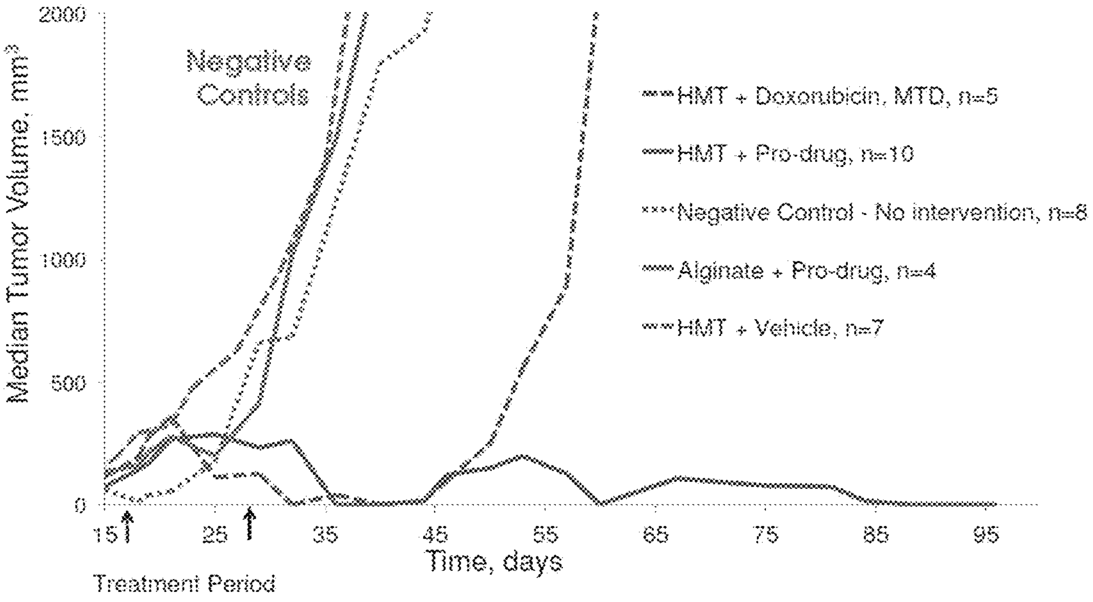
FIG. 20 shows negative controls for therapeutic effect of doxorubicin pro-drug in a xenograft model of soft tissue sarcoma. NCR/nu: nu mice were injected with human HT-1080 fibrosarcoma cells at day 0. Tumors were then injected with HMT and started on intravenous doses of either doxorubicin pro-drug or a maximum tolerable dose of doxorubicin. Tumor sizes were monitored for more than 16 weeks (n=5-10). The control groups included (i) no intervention, (ii) regular alginate implantation and treatment with doxorubicin pro-drug, (iii) HMT implantation with vehicle treatment. No significant difference was noted between any of the control groups.
Figure 21:
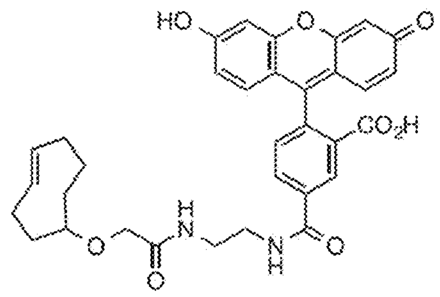
FIG. 21 shows fluorescently labeled TCO compounds that were used to study stability of HMT and in vivo properties of the ‘catch and release’ system.
Figure 21:
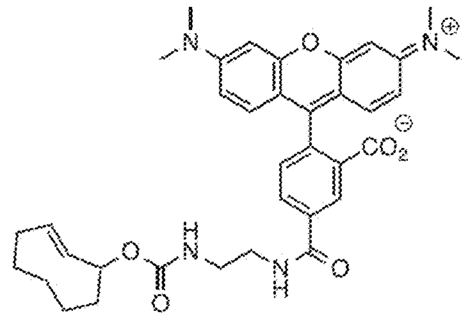
Figure 22:
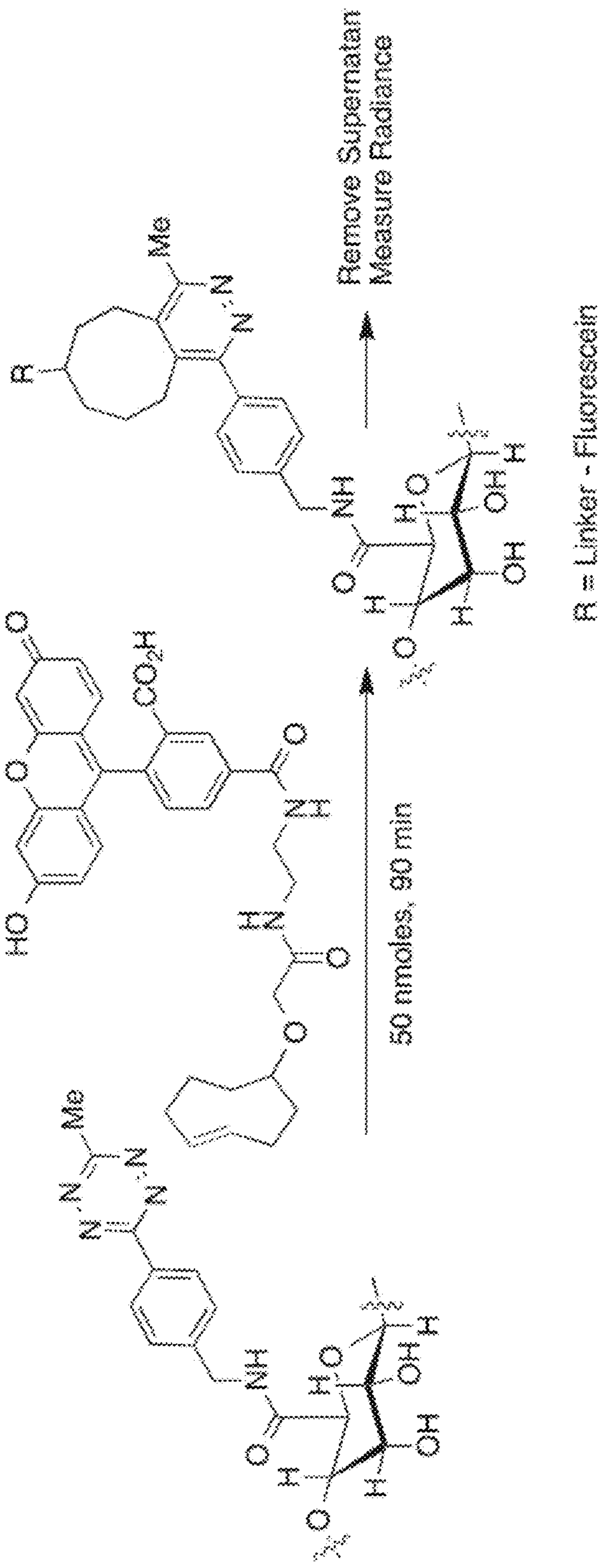
FIG. 22 and FIG. 23 show a functional assay to determine stability of HMT in PBS over 14 days in 37° C.
Figure 23:
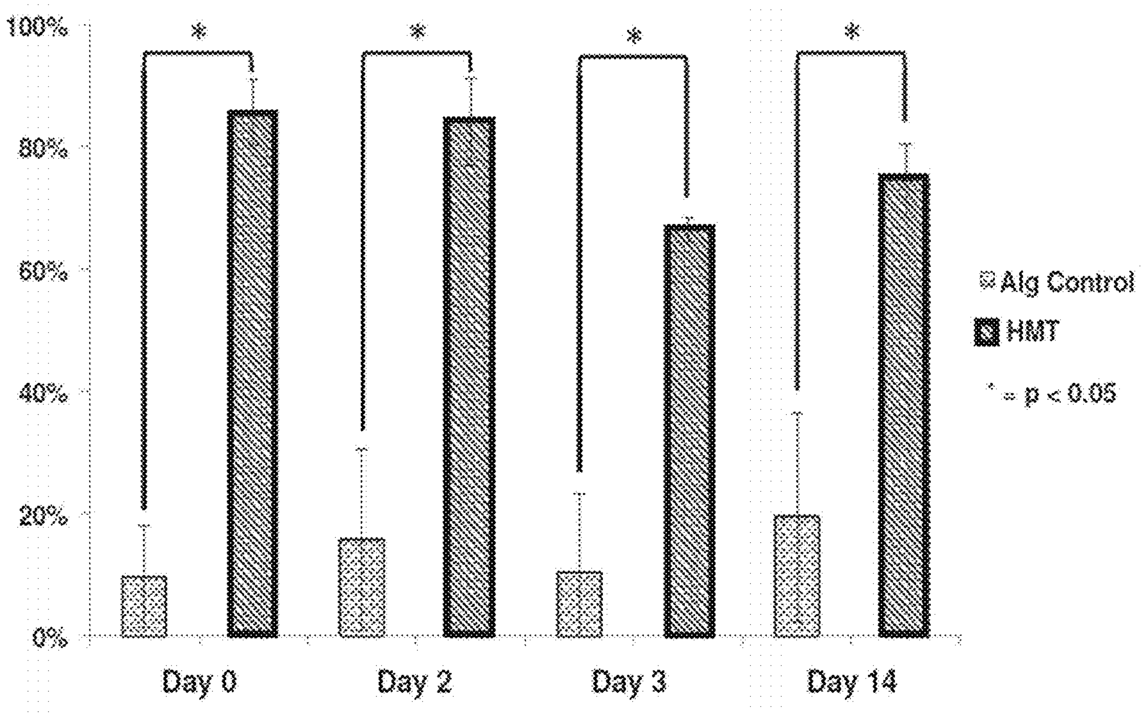
Figure 24:
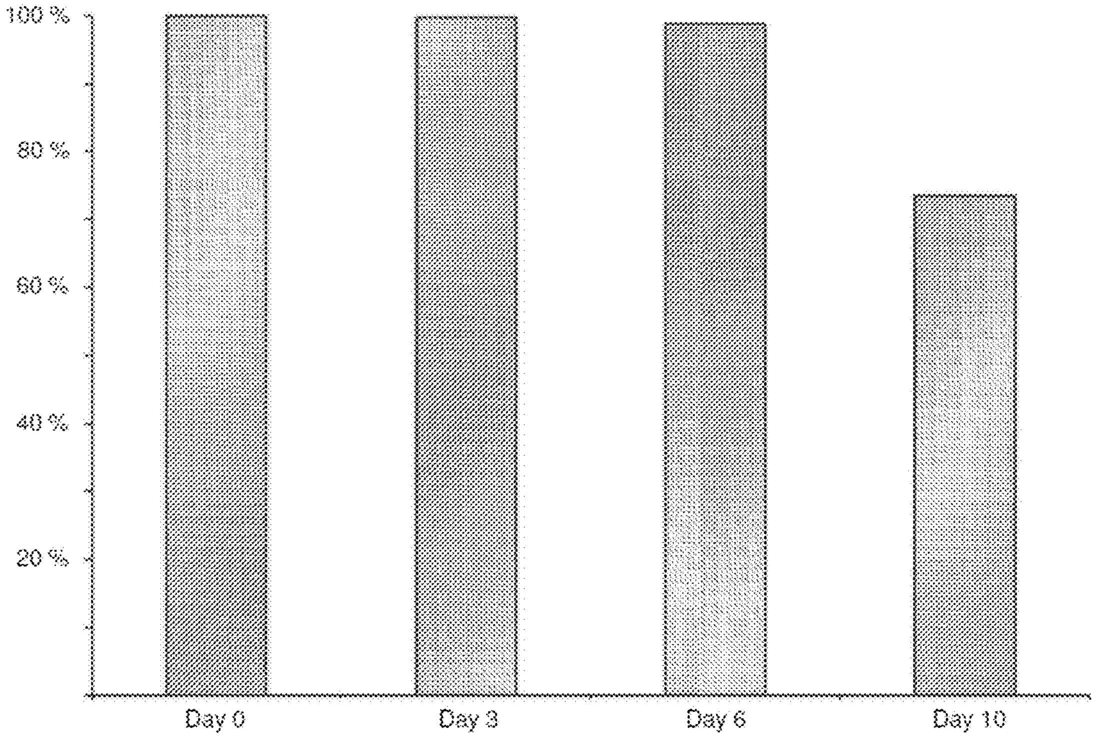
FIG. 24 shows a functional assay to determine stability of HMT in cell lysate. Activity of HMT treated with cell lysate for 3, 6, and 10 days relative to the untreated HMT (day 0). HMT and was challenged with non-releasable fluorescently labeled TCO to determine the functional amount of tetrazines that remain active after incubation in cell lysate at 37° C. for different time periods (3, 6, 10 days). In short, the hydrogels were prepared as outlined above for in-vitro analysis. Disks of hydrogel (50 mg) were placed in spin columns containing 200 μL of cell lysate (MDA-MB-231 cells). The spin columns were maintained at a 37° C. incubator until the period was over. Then, the cell lysate was removed by centrifugation and HMT was washed with $H_2O$ (3×200 μL). HMT was challenged with 50 nmoles of an aqueous solution of TCO-NRF1 for 90 min in a shaker. The resulting supernatant was collected after centrifugation and analyzed by HPLC. The data (n=1 per time point) suggest that 73% of the tetrazine moieties remain stable and reactive even after 10 days of incubation in cell lysate.

Control cohorts for Inhibition of HT1080 Xenograft Growth. The exact same protocol as described in the paper was used, except that mice were separated into three additional cohorts: (i) an unmodified alginate gel was placed near the tumor and the mice were treated with 7 μmoles/kg of doxorubicin pro-drug every other day for 4 doses, (ii) HMT gel was placed near the tumor side and the cohort was treated only with vehicle, (iii) after tumor implantation the mice were not given any further interventions to monitor the natural progression of the disease. No statistical significant differences were detected between any of these cohorts (FIG. 20).

Figure 9A:
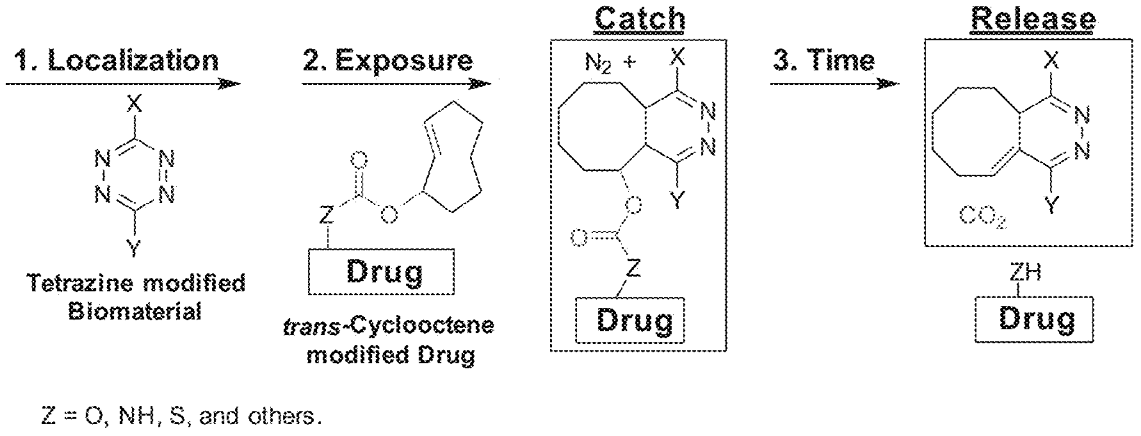
FIG. 9A shows one exemplary embodiment for the catch and release of a payload to a targeted location.
Figure 9B:
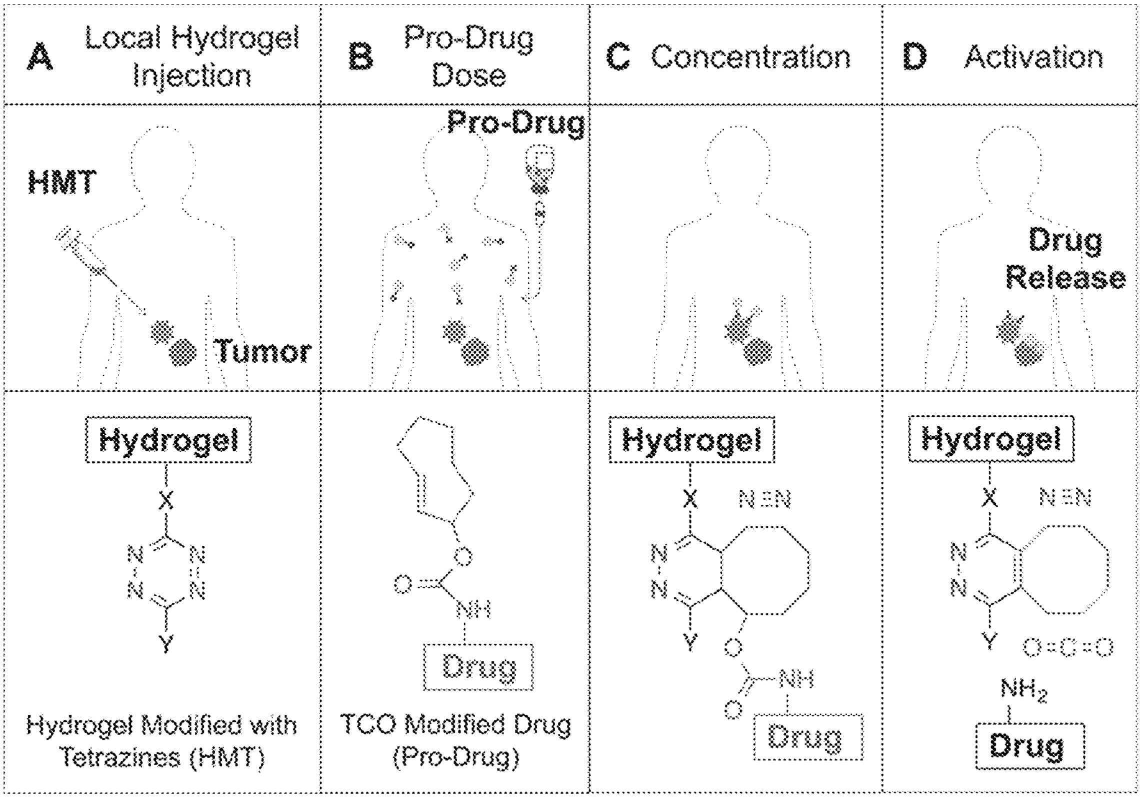
FIG. 9B shows in vivo bioorthongal chemistry for the concentration and activation of systemic prodrugs. (A) A hydrogel modified with Tz (HMT) is injected into the area where the drugs are needed. (B) A drug covalently modified with a TCO carbamate (pro-drug) is given to the patient. (C) When the pro-drug and the material come into contact, the rapid cycloaddition reaction enhances the amount of drug present at the desired location with the concomitant release of a molecule of nitrogen. (D) The resulting cycloadduct isomerizes in vivo leading to decomposition of the self-immolable carbamate linker, releasing an equivalent of carbon dioxide and most importantly the drug at the local site to perform its therapeutic function.

In-vitro Activation of Doxorubicin Pro-drug. The strategy illustrated in FIG. 9B was first tested in vitro. The alginate hydrogel was prepared by crosslinking 160 μL of tetrazine-modified polyalginate with 40 μL CaSO4 and placed into a spin column. The hydrogel was treated with a 30 μL aqueous solution of doxorubicin pro-drug (14 nmol). After 30 min, the supernatant was collected after centrifugation and the hydrogel was resuspended in PBS (30 μL). The supernatants were collected at regular time intervals and analyzed by HPLC.

Animal Studies. All studies involving animals were approved by the appropriate Institutional Animal Care and Use Committee before initiation. All animals used in efficacy studies were allowed to acclimate for at least 1 wk in the animal facilities before experimentation. Animals were exposed to a 12-h light/dark cycle and received food and water ad libitum through the studies.

Inhibition of HT1080 Xenograft Growth. Tumors were created by injecting 2.5×105 HT1080 cells (American Type Culture Collection) combined with Matrigel (BD Biosciences) to a total volume of 100 μL (50 μL PBS and 50 μL Matrigel) into the flank region of 5-7-wk-old NCR: nu/nu male mice (Charles River Laboratories). Eighteen days following tumor inoculation, mice were separated into two cohorts with the same median tumor size and a similar tumor size distribution (FIG. 17B). 100 μg of 2.5% w/w HMT was injected near the tumor site. The intravenous therapy consisted of either maximum tolerable dose of doxorubicin (3 doses of 14 μmoles/kg every 4 days) or doxorubicin pro-drug (14 μmoles daily for 10 days). Throughout the study, tumor area was measured twice per week with digital calipers. Mice that died or had to be euthanized before completion of the experiment were not included in the analysis.

Reticulocyte measurements. Two mice per condition were anesthetized with isoflurane anesthesia 3 days after the last treatment during the nadir of reticulocyte decrease. (27)

Blood was collected by cardiac puncture in a syringe containing lithium heparin to prevent coagulation. RBC and reticulocyte concentrations were determined the same day using a DEXX ProCyte Dx Hematology Analyzer (IDEXX Laboratories, Inc.).

Statistical Analyses. Data are expressed as means±SEM, unless otherwise noted. Unpaired t tests were used to make comparisons of continuous values between groups. Unadjusted P values are reported for pairwise comparisons when an overall difference was detected.

Results

Figure 17A:
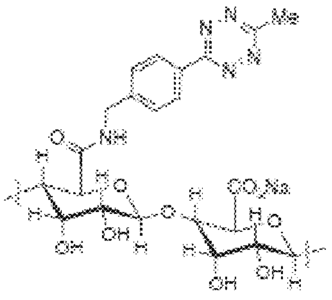
Figure 17A:
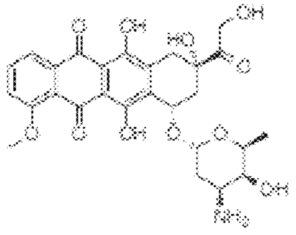
Figure 17A:
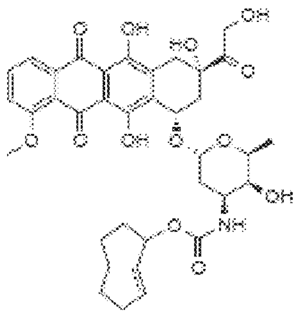
Figure 19A:
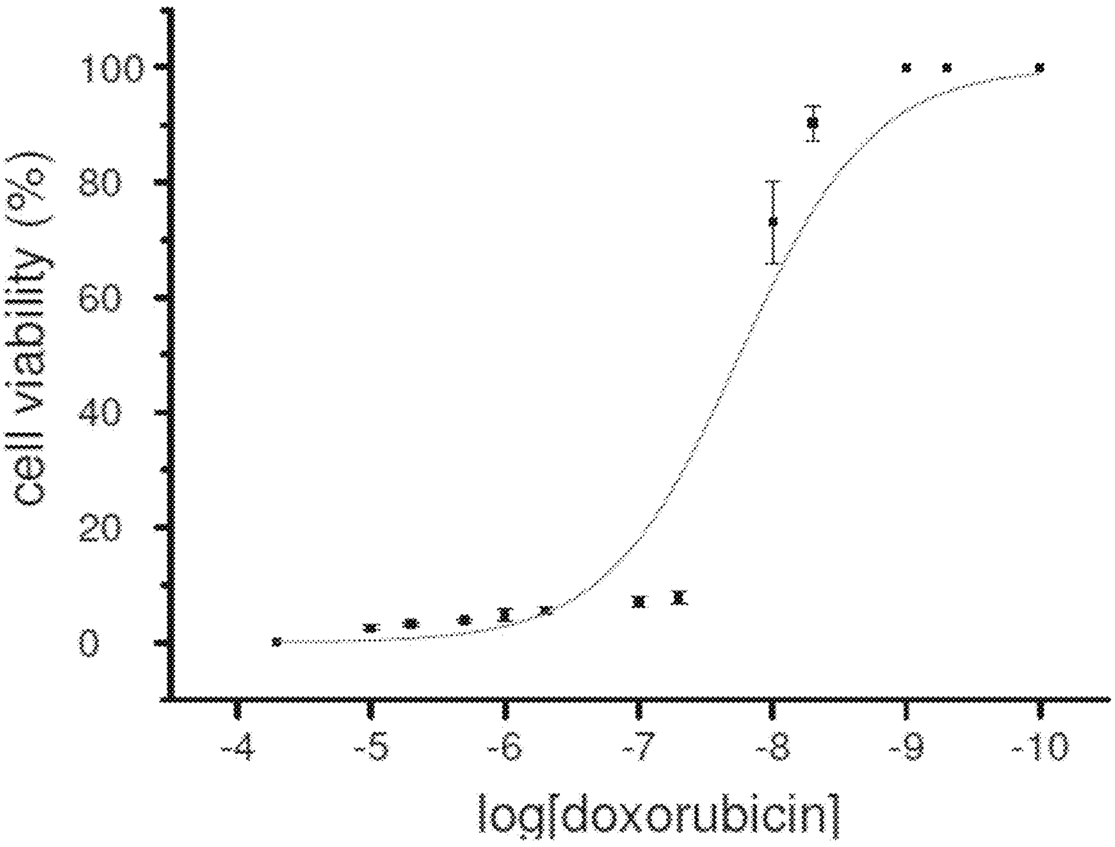
FIG. 19A and FIG. 19B show dose-response curve of HT1080 cells treated with different concentrations of doxorubicin (FIG. 19A) and doxorubicin pro-drug (FIG. 19B) as measured by the MTT assay. Cells were treated with the drug or the pro-drug for 48 h, followed by additional 48 h in DMEM, prior to measuring their viability. The 50% growth inhibitory concentration (IC50) values determined from these data are doxorubicin: 0.018 μM; doxorubicin: 1.02 μM.
Figure 19B:
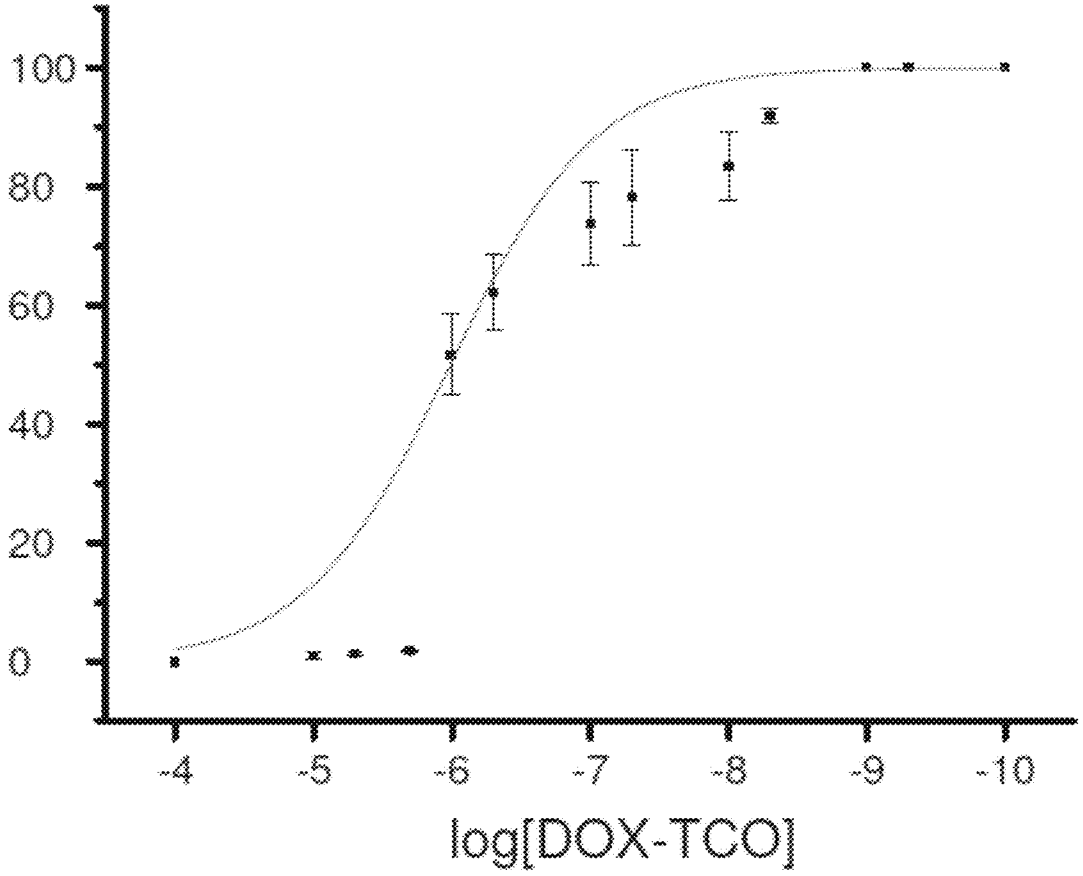
Figure 25:
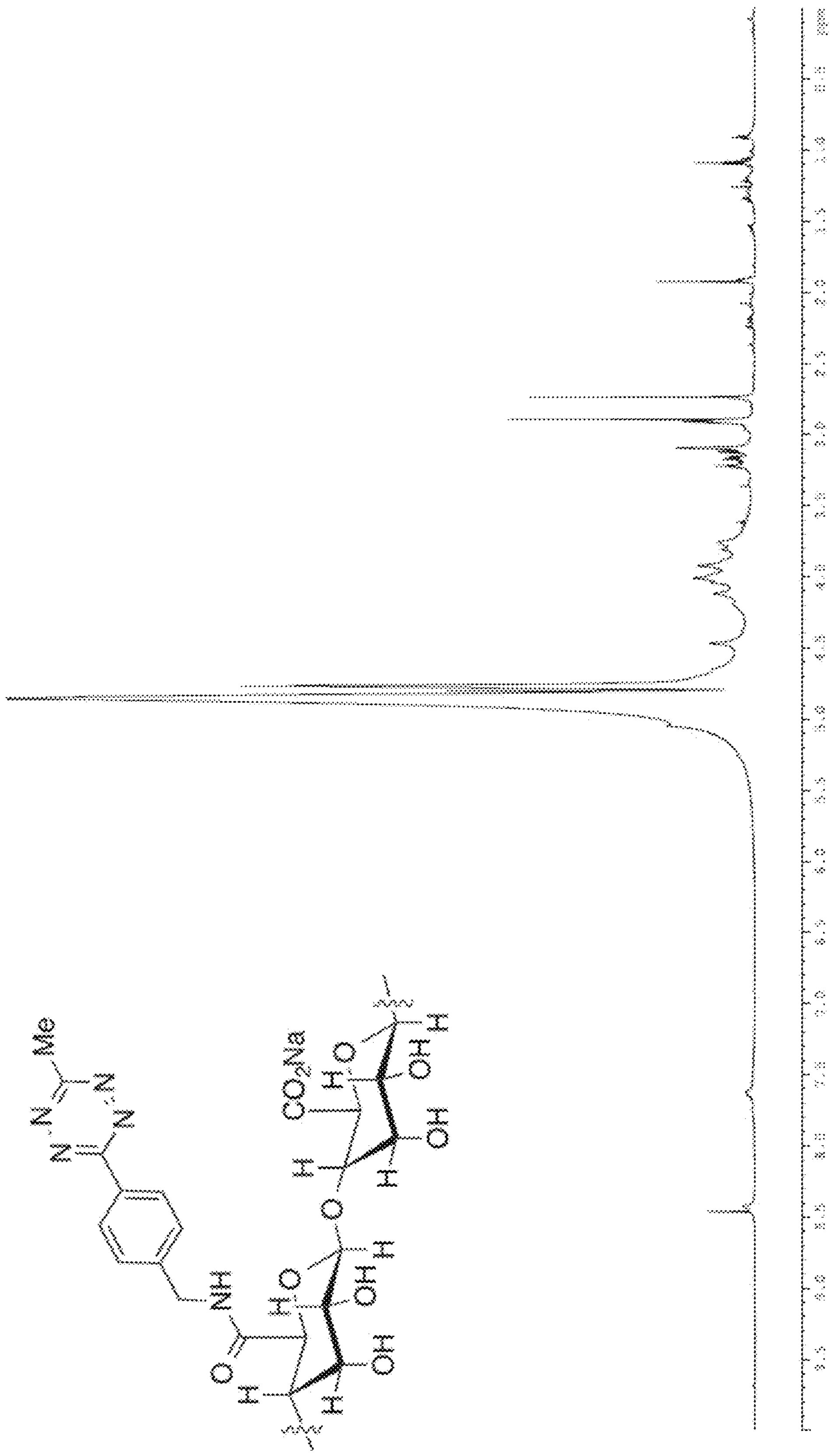
FIG. 25 shows an NMR spectrum of the hydrogel modified tetrazine (HMT). The peaks at 8.4 and 7.6 ppm correspond to the aryl protons of the tetrazine group, while the broad multiplet 4.3-3.6 ppm corresponds to the polyalginate protons.
Figure 26:
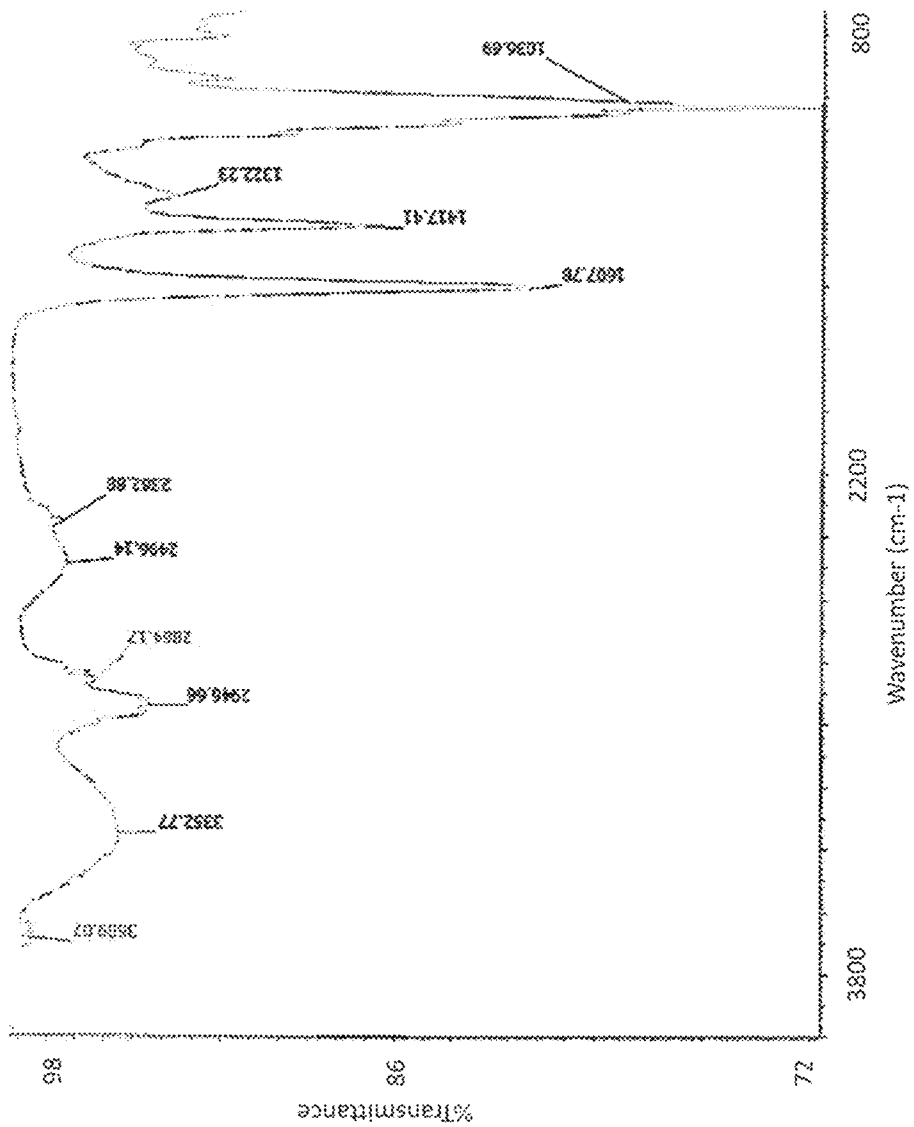
FIG. 26 shows an IR spectrum of the hydrogel modified tetrazine (HMT).

Local Concentration and Activation Approach. An alginate hydrogel was modified with tetrazine moieties (HMT, FIG. 17A). HMT contains about 120 nmoles of tetrazine per milligram of material based on 1H NMR analysis (FIG. 25). Doxorubicin was covalently modified into a pro-drug by covalent modification with a trans-cyclooctene moiety. This modification resulted in an agent that is 57 times less active against HT1080 than regular doxorubicin (FIG. 19A and FIG. 19B).

Figure 17B:
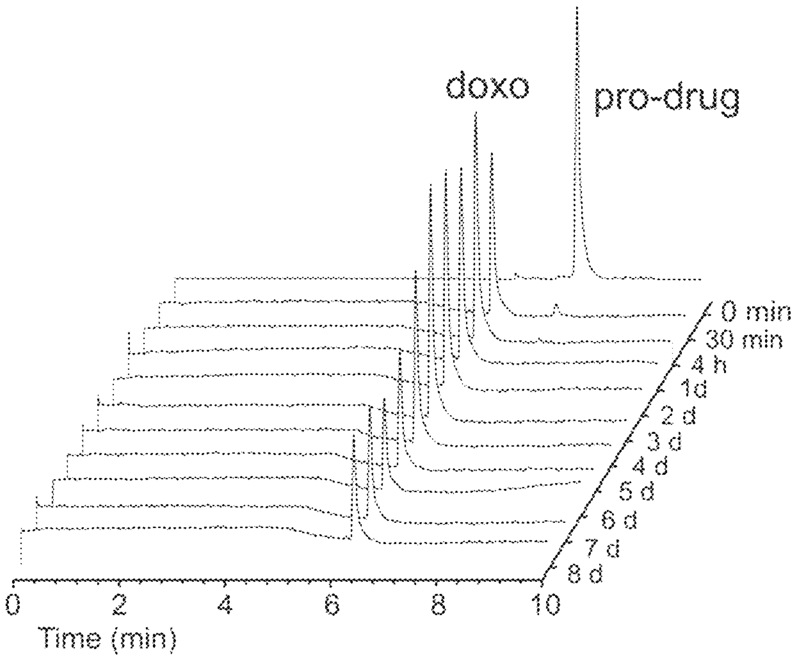
FIG. 17B shows sample data from high-pressure liquid chromatography analysis of the supernatant after mixing HTM with doxorubicin pro-drug for 30 minutes.
Figure 17C:
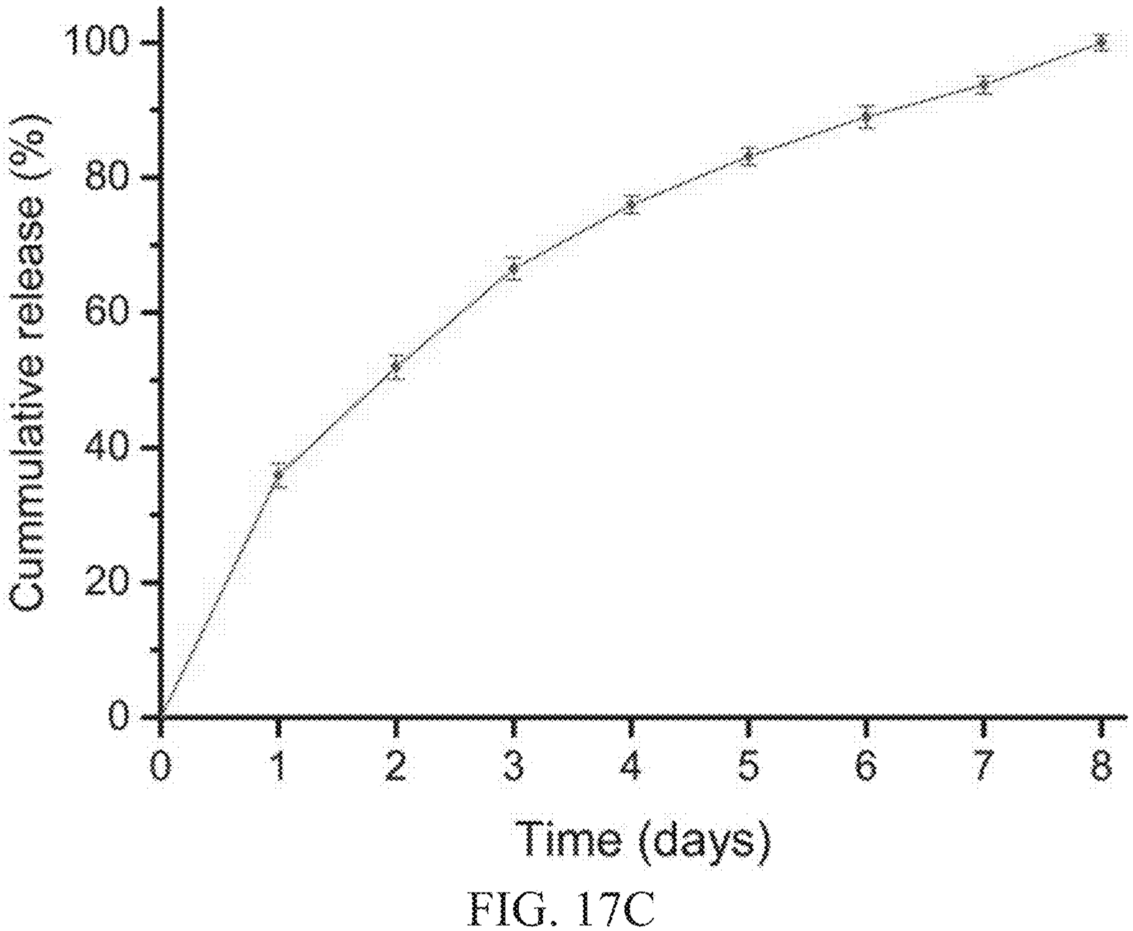
FIG. 17C shows cumulative release of doxorubicin after mixing HTM with doxorubicin pro-drug. For HPLC analysis, the concentration of the pro-drug shown at t=0 was diluted 10-fold. Data are averages±SEM, n=3.

Doxorubicin Pro-drug in-vitro Activation. When the HMT and the doxorubicin pro-drug were mixed in vitro for 30 minutes at room temperature, >99% of the compounds detected in the supernatant were regular doxorubicin as confirmed by high performance liquid chromatography (FIG. 17B). Subsequent daily measurements during a week detected only regular doxorubicin release (FIG. 17B and FIG. 17C). This confirms that the doxorubicin pro-drug is rapidly captured by the HMT and that the product released from the material is unmodified doxorubicin.

Figure 18A:
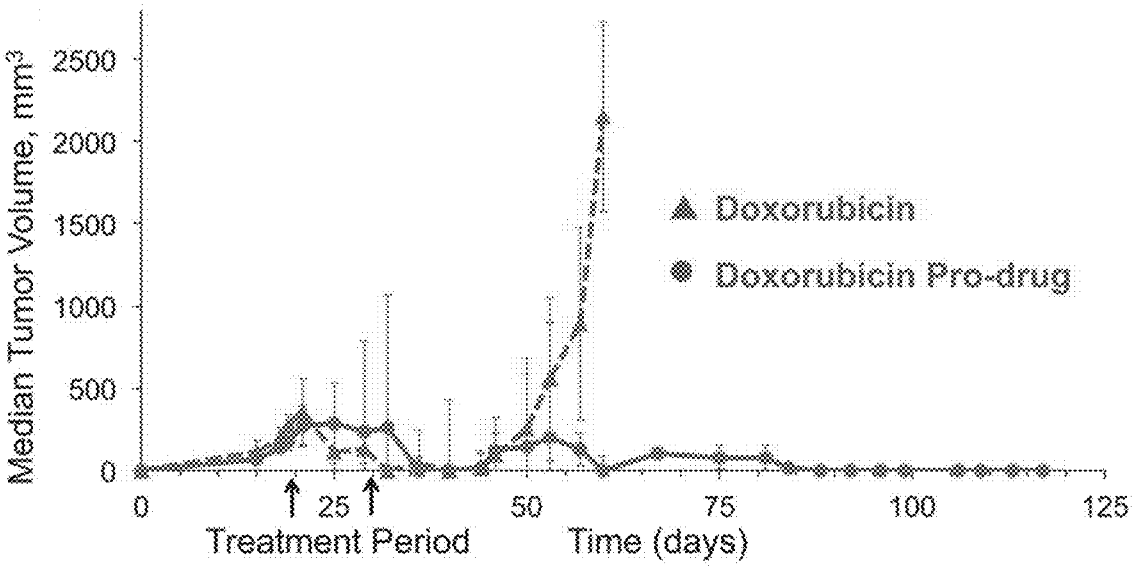
FIG. 18A, FIG. 18B, FIG. 18C, and FIG. 18D show the therapeutic effect of doxorubicin pro-drug in a xenograft model of soft tissue sarcoma.
Figure 18B:
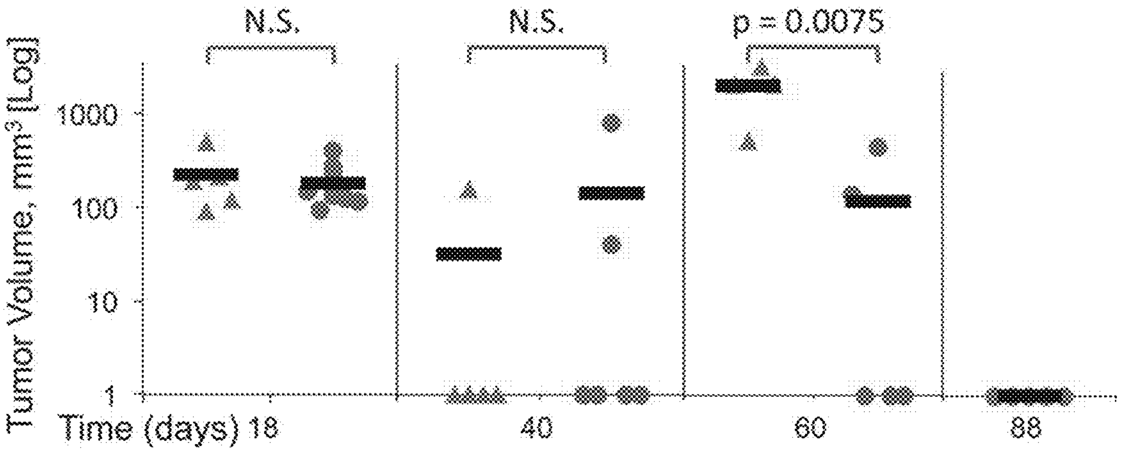
Figure 18C:
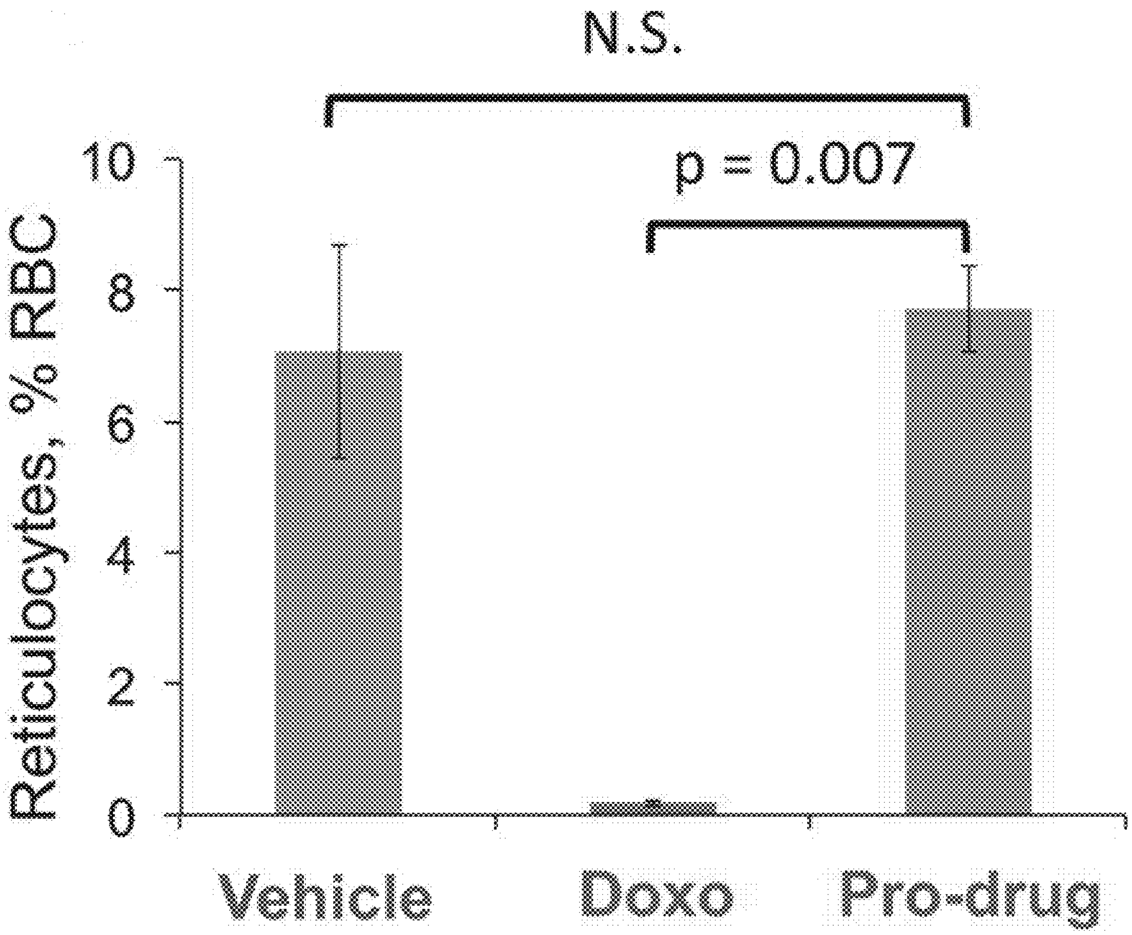
Figure 18D:
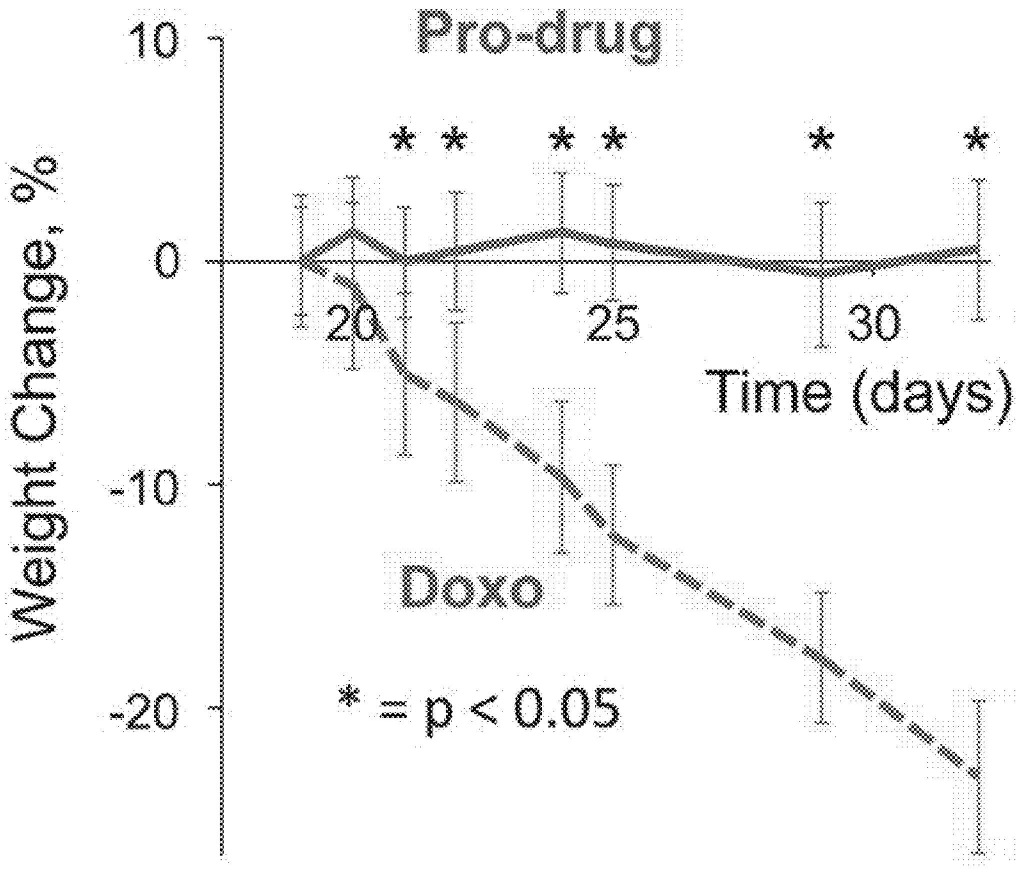

Doxorubicin Pro-drug Promotes Tumor Regression. To evaluate the antitumor activity of doxorubicin pro-drug when the HMT is injected near the tumor, we performed efficacy studies with athymic nude mice bearing human soft tissue sarcoma (HT-1080) xenografts. HMT was injected near the palpable soft tissue sarcoma tumors after 18 days when their size reached an average of 195 mm3 (range, 90-500 mm3). The mice were separated into two cohorts: (i) 3 intravenous doses of 14 μmoles/kg of doxorubicin every 4 days (maximum tolerable dose), (27, 49) or (ii) daily doses of 14 μmoles/kg of doxorubicin for 10 days (FIG. 18B). Tumor volumes were measured twice a week for 13 weeks (FIG. 18A). No further therapies were given to the subjects 28 days post tumoral implantation (dpi).

For both groups the median tumor size was undetectable 2 weeks after the last treatment dose (40 dpi). At this point 4/10 mice had not responded to the pro-drug therapy, while 1/5 in' the doxorubicin group had a mild response. 30 days after the last treatment dose (60 dpi) the median tumor size of the doxorubicin cohort was greater than 2000 $mm^3$, while the median tumor size of the tumors treated with the pro-drug remained undetectable (P=0.021). None of the tumor beds of the remaining mice (5/10) in the pro-drug cohort at 88 dpi showed any detectable tumors and remained that way until the end of the study, while all of the mice (5/5) in the doxorubicin group had reached the study endpoint of 2000 mm3 (FIG. 18B).

In order to exclude issues such as non-specific in-vivo activation of the pro-drug or microenvironment changes due to the placement of an alginate polymer, multiple additional controls were tested (FIG. 20). No differences in tumor volume were observed between untreated mice and mice treated with (i) local injection of alginate modified with tetrazine and i.v. administration of saline, or (ii) local injection of unmodified alginate and i.v. doxorubicin pro-drug administration. This confirms that the pro-drug does not spontaneously turn into the regular doxorubicin without the presence of the gel in clinically meaningful quantities.

Doxorubicin Pro-drug Does Not Cause Obvious Evidence of Tissue Toxicity. Myelosuppression is the dose-limiting toxicity of doxorubicin. A standard measure for this side effect is reticulocyte count, based on a short-lived precursor of red blood cells that is easily quantified. The maximum immunosuppression of doxorubicin therapy occurs 3 days after the end of therapy. The cohort treated with doxorubicin pro-drug showed reticulocyte counts similar to saline treated mice. As expected the doxorobucin-treated cohort showed a dramatic decrease in reticulocytes (P=0.007). Furthermore, mice treated with doxorubicin prodrug did not show any overt signs of toxicity, including weight loss or changes in coat texture, while the regular doxorubicin cohort lost about 20% of body weight. See FIGS. 18A-18D.

Discussion

Here, we show that local HMT increases the efficacy of a pro-drug modified with a TCO moiety limiting systemic toxicity. The local concentration and activation of the cytotoxic agent resulted in a better tumor response and tolerability, as measured by the lack of bone marrow suppression and body weight increase compared to the existing clinical standard of care.

Our combination approach increases the efficacy of doxorubicin, by harnessing the benefits of exogenous local activation, minimizing systemic toxicity and optimizing the local and regional therapeutic effects. Improved delivery of the most effective cytotoxic agent to a desired area may increase the number of patients with resectable tumors, as well as the number of resected tumors with clean margins, improving patient outcomes. With regards to distant micrometastasis, the low level of systemic toxicity of the approach would not preclude the concomitant use of systemic doxorubicin.

The values and limitations of animal xenograft models with regards to clinical efficacy have been well documented. (52-56) We attempted to minimize the limitations of our study by (i) using an aggressive cell line commonly used to evaluate new STS therapies, (27, 49, 50) (ii) implanting the cells in a relevant anatomical location, (iii) starting treatment at a representative advanced stage (54) and finally (iv) using a pro-drug of the cytotoxic agent with the best clinical efficacy for STS (3, 57) and that has shown a clinical drug dose response. (14) Most importantly our approach is not inherently dependent on enzymatic activity, pH, oxygen levels or other endogenous factor of the animal or tumor, but rather on an effective circulatory system and the placement of agents exogenous to the body.

We need further studies to evaluate nonresponders and the variables that prevent use from achieving a 100% response rate. It is possible that the optimal dosing schedule needs to be elucidated. Given the low level of toxicity observed, shorter courses with higher doses, or longer courses with smaller doses may be even more effective as has been recently suggested in the literature. (58-60) More studies are also needed to establish the dose limiting toxicities of the pro-drug as well as the HMT and the effect of the native tumor microenvironment on this approach.

The specificity of chemotherapies and the precision of radiation therapy have seen major improvements in the last 4 decades. Despite clear successes, many cancers, such as soft tissue sarcoma, only achieve a partial response to those treatment modalities at the costs of greater toxicity when used in combination. (61, 62) As the limitations of systemic maximum tolerable dose chemotherapy (9, 58-60), radiotherapy (61-64) and their combination become clear, there is an increasing need for new treatment modalities that minimize morbidity and optimize the outcomes of soft tissue sarcoma patients.

The potential applications of a modified therapeutic agent that is concentrated and activated via bioorthogonal chemistry by a pre-injected HMT, extend well beyond soft tissue sarcoma and doxorubicin. In cancers with limited response, this approach could be applied to a number of other therapeutic agents, such as other cytotoxics, immunomodulating drugs and radiosensitizing entities. Decreased toxicity may improve patient compliance for cytotoxic agents, enable therapies for people who are too frail to receive them or allow new pro-drug regimens to be evaluated in combination that were previously impossible due to dose limiting toxicities. This approach has tremendous potential to improve the outcomes of challenging neoplasms.

Example 3

Enhancing Systemic Therapies by Local Concentration and Activation of Therapeutic Agents Disclosed herein is a non-stochastic effect of TCO-doxorubicin in a soft tissue sarcoma model in mice. As one can appreciate from FIGS. 6-9, TCO-Doxorubicin is more effective than the maximum tolerable dose of doxorubicin with fewer side effects as evaluated by no weight loss. Furthermore, the disclosed studies suggest that TCO-doxorubicin in the absence of Tz-gel has no long term effect on the tumor growth suggesting that the TCO-doxorubicin construct maintains its integrity while in the body and does not release regular doxorubicin. Given the non-stochastic effect of the local TCO-doxorubicin concentration and activation leading to tumor inhibition and potential regression, this is an ideal therapy to combine with existing immunotherapy approaches.

As documented by Emmens and Middleton, immune checkpoint antagonists act on negative signals that diminish T-cell activation during the priming process, or inhibit effector T-cell activity at the tumor site. "Tumors co-opt these immunoregulatory pathways to circumvent immune surveillance and promote their growth and progression. Blocking immune checkpoints with antagonist monoclonal antibodies "takes the brakes off," restoring immune surveillance and unleashing T-cell function. Ipilimumab (Yervoy; Bristol-Myers Squibb) is a humanized IgG1 monoclonal antibody that blocks CTLA-4 signaling and is FDA approved for advanced melanoma. Pembrolizumab (Keytruda; Merck) and nivolumab (Opdivo; Bristol-Myers Squibb) are humanized IgG4 monoclonal antibodies that are FDA approved for metastatic melanoma; nivolumab received FDA approval in March of 2015 for squamous non-small cell lung cancer (NSCLC). Agents that target the PD-1 pathway also have clinical activity in a range of other cancer types, including some (urothelial bladder cancer and triple-negative breast cancer) that have been traditionally considered immunologically inert."

The disclosed system with anthracyclines, taxanes, gemcitabine and other agents mentioned in the Emmens paper, would enhance the efficacy of the aforementioned ipilimunab, nivolumab, pembrolizumab, avelumab (also known as MSB0010718C; Pfizer) and other checkpoint inhibitors.

Furthermore, the disclosed compositions and methods provide the ability to place particles at the time of the biopsy. When the results return, the practitioner can deliver through our system to the biopsy site chemokines (agents that attract cancerous cells and/or immune cells) and adjuvants to enhance the immune system with fewer side effects as well as the chemotherapeutics agents mentioned combined with immunotherapy agents. This combination approach would be beneficial to patients. The chemotherapy agent would treat the solid tumor or specific location, while the enhanced response of the immunotherapy would help with distant metastatic sites.

Another potential use of our approach is with any type of solid tumor. In particular our approach lends itself well as an adjuvant/neoadjuvant system. The particles could be placed during the biopsy, once the results from the study come back, the practitioner could deliver the appropriate cocktail to the desired site in the body. This would minimize the size of the tumor particularly in the context of a surgically resectable tumor. Then at the end of the surgery, the surgeon could place more particles around the surgical cavity and treat the patient with further doses of treatment (e.g. chemotherapy through the Shasqi approach) to minimize the risk of any cancer cells that may have been missed in the surgical margins.

Examples of solid tumors include but are not limited to melanoma (e.g., unresectable, metastatic melanoma), renal cancer (e.g., renal cell carcinoma), prostate cancer (e.g., metastatic castration resistant prostate cancer), ovarian cancer (e.g., epithelial ovarian cancer, such as metastatic epithelial ovarian cancer), breast cancer (e.g., triple negative breast cancer), glioblastoma, and lung cancer (e.g., non-small cell lung cancer), soft tissue sarcoma, fibrosarcoma, osteosarcoma, pancreatic cancer, among others.

Example 4

Delivery of Radionuclides

Disclosed are a biodegradable, cytocompatible implantable biomaterials that use bio-orthogonal chemistry to concentrate systemic molecular payloads to the biomaterial after implantation. This technology would be ideal for delivering radionuclides to pretargeting tumors that are traditionally difficult to target molecularly.

Figure 9C:
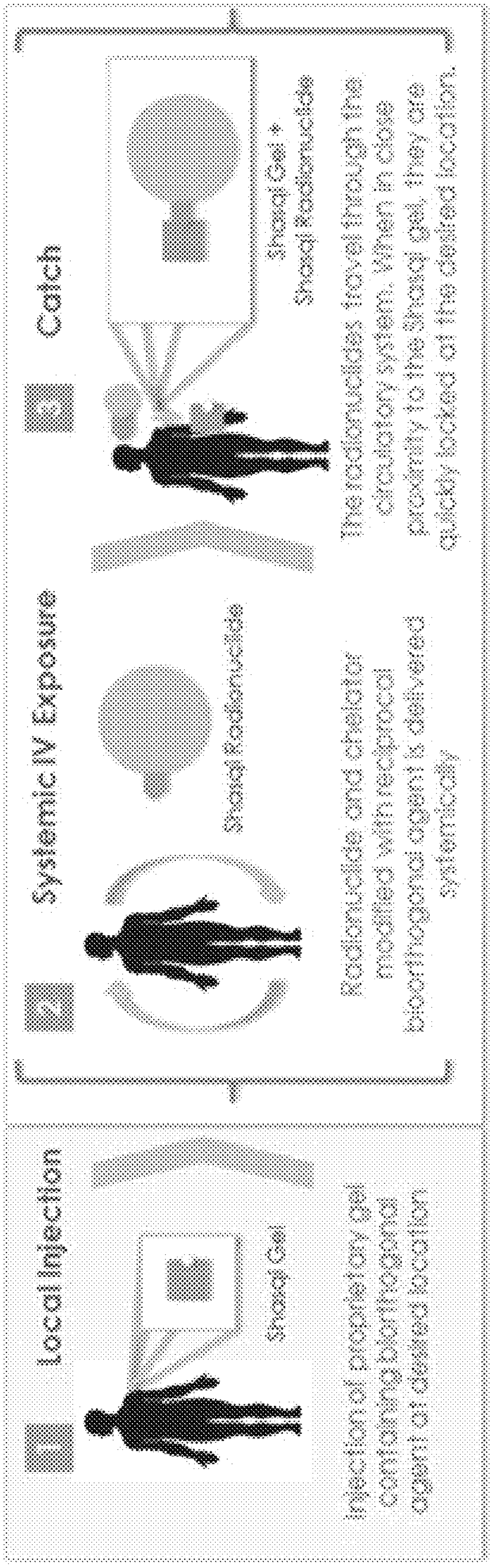
FIG. 9C shows one exemplary embodiment for a therapeutic process.
Figure 10A:
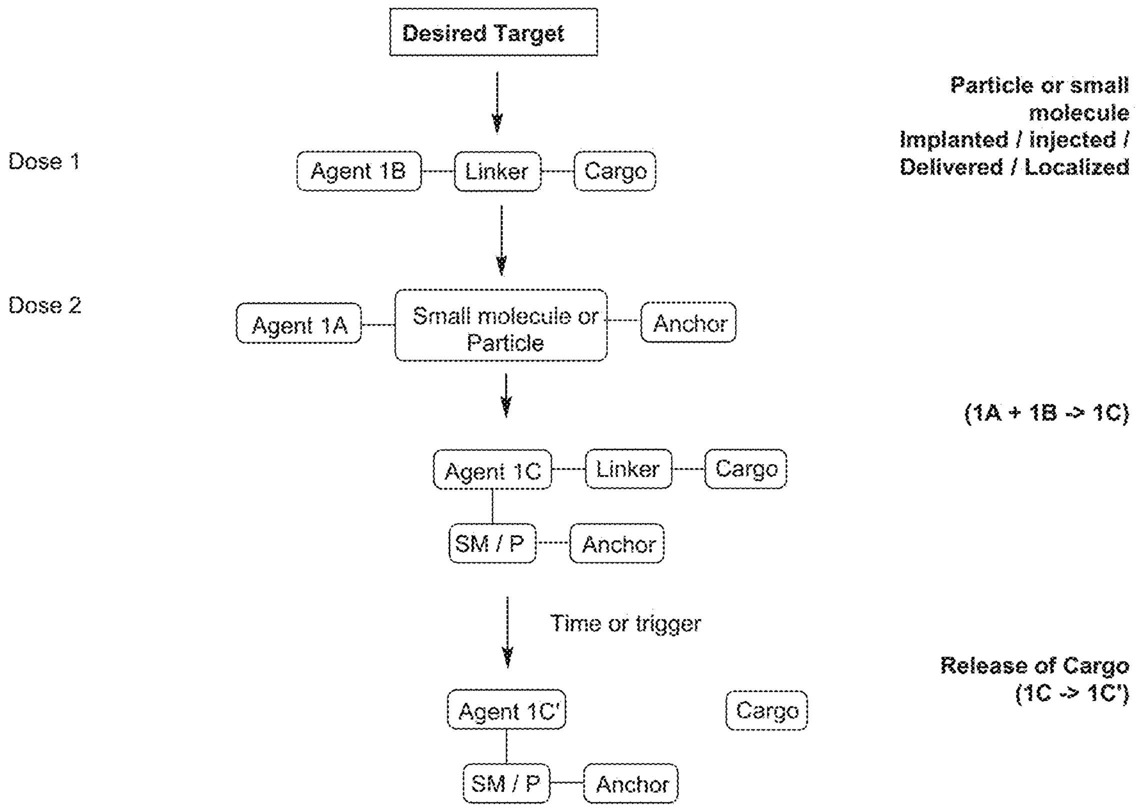
FIG. 10A a schematic of an administration protocol using support compositions and functionalized payloads, according to embodiments of the present disclosure.
Figure 10B:
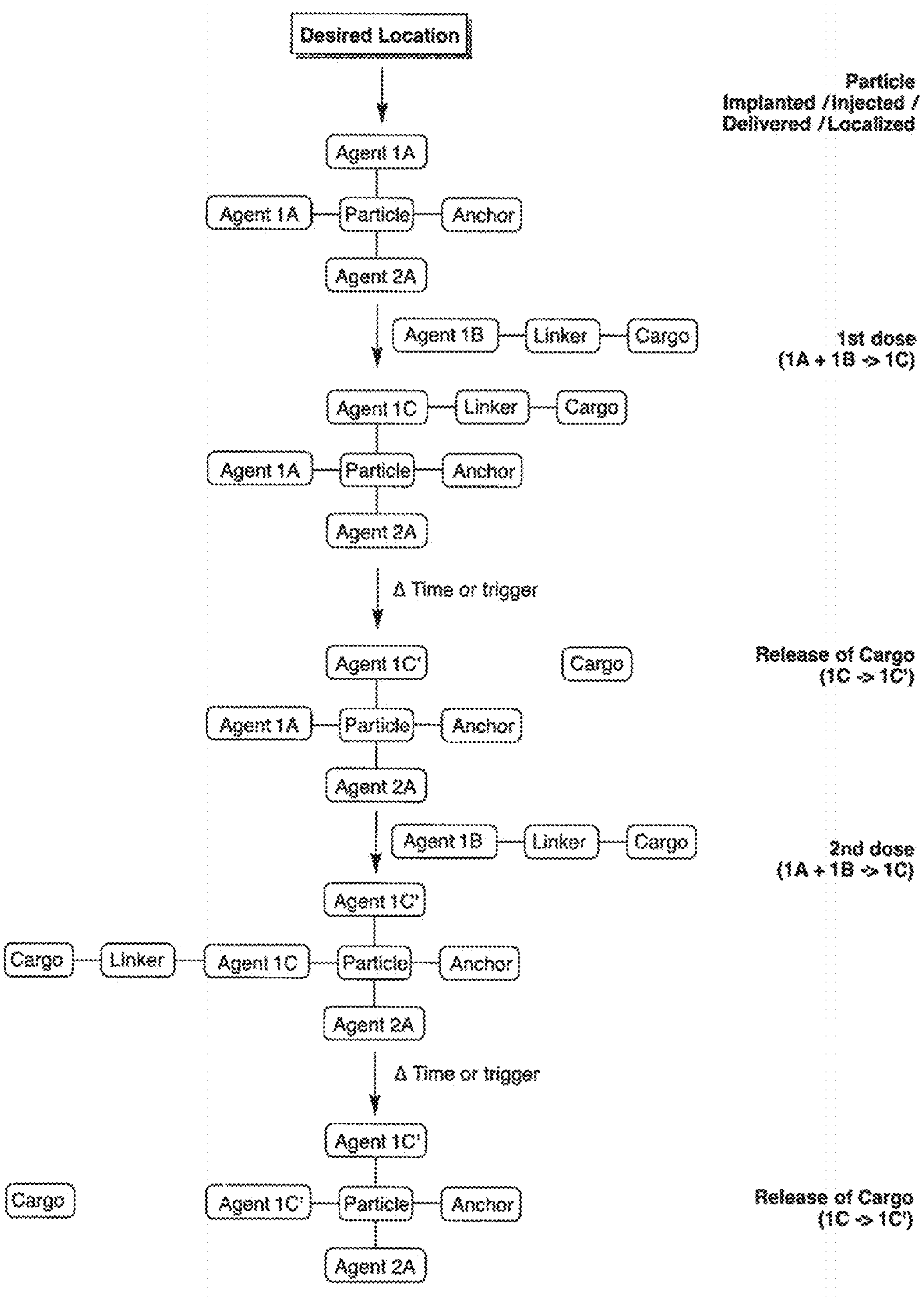
FIG. 10B a schematic of an administration protocol using support compositions and functionalized payloads, according to embodiments of the present disclosure.
Figure 10C:
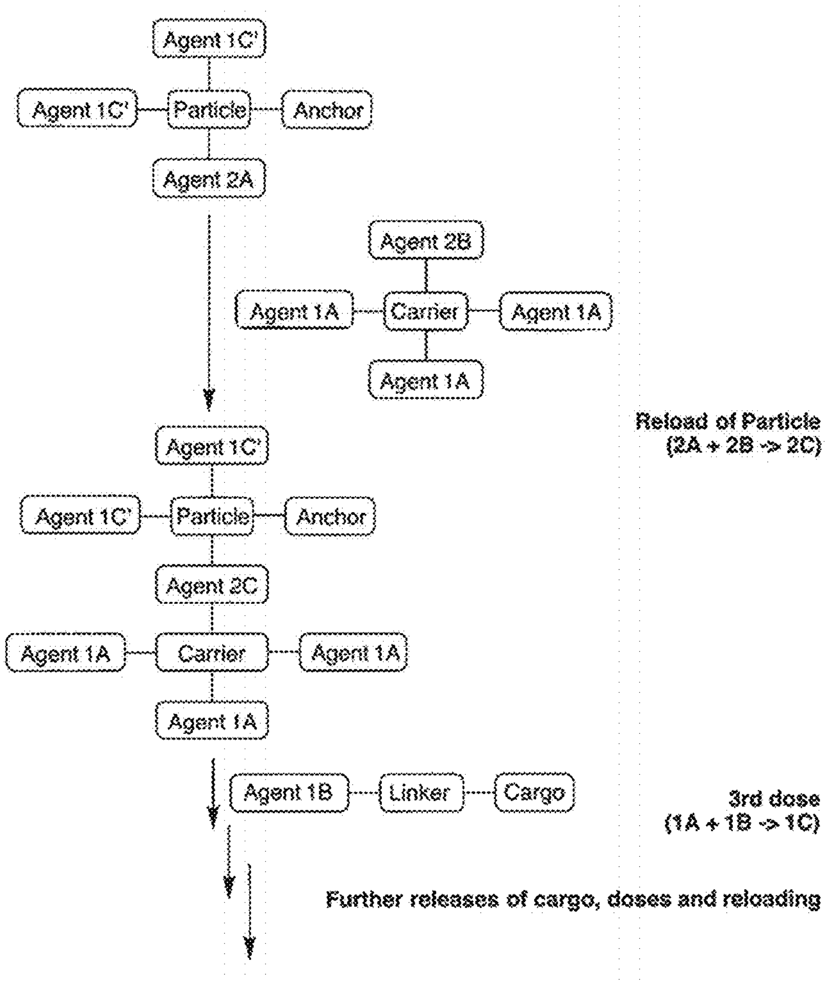
FIG. 10C shows a schematic of an administration protocol using support compositions and functionalized payloads, according to embodiments of the present disclosure.

The biomaterial can be injected or implanted at a desired location of the body ("local injection"), in this case during biopsy (neoadjuvant) or after resection (adjuvant). Then the radionuclide, chelated to a bioorthogonal reaction partner, is injected into the blood stream whenever it is needed ("systemic exposure"). The modified radionuclide would spread throughout the body, but when it comes near the gel they quickly attach covalently to each other ("capture"), thus concentrating the radionuclide at the desired location. The radionuclide would remain irreversibly attached at the implanted biomaterial, destroying the tumor. This technology effectively turns systemic radionuclides into molecularly targeted agents, with the caveat that the physician directs where the treatment goes by placing the gel (FIG. 9C).

Preliminary studies have shown that more radionuclides can be retained at the targeted region than the kidneys, suggesting lower rates of kidney toxicities that are associated with small molecule therapies. This is particularly compelling as indium-111 was used, a common imaging surrogate for yttrium-90. The non-invasive approach also would limit post-operative wound complications seen with brachytherapy or external beam radiation therapy.

The disclosed technology is expected to deliver a higher dose of radionuclide than what can be given alone or with other targeting approaches. This is expected to increase the drug's therapeutic index, resulting in both reduced side effects and increased survival rates. Further, by injecting or implanting a gel at the site of surgery or biopsy, the drug will be able to accumulate around the tumors where the dose of the radiation can be maintained away from the dermis preventing wound breakdown, which is a big problem with brachytherapy and external beam radiation therapy.

Example 5

Delivery of Antibiotics

While infections may have an initial locus of infection or entry point, in many cases, the bacteria disseminates from that entry point to other areas potentially leading to sepsis, which is a widespread infection. Systemic particles are delivered via the circulatory system and reach areas beyond the initial locus of infection. Targeting agents (such as monoclonal antibodies or affinity binding to specific targets on the surface of the pathogens) are used to selectively deliver support compositions as described herein to the surface of the bacteria. Once localized to the bacteria, the support composition is used to deliver therapeutic and/or diagnostic agents over multiple days using bioorthogonal TCO-Tz binding. If therapy is needed for more than 10 days, then the Tz functionalized payloads are recharged via a bioorthogonal binding agent, for example using azide-alkyne chemistry. The azide-alkyne bioorthogonal binding agents are used to deliver particles containing multiple reactive Tz binding agents over a period of months.

Example 6

Delivery of Chemotherapeutic Agents to Primary Tumor Sites

Tumor growth typically starts at a specific location in the body of a subject. A support composition (e.g., particle) that either remains in situ or has a targeting agent that attaches the support composition to the tumor cells is injected directly to the main tumor site, e.g., during biopsy. The support composition may also include diagnostic agents, such as radioactive moieties or optical imaging moieties to facilitate diagnosis. Using a Tz functionalized payload attached to the support composition, a therapeutic agent modified with TCO is delivered to the tumor site. The TCO and Tz agents react with each other leading to the delivery of the therapeutic agent to the targeted areas of the tumor. If therapy is needed for more than 10 days, the Tz active agents are recharged via a bioorthogonal binding agent, for example using azide-alkyne chemistry. The azide-alkyne bioorthogonal binding agents are used to deliver particles containing multiple Tz binding agents over a period of months.

Example 7

Delivery of Chemotherapeutic Agents to Sites of Metastasis

In some subjects, tumor growth starts localized and then spreads to other organs or areas of the body (metastasis). A support composition (e.g., particle) that targets markers (e.g., proteins, peptides) on the surface of the cancerous cells is systemically administered to the subject. The particles have a targeting agent that attaches the particles to the cancerous cells, thus localizing the particles to the sites of metastasis and clearing the particles from the circulatory system of the subject. The particles may also include diagnostic agents, such as radioactive moieties or optical imaging moieties to facilitate diagnosis. Using a Tz functionalized payload attached to the particles, a therapeutic agent attached to TCO is delivered to the cancerous cells. The TCO and Tz react with each other leading to the delivery of the therapeutic agent to the areas of metastasis. If therapy is needed for more than 10 days, the Tz active agents are recharged via a bioorthogonal binding agent, for example using azide-alkyne chemistry. The azide-alkyne bioorthogonal binding agents are used to deliver particles containing multiple Tz binding agents over a period of months.

Example 8

TCO-Gemcitabine

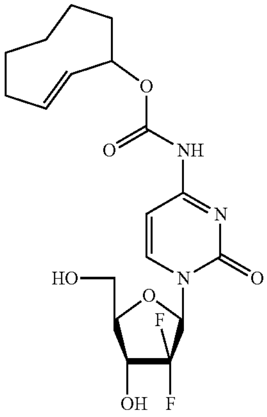

A functionalized payload of (E)-cyclooct-2-ene Gemcitabine was prepared as described below.

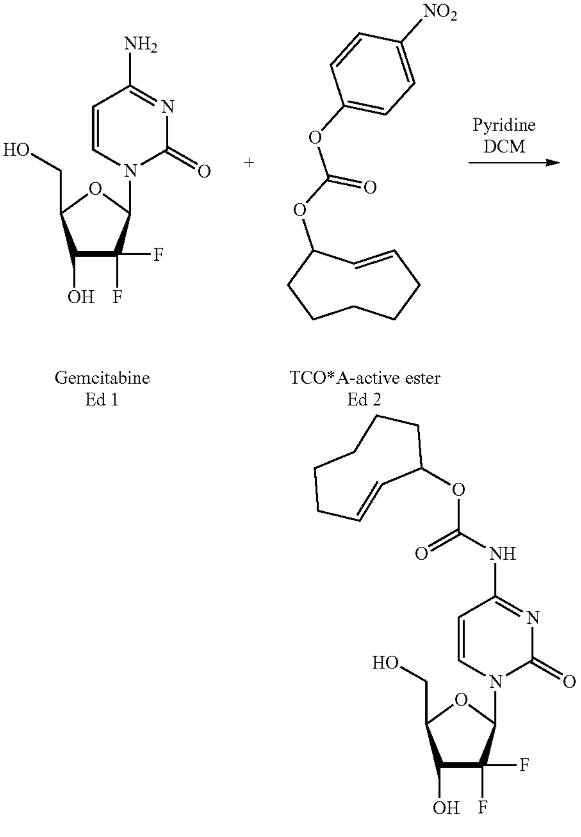

Gemcitabine
Ed 1

TCO*A-active ester
Ed 2

Figure 11:
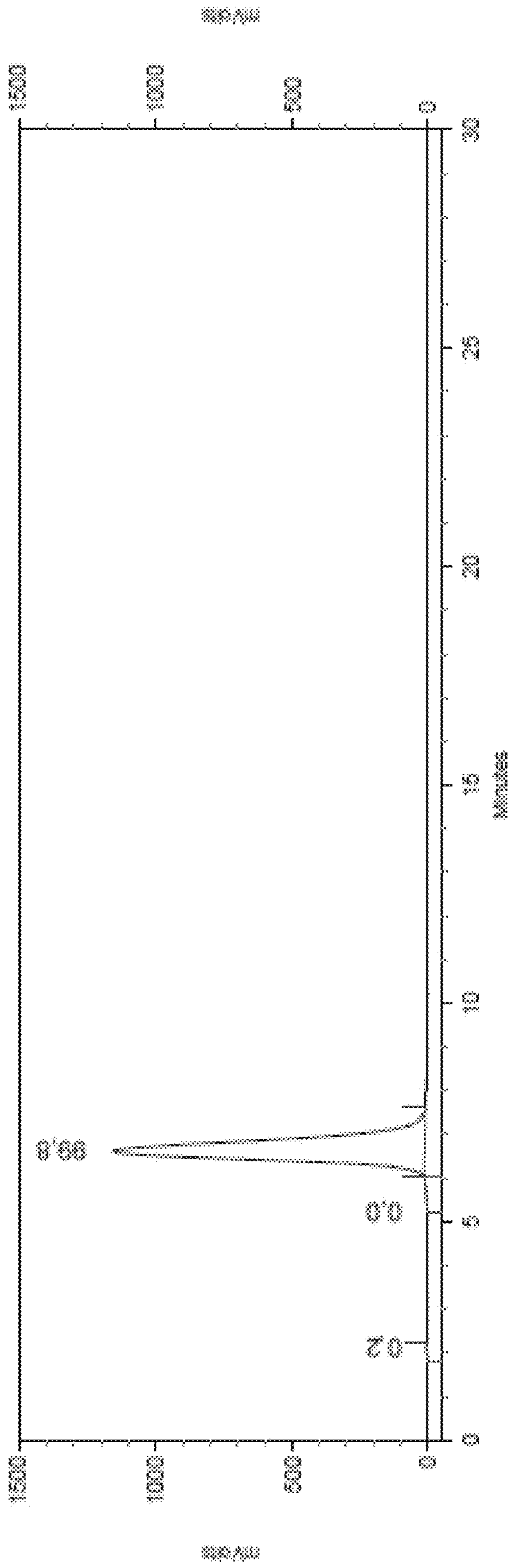
FIG. 11 shows an HPLC of a TCO-gemcitabine.
Figure 12:
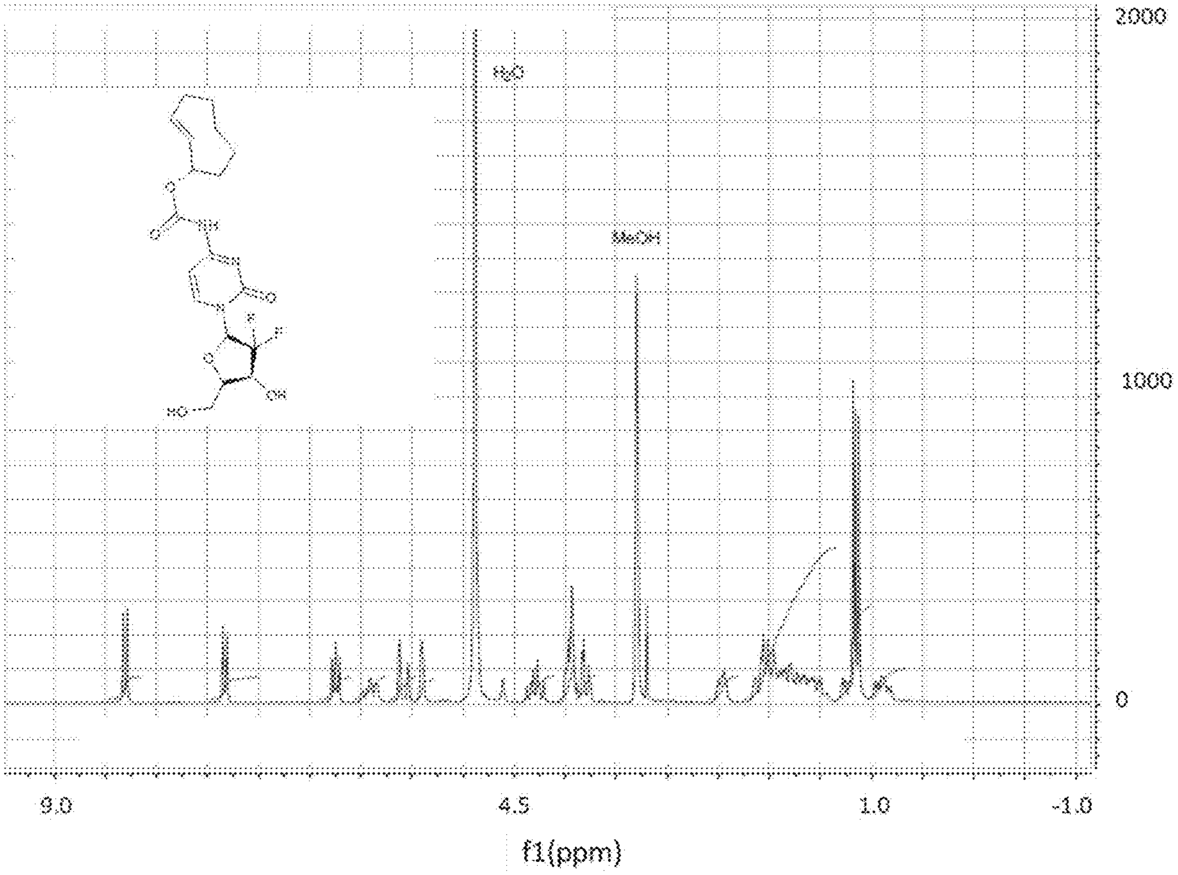
FIG. 12 shows a $^1$H-NMR of a TCO-gemcitabine.
Figure 13:
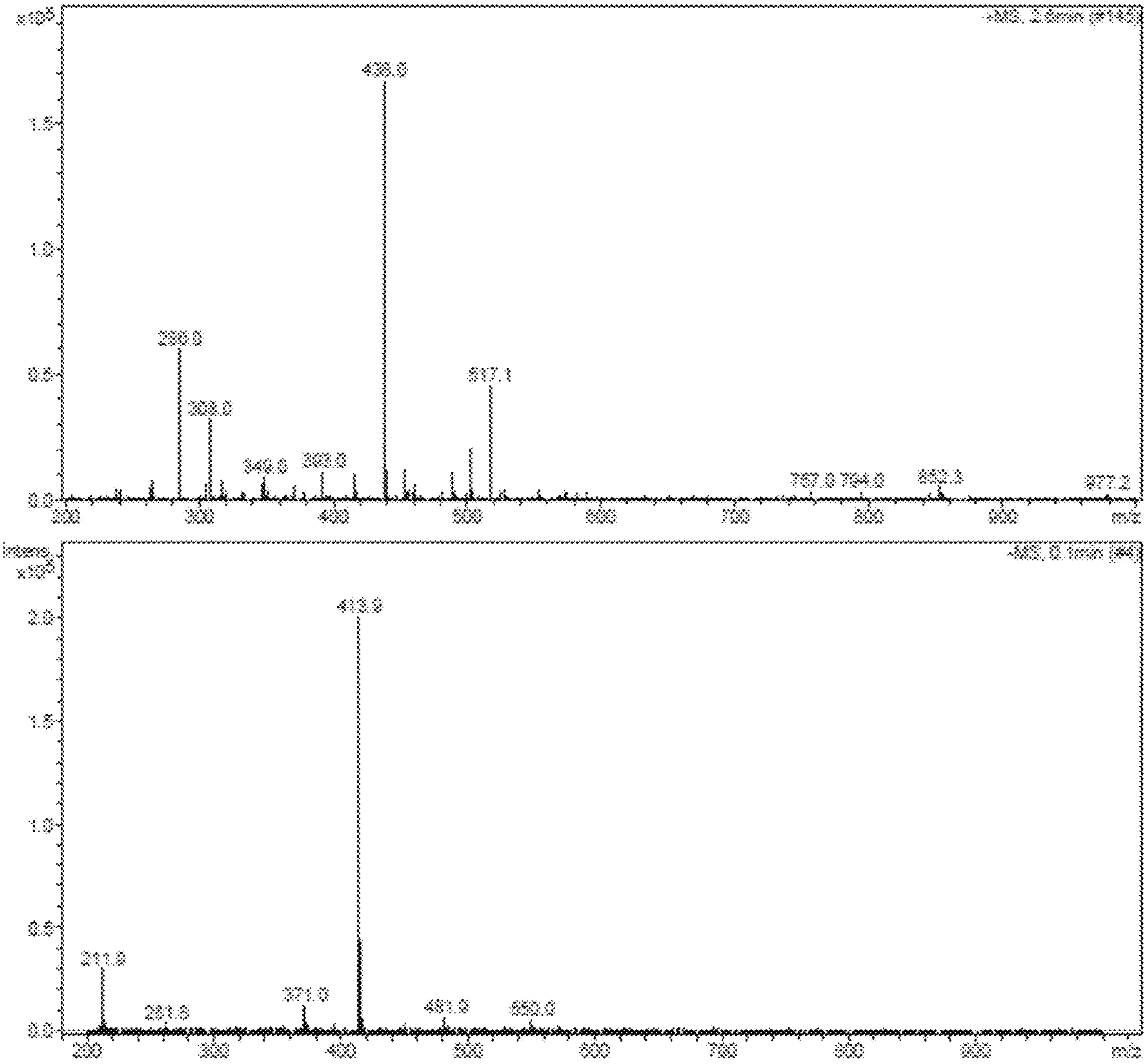
FIG. 13 shows an electrospray ionization mass spectrogram of TCO-gemcitabine.

Pr 1 g of Gemcitabine (3.8 mmol, 1 eq) and axial TCO active ester (1.2 grams, 4.2 mmol, 1.1 eq) were dissolved in a mixture of pyridine (50 mL, 620 mmol, 163 eq) and molecular sieve dried dichloromethane. The reaction mixture was allowed to stir at r.t. for 3 days under a blanket of nitrogen. The solution was concentrated to dryness under reduced pressure. The solid yellowish residue was redissolved in the eluent (70% methanol, 30% water) and purified by RP-HPLC. The result was 0.22 g (0.53 mmol, 14% yield) of the product. The product was obtained in a purity of ≥99% (HPLC, NMR) and confirmed by $^{1}$H-NMR, 200 MHZ ($CD_3OD$), $^{13}$C-NMR, 200 MHz ($CD_3OD$), and electrospray ionization mass spectrometry (ESI-MS). See FIGS. 11-13.

Example 9

TCO-Docetaxel

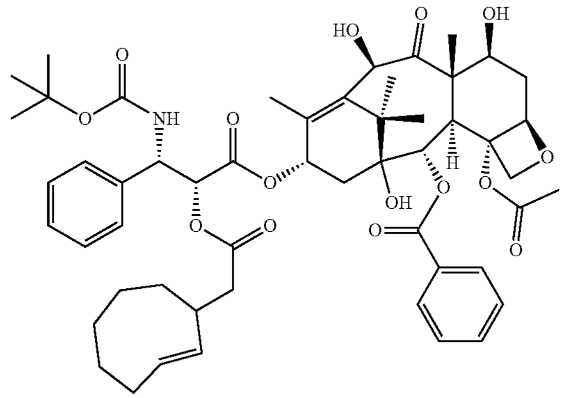

A functionalized payload of TCO-docetaxel was prepared as described below.

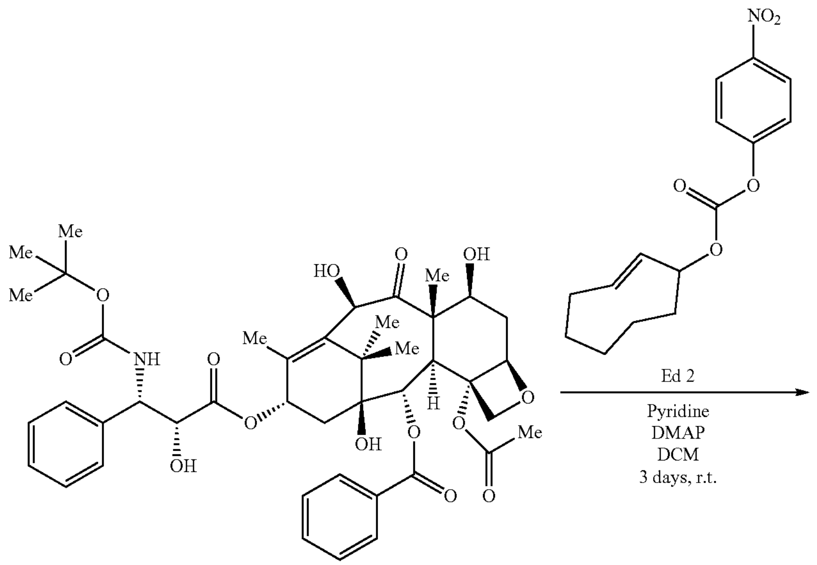

Docetaxel
Ed 1

-continued

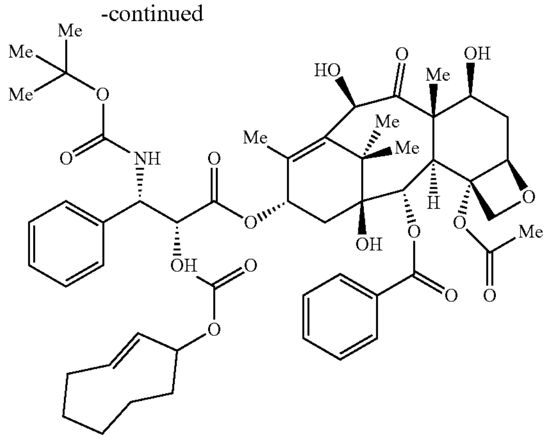

TCO*A-Docetaxel
Pr 1

Figure 14:
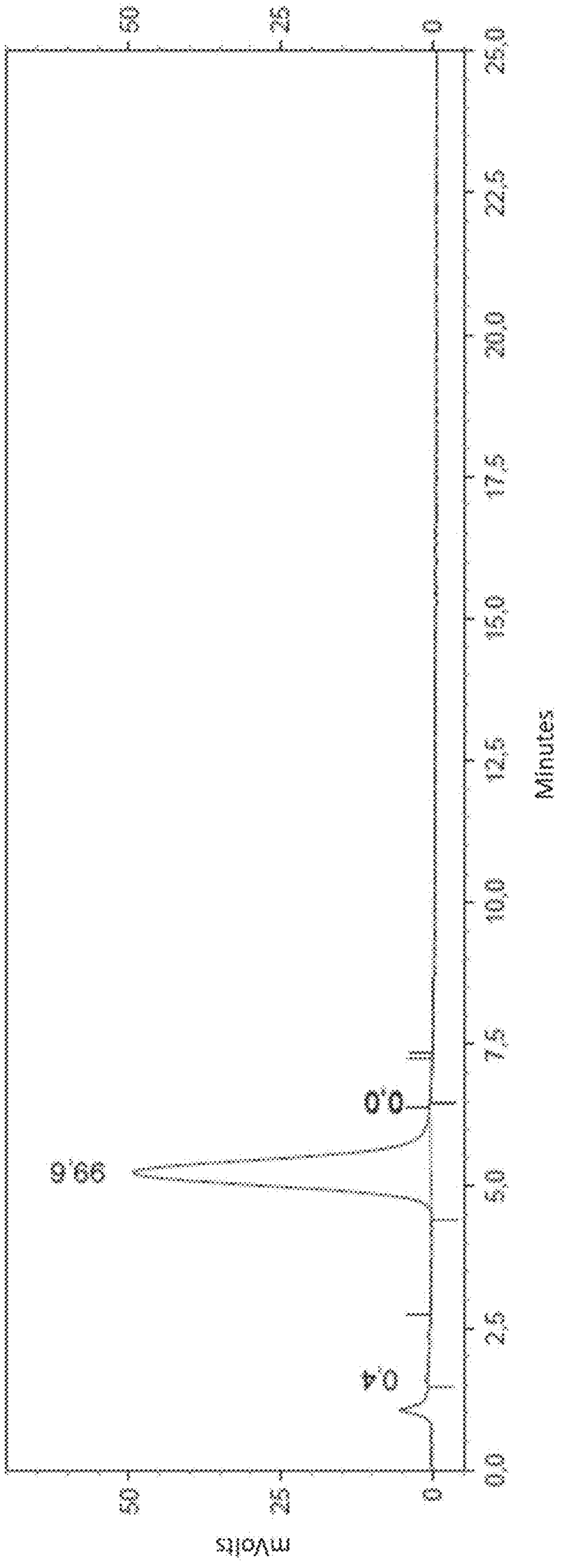
FIG. 14 shows an HPLC of a TCO-docetaxel.
Figure 15:
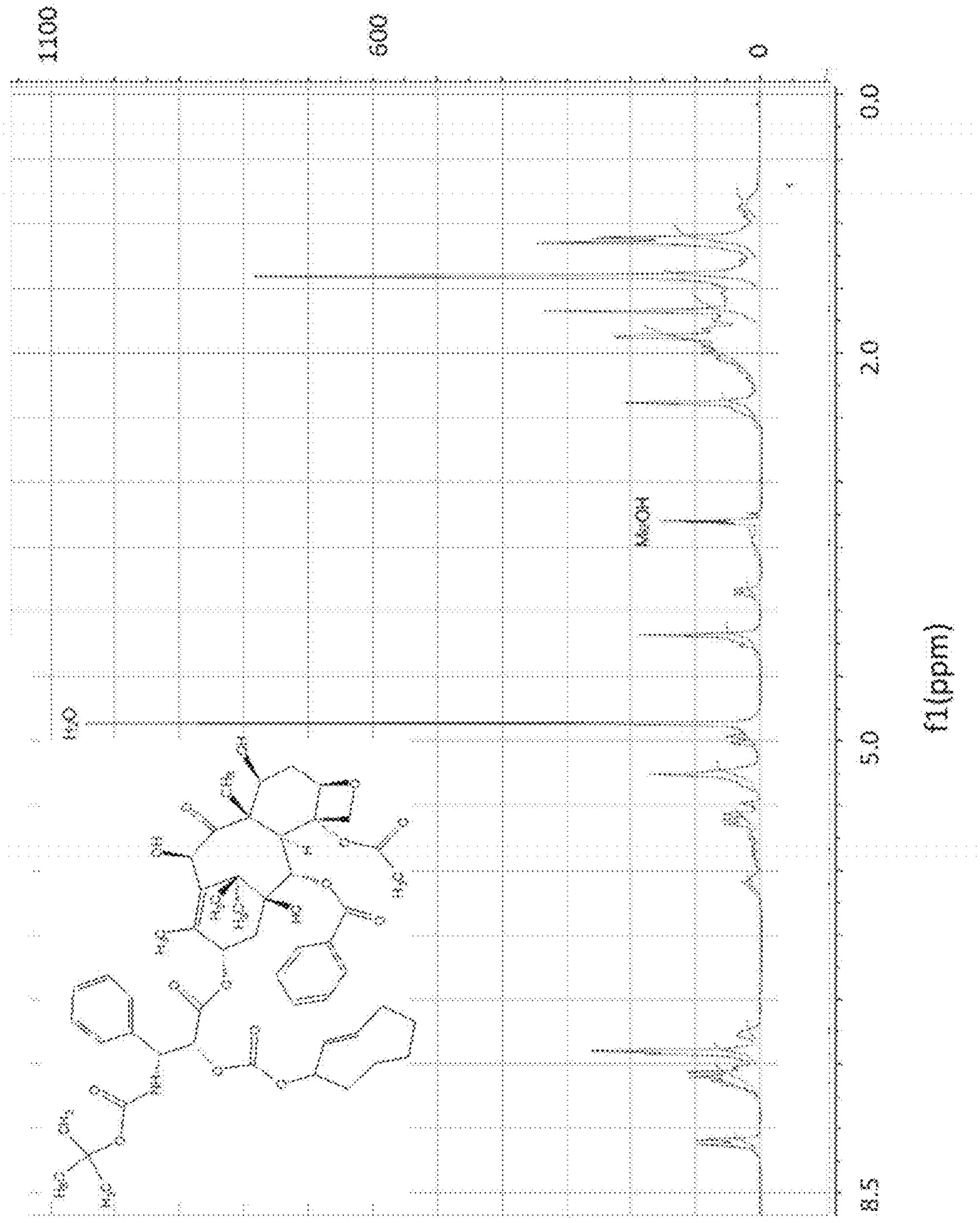
FIG. 15 shows a $^1$H-NMR of a TCO-docetaxel.
Figure 16:
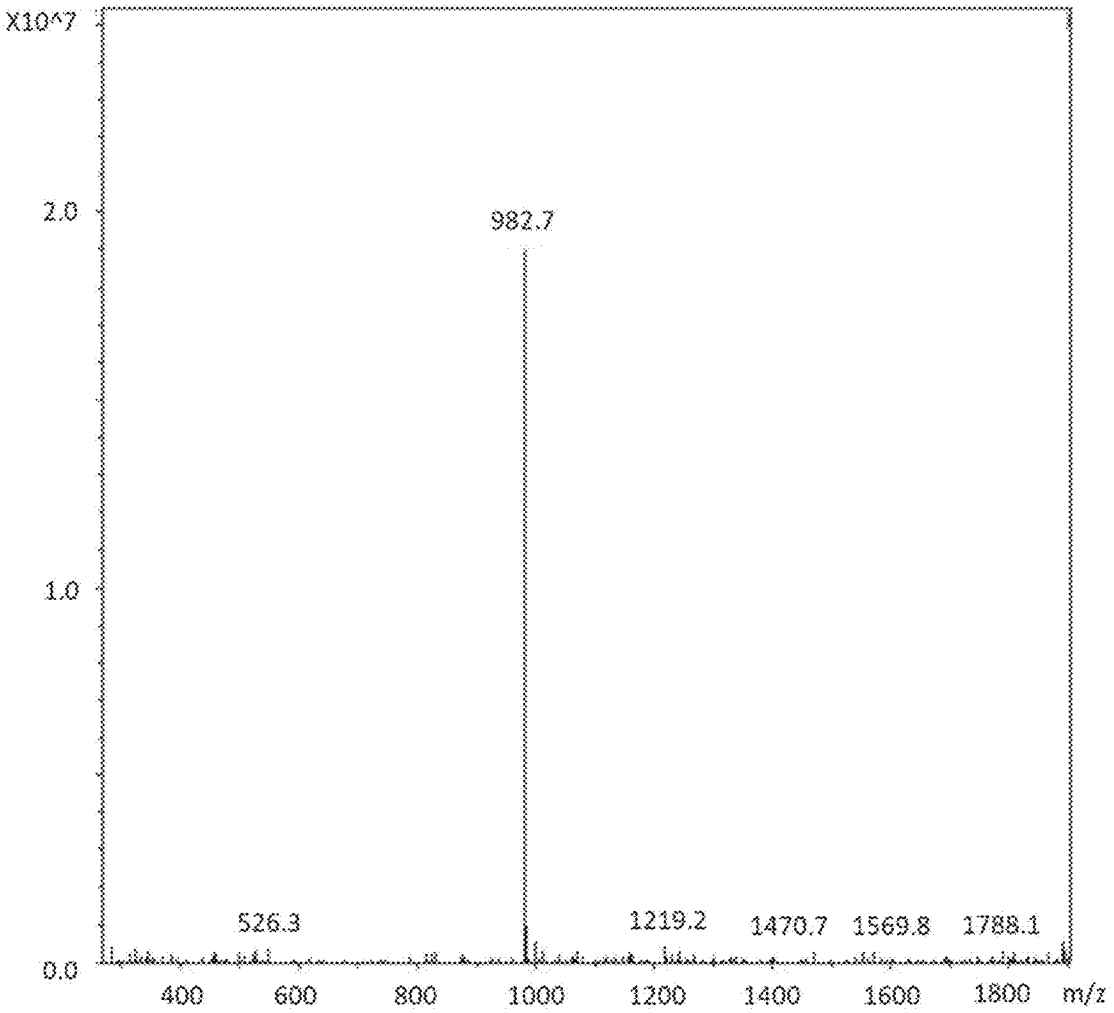
FIG. 16 shows an electrospray ionization mass spectrogram of TCO-docetaxel.

Docetaxel (Ed1, 0.4 grams, 0.49 mmol, 1 eq) was dissolved in pyridine (6.5 ml, 80.76 mmol, 163 eq) at room temperature. The obtained solution was cooled down to 0° C. (ice/water bath). A solution of the activated TCO (Ed 2, 0.158 grams, 0.54 mmol, 1.1 eq) in 5 ml of molecular sieve dried dichloromethane was dropped in within 2 minutes followed by the addition of 4-dimethylaminopyridine (0.006 grams, 0.049 mmol, 0.1 eq) at once. The yellow solution was allowed to warm to room temperature and stirred for 3 days. The reaction mixture was concentrated to constant weight under reduced pressure, delivering 0.58 grams of a dark yellow oily residue. The oily residue (0.58 grams) was dissolved in 20 ml of eluent and injected in one shot into a preparative HPLC (Eluent: 80% methanol, 20% water, isocratic, 55 ml/min; Column: YMC Triart C180-S, RP 250×50 nm). The white solid was obtained in 29.8% yield (0.140 g, 0.015 mmol) in a purity of ≥99% (HPLC, NMR) and confirmed by $^1$H-NMR, 200 MHZ ($CD_3OD$), $^{13}$C-NMR, 200 MHz ($CD_3OD$), and electrospray ionization mass spectrometry (ESI-MS). See FIGS. 14-16.

Example 10

Support Composition

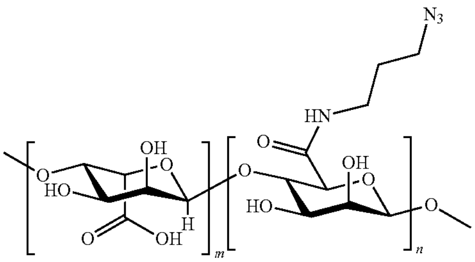

-continued

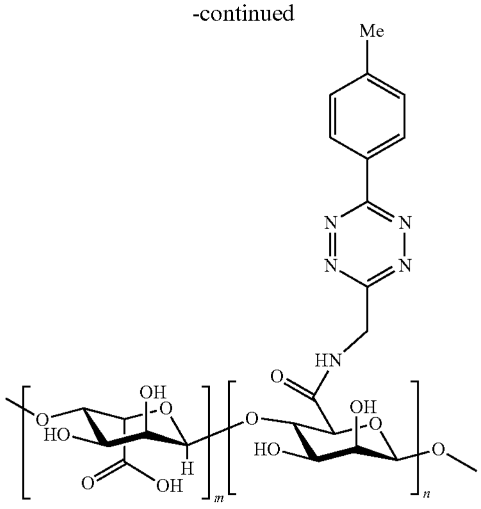

To 10 mL of MES buffer (0.1 M MES, 0.3 M NaCl, pH=6.5) was added 0.1 grams of UP MVG alginate and stirred until it dissolved (4 hours). To this, was added N-hydroxysuccinamide (23.2 mg, 0.107 mmols), N,N'-dicyclohexylcarbodiimide (41.2 mg, 0.215 mmols), (4-(6-methyl-1,2,4,5-tetrazin-3-yl)phenyl) methanamine hydrochloride (13.4 mg, 0.056 mmols), and azide-propylamine (1.0 mg, 0.010 mmols). The reaction mixture was stirred for 20 hours in the absence of light for after which time it was quenched with hydroxylamine (132.4 mg, 1.905 mmols). The alginate product was purified in the absence of light against deionized water containing a decreasing salt concentration (NaCl, 0.13 M-0.0 M) over 4 days. The alginate was filtered (0.22 μm) and lyophilized for 5 days.

Example 11

Support Composition

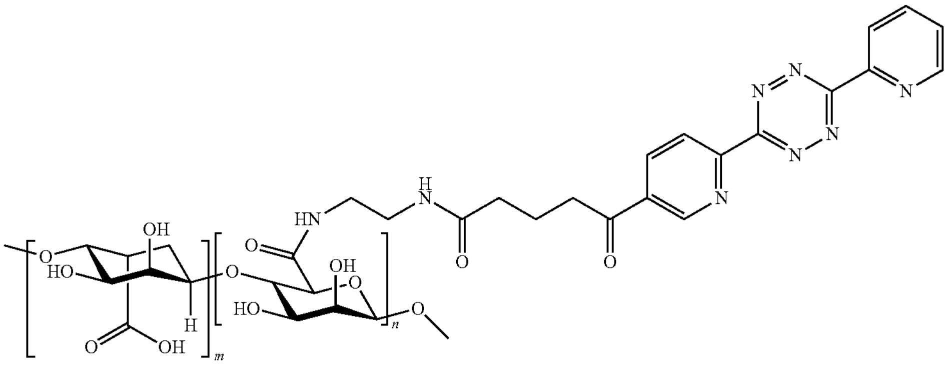

To 10 mL of MES buffer (0.1 M MES, 0.3 M NaCl, pH=6.5) was added 0.1 grams of UP MVG alginate and stirred until it dissolved (4 hours). To this, was added N-hydroxysuccinamide (46.4 mg, 0.214 mmols), N,N'-dicyclohexylcarbodiimide (82.4 mg, 0.430 mmols), and Bispirydil Tetrazine (69.6 mg, 0.134 mmols). The reaction mixture was stirred for 20 hours in the absence of light for after which time it was quenched with hydroxylamine (132 mg, 1.905 mmols). The alginate product was purified in the absence of light against deionized water containing a decreasing salt concentration (NaCl, 0.13 M-0.0 M) over 4 days. The alginate was filtered (0.22 μm) and lyophilized for 5 days.

Example 12

Support Composition

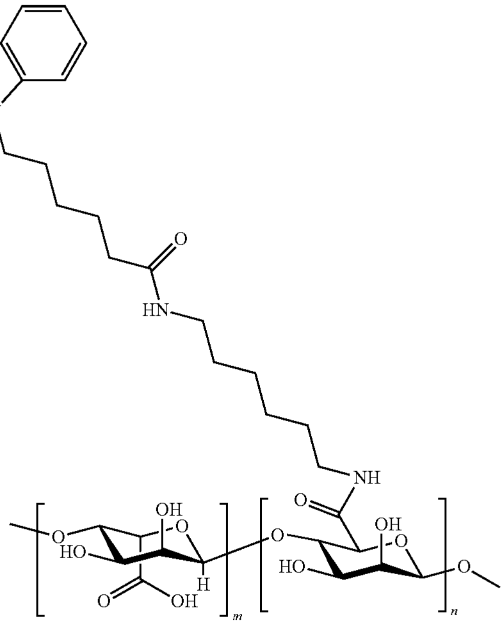

-continued

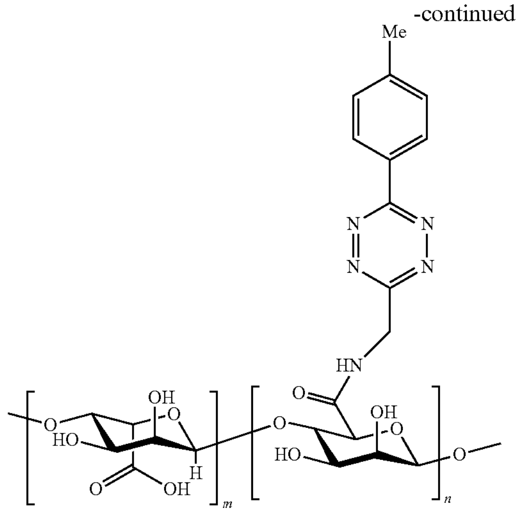

To 10 mL of MES buffer (0.1 M MES, 0.3 M NaCl, pH=6.5) was added 0.1 grams of UP MVG alginate and stirred until it dissolved (4 hours). To this, was added N-hydroxysuccinamide (46.4 mg, 0.215 mmols), N,N'-dicyclohexylcarbodiimide (82.4 mg, 0.430 mmols), (4-(6-methyl-1,2,4,5-tetrazin-3-yl)phenyl) methanamine hydrochloride (32.0 mg, 1.35 mmols), and Cyanine 5 amine (1.0 mg, 0.002 mmols, in 3 mL of MES buffer). The reaction mixture was stirred for 20 hours in the absence of light for after which time it was quenched with hydroxylamine (132.4 mg, 1.905 mmols). The alginate product was purified in the absence of light against deionized water containing a decreasing salt concentration (NaCl, 0.13 M-0.0 M) over 4 days. The alginate was filtered (0.22 μm) and lyophilized for 5 days.

Example 13

Support Composition

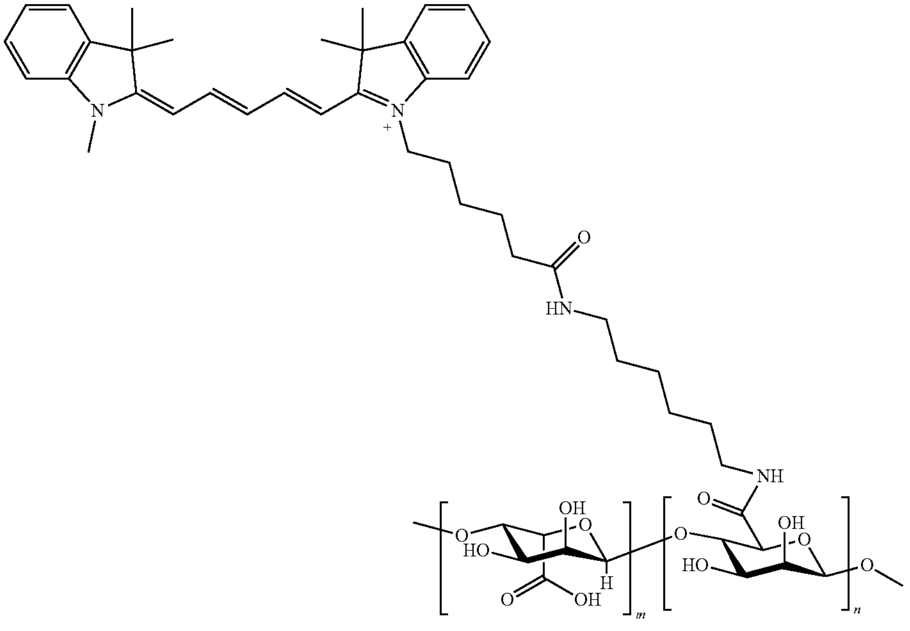

-continued

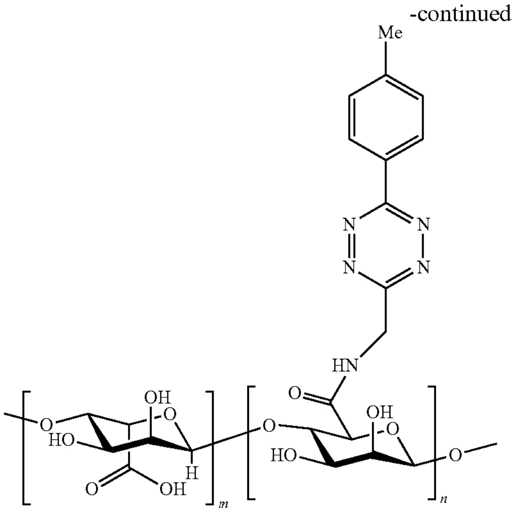

To 5 mL of MES buffer (0.1 M MES, 0.3 M NaCl, pH=6.5) was added 0.05 grams of MeTz-Gel and stirred until it dissolved (4 hours). To this, was added N-hydroxysuccinamide (4.55 mg, 0.021 mmols), N,N'-dicyclohexylcarbodiimide (8.04 mg, 0.043 mmols), and Cyanine 5 amine (1.0 mg, 0.0013 mmols, in 3 mL of MES buffer). The reaction mixture was stirred for 20 hours in the absence of light for after which time it was quenched with hydroxylamine (5.70 mg, 0.082 mmols). The alginate product was purified in the absence of light against deionized water containing a decreasing salt concentration (NaCl, 0.13 M-0.0 M) over 4 days. The alginate was filtered (0.22 μm) and lyophilized for 5 days.

Example 14

Support Composition

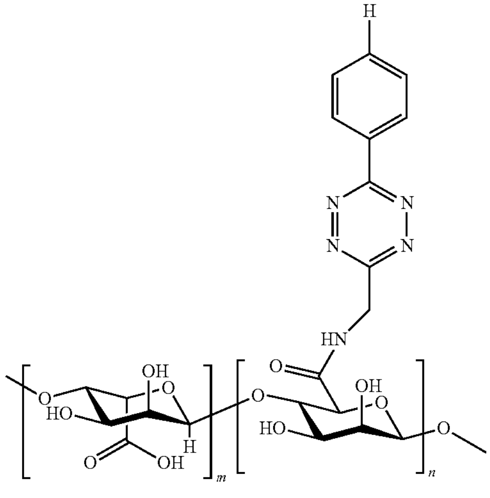

To 8.3 mL of MES buffer (0.1 M MES, 0.3 M NaCl, pH=6.5) was added 83 milligrams of UP MVG alginate and stirred until it dissolved (4 hours). To this, was added N-hydroxysuccinamide (38.6 mg, 0.178 mmols), N,N'-dicyclohexylcarbodiimide (68.5 mg, 0.356 mmols), and (1,2,4,5-tetrazin-3-yl)phenyl) methanamine hydrochloride (25.0 mg, 0.112 mmols). The reaction mixture was stirred for 20 hours in the absence of light for after which time it was quenched with hydroxylamine (110.0 mg, 1.574 mmols). The alginate product was purified in the absence of light against deionized water containing a decreasing salt concentration (NaCl, 0.13 M-0.0 M) over 4 days. The alginate was filtered (0.22 μm) and lyophilized for 5 days.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A therapeutic support composition comprising a tetrazine-containing group of formula

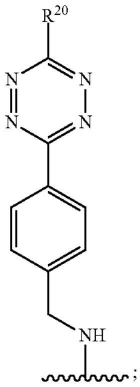

wherein $R^{20}$ is alkyl;

wherein the tetrazine-containing group is covalently attached directly to a support through an amide and the support is a hyaluronic acid.

2. The therapeutic support composition of claim 1, wherein the support is a hydrogel.

3. The therapeutic support composition of claim 1, wherein the support is a particle.

4. The therapeutic support composition of claim 3, wherein the particle is a nanoparticle.

5. The therapeutic support composition of claim 1, comprising:

an azide-containing group of formula:

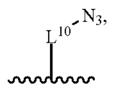

wherein $L^{10}$ is a linker; or an alkyne-containing group of formula:

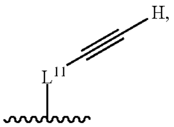

wherein $L^{11}$ is a linker.

6. The therapeutic support composition of claim 5, wherein each linker is a $C_1$-$C_{10}$-alkylene group.

7. A therapeutic support composition comprising a particle, to which a tetrazine-containing group is attached, represented by the following formula

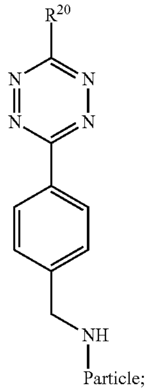

wherein:

$R^{20}$ is alkyl;

the particle is hyaluronic acid, and the tetrazine-containing group is covalently attached directly to the particle through an amide.

* * * * *